US012774477B2

(12) United States Patent
Lorántfy et al.

(10) Patent No.: US 12,774,477 B2
(45) Date of Patent: Oct. 27, 2026

(54) METHODS FOR PRODUCTION, RECOVERY AND SECRETION OF HYDROPHOBIC COMPOUNDS IN A FERMENTATION

(71) Applicant: FMC Agricultural Solutions A/S, Harboøre (DK)

(72) Inventors: Bettina Lorántfy, Harboøre (DK); Irina Borodina, Harboøre (DK)

(73) Assignee: FMC AGRICULTURAL SOLUTIONS A/S, Ronland (DK)

( * ) Notice: Subject to any disclaimer, the term of this patent is extended or adjusted under 35 U.S.C. 154(b) by 1093 days.

(21) Appl. No.: 17/767,808

(22) PCT Filed: Sep. 22, 2020

(86) PCT No.: PCT/EP2020/076351

§ 371 (c)(1),
(2) Date: Apr. 8, 2022

(87) PCT Pub. No.: WO2021/078452

PCT Pub. Date: Apr. 29, 2021

(65) Prior Publication Data

US 2024/0043880 A1 Feb. 8, 2024

(30) Foreign Application Priority Data

Oct. 22, 2019 (EP) .................................... 19204554

(51) Int. Cl.

| | |
|---|---|
| ***C12P 7/04*** | (2006.01) |
| ***C12N 1/165*** | (2026.01) |
| ***C12N 9/02*** | (2006.01) |
| ***C12N 9/10*** | (2006.01) |
| ***C12P 7/24*** | (2006.01) |
| ***C12P 7/64*** | (2022.01) |

(52) U.S. Cl.

CPC ................ *C12P 7/04* (2013.01); *C12N 1/165* (2021.05); *C12N 9/001* (2013.01); *C12N 9/1029* (2013.01); *C12P 7/24* (2013.01); *C12P 7/64* (2013.01); *C12Y 103/03006* (2013.01); *C12Y 203/01086* (2013.01)

(58) Field of Classification Search

None

See application file for complete search history.

(56) References Cited

U.S. PATENT DOCUMENTS

| | | | | |
|---|---|---|---|---|
| 7,659,097 | B2 | 2/2010 | Renninger et al. | |
| 2007/0259428 | A1 | 11/2007 | Chen et al. | |
| 2010/0151525 | A1* | 6/2010 | Hedges ................ | C07K 14/375 530/427 |
| 2018/0162916 | A1* | 6/2018 | Borodina ................. | C12P 7/24 |
| 2019/0136266 | A1 | 5/2019 | D'Espaux et al. | |

FOREIGN PATENT DOCUMENTS

| | | | |
|---|---|---|---|
| WO | 1999/54432 | A1 | 10/1999 |
| WO | WO2012/087964 | A1 | 6/2012 |
| WO | 2014/131084 | A1 | 9/2014 |
| WO | 2016/207339 | A1 | 12/2016 |
| WO | WO2017/214133 | A2 | 12/2017 |
| WO | 2018/109163 | A1 | 6/2018 |
| WO | 2018/109167 | A1 | 6/2018 |
| WO | WO 2018/187389 | A2 | 10/2018 |
| WO | WO 2018/213554 | A1 | 11/2018 |
| WO | 2020/169389 | A1 | 8/2020 |

OTHER PUBLICATIONS

Chica et al. Curr Opin Biotechnol. Aug. 2005; 16(4):378-84. (Year: 2005).*

Singh et al. Curr Protein Pept Sci. 2017, 18, 1-11 (Year: 2017).*

Kizer et al. Appl Environ Microbiol. May 2008;74(10):3229-41. (Year: 2008).*

Prather et al. Curr Opin Biotechnol. Oct. 2008; 19(5):468-74. (Year: 2008).*

Accession S4WAY4. Oct. 16, 2013 (Year: 2013).*

Accession BDL70211. Feb. 23, 2017 (Year: 2017).*

Anelli, P. et al., Fast and Selective Oxidation of Primary Alcohols to Aldehydes or to Carboxylic Acids and of Secondary Alcohols to Ketones Mediated by Oxoammonium Salts under Two-Phase Conditions, Org. Chem., 52:12, 2559-2562, 1987.

Borodina, I., Understanding metabolite transport gives an upper hand in strain development, Microbial Biotechnology, 12(1):69-70, Jan. 2019.

Corey, E. et al., A New and Highly Effective Method for the Oxidation of Primary and Secondary Alcohols to Carbonyl Compounds, Journal of the American Chemical Society., 94(21): 7586-7587, 1972.

Davies et al., Engineering limonene and bisabolene production in wild-type and a glycogen-deficient mutant of Synechococc sp. PCC 7002, Bioengineering and Biotechnology, doi:10.3389/fbioe.2014.00021, Jun. 19, 2014.

Ding et al., A plant factory for 13-15 moth pheromone production, Nature Communications, 5, Feb. 25, 2014.

Fillet et al., Fatty alcohols production by oleaginous yeast, Bioenergy/Biofuels/Biochemicals, J Ind Microbiol Biotechnol, 42:1463-1472, DOI 10.1007/s10295-015-1674-x, Aug. 29, 2015.

Fritz, J.S. et al. Acid-catalysed acetylation of organic hydroxyl groups, Anal. Chem., 31(11): 1808-1812, 1959.

Han et al., Fermentative production and direct extraction of (-)-α-bisabolol in metabolically engineered *Escherichia coli*, Microb Cell Fact, 15:185, DOI 10.1186/s12934-016-0588-2, Nov. 8, 2016.

(Continued)

*Primary Examiner* — Christian L Fronda

(74) *Attorney, Agent, or Firm* — Weston R. Gould; DINSMORE & SHOHL LLP

(57) ABSTRACT

The present invention relates to improved methods for producing a hydrophobic compound, in particular a hydrophobic compound which is a pheromone such as an insect pheromone, in a fermentation process involving cultivation of a microorganism such as a yeast, said microorganism producing said hydrophobic compound, wherein the methods facilitate recovery of the hydrophobic compound from the fermentation broth, increase the titer of the hydrophobic compound and/or increase secretion of the hydrophobic compound from the microorganism.

17 Claims, 2 Drawing Sheets

Specification includes a Sequence Listing.

(56) References Cited

OTHER PUBLICATIONS

Holkenbrink C. et al., CRISPR/Cas9-Based Synthetic Toolbox for Engineering of the Yeast Yarrowia lipolytica, Biotechnol J., 13(9):e1700543. doi:10.1002/biot.201700543, 2018.
Hoover et al., Highly Practical Copper(I)/TEMPO Catalyst System for Chemoselective Aerobic Oxidation of Primary Alcohols, .pubs. acs.org/JACS, J. Am. Chem. Soc., 133(42): 16901-16910, 2011.
Hunkova, Z. et al., Toxic Effects of Fatty Acids on Yeast Cells: Dependence of Inhibitory Effects on Fatty Acid Concentration, Biotechnology and Bioengineering, XIX: 1623-1641, 1977.
Kehat et al.: "Behavioral responses of male Heliothis armigera (Lepidoptera: Noctuidae) moths in a flight tunnel to combinations of components identified from female sex pheromone glands", Journal of Insect Behavior, 3(1):75-83, 1990.
Ley, S. et al., Tetrapropylammonium Perruthenate, Pr4N+RuO4, TPAP: A Catalytic Oxidant for Organic Synthesis, Synthesis, (7): 639-666. doi:10.1055/s-1994-25538, 1994.
Li et al., Bioreactors and in situ product recovery techniques for acetone-butanol-ethanol fermentation, FEMS Microbiology Letters, 363, fnw107, doi: 10.1093/femsle/fnw107, Apr. 19, 2016.
Marella, E. et al., A single-host fermentation process for the production of flavor lactones from non-hydroxylated fatty acids, Metabolic Engineering, 61: 427-436, 2020.
Mattson, F. et al., Esterification of hydroxy compounds by fatty acid anhydrides, J Lipid Res., 5(3): 374-7, Jul. 1964.
Omura, K. et al., Tetrahedron. 34 (11): 1651-1660. doi:10.1016/0040-4020(78)80197-5, Chemischer Informationsdienst, 9(45), Abstract 119, 1978.
Ratcliffe, R. et al., Improved Procedure for Oxidations with the Chromium Trioxide-Pyridine Complex, J. Org. Chem., 35(11): 4000-4001. doi:10.1021/jo00836a108, 1970.
Roffler et al., In Situ Extractive Fermentation of Acetone and Butanol, Department of Chemical Engineering, University of California, Berkeley, California 94720, Biotechnology and Bioengineering, 31: 135-143, 1988.
Steves et al., Copper(I)/ABNO-catalyzed aerobic alcohol oxidation: alleviating steric and electronic constraints of Cu/TEMPO catalyst systems, J Am Chem Soc., 135(42):15742-5, doi:10.1021/ja409241h, Oct. 23, 2013.
Tadsuki et al., Sex Pheromome of the Rice Stem Borer, Chilo suppressalis (Walker) (Lepidoptera:Pyraludae): the Third Component, Z-9-Hexadecenal, Applied Entomology and Zoology, 18(3): 443-446, 1983.
Wang et al., Fatty alcohol production in Lipomyces starkeyi and Yarrowia lipolytica, Biotechnol Biofuels, 9:227, DOI 10.1186/s13068-016-0647-2, Oct. 24, 2016.
Weilnhammer, C. et al., Continuous Fermentation with Product Recovery by in-situ Extraction, Chem. Eng. Technol. 17: 365-373, Nov. 23, 1993.
Xin et al., Strategies for improved isopropanol-butanol production by a Clostridium strain from glucose and hemicellulose through consolidated bioprocessing, Biotechnol Biofuels, 10:118, DOI 10.1186/s13068-017-0805-1, May 3, 2017.
Klose, M., Fermentation mit In-situ-Extraktion und In-situ-Elektroextraktion, Technical University of Munich, Dec. 6, 2000, 98 pages.
Kirby, J., et al., Use of Nonionic Surfactants for Improvement of Terpene Production in Saccharomyces cerevisiae, Applied and Environmental Microbiology, 80: 6685-6693, 2014.
Kar, et al., Scale-down assessment of the sensitivity of Yarrowia lipolytica to oxygen transfer and foam management in bioreactors: investigation of the underlying physiological mechanisms, J Ind Microbiol Biotechnol, 39(2): 337-346, 2012.
Routledge, Beyond de-foaming: the effects of antifoams on bioprocess productivity, Computational and Structural Biotechnology Journal, 3(4), Oct. 2012, e201210014, 7 pages.

* cited by examiner

A B C D

SEQUENCE LISTING

```
<160> NUMBER OF SEQ ID NOS: 50

<210> SEQ ID NO 1
<211> LENGTH: 326
<212> TYPE: PRT
<213> ORGANISM: Amyelois transitella

<400> SEQUENCE: 1

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
        115                 120                 125

Asp Thr Asp Ala Asp Pro His Asn Ala Thr Arg Gly Phe Phe Tyr Ser
    130                 135                 140

His Val Gly Trp Leu Leu Val Lys Lys His Pro Glu Val Lys Ala Arg
145                 150                 155                 160
```

Gly Lys Tyr Leu Ser Leu Asp Asp Leu Lys Asn Asn Pro Leu Leu Lys
165 170 175

Phe Gln Lys Lys Tyr Ala Ile Leu Val Ile Gly Thr Leu Cys Phe Leu
180 185 190

Met Pro Thr Phe Val Pro Val Tyr Phe Trp Gly Glu Gly Ile Ser Thr
195 200 205

Ala Trp Asn Ile Asn Leu Leu Arg Tyr Val Met Asn Leu Asn Met Thr
210 215 220

Phe Leu Val Asn Ser Ala Ala His Ile Phe Gly Asn Lys Pro Tyr Asp
225 230 235 240

Lys Ser Ile Ala Ser Val Gln Asn Ile Ser Val Ser Leu Ala Thr Phe
245 250 255

Gly Glu Gly Phe His Asn Tyr His His Thr Tyr Pro Trp Asp Tyr Arg
260 265 270

Ala Ala Glu Leu Gly Asn Asn Arg Leu Asn Met Thr Thr Ala Phe Ile
275 280 285

Asp Phe Phe Ala Trp Ile Gly Trp Ala Tyr Asp Leu Lys Ser Val Pro
290 295 300

Gln Glu Ala Ile Ala Lys Arg Cys Ala Lys Thr Gly Asp Gly Thr Asp
305 310 315 320

Met Trp Gly Arg Lys Arg
325

<210> SEQ ID NO 2
<211> LENGTH: 338
<212> TYPE: PRT
<213> ORGANISM: Spodoptera littoralis

<400> SEQUENCE: 2

Met Ala Gln Cys Val Gln Thr Thr Thr Ile Leu Glu Gln Lys Glu Glu
1 5 10 15

Lys Thr Val Thr Leu Leu Val Pro Gln Ala Gly Lys Arg Lys Phe Glu
20 25 30

Ile Val Tyr Phe Asn Ile Ile Thr Phe Ala Tyr Trp His Ile Ala Gly
35 40 45

Leu Tyr Gly Leu Tyr Leu Cys Phe Thr Ser Thr Lys Trp Ala Thr Val
50 55 60

Leu Phe Ser Phe Phe Leu Phe Val Val Ala Glu Val Gly Val Thr Ala
65 70 75 80

Gly Ser His Arg Leu Trp Ser His Lys Thr Tyr Lys Ala Lys Leu Pro
85 90 95

Leu Gln Ile Leu Leu Met Val Met Asn Ser Leu Ala Phe Gln Asn Thr
100 105 110

Val Ile Asp Trp Val Arg Asp His Arg Leu His His Lys Tyr Ser Asp
115 120 125

Thr Asp Ala Asp Pro His Asn Ala Ser Arg Gly Phe Phe Tyr Ser His
130 135 140

Val Gly Trp Leu Leu Val Arg Lys His Pro Asp Val Lys Lys Arg Gly
145 150 155 160

Lys Glu Ile Asp Ile Ser Asp Ile Tyr Asn Asn Pro Val Leu Arg Phe
165 170 175

Gln Lys Lys Tyr Ala Ile Pro Phe Ile Gly Ala Val Cys Phe Val Leu
180 185 190

Pro Thr Leu Ile Pro Val Tyr Gly Trp Gly Glu Thr Trp Thr Asn Ala
195 200 205

```
Trp His Val Ala Met Leu Arg Tyr Ile Met Asn Leu Asn Val Thr Phe
    210                 215                 220

Leu Val Asn Ser Ala Ala His Ile Tyr Gly Lys Arg Pro Tyr Asp Lys
225                 230                 235                 240

Lys Ile Leu Pro Ser Gln Asn Ile Ala Val Ser Ile Ala Thr Phe Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Phe Pro Thr Lys Phe Ile Asp
        275                 280                 285

Phe Phe Ala Trp Ile Gly Trp Ala Tyr Asp Leu Lys Thr Val Ser Lys
    290                 295                 300

Glu Met Ile Lys Gln Arg Ser Lys Arg Thr Gly Asp Gly Thr Asn Leu
305                 310                 315                 320

Trp Gly Leu Glu Asp Val Asp Thr Pro Glu Asp Leu Lys Asn Thr Lys
                325                 330                 335

Gly Glu


<210> SEQ ID NO 3
<211> LENGTH: 336
<212> TYPE: PRT
<213> ORGANISM: Agrotis segetum

<400> SEQUENCE: 3

Met Ala Gln Gly Val Gln Thr Thr Thr Ile Leu Arg Glu Glu Glu Pro
1               5                   10                  15

Ser Leu Thr Phe Val Val Pro Gln Glu Pro Arg Lys Tyr Gln Ile Val
            20                  25                  30

Tyr Pro Asn Leu Ile Thr Phe Gly Tyr Trp His Ile Ala Gly Leu Tyr
        35                  40                  45

Gly Leu Tyr Leu Cys Phe Thr Ser Ala Lys Trp Gln Thr Ile Leu Phe
    50                  55                  60

Ser Phe Met Leu Val Val Leu Ala Glu Leu Gly Ile Thr Ala Gly Ala
65                  70                  75                  80

His Arg Leu Trp Ala His Lys Thr Tyr Lys Ala Lys Leu Pro Leu Gln
                85                  90                  95

Ile Ile Leu Met Ile Leu Asn Ser Ile Ala Phe Gln Asn Ser Ala Ile
            100                 105                 110

Asp Trp Val Arg Asp His Arg Leu His His Lys Tyr Ser Asp Thr Asp
        115                 120                 125

Ala Asp Pro His Asn Ala Thr Arg Gly Phe Phe Tyr Ser His Val Gly
    130                 135                 140

Trp Leu Leu Val Arg Lys His Pro Glu Val Lys Arg Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
    210                 215                 220

Asn Ser Ala Ala His Ile Trp Gly Tyr Lys Pro Tyr Asp Ile Lys Ile
225                 230                 235                 240
```

```
Leu Pro Ala Gln Asn Ile Ala Val Ser Ile Val Thr Gly Gly Glu Val
                245                 250                 255

Ser Ile Thr Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
    290                 295                 300

Ile Lys Ser Lys Ala Glu Arg Thr Gly Asp Gly Thr Asn Leu Trp Gly
305                 310                 315                 320

Leu Glu Asp Lys Gly Glu Glu Asp Phe Leu Lys Ile Trp Lys Asp Asn
                325                 330                 335


<210> SEQ ID NO 4
<211> LENGTH: 349
<212> TYPE: PRT
<213> ORGANISM: Trichoplusia ni

<400> SEQUENCE: 4

Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
            20                  25                  30

Lys Tyr Lys Tyr Ile Tyr Thr Asn Phe Leu Thr Phe Ser Tyr Ala His
        35                  40                  45

Leu Ala Ala Leu Tyr Gly Leu Tyr Leu Cys Phe Thr Ser Ala Lys Trp
    50                  55                  60

Glu Thr Leu Leu Phe Ser Phe Val Leu Phe His Met Ser Asn Ile Gly
65                  70                  75                  80

Ile Thr Ala Gly Ala His Arg Leu Trp Thr His Lys Thr Phe Lys Ala
                85                  90                  95

Lys Leu Pro Leu Glu Ile Val Leu Met Ile Phe Asn Ser Leu Ala Phe
            100                 105                 110

Gln Asn Thr Ala Ile Thr Trp Ala Arg Glu His Arg Leu His His Lys
        115                 120                 125

Tyr Ser Asp Thr Asp Ala Asp Pro His Asn Ala Ser Arg Gly Phe Phe
    130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
            180                 185                 190

Phe Ala Leu Pro Thr Leu Ile Pro Val Tyr Cys Trp Gly Glu Ser Trp
        195                 200                 205

Asn Asn Ala Trp His Ile Ala Leu Phe Arg Tyr Ile Phe Asn Leu Asn
    210                 215                 220

Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
            260                 265                 270

Tyr Arg Thr Ala Glu Leu Gly Asn Asn Phe Leu Asn Leu Thr Thr Leu
```

275 280 285

Phe Ile Asp Phe Cys Ala Trp Phe Gly Trp Ala Tyr Asp Leu Lys Ser
290 295 300

Val Ser Glu Asp Ile Ile Lys Gln Arg Ala Lys Arg Thr Gly Asp Gly
305 310 315 320

Ser Ser Gly Val Ile Trp Gly Trp Asp Asp Lys Asp Met Asp Arg Asp
325 330 335

Ile Lys Ser Lys Ala Asn Ile Phe Tyr Ala Lys Lys Glu
340 345

<210> SEQ ID NO 5
<211> LENGTH: 455
<212> TYPE: PRT
<213> ORGANISM: Helicoverpa armigera

<400> SEQUENCE: 5

Met Val Val Leu Thr Ser Lys Glu Thr Lys Pro Ser Val Ala Glu Phe
1 5 10 15

Tyr Ala Gly Lys Ser Val Phe Ile Thr Gly Gly Thr Gly Phe Leu Gly
20 25 30

Lys Val Phe Ile Glu Lys Leu Leu Tyr Ser Cys Pro Asp Ile Gly Asn
35 40 45

Ile Tyr Met Leu Ile Arg Glu Lys Lys Gly Leu Ser Val Ser Glu Arg
50 55 60

Ile Lys His Phe Leu Asp Asp Pro Leu Phe Thr Arg Leu Lys Glu Lys
65 70 75 80

Arg Pro Ala Asp Leu Glu Lys Ile Val Leu Ile Pro Gly Asp Ile Thr
85 90 95

Ala Pro Asp Leu Gly Ile Thr Ser Glu Asn Glu Lys Met Leu Ile Glu
100 105 110

Lys Val Ser Val Ile Ile His Ser Ala Ala Thr Val Lys Phe Asn Glu
115 120 125

Pro Leu Pro Thr Ala Trp Lys Ile Asn Val Glu Gly Thr Arg Met Met
130 135 140

Leu Ala Leu Ser Arg Arg Met Lys Arg Ile Glu Val Phe Ile His Ile
145 150 155 160

Ser Thr Ala Tyr Thr Asn Thr Asn Arg Glu Val Val Asp Glu Ile Leu
165 170 175

Tyr Pro Ala Pro Ala Asp Ile Asp Gln Val His Arg Tyr Val Lys Asp
180 185 190

Gly Ile Ser Glu Glu Glu Thr Glu Lys Ile Leu Asn Gly Arg Pro Asn
195 200 205

Thr Tyr Thr Phe Thr Lys Ala Leu Thr Glu His Leu Val Ala Glu Asn
210 215 220

Gln Ala Tyr Val Pro Thr Ile Ile Val Arg Pro Ser Val Val Ala Ala
225 230 235 240

Ile Lys Asp Glu Pro Ile Lys Gly Trp Leu Gly Asn Trp Tyr Gly Ala
245 250 255

Thr Gly Leu Thr Val Phe Thr Ala Lys Gly Leu Asn Arg Val Ile Tyr
260 265 270

Gly His Ser Ser Asn Ile Val Asp Leu Ile Pro Val Asp Tyr Val Ala
275 280 285

Asn Leu Val Ile Ala Ala Gly Ala Lys Ser Ser Lys Ser Thr Glu Leu
290 295 300

```
Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Ser Tyr Glu
    450                 455


<210> SEQ ID NO 6
<211> LENGTH: 453
<212> TYPE: PRT
<213> ORGANISM: Heliothis subflexa

<400> SEQUENCE: 6

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220
```

```
Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Val Asn Ile
            420                 425                 430

Asn Trp Arg Gln Tyr Ile Gln Asp Tyr Cys Trp Gly Val Arg His Phe
        435                 440                 445

Leu Glu Lys Lys Thr
    450
```

<210> SEQ ID NO 7
<211> LENGTH: 456
<212> TYPE: PRT
<213> ORGANISM: Helicoverpa assulta

<400> SEQUENCE: 7

```
Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Ile Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys Gln Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
```

```
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Val Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Thr Thr Asn Lys
    450                 455


<210> SEQ ID NO 8
<211> LENGTH: 700
<212> TYPE: PRT
<213> ORGANISM: Saccharomyces cerevisiae

<400> SEQUENCE: 8

Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45
```

```
Cys Phe Gln Lys Asn Lys Asn Ser Asn Ala Met Gly Trp Arg Asp Val
    50                  55                  60

Lys Glu Ile His Glu Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

Gly Arg Gly Leu Val Lys Ile Gly Leu Lys Pro Asn Asp Asp Asp Lys
        115                 120                 125

Leu His Leu Tyr Ala Ala Thr Ser His Lys Trp Met Lys Met Phe Leu
    130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270

Ser Thr Gly Glu Pro Lys Gly Val Val Leu Lys His Ser Asn Val Val
        275                 280                 285

Ala Gly Val Gly Gly Ala Ser Leu Asn Val Leu Lys Phe Val Gly Asn
    290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Ser Val Arg Asn Cys Gln Gly Asp
            340                 345                 350

Leu Gln Glu Phe Lys Pro Thr Ile Met Val Gly Val Ala Ala Val Trp
        355                 360                 365

Glu Thr Val Arg Lys Gly Ile Leu Asn Gln Ile Asp Asn Leu Pro Phe
    370                 375                 380

Leu Thr Lys Lys Ile Phe Trp Thr Ala Tyr Asn Thr Lys Leu Asn Met
385                 390                 395                 400

Gln Arg Leu His Ile Pro Gly Gly Gly Ala Leu Gly Asn Leu Val Phe
                405                 410                 415

Lys Lys Ile Arg Thr Ala Thr Gly Gly Gln Leu Arg Tyr Leu Leu Asn
            420                 425                 430

Gly Gly Ser Pro Ile Ser Arg Asp Ala Gln Glu Phe Ile Thr Asn Leu
        435                 440                 445

Ile Cys Pro Met Leu Ile Gly Tyr Gly Leu Thr Glu Thr Cys Ala Ser
    450                 455                 460

Thr Thr Ile Leu Asp Pro Ala Asn Phe Glu Leu Gly Val Ala Gly Asp
```

```
465                 470                 475                 480

Leu Thr Gly Cys Val Thr Val Lys Leu Val Asp Val Glu Glu Leu Gly
                485                 490                 495

Tyr Phe Ala Lys Asn Asn Gln Gly Glu Val Trp Ile Thr Gly Ala Asn
            500                 505                 510

Val Thr Pro Glu Tyr Tyr Lys Asn Glu Glu Glu Thr Ser Gln Ala Leu
        515                 520                 525

Thr Ser Asp Gly Trp Phe Lys Thr Gly Asp Ile Gly Glu Trp Glu Ala
    530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
                565                 570                 575

Ser Asn Glu Tyr Val Ala Asn Ile Cys Val Tyr Ala Asp Gln Ser Lys
            580                 585                 590

Thr Lys Pro Val Gly Ile Ile Val Pro Asn His Ala Pro Leu Thr Lys
        595                 600                 605

Leu Ala Lys Lys Leu Gly Ile Met Glu Gln Lys Asp Ser Ser Ile Asn
    610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
                645                 650                 655

Leu Ala Gly Ile Val Phe Phe Asp Gly Glu Trp Thr Pro Gln Asn Gly
            660                 665                 670

Phe Val Thr Ser Ala Gln Lys Leu Lys Arg Lys Asp Ile Leu Asn Ala
        675                 680                 685

Val Lys Asp Lys Val Asp Ala Val Tyr Ser Ser Ser
    690                 695                 700


<210> SEQ ID NO 9
<211> LENGTH: 690
<212> TYPE: PRT
<213> ORGANISM: Yarrowia lipolytica

<400> SEQUENCE: 9

Met Val Gly Tyr Thr Ile Ser Ser Lys Pro Val Ser Val Glu Val Gly
1               5                   10                  15

Pro Ala Lys Pro Gly Glu Thr Ala Pro Arg Arg Asn Val Ile Ala Lys
            20                  25                  30

Asp Ala Pro Val Val Phe Pro Asp Asn Asp Ser Ser Leu Thr Thr Val
        35                  40                  45

Tyr Lys Leu Phe Lys Lys Tyr Ala Glu Ile Asn Ser Glu Arg Lys Ala
    50                  55                  60

Met Gly Trp Arg Asp Thr Ile Asp Ile His Val Glu Thr Lys Gln Val
65                  70                  75                  80

Thr Lys Val Val Asp Gly Val Glu Lys Lys Val Pro Lys Glu Trp Lys
                85                  90                  95

Tyr Phe Glu Met Gly Pro Tyr Lys Trp Leu Ser Tyr Lys Glu Ala Leu
            100                 105                 110

Lys Leu Val His Asp Tyr Gly Ala Gly Leu Arg His Leu Gly Ile Lys
        115                 120                 125

Pro Lys Glu Lys Met His Ile Tyr Ala Gln Thr Ser His Arg Trp Met
    130                 135                 140
```

-continued

```
Leu Ser Gly Leu Ala Ser Leu Ser Gln Gly Ile Pro Ile Val Thr Ala
145                 150                 155                 160

Tyr Asp Thr Leu Gly Glu Glu Gly Leu Thr Arg Ser Leu Gln Glu Thr
                165                 170                 175

Asn Ser Val Ile Met Phe Thr Asp Lys Ala Leu Leu Ser Ser Leu Lys
            180                 185                 190

Val Ser Leu Lys Lys Gly Thr Asp Leu Arg Ile Ile Ile Tyr Gly Gly
        195                 200                 205

Asp Leu Thr Pro Asp Asp Lys Lys Ala Gly Asn Thr Glu Ile Asp Ala
    210                 215                 220

Ile Lys Glu Ile Val Pro Asp Met Lys Ile Tyr Thr Met Asp Glu Val
225                 230                 235                 240

Val Ala Leu Gly Arg Glu His Pro His Pro Val Glu Glu Val Asp Tyr
                245                 250                 255

Glu Asp Leu Ala Phe Ile Met Tyr Thr Ser Gly Ser Thr Gly Val Pro
            260                 265                 270

Lys Gly Val Val Leu Gln His Lys Gln Ile Leu Ala Ser Val Ala Gly
        275                 280                 285

Val Thr Lys Ile Ile Asp Arg Ser Ile Ile Gly Asn Thr Asp Arg Leu
    290                 295                 300

Leu Asn Phe Leu Pro Leu Ala His Ile Phe Glu Phe Val Phe Glu Met
305                 310                 315                 320

Val Thr Phe Trp Trp Gly Ala Ser Leu Gly Tyr Gly Thr Val Lys Thr
                325                 330                 335

Ile Ser Asp Leu Ser Met Lys Asn Cys Lys Gly Asp Ile Arg Glu Leu
            340                 345                 350

Lys Pro Thr Ile Met Val Gly Val Pro Ala Val Trp Glu Pro Met Arg
        355                 360                 365

Lys Gly Ile Leu Gly Lys Ile Lys Glu Leu Ser Pro Leu Met Gln Arg
    370                 375                 380

Val Phe Trp Ala Ser Phe Ala Ala Lys Gln Arg Leu Asp Glu Asn Gly
385                 390                 395                 400

Leu Pro Gly Gly Ser Ile Leu Asp Ser Leu Ile Phe Lys Lys Val Lys
                405                 410                 415

Asp Ala Thr Gly Gly Cys Leu Arg Tyr Val Cys Asn Gly Gly Ala Pro
            420                 425                 430

Val Ser Val Asp Thr Gln Lys Phe Ile Thr Thr Leu Ile Cys Pro Met
        435                 440                 445

Leu Ile Gly Cys Gly Leu Thr Glu Thr Thr Ala Asn Thr Thr Ile Met
    450                 455                 460

Ser Pro Lys Ser Tyr Ala Phe Gly Thr Ile Gly Glu Pro Thr Ala Ala
465                 470                 475                 480

Val Thr Leu Lys Leu Ile Asp Val Pro Glu Ala Gly Tyr Phe Ala Glu
                485                 490                 495

Asn Asn Gln Gly Glu Leu Cys Ile Lys Gly Asn Val Val Met Lys Glu
            500                 505                 510

Tyr Tyr Lys Asn Glu Glu Glu Thr Lys Lys Ala Phe Ser Asp Asp Gly
        515                 520                 525

Tyr Phe Leu Thr Gly Asp Ile Ala Glu Trp Thr Ala Asn Gly Gln Leu
    530                 535                 540

Arg Ile Ile Asp Arg Arg Lys Asn Leu Val Lys Thr Gln Asn Gly Glu
545                 550                 555                 560

Tyr Ile Ala Leu Glu Lys Leu Glu Thr Gln Tyr Arg Ser Ser Ser Tyr
```

565 570 575

Val Ala Asn Leu Cys Val Tyr Ala Asp Gln Asn Arg Val Lys Pro Ile
580 585 590

Ala Leu Val Ile Pro Asn Glu Gly Pro Thr Lys Lys Leu Gln Ser Leu
595 600 605

Gly Val Asp Ser Asp Asp Trp Asp Ala Val Cys Ser Asn Lys Lys Val
610 615 620

Val Lys Ala Val Leu Lys Asp Met Leu Asp Thr Gly Arg Ser Leu Gly
625 630 635 640

Leu Ser Gly Ile Glu Leu Leu Gln Gly Ile Val Leu Leu Pro Gly Glu
645 650 655

Trp Thr Pro Gln Asn Ser Tyr Leu Thr Ala Ala Gln Lys Leu Asn Arg
660 665 670

Lys Lys Ile Val Asp Asp Asn Lys Lys Glu Ile Asp Glu Cys Tyr Glu
675 680 685

Gln Ser
690

<210> SEQ ID NO 10
<211> LENGTH: 525
<212> TYPE: PRT
<213> ORGANISM: Saccharomyces cerevisiae

<400> SEQUENCE: 10

Met Asn Glu Ile Asp Glu Lys Asn Gln Ala Pro Val Gln Gln Glu Cys
1 5 10 15

Leu Lys Glu Met Ile Gln Asn Gly His Ala Arg Arg Met Gly Ser Val
20 25 30

Glu Asp Leu Tyr Val Ala Leu Asn Arg Gln Asn Leu Tyr Arg Asn Phe
35 40 45

Cys Thr Tyr Gly Glu Leu Ser Asp Tyr Cys Thr Arg Asp Gln Leu Thr
50 55 60

Leu Ala Leu Arg Glu Ile Cys Leu Lys Asn Pro Thr Leu Leu His Ile
65 70 75 80

Val Leu Pro Thr Arg Trp Pro Asn His Glu Asn Tyr Tyr Arg Ser Ser
85 90 95

Glu Tyr Tyr Ser Arg Pro His Pro Val His Asp Tyr Ile Ser Val Leu
100 105 110

Gln Glu Leu Lys Leu Ser Gly Val Val Leu Asn Glu Gln Pro Glu Tyr
115 120 125

Ser Ala Val Met Lys Gln Ile Leu Glu Glu Phe Lys Asn Ser Lys Gly
130 135 140

Ser Tyr Thr Ala Lys Ile Phe Lys Leu Thr Thr Thr Leu Thr Ile Pro
145 150 155 160

Tyr Phe Gly Pro Thr Gly Pro Ser Trp Arg Leu Ile Cys Leu Pro Glu
165 170 175

Glu His Thr Glu Lys Trp Lys Lys Phe Ile Phe Val Ser Asn His Cys
180 185 190

Met Ser Asp Gly Arg Ser Ser Ile His Phe Phe His Asp Leu Arg Asp
195 200 205

Glu Leu Asn Asn Ile Lys Thr Pro Pro Lys Lys Leu Asp Tyr Ile Phe
210 215 220

Lys Tyr Glu Glu Asp Tyr Gln Leu Leu Arg Lys Leu Pro Glu Pro Ile
225 230 235 240

Glu Lys Val Ile Asp Phe Arg Pro Pro Tyr Leu Phe Ile Pro Lys Ser
245 250 255

Leu Leu Ser Gly Phe Ile Tyr Asn His Leu Arg Phe Ser Ser Lys Gly
260 265 270

Val Cys Met Arg Met Asp Asp Val Glu Lys Thr Asp Asp Val Val Thr
275 280 285

Glu Ile Ile Asn Ile Ser Pro Thr Glu Phe Gln Ala Ile Lys Ala Asn
290 295 300

Ile Lys Ser Asn Ile Gln Gly Lys Cys Thr Ile Thr Pro Phe Leu His
305 310 315 320

Val Cys Trp Phe Val Ser Leu His Lys Trp Gly Lys Phe Phe Lys Pro
325 330 335

Leu Asn Phe Glu Trp Leu Thr Asp Ile Phe Ile Pro Ala Asp Cys Arg
340 345 350

Ser Gln Leu Pro Asp Asp Asp Glu Met Arg Gln Met Tyr Arg Tyr Gly
355 360 365

Ala Asn Val Gly Phe Ile Asp Phe Thr Pro Trp Ile Ser Glu Phe Asp
370 375 380

Met Asn Asp Asn Lys Glu Asn Phe Trp Pro Leu Ile Glu His Tyr His
385 390 395 400

Glu Val Ile Ser Glu Ala Leu Arg Asn Lys Lys His Leu His Gly Leu
405 410 415

Gly Phe Asn Ile Gln Gly Phe Val Gln Lys Tyr Val Asn Ile Asp Lys
420 425 430

Val Met Cys Asp Arg Ala Ile Gly Lys Arg Arg Gly Gly Thr Leu Leu
435 440 445

Ser Asn Val Gly Leu Phe Asn Gln Leu Glu Glu Pro Asp Ala Lys Tyr
450 455 460

Ser Ile Cys Asp Leu Ala Phe Gly Gln Phe Gln Gly Ser Trp His Gln
465 470 475 480

Ala Phe Ser Leu Gly Val Cys Ser Thr Asn Val Lys Gly Met Asn Ile
485 490 495

Val Val Ala Ser Thr Lys Asn Val Val Gly Ser Gln Glu Ser Leu Glu
500 505 510

Glu Leu Cys Ser Ile Tyr Lys Ala Leu Leu Leu Gly Pro
515 520 525

<210> SEQ ID NO 11
<211> LENGTH: 609
<212> TYPE: PRT
<213> ORGANISM: Yarrowia lipolytica

<400> SEQUENCE: 11

Met Ser Asp Asp Lys His Thr Phe Asp Phe Ile Ile Val Gly Gly Gly
1 5 10 15

Thr Ala Gly Pro Thr Leu Ala Arg Arg Leu Ala Asp Ala Trp Ile Ser
20 25 30

Gly Lys Lys Leu Lys Val Leu Leu Leu Glu Ser Gly Pro Ser Ser Glu
35 40 45

Gly Val Asp Asp Ile Arg Cys Pro Gly Asn Trp Val Asn Thr Ile His
50 55 60

Ser Glu Tyr Asp Trp Ser Tyr Glu Val Asp Glu Pro Tyr Leu Ser Thr
65 70 75 80

Asp Gly Glu Glu Arg Arg Leu Cys Gly Ile Pro Arg Gly His Cys Leu
85 90 95

```
Gly Gly Ser Ser Cys Leu Asn Thr Ser Phe Val Ile Arg Gly Thr Arg
            100                 105                 110

Gly Asp Phe Asp Arg Ile Glu Glu Glu Thr Gly Ala Lys Gly Trp Gly
        115                 120                 125

Trp Asp Asp Leu Phe Pro Tyr Phe Arg Lys His Glu Cys Tyr Val Pro
    130                 135                 140

Gln Gly Ser Ala His Glu Pro Lys Leu Ile Asp Phe Asp Thr Tyr Asp
145                 150                 155                 160

Tyr Lys Lys Phe His Gly Asp Ser Gly Pro Ile Lys Val Gln Pro Tyr
                165                 170                 175

Asp Tyr Ala Pro Ile Ser Lys Lys Phe Ser Glu Ser Leu Ala Ser Phe
            180                 185                 190

Gly Tyr Pro Tyr Asn Pro Glu Ile Phe Val Asn Gly Gly Ala Pro Gln
        195                 200                 205

Gly Trp Gly His Val Val Arg Ser Thr Ser Asn Gly Val Arg Ser Thr
    210                 215                 220

Gly Tyr Asp Ala Leu Val His Ala Pro Lys Asn Leu Asp Ile Val Thr
225                 230                 235                 240

Gly His Ala Val Thr Lys Ile Leu Phe Glu Lys Ile Gly Gly Lys Gln
                245                 250                 255

Thr Ala Val Gly Val Glu Thr Tyr Asn Arg Ala Ala Glu Glu Ala Gly
            260                 265                 270

Pro Thr Tyr Lys Ala Arg Tyr Glu Val Val Val Cys Cys Gly Ser Tyr
        275                 280                 285

Ala Ser Pro Gln Leu Leu Met Val Ser Gly Val Gly Pro Lys Lys Glu
    290                 295                 300

Leu Glu Glu Val Gly Val Lys Asp Ile Ile Leu Asp Ser Pro Tyr Val
305                 310                 315                 320

Gly Lys Asn Leu Gln Asp His Leu Ile Cys Gly Ile Phe Val Glu Ile
                325                 330                 335

Lys Glu Pro Gly Tyr Thr Arg Asp His Gln Phe Phe Asp Asp Glu Gly
            340                 345                 350

Leu Asp Lys Ser Thr Glu Glu Trp Lys Thr Lys Arg Thr Gly Phe Phe
        355                 360                 365

Ser Asn Pro Pro Gln Gly Ile Phe Ser Tyr Gly Arg Ile Asp Asn Leu
    370                 375                 380

Leu Lys Asp Asp Pro Val Trp Lys Glu Ala Cys Glu Lys Gln Lys Ala
385                 390                 395                 400

Leu Asn Pro Arg Arg Asp Pro Met Gly Asn Asp Pro Ser Gln Pro His
                405                 410                 415

Phe Glu Ile Trp Asn Ala Glu Leu Tyr Ile Glu Leu Glu Met Thr Gln
            420                 425                 430

Ala Pro Asp Glu Gly Gln Ser Val Met Thr Val Ile Gly Glu Ile Leu
        435                 440                 445

Pro Pro Arg Ser Lys Gly Tyr Val Lys Leu Leu Ser Pro Asp Pro Met
    450                 455                 460

Glu Asn Pro Glu Ile Val His Asn Tyr Leu Gln Asp Pro Val Asp Ala
465                 470                 475                 480

Arg Val Phe Ala Ala Ile Met Lys His Ala Ala Asp Val Ala Thr Asn
                485                 490                 495

Gly Ala Gly Thr Lys Asp Leu Val Lys Ala Arg Trp Pro Pro Glu Ser
            500                 505                 510
```

```
Lys Pro Phe Glu Glu Met Ser Ile Glu Glu Trp Glu Thr Tyr Val Arg
        515                 520                 525

Asp Lys Ser His Thr Cys Phe His Pro Cys Gly Thr Val Lys Leu Gly
    530                 535                 540

Gly Ala Asn Asp Lys Glu Ala Val Val Asp Glu Arg Leu Arg Val Lys
545                 550                 555                 560

Gly Val Asp Gly Leu Arg Val Ala Asp Val Ser Val Leu Pro Arg Val
                565                 570                 575

Pro Asn Gly His Thr Gln Ala Phe Ala Tyr Ala Val Gly Glu Lys Ala
            580                 585                 590

Ala Asp Leu Ile Leu Ala Asp Ile Ala Gly Lys Asp Leu Arg Pro Arg
        595                 600                 605

Ile


<210> SEQ ID NO 12
<211> LENGTH: 519
<212> TYPE: PRT
<213> ORGANISM: Yarrowia lipolytica

<400> SEQUENCE: 12

Met Ser Thr Phe Asp Trp Glu Ser Ile Val Pro Ala Thr Pro Leu Asp
1               5                   10                  15

Gln Ile Pro Gly Asp Ile Gln Arg Leu Arg Lys Gly Phe Arg Ser Gly
            20                  25                  30

Lys Thr Leu Asp Leu Asn Tyr Arg Leu Asp Gln Ile Arg Asn Leu His
        35                  40                  45

Tyr Val Leu Arg Asp Asn Val Glu Ala Ile Lys Asp Ala Val Tyr Lys
    50                  55                  60

Asp Leu Gly Arg Pro Lys His Glu Thr Asp Leu Cys Glu Val Gly Phe
65                  70                  75                  80

Leu Trp Gly Glu Phe Asn Asn Val Val Ala Asn Leu Lys Lys Trp Ala
                85                  90                  95

Ala Asp Glu Asp Val Lys Thr Asn Leu Gln Tyr Ser Ile Ser Ser Pro
            100                 105                 110

Lys Ile Arg Lys Arg Pro Leu Gly Asn Val Leu Ile Ile Ser Pro Trp
        115                 120                 125

Asn Tyr Pro Phe Met Leu Thr Val Ser Pro Leu Ile Gly Ala Leu Ala
    130                 135                 140

Ala Gly Asn Thr Val Ala Val Lys Phe Ser Glu Met Ala Pro His Thr
145                 150                 155                 160

Ser Lys Ile Val Gly Asp Leu Cys Thr Lys Ala Leu Asp Pro Asp Val
                165                 170                 175

Phe Gln Ala Ile Gln Gly Gly Val Pro Val Val Thr Lys Thr Leu Glu
            180                 185                 190

Gln Lys Phe Asp Lys Ile Met Tyr Thr Gly Asn His Thr Val Gly Lys
        195                 200                 205

Ile Ile Ala Thr Ala Ala Asn Lys Tyr Leu Thr Pro Val Ile Leu Glu
    210                 215                 220

Leu Gly Gly Lys Ser Pro Val Phe Val Thr Lys Asn Cys Lys Asn Ile
225                 230                 235                 240

Lys Leu Ala Ala Lys Arg Ala Leu Trp Gly Lys Val Val Asn Ala Gly
                245                 250                 255

Gln Thr Cys Val Ala Pro Asp Tyr Val Ile Val Glu Pro Glu Val Glu
            260                 265                 270
```

```
Gln Glu Phe Ile Asp Ala Cys Lys Tyr Trp Ile Asn Glu Phe Tyr Ser
        275                 280                 285

Gly Lys Ile Asp Gln Tyr Asn Pro Asp Phe Ala Lys Ile Ala Thr Pro
    290                 295                 300

Asn His Trp Asn Arg Leu Thr Ser Met Leu Ser Lys Ser Lys Gly Glu
305                 310                 315                 320

Ile Ile Thr Gly Gly Asn Thr Asp Glu Lys Thr Arg Phe Ile Ala Pro
                325                 330                 335

Thr Val Val Ala Lys Val Pro Asp Asn Asp Ser Leu Met Glu Asp Glu
            340                 345                 350

Ile Phe Gly Pro Leu Leu Pro Ile Leu Thr Ala Arg Ser Val Glu Glu
        355                 360                 365

Gly Ile Lys Tyr Val His Glu Asn His Asp Thr Pro Leu Ala Met Tyr
    370                 375                 380

Val Phe Thr Asp Lys Ala Ser Glu Gly Asp Tyr Ile Gln Ser Gln Ile
385                 390                 395                 400

Asn Ser Gly Gly Leu Ile Phe Asn Asp Thr Leu Ile His Val Gly Cys
                405                 410                 415

Val Gln Ala Pro Phe Gly Gly Val Gly Met Ser Gly Tyr Gly Ala Tyr
            420                 425                 430

His Gly Glu Asp Ser Phe Leu Ala Phe Thr His Arg Gln Thr Tyr Leu
        435                 440                 445

Asn Gln Pro Lys Leu Leu Glu Pro Leu Gln Asp Val Arg Tyr Ala Pro
    450                 455                 460

Tyr Thr Lys Thr Lys Arg Ser Met Val Lys Asn Leu Leu Leu Val Gly
465                 470                 475                 480

Pro Ile Phe Pro Arg Thr Gly Ser Val Tyr Pro Asn Val Leu Ile Arg
                485                 490                 495

Ile Phe Arg Lys Ile Trp Phe Trp Val Leu Ile Val Ala Ile Gly Ala
            500                 505                 510

Ala Gly Ala Lys Ala Leu Leu
        515
```

<210> SEQ ID NO 13
<211> LENGTH: 529
<212> TYPE: PRT
<213> ORGANISM: Yarrowia lipolytica

<400> SEQUENCE: 13

```
Met Thr Thr Thr Ala Thr Glu Thr Pro Thr Thr Asn Val Thr Pro Thr
1               5                   10                  15

Thr Ser Leu Pro Lys Glu Thr Ala Ser Pro Gly Gly Thr Ala Ser Val
            20                  25                  30

Asn Thr Ser Phe Asp Trp Glu Ser Ile Cys Gly Lys Thr Pro Leu Glu
        35                  40                  45

Glu Ile Glu Ser Asp Ile Ser Arg Leu Lys Lys Thr Phe Arg Ser Gly
    50                  55                  60

Lys Thr Leu Asp Leu Asp Tyr Arg Leu Asp Gln Ile Arg Asn Leu Ala
65                  70                  75                  80

Tyr Ala Ile Arg Asp Asn Glu Asn Lys Ile Arg Asp Ala Ile Lys Ala
                85                  90                  95

Asp Leu Lys Arg Pro Asp Phe Glu Thr Met Ala Ala Glu Phe Ser Val
            100                 105                 110

Gln Met Gly Glu Phe Asn Tyr Val Val Lys Asn Leu Pro Lys Trp Val
        115                 120                 125
```

```
Lys Asp Glu Lys Val Lys Gly Thr Ser Met Ala Tyr Trp Asn Ser Ser
    130                 135                 140

Pro Lys Ile Arg Lys Arg Pro Leu Gly Ser Val Leu Val Ile Thr Pro
145                 150                 155                 160

Trp Asn Tyr Pro Leu Ile Leu Ala Val Ser Pro Val Leu Gly Ala Ile
                165                 170                 175

Ala Ala Gly Asn Thr Val Ala Leu Lys Met Ser Glu Met Ser Pro Asn
            180                 185                 190

Ala Ser Lys Val Ile Gly Asp Ile Met Thr Ala Ala Leu Asp Pro Gln
        195                 200                 205

Leu Phe Gln Cys Phe Phe Gly Gly Val Pro Glu Thr Thr Glu Ile Leu
    210                 215                 220

Lys His Arg Trp Asp Lys Ile Met Tyr Thr Gly Asn Gly Lys Val Gly
225                 230                 235                 240

Arg Ile Ile Cys Glu Ala Ala Asn Lys Tyr Leu Thr Pro Val Glu Leu
                245                 250                 255

Glu Leu Gly Gly Lys Ser Pro Val Phe Val Thr Lys His Cys Ser Asn
            260                 265                 270

Leu Glu Met Ala Ala Arg Arg Ile Ile Trp Gly Lys Phe Val Asn Gly
        275                 280                 285

Gly Gln Thr Cys Val Ala Pro Asp Tyr Val Leu Val Cys Pro Glu Val
    290                 295                 300

His Asp Lys Phe Val Ala Ala Cys Gln Lys Val Leu Asp Lys Phe Tyr
305                 310                 315                 320

Pro Asn Asn Ser Ala Glu Ser Glu Met Ala His Ile Ala Thr Pro Leu
                325                 330                 335

His Tyr Glu Arg Leu Thr Gly Leu Leu Asn Ser Thr Arg Gly Lys Val
            340                 345                 350

Val Ala Gly Gly Thr Phe Asn Ser Ala Thr Arg Phe Ile Ala Pro Thr
        355                 360                 365

Ile Val Asp Gly Val Asp Ala Asn Asp Ser Leu Met Gln Gly Glu Leu
    370                 375                 380

Phe Gly Pro Leu Leu Pro Ile Val Lys Ala Met Ser Thr Glu Ala Ala
385                 390                 395                 400

Cys Asn Phe Val Leu Glu His His Pro Thr Pro Leu Ala Glu Tyr Ile
                405                 410                 415

Phe Ser Asp Asn Asn Ser Glu Ile Asp Tyr Ile Arg Asp Arg Val Ser
            420                 425                 430

Ser Gly Gly Leu Val Ile Asn Asp Thr Leu Ile His Val Gly Cys Val
        435                 440                 445

Gln Ala Pro Phe Gly Gly Val Gly Asp Ser Gly Asn Gly Gly Tyr His
    450                 455                 460

Gly Lys His Thr Phe Asp Leu Phe Ser His Ser Gln Thr Val Leu Arg
465                 470                 475                 480

Gln Pro Gly Trp Val Glu Met Leu Gln Lys Lys Arg Tyr Pro Pro Tyr
                485                 490                 495

Asn Lys Ser Asn Glu Lys Phe Val Arg Arg Met Val Val Pro Ser Pro
            500                 505                 510

Gly Phe Pro Arg Glu Gly Asp Val Arg Gly Phe Trp Ser Arg Leu Phe
        515                 520                 525

Asn
```

<210> SEQ ID NO 14
<211> LENGTH: 377
<212> TYPE: PRT
<213> ORGANISM: Yarrowia lipolytica

<400> SEQUENCE: 14

```
Met Trp Gly Ser Ser His Ala Phe Ala Gly Glu Ser Asp Leu Thr Leu
1               5                   10                  15

Gln Leu His Thr Arg Ser Asn Met Ser Asp Asn Thr Thr Ile Lys Lys
            20                  25                  30

Pro Ile Arg Pro Lys Pro Ile Arg Thr Glu Arg Leu Pro Tyr Ala Gly
        35                  40                  45

Ala Ala Glu Ile Ile Arg Ala Asn Gln Lys Asp His Tyr Phe Glu Ser
    50                  55                  60

Val Leu Glu Gln His Leu Val Thr Phe Leu Gln Lys Trp Lys Gly Val
65                  70                  75                  80

Arg Phe Ile His Gln Tyr Lys Glu Glu Leu Glu Thr Ala Ser Lys Phe
                85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175

Pro Glu Thr Trp Lys Glu Arg Val Ile Lys Thr Phe Val Asn Lys Phe
            180                 185                 190

Asp Lys Phe Thr Ala Leu Glu Gly Phe Thr Ala Ile His Leu Ala Ile
        195                 200                 205

Phe Tyr Val Tyr Gly Ser Tyr Tyr Gln Leu Ser Lys Arg Ile Trp Gly
    210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
                245                 250                 255

Phe Val Gln Thr Gly Arg Glu Tyr Leu Gly Ala Leu Leu Glu Lys Ser
            260                 265                 270

Val Glu Lys Glu Ala Gly Glu Lys Glu Asp Glu Lys Glu Ala Val Val
        275                 280                 285

Pro Lys Lys Lys Ser Ser Ile Pro Phe Ile Glu Asp Thr Glu Gly Glu
    290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
                325                 330                 335

Pro Ala Cys Thr Pro Cys Gly His Phe Phe Cys Trp Asp Cys Ile Ser
            340                 345                 350

Glu Trp Val Arg Glu Lys Pro Glu Cys Pro Leu Cys Arg Gln Gly Val
        355                 360                 365

Arg Glu Gln Asn Leu Leu Pro Ile Arg
    370                 375
```

<210> SEQ ID NO 15
<211> LENGTH: 727
<212> TYPE: PRT
<213> ORGANISM: Yarrowia lipolytica

<400> SEQUENCE: 15

```
Met Ser Glu Thr Asp His Leu Leu Ala Ala Glu Pro Val Ala Glu Tyr
1               5                   10                  15

Pro Gln Tyr Thr Pro Trp Pro Asn Ser Arg Lys Ser Val Asp Thr Glu
            20                  25                  30

Phe Ser Ala Thr Ser Trp Ile Tyr Asp Leu Val Leu Trp Ile Phe Thr
        35                  40                  45

Ala Cys Phe Asp Ile Phe Phe Arg Glu Ile Arg Pro Arg Gly Ala Phe
    50                  55                  60

Arg Ile Pro Arg Lys Gly Pro Val Leu Phe Val Ala Ala Pro His Ala
65                  70                  75                  80

Asn Gln Phe Val Asp Pro Val Ile Leu Met Asn Gln Val Lys Gln Glu
                85                  90                  95

Ala Gly Arg Arg Ile Ser Phe Leu Val Ala Glu Lys Ser Met Arg Arg
            100                 105                 110

Ala Ala Val Gly Arg Met Ala Arg Ser Met Asn Ser Ile Pro Val Val
        115                 120                 125

Arg Ala Gln Asp Asn Ala Lys Lys Gly Glu Gly Lys Ile Tyr Val Asp
    130                 135                 140

Ala Glu Asp Pro Thr Lys Ile His Gly Ile Gly Thr Gln Phe Thr Lys
145                 150                 155                 160

Gln Cys Glu Val Arg Gly Leu Val Val Cys Ser Ser Ser Val Gly Ser
                165                 170                 175

Ile Asp Val Ala Glu Ile Val Ser Asp Thr Leu Leu Ile Ala Arg Lys
            180                 185                 190

Glu Phe Lys Gly Pro Lys Ala Lys Glu Ala Leu Lys Glu Ser Asn Gly
        195                 200                 205

Gly Ile Thr Tyr Lys Tyr Ala Asp Tyr Val Asn Gln Ala Thr Val Tyr
    210                 215                 220

Arg Ser Val Phe Asp Lys Leu His His Gly Gly Cys Val Gly Ile Phe
225                 230                 235                 240

Pro Glu Gly Gly Ser His Asp Arg Thr Glu Leu Leu Pro Leu Lys Ala
                245                 250                 255

Gly Val Ala Ile Met Ala Leu Gly Ala Leu Ala Glu Asp Pro Ser Cys
            260                 265                 270

Gly Val Arg Ile Val Pro Cys Gly Leu Asn Tyr Phe His Ala His Lys
        275                 280                 285

Phe Arg Ser Arg Ala Val Val Glu Phe Gly Ser Pro Ile Ala Ile Pro
    290                 295                 300

Pro Asp Leu Val Glu Lys Tyr Lys Ala Gly Gly Glu Ala Lys Arg Glu
305                 310                 315                 320

Ala Val Lys Thr Val Leu Asp Ile Thr Ala Ala Gly Leu Lys Ser Val
                325                 330                 335

Thr Val Gln Val Gln Asp Phe Asp Thr Leu Met Leu Ile Gln Ala Ile
            340                 345                 350

Arg Arg Leu Tyr Arg Pro Pro Gly Lys Lys Ile Pro Leu Pro Met Val
        355                 360                 365

Val Glu Leu Asn Arg Arg Leu Val Tyr Ala Tyr Asn His Tyr Lys Asp
    370                 375                 380
```

Asp Pro Arg Ile Glu Glu Met Lys Gln Glu Ile Arg Lys Tyr Asn Lys
385 390 395 400

Phe Leu Gln Ala Met Gly Leu Lys Asp His Gln Val Glu Lys Ala Arg
405 410 415

Ile Ser Lys Ile Glu Ile Leu Gly Arg Leu Leu Tyr Arg Ser Ile Lys
420 425 430

Leu Val Phe Leu Ser Ile Gly Cys Leu Pro Gly Leu Leu Leu Phe Ser
435 440 445

Pro Ile Phe Ile Ile Ser Lys Ser Ile Ser Lys Thr Lys Ala Lys Glu
450 455 460

Ala Leu Lys Ala Ser Ser Val Lys Ile Lys Ala Asn Asp Val Val Ala
465 470 475 480

Thr Trp Lys Val Leu Val Ala Met Gly Leu Thr Pro Val Leu Tyr Ile
485 490 495

Leu Tyr Ser Leu Val Gly Ser Val Val Ile Arg Lys Leu Asp Leu Ile
500 505 510

Ser Trp Phe Pro Thr Ile Leu Leu Pro Gly Leu Val Leu Ser Ile Ile
515 520 525

Ile Thr Thr Ser Tyr Ala Ala Leu Ala Met Gly Glu Ala Gly Met Asp
530 535 540

Ile Phe Lys Ser Leu Arg Pro Leu Ala Leu Ala Leu Asn Pro Ser Thr
545 550 555 560

Lys Asn Ser Leu Leu Lys Leu Gln Asn Glu Arg Lys Arg Leu Val Leu
565 570 575

Lys Ser Ser Glu Leu Val Thr Ser Leu Gly Pro Glu Leu Phe Pro Asp
580 585 590

Phe Pro Glu Asn Ser Ile Leu Gln Gly Ser Asp Lys Phe Glu Asp Glu
595 600 605

Glu Asn Tyr Glu Asn Glu Lys Arg Ser His Ser Arg Ser Thr Ser Ala
610 615 620

Thr Ser Leu Ser Ala Met Ser Glu Gly Asp Gly Asp Glu Leu Val Arg
625 630 635 640

Glu Val Arg Lys Gly Ala Ser Tyr Phe Pro Val Ser Thr Ile Ser Glu
645 650 655

Asp Glu Asp Gln Ala Ile Ser Arg Val Gly Ser Glu Ala Ser Leu Ala
660 665 670

Asp Ile Pro Leu Phe Gly Met Ser Arg Ser Gln Ser Gly Ala Ser Leu
675 680 685

Ser Glu Ala Ser Thr His Gly Ser Ser Thr Gly Ala Asp Ala Glu Glu
690 695 700

Ala Lys Thr Glu Val Thr Arg Arg Ile Ala Leu Ala Met Glu Glu Lys
705 710 715 720

Arg Arg Glu Gln Asp Glu Glu
725

<210> SEQ ID NO 16
<211> LENGTH: 361
<212> TYPE: PRT
<213> ORGANISM: Drosophila melanogaster

<400> SEQUENCE: 16

Met Ala Pro Tyr Ser Arg Ile Tyr His Gln Asp Lys Ser Ser Arg Glu
1 5 10 15

Thr Gly Val Leu Phe Glu Asp Asp Ala Gln Thr Val Asp Ser Asp Leu

```
            20                  25                  30

Thr Thr Asp Arg Phe Gln Leu Lys Arg Ala Glu Lys Arg Arg Leu Pro
        35                  40                  45

Leu Val Trp Arg Asn Ile Ile Leu Phe Ala Leu Val His Leu Ala Ala
    50                  55                  60

Leu Tyr Gly Leu His Ser Ile Phe Thr Arg Ala Lys Leu Ala Thr Thr
65                  70                  75                  80

Leu Phe Ala Ala Gly Leu Tyr Ile Ile Gly Met Leu Gly Val Thr Ala
                85                  90                  95

Gly Ala His Arg Leu Trp Ala His Arg Thr Tyr Lys Ala Lys Trp Pro
            100                 105                 110

Leu Arg Leu Leu Leu Val Ile Phe Asn Thr Ile Ala Phe Gln Asp Ala
        115                 120                 125

Val Tyr His Trp Ala Arg Asp His Arg Val His His Lys Tyr Ser Glu
    130                 135                 140

Thr Asp Ala Asp Pro His Asn Ala Thr Arg Gly Phe Phe Phe Ser His
145                 150                 155                 160

Val Gly Trp Leu Leu Cys Lys Lys His Pro Asp Ile Lys Glu Lys Gly
                165                 170                 175

Arg Gly Leu Asp Leu Ser Asp Leu Arg Ala Asp Pro Ile Leu Met Phe
            180                 185                 190

Gln Arg Lys His Tyr Tyr Ile Leu Met Pro Leu Ala Cys Phe Val Leu
        195                 200                 205

Pro Thr Val Ile Pro Met Val Tyr Trp Asn Glu Thr Leu Ala Ser Ser
    210                 215                 220

Trp Phe Val Ala Thr Met Phe Arg Trp Cys Phe Gln Leu Asn Met Thr
225                 230                 235                 240

Trp Leu Val Asn Ser Ala Ala His Lys Phe Gly Asn Arg Pro Tyr Asp
                245                 250                 255

Lys Thr Met Asn Pro Thr Gln Asn Ala Phe Val Ser Ala Phe Thr Phe
            260                 265                 270

Gly Glu Gly Trp His Asn Tyr His His Ala Phe Pro Trp Asp Tyr Lys
        275                 280                 285

Thr Ala Glu Trp Gly Cys Tyr Ser Leu Asn Ile Thr Thr Ala Phe Ile
    290                 295                 300

Asp Leu Phe Ala Lys Ile Gly Trp Ala Tyr Asp Leu Lys Thr Val Ala
305                 310                 315                 320

Pro Asp Val Ile Gln Arg Arg Val Leu Arg Thr Gly Asp Gly Ser His
                325                 330                 335

Glu Leu Trp Gly Trp Gly Asp Lys Asp Leu Thr Ala Glu Asp Ala Arg
            340                 345                 350

Asn Val Leu Leu Val Asp Lys Ser Arg
        355                 360


<210> SEQ ID NO 17
<211> LENGTH: 478
<212> TYPE: PRT
<213> ORGANISM: Bicyclus anynana

<400> SEQUENCE: 17

Met Tyr Arg Asn Val Asn Asn Asn Tyr Lys Gly His Ser Val Tyr Thr
1               5                   10                  15

Asn Gly Ala Gly Ser Arg Val Lys Ser Leu Leu Ser Ser Ala Thr Asp
            20                  25                  30
```

```
Asn Thr Asn Glu Tyr Gln Ser Ile Ala Glu Cys Tyr Lys Gly Gln Ser
        35                  40                  45

Val Phe Ile Thr Gly Gly Thr Gly Phe Val Gly Lys Val Leu Leu Glu
    50                  55                  60

Lys Leu Leu Tyr Ser Cys Pro Gly Ile Asp Lys Val Tyr Leu Leu Val
65                  70                  75                  80

Arg Glu Thr Gln Gly Ala Thr Ala His Gln Arg Met Gln Lys Leu Leu
                85                  90                  95

Glu Glu Pro Ala Phe Ser Arg Ile Lys Glu Glu Asn Pro Gln Ala Phe
            100                 105                 110

Glu Lys Val Ile Pro Ile Val Gly Asp Ile Thr Gln Pro Gln Leu Gly
        115                 120                 125

Ile Met Ala Glu Asn Glu Glu Leu Leu Ile Lys Glu Val Ser Phe Val
    130                 135                 140

Tyr His Val Ala Ala Thr Thr Lys Phe Asn Glu Thr Leu Asp Ile Ala
145                 150                 155                 160

Met Asn Val Asn Val Ala Gly Thr Gly Arg Val Leu Asp Leu Ser Lys
                165                 170                 175

Arg Met Glu Asn Ile Lys Ala Phe Val Tyr Val Ser Thr Ala Tyr Ser
            180                 185                 190

Asn Thr Asp Arg Glu Val Val Glu Glu Val Leu Tyr Pro Ala Pro Val
        195                 200                 205

Ser Leu Asn Glu Val His Lys Leu Leu Lys Ile Gly Ile Thr Asp Ala
    210                 215                 220

Gln Val Lys Glu Leu Ile Lys Gly Arg Pro Asn Thr Tyr Thr Phe Thr
225                 230                 235                 240

Lys Ala Leu Ala Glu Asn Leu Val Ala Asp Asn His Gly His Val Pro
                245                 250                 255

Ala Ile Ile Val Arg Pro Ser Ile Val Ser Ser Ser Lys Lys Glu Pro
            260                 265                 270

Ile Thr Gly Trp Ile Asp Ser Trp Tyr Gly Ala Thr Phe Leu Ala Thr
        275                 280                 285

Val Thr Met Lys Gly Phe Asn Arg Val Phe Val Ser Ser Tyr Glu Tyr
    290                 295                 300

Asn Leu Asp Phe Ile Pro Val Asp Tyr Val Ser Asn Leu Ile Ile Val
305                 310                 315                 320

Ala Ala Ala Arg Cys Lys Cys Ser Asp Lys Val Asp Val Tyr Asn Ser
                325                 330                 335

Ser Thr Ser Gly Glu Asn Pro Leu Lys Ile Gly Ala Phe Phe Asp Asp
            340                 345                 350

Ile Ile Ala Tyr Ser Cys Lys His Lys Phe Tyr Asp Ile Pro Leu Pro
        355                 360                 365

Met Ala Tyr Leu Thr Arg Tyr Arg Trp Val Met Phe Leu Ile Thr Leu
    370                 375                 380

Leu Leu Gln Thr Leu Pro Ala Tyr Ile Ala Asp Leu Phe Leu Leu Ile
385                 390                 395                 400

Val Gly Lys Lys Pro Arg Tyr Val Lys Leu Ala Ser Lys Ile Ser Ala
                405                 410                 415

Ala His Glu Val Leu Asp Tyr Phe Pro Ser Arg Thr Trp Ser Met Ser
            420                 425                 430

Ala Arg Gln Thr Thr Ala Leu Phe Gln Ser Leu Ser Pro Ser Asp Arg
        435                 440                 445

Asp Gln Phe Pro Cys Asp Pro Thr Asp Ile Asp Trp Lys Glu Tyr Ile
```

```
    450                 455                 460

Val Thr Tyr Cys Gln Gly Ile Arg Gln Phe Leu Cys Lys Ser
465                 470                 475


<210> SEQ ID NO 18
<211> LENGTH: 353
<212> TYPE: PRT
<213> ORGANISM: Spodoptera litura

<400> SEQUENCE: 18

Met Ala Pro Asn Ile Ser Glu Asp Val Asn Gly Val Leu Phe Glu Ser
1               5                   10                  15

Asp Ala Ala Thr Pro Asp Leu Ala Leu Ala Arg Pro Pro Val Gln Lys
            20                  25                  30

Ala Asp Asn Lys Pro Lys Gln Leu Val Trp Arg Asn Ile Ile Leu Phe
        35                  40                  45

Ala Tyr Leu His Leu Ala Ala Leu Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Lys Val Ile Leu Ile Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Val Leu Arg Phe Gln Lys Lys Tyr Tyr Leu Leu Leu Met
            180                 185                 190

Pro Leu Ala Cys Phe Val Met Pro Thr Val Ile Pro Val Tyr Leu Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Met
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Phe Gly Asn Asn Lys Leu
        275                 280                 285

Asn Phe Thr Thr Ala Phe Ile Asn Phe Phe Ala Lys Ile Gly Trp Ala
    290                 295                 300

Tyr Asp Met Lys Thr Val Ser Glu Asp Ile Val Lys Asn Arg Val Lys
305                 310                 315                 320

Arg Thr Gly Asp Gly Ser His His Leu Trp Gly Trp Gly Asp Glu Asn
                325                 330                 335

Gln Pro Lys Glu Glu Ile Glu Ala Ala Ile Arg Ile Asn Pro Lys Asp
            340                 345                 350
```

Asp

<210> SEQ ID NO 19
<211> LENGTH: 677
<212> TYPE: PRT
<213> ORGANISM: Yarrowia lipolytica

<400> SEQUENCE: 19

Met Ala Lys Glu Arg Gly Lys Thr Gln Phe Thr Val Arg Asp Val Thr
1               5                   10                  15

Asn Phe Leu Asn Gly Gly Glu Glu Glu Thr Gln Ile Val Glu Lys Ile
            20                  25                  30

Met Ser Ser Ile Glu Arg Asp Pro Val Leu Ser Val Thr Ala Asp Tyr
        35                  40                  45

Asp Cys Asn Leu Gln Gln Ala Arg Lys Gln Thr Met Glu Arg Val Ala
    50                  55                  60

Ala Leu Ser Pro Tyr Leu Val Thr Asp Thr Glu Lys Leu Ser Leu Trp
65                  70                  75                  80

Arg Ala Gln Leu His Gly Met Val Asp Met Ser Thr Arg Thr Arg Leu
                85                  90                  95

Ser Ile His Asn Asn Leu Phe Ile Gly Ser Ile Arg Gly Ser Gly Thr
            100                 105                 110

Pro Glu Gln Phe Lys Tyr Trp Val Lys Lys Gly Ala Val Ala Val Lys
        115                 120                 125

Gln Phe Tyr Gly Cys Phe Ala Met Thr Glu Leu Gly His Gly Ser Asn
    130                 135                 140

Leu Lys Gly Leu Glu Thr Thr Ala Thr Tyr Asp Gln Asp Ser Asp Gln
145                 150                 155                 160

Phe Ile Ile Asn Thr Pro His Ile Gly Ala Thr Lys Trp Trp Ile Gly
                165                 170                 175

Gly Ala Ala His Thr Ser Thr His Cys Val Cys Phe Ala Lys Leu Ile
            180                 185                 190

Val His Gly Lys Asp Tyr Gly Thr Arg Asn Phe Val Val Pro Leu Arg
        195                 200                 205

Asn Val His Asp His Ser Leu Lys Val Gly Val Ser Ile Gly Asp Ile
    210                 215                 220

Gly Lys Lys Met Gly Arg Asp Gly Val Asp Asn Gly Trp Ile Gln Phe
225                 230                 235                 240

Thr Asn Val Arg Ile Pro Arg Gln Asn Met Leu Met Arg Tyr Ala Lys
                245                 250                 255

Val Ser Asp Thr Gly Val Val Thr Lys Pro Ala Leu Asp Gln Leu Thr
            260                 265                 270

Tyr Gly Ala Leu Ile Arg Gly Arg Val Ser Met Ile Ala Asp Ser Phe
        275                 280                 285

His Val Ser Lys Arg Phe Leu Thr Ile Ala Leu Arg Tyr Ala Cys Val
    290                 295                 300

Arg Arg Gln Phe Gly Thr Ser Gly Asp Thr Lys Glu Thr Lys Ile Ile
305                 310                 315                 320

Asp Tyr Pro Tyr His Gln Arg Arg Leu Leu Pro Leu Leu Ala Tyr Cys
                325                 330                 335

Tyr Ala Met Lys Met Gly Ala Asp Glu Ala Gln Lys Thr Trp Ile Glu
            340                 345                 350

Thr Thr Asp Arg Ile Leu Ala Leu Asn Pro Asn Asp Pro Ala Gln Lys
        355                 360                 365

Asn Asp Leu Glu Lys Ala Val Thr Asp Thr Lys Glu Leu Phe Ala Ala
370 375 380

Ser Ala Gly Met Lys Ala Phe Thr Thr Trp Gly Cys Ala Lys Ile Ile
385 390 395 400

Asp Glu Cys Arg Gln Ala Cys Gly Gly His Gly Tyr Ser Gly Tyr Asn
405 410 415

Gly Phe Gly Gln Gly Tyr Ala Asp Trp Val Val Gln Cys Thr Trp Glu
420 425 430

Gly Asp Asn Asn Val Leu Cys Leu Ser Met Gly Arg Gly Leu Val Gln
435 440 445

Ser Ala Leu Gln Ile Leu Ala Gly Lys His Val Gly Ala Ser Ile Gln
450 455 460

Tyr Val Gly Asp Lys Ser Lys Ile Ser Gln Asn Gly Gln Gly Thr Pro
465 470 475 480

Arg Glu Gln Leu Leu Ser Pro Glu Phe Leu Val Glu Ala Phe Arg Thr
485 490 495

Ala Ser Arg Asn Asn Ile Leu Arg Thr Thr Asp Lys Tyr Gln Glu Leu
500 505 510

Val Lys Thr Leu Asn Pro Asp Gln Ala Phe Glu Glu Leu Ser Gln Gln
515 520 525

Arg Phe Gln Cys Ala Arg Ile His Thr Arg Gln His Leu Ile Ser Ser
530 535 540

Phe Tyr Ala Arg Ile Ala Thr Ala Lys Asp Asp Ile Lys Pro His Leu
545 550 555 560

Leu Lys Leu Ala Asn Leu Phe Ala Leu Trp Ser Ile Glu Glu Asp Thr
565 570 575

Gly Ile Phe Leu Arg Glu Asn Ile Leu Thr Pro Gly Asp Ile Asp Leu
580 585 590

Ile Asn Ser Leu Val Asp Glu Leu Cys Val Ala Val Arg Asp Gln Val
595 600 605

Ile Gly Leu Thr Asp Ala Phe Gly Leu Ser Asp Phe Phe Ile Asn Ala
610 615 620

Pro Ile Gly Ser Tyr Asp Gly Asn Val Tyr Glu Lys Tyr Phe Ala Lys
625 630 635 640

Val Asn Gln Gln Asn Pro Ala Thr Asn Pro Arg Pro Pro Tyr Tyr Glu
645 650 655

Ser Thr Leu Lys Pro Phe Leu Phe Arg Glu Glu Glu Asp Asp Glu Ile
660 665 670

Cys Asp Leu Asp Glu
675

<210> SEQ ID NO 20
<211> LENGTH: 700
<212> TYPE: PRT
<213> ORGANISM: Yarrowia lipolytica

<400> SEQUENCE: 20

Met Asn Pro Asn Asn Thr Gly Thr Ile Glu Ile Asn Gly Lys Glu Tyr
1 5 10 15

Asn Thr Phe Thr Glu Pro Pro Val Ala Met Ala Gln Glu Arg Ala Lys
20 25 30

Thr Ser Phe Pro Val Arg Glu Met Thr Tyr Phe Leu Asp Gly Gly Glu
35 40 45

Lys Asn Thr Leu Lys Asn Glu Gln Ile Met Glu Glu Ile Glu Arg Asp
50 55 60

```
Pro Leu Phe Asn Asn Asp Asn Tyr Tyr Asp Leu Asn Lys Glu Gln Ile
65                  70                  75                  80

Arg Glu Leu Thr Met Glu Arg Val Ala Lys Leu Ser Leu Phe Val Arg
                85                  90                  95

Asp Gln Pro Glu Asp Asp Ile Lys Lys Arg Phe Ala Leu Ile Gly Ile
            100                 105                 110

Ala Asp Met Gly Thr Tyr Thr Arg Leu Gly Val His Tyr Gly Leu Phe
        115                 120                 125

Phe Gly Ala Val Arg Gly Thr Gly Thr Ala Glu Gln Phe Gly His Trp
    130                 135                 140

Ile Ser Lys Gly Ala Gly Asp Leu Arg Lys Phe Tyr Gly Cys Phe Ser
145                 150                 155                 160

Met Thr Glu Leu Gly His Gly Ser Asn Leu Ala Gly Leu Glu Thr Thr
                165                 170                 175

Ala Ile Tyr Asp Glu Glu Thr Asp Glu Phe Ile Ile Asn Thr Pro His
            180                 185                 190

Ile Ala Ala Thr Lys Trp Trp Ile Gly Gly Ala Ala His Thr Ala Thr
        195                 200                 205

His Thr Val Val Phe Ala Arg Leu Ile Val Lys Gly Lys Asp Tyr Gly
    210                 215                 220

Val Lys Thr Phe Val Val Gln Leu Arg Asn Ile Asn Asp His Ser Leu
225                 230                 235                 240

Lys Val Gly Ile Ser Ile Gly Asp Ile Gly Lys Lys Met Gly Arg Asp
                245                 250                 255

Gly Ile Asp Asn Gly Trp Ile Gln Phe Thr Asn Val Arg Ile Pro Arg
            260                 265                 270

Gln Asn Leu Leu Met Lys Tyr Thr Lys Val Asp Arg Glu Gly Asn Val
        275                 280                 285

Thr Gln Pro Pro Leu Ala Gln Leu Thr Tyr Gly Ser Leu Ile Thr Gly
    290                 295                 300

Arg Val Ser Met Ala Ser Asp Ser His Gln Val Gly Lys Arg Phe Ile
305                 310                 315                 320

Thr Ile Ala Leu Arg Tyr Ala Cys Ile Arg Arg Gln Phe Ser Thr Thr
                325                 330                 335

Pro Gly Gln Pro Glu Thr Lys Ile Ile Asp Tyr Pro Tyr His Gln Arg
            340                 345                 350

Arg Leu Leu Pro Leu Leu Ala Tyr Val Tyr Ala Leu Lys Met Thr Ala
        355                 360                 365

Asp Glu Val Gly Ala Leu Phe Ser Arg Thr Met Leu Lys Met Asp Asp
    370                 375                 380

Leu Lys Pro Asp Asp Lys Ala Gly Leu Asn Glu Val Val Ser Asp Val
385                 390                 395                 400

Lys Glu Leu Phe Ser Val Ser Ala Gly Leu Lys Ala Phe Ser Thr Trp
                405                 410                 415

Ala Cys Ala Asp Val Ile Asp Lys Thr Arg Gln Ala Cys Gly Gly His
            420                 425                 430

Gly Tyr Ser Gly Tyr Asn Gly Phe Gly Gln Ala Tyr Ala Asp Trp Val
        435                 440                 445

Val Gln Cys Thr Trp Glu Gly Asp Asn Asn Ile Leu Thr Leu Ser Ala
    450                 455                 460

Gly Arg Ala Leu Ile Gln Ser Ala Val Ala Leu Arg Lys Gly Glu Pro
465                 470                 475                 480
```

Val Gly Asn Ala Val Ser Tyr Leu Lys Arg Tyr Lys Asp Leu Ala Asn
485 490 495

Ala Lys Leu Asn Gly Arg Ser Leu Thr Asp Pro Lys Val Leu Val Glu
500 505 510

Ala Trp Glu Val Ala Ala Gly Asn Ile Ile Asn Arg Ala Thr Asp Gln
515 520 525

Tyr Glu Lys Leu Ile Gly Glu Gly Leu Asn Ala Asp Gln Ala Phe Glu
530 535 540

Val Leu Ser Gln Gln Arg Phe Gln Ala Ala Lys Val His Thr Arg Arg
545 550 555 560

His Leu Ile Ala Ala Phe Phe Ser Arg Ile Asp Thr Glu Ala Gly Glu
565 570 575

Ala Ile Lys Gln Pro Leu Leu Asn Leu Ala Leu Leu Phe Ala Leu Trp
580 585 590

Ser Ile Glu Glu Asp Ser Gly Leu Phe Leu Arg Glu Gly Phe Leu Glu
595 600 605

Pro Lys Asp Ile Asp Thr Val Thr Glu Leu Val Asn Lys Tyr Cys Thr
610 615 620

Thr Val Arg Glu Glu Val Ile Gly Tyr Thr Asp Ala Phe Asn Leu Ser
625 630 635 640

Asp Tyr Phe Ile Asn Ala Pro Ile Gly Cys Tyr Asp Gly Asp Ala Tyr
645 650 655

Arg His Tyr Phe Gln Lys Val Asn Glu Gln Asn Pro Ala Arg Asp Pro
660 665 670

Arg Pro Pro Tyr Tyr Ala Ser Thr Leu Lys Pro Phe Leu Phe Arg Glu
675 680 685

Glu Glu Asp Asp Asp Ile Cys Glu Leu Asp Glu Glu
690 695 700

<210> SEQ ID NO 21
<211> LENGTH: 700
<212> TYPE: PRT
<213> ORGANISM: Yarrowia lipolytica

<400> SEQUENCE: 21

Met Ile Ser Pro Asn Leu Thr Ala Asn Val Glu Ile Asp Gly Lys Gln
1 5 10 15

Tyr Asn Thr Phe Thr Glu Pro Pro Lys Ala Leu Ala Gly Glu Arg Ala
20 25 30

Lys Val Lys Phe Pro Ile Lys Asp Met Thr Glu Phe Leu His Gly Gly
35 40 45

Glu Glu Asn Val Thr Met Ile Glu Arg Leu Met Thr Glu Leu Glu Arg
50 55 60

Asp Pro Val Leu Asn Val Ser Gly Asp Tyr Asp Met Pro Lys Glu Gln
65 70 75 80

Leu Arg Glu Thr Ala Val Ala Arg Ile Ala Ala Leu Ser Gly His Trp
85 90 95

Lys Lys Asp Thr Glu Lys Glu Ala Leu Leu Arg Ser Gln Leu His Gly
100 105 110

Ile Val Asp Met Gly Thr Arg Ile Arg Leu Gly Val His Thr Gly Leu
115 120 125

Phe Met Gly Ala Ile Arg Gly Ser Gly Thr Lys Glu Gln Tyr Asp Tyr
130 135 140

Trp Val Arg Lys Gly Ala Ala Asp Val Lys Gly Phe Tyr Gly Cys Phe
145 150 155 160

```
Ala Met Thr Glu Leu Gly His Gly Ser Asn Val Ala Gly Leu Glu Thr
                165                 170                 175

Thr Ala Thr Tyr Ile Gln Asp Thr Asp Glu Phe Ile Ile Asn Thr Pro
            180                 185                 190

Asn Thr Gly Ala Thr Lys Trp Trp Ile Gly Gly Ala Ala His Ser Ala
        195                 200                 205

Thr His Thr Ala Cys Phe Ala Arg Leu Leu Val Asp Gly Lys Asp Tyr
    210                 215                 220

Gly Val Lys Ile Phe Val Val Gln Leu Arg Asp Val Ser Ser His Ser
225                 230                 235                 240

Leu Met Pro Gly Ile Ala Leu Gly Asp Ile Gly Lys Lys Met Gly Arg
                245                 250                 255

Asp Ala Ile Asp Asn Gly Trp Ile Gln Phe Thr Asn Val Arg Ile Pro
            260                 265                 270

Arg Gln Asn Met Leu Met Lys Tyr Ala Lys Val Ser Ser Thr Gly Lys
        275                 280                 285

Val Ser Gln Pro Pro Leu Ala Gln Leu Thr Tyr Gly Ala Leu Ile Gly
    290                 295                 300

Gly Arg Val Thr Met Ile Ala Asp Ser Phe Phe Val Ser Gln Arg Phe
305                 310                 315                 320

Ile Thr Ile Ala Leu Arg Tyr Ala Cys Val Arg Arg Gln Phe Gly Thr
                325                 330                 335

Thr Pro Gly Gln Pro Glu Thr Lys Ile Ile Asp Tyr Pro Tyr His Gln
            340                 345                 350

Arg Arg Leu Leu Pro Leu Leu Ala Phe Thr Tyr Ala Met Lys Met Ala
        355                 360                 365

Ala Asp Gln Ser Gln Ile Gln Tyr Asp Gln Thr Thr Asp Leu Leu Gln
    370                 375                 380

Thr Ile Asp Pro Lys Asp Lys Gly Ala Leu Gly Lys Ala Ile Val Asp
385                 390                 395                 400

Leu Lys Glu Leu Phe Ala Ser Ser Ala Gly Leu Lys Ala Phe Thr Thr
                405                 410                 415

Trp Thr Cys Ala Asn Ile Ile Asp Gln Cys Arg Gln Ala Cys Gly Gly
            420                 425                 430

His Gly Tyr Ser Gly Tyr Asn Gly Phe Gly Gln Ala Tyr Ala Asp Trp
        435                 440                 445

Val Val Gln Cys Thr Trp Glu Gly Asp Asn Asn Val Leu Cys Leu Ser
    450                 455                 460

Met Gly Arg Gly Leu Ile Gln Ser Cys Leu Gly His Arg Lys Gly Lys
465                 470                 475                 480

Pro Leu Gly Ser Ser Val Gly Tyr Leu Ala Asn Lys Gly Leu Glu Gln
                485                 490                 495

Ala Thr Leu Ser Gly Arg Asp Leu Lys Asp Pro Lys Val Leu Ile Glu
            500                 505                 510

Ala Trp Glu Lys Val Ala Asn Gly Ala Ile Gln Arg Ala Thr Asp Lys
        515                 520                 525

Phe Val Glu Leu Thr Lys Gly Gly Leu Ser Pro Asp Gln Ala Phe Glu
    530                 535                 540

Glu Leu Ser Gln Gln Arg Phe Gln Cys Ala Lys Ile His Thr Arg Lys
545                 550                 555                 560

His Leu Val Thr Ala Phe Tyr Glu Arg Ile Asn Ala Ser Ala Lys Ala
                565                 570                 575
```

```
Asp Val Lys Pro Tyr Leu Ile Asn Leu Ala Asn Leu Phe Thr Leu Trp
            580                 585                 590

Ser Ile Glu Glu Asp Ser Gly Leu Phe Leu Arg Glu Gly Phe Leu Gln
        595                 600                 605

Pro Lys Asp Ile Asp Gln Val Thr Glu Leu Val Asn His Tyr Cys Lys
    610                 615                 620

Glu Val Arg Asp Gln Val Ala Gly Tyr Thr Asp Ala Phe Gly Leu Ser
625                 630                 635                 640

Asp Trp Phe Ile Asn Ala Pro Ile Gly Asn Tyr Asp Gly Asp Val Tyr
                645                 650                 655

Lys His Tyr Phe Ala Lys Val Asn Gln Gln Asn Pro Ala Gln Asn Pro
            660                 665                 670

Arg Pro Pro Tyr Tyr Glu Ser Thr Leu Arg Pro Phe Leu Phe Arg Glu
        675                 680                 685

Asp Glu Asp Asp Asp Ile Cys Glu Leu Asp Glu Glu
    690                 695                 700


<210> SEQ ID NO 22
<211> LENGTH: 701
<212> TYPE: PRT
<213> ORGANISM: Yarrowia lipolytica

<400> SEQUENCE: 22

Met Ile Thr Pro Asn Pro Ala Asn Asp Ile Val His Asp Gly Lys Leu
1               5                   10                  15

Tyr Asp Thr Phe Thr Glu Pro Pro Lys Leu Met Ala Gln Glu Arg Ala
            20                  25                  30

Gln Leu Asp Phe Asp Pro Arg Asp Ile Thr Tyr Phe Leu Asp Gly Ser
        35                  40                  45

Lys Glu Glu Thr Glu Leu Leu Glu Ser Leu Met Leu Met Tyr Glu Arg
    50                  55                  60

Asp Pro Leu Phe Asn Asn Gln Asn Glu Tyr Asp Glu Ser Phe Glu Thr
65                  70                  75                  80

Leu Arg Glu Arg Ser Val Lys Arg Ile Phe Gln Leu Ser Lys Ser Ile
                85                  90                  95

Ala Met Asp Pro Glu Pro Met Ser Phe Arg Lys Ile Gly Phe Leu Gly
            100                 105                 110

Ile Leu Asp Met Gly Thr Tyr Ala Arg Leu Gly Val His Tyr Ala Leu
        115                 120                 125

Phe Cys Asn Ser Ile Arg Gly Gln Gly Thr Pro Asp Gln Leu Met Tyr
    130                 135                 140

Trp Leu Asp Gln Gly Ala Met Val Ile Lys Gly Phe Tyr Gly Cys Phe
145                 150                 155                 160

Ala Met Thr Glu Met Gly His Gly Ser Asn Leu Ser Arg Leu Glu Thr
                165                 170                 175

Ile Ala Thr Phe Asp Lys Glu Thr Asp Glu Phe Ile Ile Asn Thr Pro
            180                 185                 190

His Val Gly Ala Thr Lys Trp Trp Ile Gly Gly Ala Ala His Thr Ala
        195                 200                 205

Thr His Thr Leu Ala Phe Ala Arg Leu Gln Val Asp Gly Lys Asp Tyr
    210                 215                 220

Gly Val Lys Ser Phe Val Val Pro Leu Arg Asn Leu Asp Asp His Ser
225                 230                 235                 240

Leu Arg Pro Gly Ile Ala Thr Gly Asp Ile Gly Lys Lys Met Gly Arg
                245                 250                 255
```

```
Asp Ala Val Asp Asn Gly Trp Ile Gln Phe Thr Asn Val Arg Val Pro
            260                 265                 270

Arg Asn Tyr Met Leu Met Lys His Thr Lys Val Leu Arg Asp Gly Thr
        275                 280                 285

Val Lys Gln Pro Pro Leu Ala Gln Leu Thr Tyr Gly Ser Leu Ile Thr
    290                 295                 300

Gly Arg Val Gln Met Thr Thr Asp Ser His Asn Val Ser Lys Lys Phe
305                 310                 315                 320

Leu Thr Ile Ala Leu Arg Tyr Ala Thr Ile Arg Arg Gln Phe Ser Ser
                325                 330                 335

Thr Pro Gly Glu Pro Glu Thr Arg Leu Ile Asp Tyr Leu Tyr His Gln
            340                 345                 350

Arg Arg Leu Leu Pro Leu Met Ala Tyr Ser Tyr Ala Met Lys Leu Ala
        355                 360                 365

Gly Asp His Val Arg Glu Leu Phe Phe Ala Ser Gln Glu Lys Ala Glu
    370                 375                 380

Ser Leu Lys Glu Asp Asp Lys Ala Gly Val Glu Ser Tyr Val Gln Asp
385                 390                 395                 400

Ile Lys Glu Leu Phe Ser Val Ser Ala Gly Leu Lys Ala Ala Thr Thr
                405                 410                 415

Trp Ala Cys Ala Asp Ile Ile Asp Lys Ala Arg Gln Ala Cys Gly Gly
            420                 425                 430

His Gly Tyr Ser Ala Tyr Asn Gly Phe Gly Gln Ala Phe Gln Asp Trp
        435                 440                 445

Val Val Gln Cys Thr Trp Glu Gly Asp Asn Thr Val Leu Thr Leu Ser
    450                 455                 460

Ala Gly Arg Ala Leu Ile Gln Ser Ala Leu Val Tyr Arg Lys Glu Gly
465                 470                 475                 480

Lys Leu Gly Asn Ala Thr Lys Tyr Leu Ser Arg Ser Lys Glu Leu Ala
                485                 490                 495

Asn Ala Lys Arg Asn Gly Arg Ser Leu Glu Asp Pro Lys Leu Leu Val
            500                 505                 510

Glu Ala Trp Glu Ala Val Ser Ala Gly Ala Ile Asn Ala Ala Thr Asp
        515                 520                 525

Ala Tyr Glu Glu Leu Ser Lys Gln Gly Val Ser Val Asp Glu Cys Phe
    530                 535                 540

Glu Gln Val Ser Gln Glu Arg Phe Gln Ala Ala Arg Ile His Thr Arg
545                 550                 555                 560

Arg Ala Leu Ile Glu Ala Phe Tyr Ser Arg Ile Ala Thr Ala Asp Glu
                565                 570                 575

Lys Val Lys Pro His Leu Ile Pro Leu Ala Asn Leu Phe Ala Leu Trp
            580                 585                 590

Ser Ile Glu Glu Asp Ser Ala Leu Phe Leu Ala Glu Gly Tyr Phe Glu
        595                 600                 605

Pro Glu Asp Ile Ile Glu Val Thr Ser Leu Val Asn Lys Tyr Cys Gly
    610                 615                 620

Ile Val Arg Lys Asn Val Ile Gly Tyr Thr Asp Ala Phe Asn Leu Ser
625                 630                 635                 640

Asp Tyr Phe Ile Asn Ala Ala Ile Gly Arg Tyr Asp Gly Asp Val Tyr
                645                 650                 655

Lys Asn Tyr Phe Glu Lys Val Lys Gln Gln Tyr Pro Pro Glu Gly Gly
            660                 665                 670
```

```
Lys Pro His Tyr Tyr Glu Asp Val Met Lys Pro Phe Leu His Arg Glu
        675                 680                 685

Arg Ile Pro Asp Val Pro Met Glu Pro Glu Asp Ile Gln
    690                 695                 700


<210> SEQ ID NO 23
<211> LENGTH: 699
<212> TYPE: PRT
<213> ORGANISM: Yarrowia lipolytica

<400> SEQUENCE: 23

Met Asn Asn Asn Pro Thr Asn Val Ile Leu Gly Gly Lys Glu Tyr Asp
1               5                   10                  15

Thr Phe Thr Glu Pro Pro Ala Gln Met Glu Leu Glu Arg Ala Lys Thr
            20                  25                  30

Gln Phe Lys Val Arg Asp Val Thr Asn Phe Leu Thr Gly Ser Glu Gln
        35                  40                  45

Glu Thr Leu Leu Thr Glu Arg Ile Met Arg Glu Ile Glu Arg Asp Pro
    50                  55                  60

Val Leu Asn Val Ala Gly Asp Tyr Asp Ala Asp Leu Pro Thr Lys Arg
65                  70                  75                  80

Arg Gln Ala Val Glu Arg Ile Gly Ala Leu Ala Arg Tyr Leu Pro Lys
                85                  90                  95

Asp Ser Glu Lys Glu Ala Ile Leu Arg Gly Gln Leu His Gly Ile Val
            100                 105                 110

Asp Met Gly Thr Arg Thr Arg Ile Ala Val His Tyr Gly Leu Phe Met
        115                 120                 125

Gly Ala Ile Arg Gly Ser Gly Thr Lys Glu Gln Tyr Asp Tyr Trp Val
    130                 135                 140

Ala Lys Gly Ala Ala Thr Leu His Lys Phe Tyr Gly Cys Phe Ala Met
145                 150                 155                 160

Thr Glu Leu Gly His Gly Ser Asn Val Ala Gly Leu Glu Thr Thr Ala
                165                 170                 175

Thr Leu Asp Lys Asp Thr Asp Glu Phe Ile Ile Asn Thr Pro Asn Ser
            180                 185                 190

Gly Ala Thr Lys Trp Trp Ile Gly Gly Ala Ala His Ser Ala Thr His
        195                 200                 205

Thr Ala Cys Leu Ala Arg Leu Ile Val Asp Gly Lys Asp Tyr Gly Val
    210                 215                 220

Lys Ile Phe Ile Val Gln Leu Arg Asp Leu Asn Ser His Ser Leu Leu
225                 230                 235                 240

Asn Gly Ile Ala Ile Gly Asp Ile Gly Lys Lys Met Gly Arg Asp Ala
                245                 250                 255

Ile Asp Asn Gly Trp Ile Gln Phe Thr Asp Val Arg Ile Pro Arg Gln
            260                 265                 270

Asn Met Leu Met Arg Tyr Asp Arg Val Ser Arg Asp Gly Glu Val Thr
        275                 280                 285

Thr Ser Glu Leu Ala Gln Leu Thr Tyr Gly Ala Leu Leu Ser Gly Arg
    290                 295                 300

Val Thr Met Ile Ala Glu Ser His Leu Leu Ser Ala Arg Phe Leu Thr
305                 310                 315                 320

Ile Ala Leu Arg Tyr Ala Cys Ile Arg Arg Gln Phe Gly Ala Val Pro
                325                 330                 335

Asp Lys Pro Glu Thr Lys Leu Ile Asp Tyr Pro Tyr His Gln Arg Arg
            340                 345                 350
```

```
Leu Leu Pro Leu Leu Ala Tyr Thr Tyr Ala Met Lys Met Gly Ala Asp
        355                 360                 365

Glu Ala Gln Gln Gln Tyr Asn Ser Ser Phe Gly Ala Leu Leu Lys Leu
    370                 375                 380

Asn Pro Val Lys Asp Ala Glu Lys Phe Ala Val Ala Thr Ala Asp Leu
385                 390                 395                 400

Lys Ala Leu Phe Ala Ser Ser Ala Gly Met Lys Ala Phe Thr Thr Trp
                405                 410                 415

Ala Ala Ala Lys Ile Ile Asp Glu Cys Arg Gln Ala Cys Gly Gly His
            420                 425                 430

Gly Tyr Ser Gly Tyr Asn Gly Phe Gly Gln Ala Tyr Ala Asp Trp Val
        435                 440                 445

Val Gln Cys Thr Trp Glu Gly Asp Asn Asn Val Leu Cys Leu Ser Met
    450                 455                 460

Gly Arg Ser Leu Ile Gln Ser Cys Ile Ala Met Arg Lys Lys Lys Gly
465                 470                 475                 480

His Val Gly Lys Ser Val Glu Tyr Leu Gln Arg Arg Asp Glu Leu Gln
                485                 490                 495

Asn Ala Arg Val Asp Asn Lys Pro Leu Thr Asp Pro Ala Val Leu Ile
            500                 505                 510

Thr Ala Trp Glu Lys Val Ala Cys Glu Ala Ile Asn Arg Ala Thr Asp
        515                 520                 525

Ser Phe Ile Lys Leu Thr Gln Glu Gly Leu Ser Pro Asp Gln Ala Phe
    530                 535                 540

Glu Glu Leu Ser Gln Gln Arg Phe Glu Cys Ala Arg Ile His Thr Arg
545                 550                 555                 560

Lys His Leu Ile Thr Ser Phe Tyr Ala Arg Ile Ser Lys Ala Lys Ala
                565                 570                 575

Arg Val Lys Pro His Leu Thr Val Leu Ala Asn Leu Phe Ala Val Trp
            580                 585                 590

Ser Ile Glu Glu Asp Ser Gly Leu Phe Leu Arg Glu Gly Cys Phe Glu
        595                 600                 605

Pro Ala Glu Met Asp Glu Ile Thr Ala Leu Val Asp Glu Leu Cys Cys
    610                 615                 620

Glu Ala Arg Glu Gln Val Ile Gly Phe Thr Asp Ala Phe Asn Leu Ser
625                 630                 635                 640

Asp Phe Phe Ile Asn Ala Pro Ile Gly Arg Phe Asp Gly Asp Ala Tyr
                645                 650                 655

Lys His Tyr Met Asp Glu Val Lys Ala Ala Asn Asn Pro Arg Asn Thr
            660                 665                 670

His Ala Pro Tyr Tyr Glu Thr Lys Leu Arg Pro Phe Leu Phe Arg Pro
        675                 680                 685

Asp Glu Asp Glu Glu Ile Cys Asp Leu Asp Glu
    690                 695
```

<210> SEQ ID NO 24
<211> LENGTH: 689
<212> TYPE: PRT
<213> ORGANISM: Yarrowia lipolytica

<400> SEQUENCE: 24

```
Met Leu Ser Gln Gln Ser Leu Asn Thr Phe Thr Glu Pro Pro Val Glu
1               5                   10                  15

Met Ala Arg Glu Arg Asn Gln Thr Ser Phe Asn Pro Arg Leu Leu Thr
```

-continued

```
            20                  25                  30

Tyr Phe Leu Asp Gly Gly Glu Lys Asn Thr Leu Leu Met Asp Arg Leu
        35                  40                  45

Met Gln Glu Tyr Glu Arg Asp Pro Val Phe Arg Asn Glu Gly Asp Tyr
    50                  55                  60

Asp Ile Thr Asp Val Ala Gln Ser Arg Glu Leu Ala Phe Lys Arg Ile
65                  70                  75                  80

Ala Lys Leu Ile Glu Tyr Val His Thr Asp Asp Glu Glu Thr Tyr Leu
                85                  90                  95

Tyr Arg Cys Met Leu Leu Gly Gln Ile Asp Met Gly Ala Phe Ala Arg
            100                 105                 110

Tyr Ala Ile His His Gly Val Trp Gly Gly Ala Ile Arg Gly Ala Gly
        115                 120                 125

Thr Pro Glu Gln Tyr Glu Phe Trp Val Lys Lys Gly Ser Leu Ser Val
    130                 135                 140

Lys Lys Phe Tyr Gly Ser Phe Ser Met Thr Glu Leu Gly His Gly Ser
145                 150                 155                 160

Asn Leu Val Gly Leu Glu Thr Thr Ala Thr Leu Asp Lys Asn Ala Asp
                165                 170                 175

Glu Phe Val Ile Asn Thr Pro Asn Val Ala Ala Thr Lys Trp Trp Ile
            180                 185                 190

Gly Gly Ala Ala Asp Thr Ala Thr His Thr Ala Val Phe Ala Arg Leu
        195                 200                 205

Ile Val Asp Gly Glu Asp His Gly Val Lys Thr Phe Val Val Gln Leu
    210                 215                 220

Arg Asp Val Glu Thr His Asn Leu Met Pro Gly Ile Ala Ile Gly Asp
225                 230                 235                 240

Cys Gly Lys Lys Met Gly Arg Gln Gly Thr Asp Asn Gly Trp Ile Gln
                245                 250                 255

Phe Thr His Val Arg Ile Pro Arg Gln Asn Met Leu Met Arg Tyr Cys
            260                 265                 270

His Val Asp Ser Asp Gly Asn Val Thr Glu Pro Met Met Ala Gln Met
        275                 280                 285

Ala Tyr Gly Ala Leu Leu Ala Gly Arg Val Gly Met Ala Met Asp Ser
    290                 295                 300

Tyr Phe Thr Ser Arg Lys Phe Leu Thr Ile Ala Leu Arg Tyr Ala Thr
305                 310                 315                 320

Ile Arg Arg Ala Phe Ala Ala Gly Gly Gly Gln Glu Thr Lys Leu Ile
                325                 330                 335

Asp Tyr Pro Tyr His Gln Arg Arg Leu Leu Pro Leu Met Ala Gln Thr
            340                 345                 350

Tyr Ala Ile Lys Cys Thr Ala Asp Lys Val Arg Asp Gln Phe Val Lys
        355                 360                 365

Val Thr Asp Met Leu Leu Asn Leu Asp Val Ser Asp Gln Glu Ala Val
    370                 375                 380

Pro Lys Ala Ile Ala Glu Ala Lys Glu Leu Phe Ser Val Ser Ala Gly
385                 390                 395                 400

Val Lys Ala Thr Thr Thr Trp Ala Cys Ala His Thr Ile Asp Gln Cys
                405                 410                 415

Arg Gln Ala Cys Gly Gly His Gly Tyr Ser Ala Tyr Asn Gly Phe Gly
            420                 425                 430

Arg Ala Tyr Ser Asp Trp Val Ile Gln Cys Thr Trp Glu Gly Asp Asn
        435                 440                 445
```

Asn Ile Leu Cys Leu Ser Ala Gly Arg Ala Leu Val Gln Ser Asn Arg
450 455 460

Ala Val Arg Ala Gly Lys Pro Ile Gly Gly Pro Thr Ala Tyr Leu Ala
465 470 475 480

Ala Pro Ala Gly Ser Pro Lys Leu Ala Gly Arg Asn Leu Tyr Asp Pro
485 490 495

Lys Val Met Ile Gly Ala Trp Glu Thr Val Ser Arg Ala Leu Ile Asn
500 505 510

Arg Thr Thr Asp Glu Phe Glu Val Leu Ala Lys Lys Gly Leu Ser Thr
515 520 525

Ala Gln Ala Tyr Glu Glu Leu Ser Gln Gln Arg Phe Leu Cys Thr Arg
530 535 540

Ile His Thr Arg Leu Tyr Met Val Lys Asn Phe Tyr Glu Arg Ile Ala
545 550 555 560

Glu Glu Gly Thr Glu Phe Thr Lys Glu Pro Leu Thr Arg Leu Ala Asn
565 570 575

Leu Tyr Ala Phe Trp Ser Val Glu Glu Glu Ala Gly Ile Phe Leu Arg
580 585 590

Glu Gly Tyr Ile Thr Pro Gln Glu Leu Lys Tyr Ile Ser Ala Glu Ile
595 600 605

Arg Lys Gln Leu Leu Glu Val Arg Lys Asp Val Ile Gly Tyr Thr Asp
610 615 620

Ala Phe Asn Val Pro Asp Phe Phe Leu Asn Ser Ala Ile Gly Arg Ala
625 630 635 640

Asp Gly Asp Val Tyr Lys Asn Tyr Phe Lys Val Val Asn Thr Gln Asn
645 650 655

Pro Pro Gln Asp Pro Arg Pro Pro Tyr Tyr Glu Ser Val Ile Arg Pro
660 665 670

Phe Leu Phe Arg Lys Asp Glu Asp Glu Glu Ile Cys Ser Leu Glu Asp
675 680 685

Glu

<210> SEQ ID NO 25
<211> LENGTH: 695
<212> TYPE: PRT
<213> ORGANISM: Agrotis segetum

<400> SEQUENCE: 25

Met Pro Ile Phe Ile Cys Ile Ile Thr Ser Gln Ala Ile Ile Arg Ser
1 5 10 15

Asn Val Glu Arg Val Ala Val Ile Leu Asn Ile Asn Met Gly Lys Val
20 25 30

Asn Glu Asp Leu Val Arg Glu Arg Ala Lys Cys Thr Phe Asn Ile Glu
35 40 45

Glu Leu Thr Tyr Phe Leu Asp Gly Gly Lys Asp Lys Thr Leu Glu Arg
50 55 60

Lys Glu Thr Glu Arg Ala Met Leu Thr Lys Arg Glu Glu Leu Phe Gly
65 70 75 80

Gly Val Pro Asp Glu Tyr Leu Ser His Lys Glu Lys Tyr Glu Asn Ser
85 90 95

Met Arg Lys Ala Val Ile Leu Phe Gly Ile Leu Arg Lys Ile Gln Lys
100 105 110

Asp Asn Asn Thr Asp Leu Thr Asn Tyr Arg Asn Leu Leu Ser Gly Val
115 120 125

```
Leu Ser Val Ser Ile Ser Gln Asp Gly Ser Pro Phe Gly Leu His Tyr
    130                 135                 140

Ile Met Phe Met Pro Val Leu Leu Ser Gln Ala Asp Glu Lys Gln Gln
145                 150                 155                 160

Glu Lys Trp Leu Lys Arg Ala Met Asn Cys Glu Ile Ile Gly Ser Tyr
                165                 170                 175

Ala Gln Thr Glu Leu Gly His Gly Thr Phe Ile Arg Gly Leu Glu Thr
            180                 185                 190

Thr Ala Thr Tyr Asp Pro Ala Thr Gln Glu Phe Val Leu His Ser Pro
        195                 200                 205

Ala Leu Ser Ser Tyr Lys Trp Trp Pro Gly Gly Leu Gly Asn Thr Val
    210                 215                 220

Asn Tyr Cys Ile Val Ile Ala Gln Leu Tyr Ser Lys Gly Val Cys His
225                 230                 235                 240

Gly Ile His Ser Phe Ile Val Gln Val Arg Asp Glu Asp Thr His Met
                245                 250                 255

Pro Leu Pro Gly Ile Lys Val Gly Glu Ile Gly Val Lys Met Gly Leu
            260                 265                 270

Asn Ser Val Asn Asn Gly Phe Leu Gly Phe Glu Asn Val Arg Ile Pro
        275                 280                 285

Arg Val Asn Met Leu Met Lys His Ala Lys Ile Leu Glu Asp Gly Thr
    290                 295                 300

Tyr Val Lys Ser Lys Asn Asn Lys Leu Ile Tyr Gly Ala Met Val Phe
305                 310                 315                 320

Val Arg Val Val Ile Val Phe Asp Ser Val Asn Tyr Leu Ala Lys Ala
                325                 330                 335

Ile Thr Ile Gly Ala Arg Tyr Ser Leu Val Arg Arg Gln Ser Gln Leu
            340                 345                 350

Lys Ala Gly Glu Pro Glu Arg Gln Ile Leu Asp Tyr Val Thr Gln Gln
        355                 360                 365

His Lys Ile Leu Pro Ala Ile Ala Gly Cys Tyr Ala Met Lys Met Asn
    370                 375                 380

Ala Trp Arg Leu Trp Asp Thr Phe Asn Leu Ile Asn Gly Gln Leu His
385                 390                 395                 400

Gln Gly Asn Met Glu Arg Leu Gly Glu Leu His Ala Leu Ala Cys Cys
                405                 410                 415

Leu Lys Ala Ile Ser Thr Thr Asp Ala Ala Met Phe Thr Ser Leu Cys
            420                 425                 430

Arg Leu Gly Cys Gly Gly His Gly Tyr Met Thr Ser Ser Asn Leu Pro
        435                 440                 445

Pro Thr Tyr Ala Leu Thr Ser Ala Ser Cys Thr Tyr Glu Gly Asp Asn
    450                 455                 460

Thr Val Leu Leu Leu Gln Thr Ala Arg Phe Leu Leu Lys Thr Trp Arg
465                 470                 475                 480

Gln Ile Asp Thr His Pro Leu Thr Arg Thr Val Ala Tyr Leu Lys Thr
                485                 490                 495

Val Ser Ala Pro Gly Phe Ser Asp Arg Trp Glu Ser Ser Val Glu Gly
            500                 505                 510

Ile Ile Arg Gly Phe Gln Thr Val Ala Met Lys Lys Ile Ser Ser Cys
        515                 520                 525

Leu Asp Ile Met Thr Ser Lys Val Met Ser Gly Met Ser Gln Glu Asp
    530                 535                 540
```

```
Ala Trp Asn Ala Ile Ser Ile Gln Leu Val Ser Ala Ala Glu Ser His
545                 550                 555                 560

Ser Arg Gly Thr Val Ile Ser Thr Phe Tyr Glu Asp Met Ser Lys Ala
                565                 570                 575

Met Arg Ser Met Thr Ala Pro Leu Ala Lys Val Met Gly Gln Leu Val
            580                 585                 590

Glu Leu Tyr Ala Val Tyr Trp Thr Leu Glu Arg Leu Gly Asp Met Leu
        595                 600                 605

Gln Tyr Thr Ser Ile Ser His Thr Asp Val Val Asp Leu Arg Ser Trp
    610                 615                 620

Tyr Glu Glu Leu Leu Arg Lys Ile Arg Pro Asn Thr Ile Gly Leu Val
625                 630                 635                 640

Asp Ala Phe Asp Ile Ile Asp Glu Leu Leu Gln Ser Thr Leu Gly Ala
                645                 650                 655

Tyr Asp Gly Arg Val Tyr Glu Arg Leu Met Glu Glu Ala Leu Lys Ser
            660                 665                 670

Pro Leu Asn Ala Glu Pro Val Asn Gln Ser Phe His Lys Tyr Leu Lys
        675                 680                 685

Pro Phe Met Gln Ser Lys Leu
    690                 695


<210> SEQ ID NO 26
<211> LENGTH: 676
<212> TYPE: PRT
<213> ORGANISM: Arabidopsis thaliana

<400> SEQUENCE: 26

Met Glu Gly Ile Asp His Leu Ala Asp Glu Arg Asn Lys Ala Glu Phe
1               5                   10                  15

Asp Val Glu Asp Met Lys Ile Val Trp Ala Gly Ser Arg His Ala Phe
            20                  25                  30

Glu Val Ser Asp Arg Ile Ala Arg Leu Val Ala Ser Asp Pro Val Phe
        35                  40                  45

Glu Lys Ser Asn Arg Ala Arg Leu Ser Arg Lys Glu Leu Phe Lys Ser
    50                  55                  60

Thr Leu Arg Lys Cys Ala His Ala Phe Lys Arg Ile Ile Glu Leu Arg
65                  70                  75                  80

Leu Asn Glu Glu Glu Ala Gly Arg Leu Arg His Phe Ile Asp Gln Pro
                85                  90                  95

Ala Tyr Val Asp Leu His Trp Gly Met Phe Val Pro Ala Ile Lys Gly
            100                 105                 110

Gln Gly Thr Glu Glu Gln Gln Lys Lys Trp Leu Ser Leu Ala Asn Lys
        115                 120                 125

Met Gln Ile Ile Gly Cys Tyr Ala Gln Thr Glu Leu Gly His Gly Ser
    130                 135                 140

Asn Val Gln Gly Leu Glu Thr Thr Ala Thr Phe Asp Pro Lys Thr Asp
145                 150                 155                 160

Glu Phe Val Ile His Thr Pro Thr Gln Thr Ala Ser Lys Trp Trp Pro
                165                 170                 175

Gly Gly Leu Gly Lys Val Ser Thr His Ala Val Val Tyr Ala Arg Leu
            180                 185                 190

Ile Thr Asn Gly Lys Asp Tyr Gly Ile His Gly Phe Ile Val Gln Leu
        195                 200                 205

Arg Ser Leu Glu Asp His Ser Pro Leu Pro Asn Ile Thr Val Gly Asp
    210                 215                 220
```

```
Ile Gly Thr Lys Met Gly Asn Gly Ala Tyr Asn Ser Met Asp Asn Gly
225                 230                 235                 240

Phe Leu Met Phe Asp His Val Arg Ile Pro Arg Asp Gln Met Leu Met
                245                 250                 255

Arg Leu Ser Lys Val Thr Arg Glu Gly Glu Tyr Val Pro Ser Asp Val
            260                 265                 270

Pro Lys Gln Leu Val Tyr Gly Thr Met Val Tyr Val Arg Gln Thr Ile
        275                 280                 285

Val Ala Asp Ala Ser Asn Ala Leu Ser Arg Ala Val Cys Ile Ala Thr
    290                 295                 300

Arg Tyr Ser Ala Val Arg Arg Gln Phe Gly Ala His Asn Gly Gly Ile
305                 310                 315                 320

Glu Thr Gln Val Ile Asp Tyr Lys Thr Gln Gln Asn Arg Leu Phe Pro
                325                 330                 335

Leu Leu Ala Ser Ala Tyr Ala Phe Arg Phe Val Gly Glu Trp Leu Lys
            340                 345                 350

Trp Leu Tyr Thr Asp Val Thr Glu Arg Leu Ala Ala Ser Asp Phe Ala
        355                 360                 365

Thr Leu Pro Glu Ala His Ala Cys Thr Ala Gly Leu Lys Ser Leu Thr
    370                 375                 380

Thr Thr Ala Thr Ala Asp Gly Ile Glu Glu Cys Arg Lys Leu Cys Gly
385                 390                 395                 400

Gly His Gly Tyr Leu Trp Cys Ser Gly Leu Pro Glu Leu Phe Ala Val
                405                 410                 415

Tyr Val Pro Ala Cys Thr Tyr Glu Gly Asp Asn Val Val Leu Gln Leu
            420                 425                 430

Gln Val Ala Arg Phe Leu Met Lys Thr Val Ala Gln Leu Gly Ser Gly
        435                 440                 445

Lys Val Pro Val Gly Thr Thr Ala Tyr Met Gly Arg Ala Ala His Leu
    450                 455                 460

Leu Gln Cys Arg Ser Gly Val Gln Lys Ala Glu Asp Trp Leu Asn Pro
465                 470                 475                 480

Asp Val Val Leu Glu Ala Phe Glu Ala Arg Ala Leu Arg Met Ala Val
                485                 490                 495

Thr Cys Ala Lys Asn Leu Ser Lys Phe Glu Asn Gln Glu Gln Gly Phe
            500                 505                 510

Gln Glu Leu Leu Ala Asp Leu Val Glu Ala Ala Ile Ala His Cys Gln
        515                 520                 525

Leu Ile Val Val Ser Lys Phe Ile Ala Lys Leu Glu Gln Asp Ile Gly
    530                 535                 540

Gly Lys Gly Val Lys Lys Gln Leu Asn Asn Leu Cys Tyr Ile Tyr Ala
545                 550                 555                 560

Leu Tyr Leu Leu His Lys His Leu Gly Asp Phe Leu Ser Thr Asn Cys
                565                 570                 575

Ile Thr Pro Lys Gln Ala Ser Leu Ala Asn Asp Gln Leu Arg Ser Leu
            580                 585                 590

Tyr Thr Gln Val Arg Pro Asn Ala Val Ala Leu Val Asp Ala Phe Asn
        595                 600                 605

Tyr Thr Asp His Tyr Leu Asn Ser Val Leu Gly Arg Tyr Asp Gly Asn
    610                 615                 620

Val Tyr Pro Lys Leu Phe Glu Glu Ala Leu Lys Asp Pro Leu Asn Asp
625                 630                 635                 640
```

```
Ser Val Val Pro Asp Gly Tyr Gln Glu Tyr Leu Arg Pro Val Leu Gln
                645                 650                 655

Gln Gln Leu Arg Thr Ala Arg Leu Asp Gln Ile Thr Ser Val Gly Ser
            660                 665                 670

Ser Ser Lys Leu
        675


<210> SEQ ID NO 27
<211> LENGTH: 704
<212> TYPE: PRT
<213> ORGANISM: Arabidopsis thaliana

<400> SEQUENCE: 27

Met Glu Ser Arg Arg Glu Lys Asn Pro Met Thr Glu Glu Glu Ser Asp
1               5                   10                  15

Gly Leu Ile Ala Ala Arg Arg Ile Gln Arg Leu Ser Leu His Leu Ser
            20                  25                  30

Pro Ser Leu Thr Pro Ser Pro Ser Leu Pro Leu Val Gln Thr Glu Thr
        35                  40                  45

Cys Ser Ala Arg Ser Lys Lys Leu Asp Val Asn Gly Glu Ala Leu Ser
    50                  55                  60

Leu Tyr Met Arg Gly Lys His Ile Asp Ile Gln Glu Lys Ile Phe Asp
65                  70                  75                  80

Phe Phe Asn Ser Arg Pro Asp Leu Gln Thr Pro Ile Glu Ile Ser Lys
                85                  90                  95

Asp Asp His Arg Glu Leu Cys Met Asn Gln Leu Ile Gly Leu Val Arg
            100                 105                 110

Glu Ala Gly Val Arg Pro Phe Arg Tyr Val Ala Asp Asp Pro Glu Lys
        115                 120                 125

Tyr Phe Ala Ile Met Glu Ala Val Gly Ser Val Asp Met Ser Leu Gly
    130                 135                 140

Ile Lys Met Gly Val Gln Tyr Ser Leu Trp Gly Gly Ser Val Ile Asn
145                 150                 155                 160

Leu Gly Thr Lys Lys His Arg Asp Lys Tyr Phe Asp Gly Ile Asp Asn
                165                 170                 175

Leu Asp Tyr Thr Gly Cys Phe Ala Met Thr Glu Leu His His Gly Ser
            180                 185                 190

Asn Val Gln Gly Leu Gln Thr Thr Ala Thr Phe Asp Pro Leu Lys Asp
        195                 200                 205

Glu Phe Val Ile Asp Thr Pro Asn Asp Gly Ala Ile Lys Trp Trp Ile
    210                 215                 220

Gly Asn Ala Ala Val His Gly Lys Phe Ala Thr Val Phe Ala Arg Leu
225                 230                 235                 240

Ile Leu Pro Thr His Asp Ser Lys Gly Val Ser Asp Met Gly Val His
                245                 250                 255

Ala Phe Ile Val Pro Ile Arg Asp Met Lys Thr His Gln Thr Leu Pro
            260                 265                 270

Gly Val Glu Ile Gln Asp Cys Gly His Lys Val Gly Leu Asn Gly Val
        275                 280                 285

Asp Asn Gly Ala Leu Arg Phe Arg Ser Val Arg Ile Pro Arg Asp Asn
    290                 295                 300

Leu Leu Asn Arg Phe Gly Asp Val Ser Arg Asp Gly Thr Tyr Thr Ser
305                 310                 315                 320

Ser Leu Pro Thr Ile Asn Lys Arg Phe Gly Ala Thr Leu Gly Glu Leu
                325                 330                 335
```

```
Val Gly Gly Arg Val Gly Leu Ala Tyr Ala Ser Val Gly Val Leu Lys
        340                 345                 350

Ile Ser Ala Thr Ile Ala Ile Arg Tyr Ser Leu Leu Arg Gln Gln Phe
    355                 360                 365

Gly Pro Pro Lys Gln Pro Glu Val Ser Ile Leu Asp Tyr Gln Ser Gln
    370                 375                 380

Gln His Lys Leu Met Pro Met Leu Ala Ser Thr Tyr Ala Tyr His Phe
385                 390                 395                 400

Ala Thr Val Tyr Leu Val Glu Lys Tyr Ser Glu Met Lys Lys Thr His
                405                 410                 415

Asp Glu Gln Leu Val Ala Asp Val His Ala Leu Ser Ala Gly Leu Lys
            420                 425                 430

Ser Tyr Val Thr Ser Tyr Thr Ala Lys Ala Leu Ser Val Cys Arg Glu
        435                 440                 445

Ala Cys Gly Gly His Gly Tyr Ala Ala Val Asn Arg Phe Gly Ser Leu
    450                 455                 460

Arg Asn Asp His Asp Ile Phe Gln Thr Phe Glu Gly Asp Asn Thr Val
465                 470                 475                 480

Leu Leu Gln Gln Val Ala Ala Asp Leu Leu Lys Arg Tyr Lys Glu Lys
                485                 490                 495

Phe Gln Gly Gly Thr Leu Thr Val Thr Trp Ser Tyr Leu Arg Glu Ser
            500                 505                 510

Met Asn Thr Tyr Leu Ser Gln Pro Asn Pro Val Thr Ala Arg Trp Glu
        515                 520                 525

Gly Glu Asp His Leu Arg Asp Pro Lys Phe Gln Leu Asp Ala Phe Arg
    530                 535                 540

Tyr Arg Thr Ser Arg Leu Leu Gln Asn Val Ala Ala Arg Leu Gln Lys
545                 550                 555                 560

His Ser Lys Thr Leu Gly Gly Phe Gly Ala Trp Asn Arg Cys Leu Asn
                565                 570                 575

His Leu Leu Thr Leu Ala Glu Ser His Ile Glu Thr Val Ile Leu Ala
            580                 585                 590

Lys Phe Ile Glu Ala Val Lys Asn Cys Pro Asp Pro Ser Ala Lys Ala
        595                 600                 605

Ala Leu Lys Leu Ala Cys Asp Leu Tyr Ala Leu Asp Arg Ile Trp Lys
    610                 615                 620

Asp Ile Gly Thr Tyr Arg Asn Val Asp Tyr Val Ala Pro Asn Lys Ala
625                 630                 635                 640

Lys Ala Ile His Lys Leu Thr Glu Tyr Leu Ser Phe Gln Val Arg Asn
                645                 650                 655

Val Ala Lys Glu Leu Val Asp Ala Phe Glu Leu Pro Asp His Val Thr
            660                 665                 670

Arg Ala Pro Ile Ala Met Gln Ser Asp Ala Tyr Ser Gln Tyr Thr Gln
        675                 680                 685

Val Val Gly Phe Asp Gln Ile Thr Ser Val Gly Ser Ser Ser Lys Leu
    690                 695                 700


<210> SEQ ID NO 28
<211> LENGTH: 696
<212> TYPE: PRT
<213> ORGANISM: Aspergillus nidulans

<400> SEQUENCE: 28

Met Pro Asn Pro Pro Pro Ala Trp Val Gln Ala Leu Lys Pro Ala Ser
```

```
1               5                   10                  15

Pro Gln Gly Thr Glu Leu Leu Thr Gln Glu Arg Ala Gln Ser Asn Ile
            20                  25                  30

Asp Val Asp Thr Leu Gly Asp Leu Leu His Thr Lys Glu Ala Leu Lys
        35                  40                  45

Lys Gln Asp Glu Ile Leu Ser Val Leu Lys Ser Glu Lys Val Phe Asp
    50                  55                  60

Lys Ser Arg Asn His Val Leu Gly Arg Thr Glu Lys Ile Gln Leu Ala
65                  70                  75                  80

Leu Ala Arg Gly Lys Arg Leu Gln Gln Leu Lys Lys Ala His Asn Trp
                85                  90                  95

Ser Asp Glu Asp Val His Val Ala Asn Asp Leu Val Ser Glu Pro Thr
            100                 105                 110

Pro Tyr Gly Leu His Ala Ser Met Phe Leu Val Thr Leu Arg Glu Gln
        115                 120                 125

Gly Thr Pro Glu Gln His Lys Leu Phe Tyr Glu Arg Ala Arg Asn Tyr
    130                 135                 140

Glu Ile Ile Gly Cys Tyr Ala Gln Thr Glu Leu Gly His Gly Ser Asn
145                 150                 155                 160

Val Arg Gly Leu Glu Thr Thr Ala Thr Trp Asp Pro Ser Asp Gln Thr
                165                 170                 175

Phe Ile Ile His Ser Pro Thr Leu Thr Ala Ser Lys Trp Trp Ile Gly
            180                 185                 190

Ser Leu Gly Arg Thr Ala Asn His Ala Val Val Met Ala Gln Leu Tyr
        195                 200                 205

Ile Gly Gly Lys Asn Tyr Gly Pro His Pro Phe Val Val Gln Ile Arg
    210                 215                 220

Asp Met Glu Thr His Gln Pro Leu Glu Asn Val Tyr Val Gly Asp Ile
225                 230                 235                 240

Gly Pro Lys Phe Gly Tyr Asn Thr Met Asp Asn Gly Phe Leu Leu Phe
                245                 250                 255

Asn Lys Leu Lys Ile Pro His Val Asn Met Leu Ala Arg Phe Ala Gln
            260                 265                 270

Val Asp Lys Ala Thr Asn Lys Tyr Ile Arg Pro Ala Ser Pro Ser Leu
        275                 280                 285

Met Tyr Gly Thr Met Thr Trp Val Arg Ser Asn Ile Val Leu Gln Ala
    290                 295                 300

Gly Gly Val Leu Ala Arg Gly Val Thr Ile Ala Val Arg Tyr Cys Ala
305                 310                 315                 320

Val Arg Arg Gln Phe Gln Asp Arg Asp Ala Lys Ala Asn Ala Glu Glu
                325                 330                 335

Asn Gln Val Leu Asn Tyr Lys Met Val Gln Ile Arg Leu Leu Pro Leu
            340                 345                 350

Leu Ala Ala Met Tyr Ala Leu His Phe Thr Gly Arg Gly Met Met Arg
        355                 360                 365

Leu Tyr Glu Glu Asn Gln Glu Arg Met Lys Ala Ala Ala Gln Ala Asp
    370                 375                 380

Gln Glu Lys Arg Gly Ala Gly Pro Glu Gln Leu Arg Ala Gly Ser Asp
385                 390                 395                 400

Leu Leu Ala Asp Leu His Ala Thr Ser Cys Gly Leu Lys Ala Leu Ala
                405                 410                 415

Ser Thr Thr Ala Gly Glu Gly Leu Glu Val Cys Arg Arg Ala Cys Gly
            420                 425                 430
```

```
Gly His Gly Tyr Ser Asn Tyr Ser Gly Ile Gly Pro Trp Tyr Ala Asp
        435                 440                 445

Tyr Leu Pro Thr Leu Thr Trp Glu Gly Asp Asn Tyr Met Leu Thr Gln
    450                 455                 460

Gln Val Ala Arg Tyr Leu Leu Lys Ser Ala Arg Ala Val Leu Ala Gly
465                 470                 475                 480

Lys Gly Thr Ala Asn Asp Thr Ser Arg Ile Leu Gln Ala Tyr Leu Ala
                485                 490                 495

Arg Arg Asp Lys Gly Ala Ser Phe Asp Ile Leu Gly Asn Asp Ala Asp
            500                 505                 510

Ile Val Ala Ala Phe Ala Trp Arg Thr Ala His Leu Thr Phe Glu Thr
        515                 520                 525

Leu Lys Tyr Arg Asp Val Glu Lys Arg Ser Trp Asn Ser Leu Leu Ile
    530                 535                 540

Asn Phe Trp Arg Leu Ser Thr Ala Leu Ser Gln Tyr Leu Val Val Lys
545                 550                 555                 560

Asn Phe Tyr Glu Ala Val Asn Ser Pro Glu Ile Arg Ser Ser Leu Asp
                565                 570                 575

Lys Asp Thr Ala Ser Thr Leu Arg Ser Leu Phe Arg Leu His Ala Leu
            580                 585                 590

His Thr Leu Asp Arg Glu Ala Ser Glu Phe Phe Ser Ser Ala Ala Val
        595                 600                 605

Thr Val Arg Gln Ile Gly Leu Thr Gln Thr Ser Glu Val Pro Lys Leu
    610                 615                 620

Leu Asp Glu Ile Arg Pro His Ala Val Arg Leu Val Asp Ser Trp Lys
625                 630                 635                 640

Ile Pro Asp Trp Gln Leu Asp Ser Ala Leu Gly Arg Ser Asp Gly Asp
                645                 650                 655

Val Tyr Pro Asp Leu Phe Lys Arg Ala Ser Met Gln Asn Pro Val Asn
            660                 665                 670

Asp Leu Val Phe Asp Pro Tyr Pro Trp Asn Glu Asn Val Leu Lys Asn
        675                 680                 685

Ala Gly Glu Ile Lys Ser Lys Leu
    690                 695


<210> SEQ ID NO 29
<211> LENGTH: 658
<212> TYPE: PRT
<213> ORGANISM: Cucurbita maxima

<400> SEQUENCE: 29

Met Ala Ala Gly Lys Ala Lys Ala Lys Ile Glu Val Asp Met Gly Ser
1               5                   10                  15

Leu Ser Leu Tyr Met Arg Gly Lys His Arg Glu Ile Gln Glu Arg Val
            20                  25                  30

Phe Glu Tyr Phe Asn Ser Arg Pro Glu Leu Gln Thr Pro Val Gly Ile
        35                  40                  45

Ser Met Ala Asp His Arg Glu Leu Cys Met Lys Gln Leu Val Gly Leu
    50                  55                  60

Val Arg Glu Ala Gly Ile Arg Pro Phe Arg Phe Val Asn Glu Asp Pro
65                  70                  75                  80

Ala Lys Tyr Phe Ala Ile Met Glu Ala Val Gly Ser Val Asp Val Ser
                85                  90                  95

Leu Ala Ile Lys Met Gly Val Gln Phe Ser Leu Trp Gly Gly Ser Val
```

```
            100                 105                 110

Ile Asn Leu Gly Thr Lys Lys His Arg Asp Arg Phe Phe Asp Gly Ile
        115                 120                 125

Asp Asn Val Asp Tyr Pro Gly Cys Phe Ala Met Thr Glu Leu His His
    130                 135                 140

Gly Ser Asn Val Gln Gly Leu Gln Thr Thr Ala Thr Phe Asp Pro Ile
145                 150                 155                 160

Thr Asp Glu Phe Ile Ile Asn Thr Pro Asn Asp Gly Ala Ile Lys Trp
                165                 170                 175

Trp Ile Gly Asn Ala Ala Val His Gly Lys Phe Ala Thr Val Phe Ala
            180                 185                 190

Lys Leu Val Leu Pro Thr His Asp Ser Arg Lys Thr Ala Asp Met Gly
        195                 200                 205

Val His Ala Phe Ile Val Pro Ile Arg Asp Leu Lys Ser His Lys Thr
    210                 215                 220

Leu Pro Gly Ile Glu Ile His Asp Cys Gly His Lys Val Gly Leu Asn
225                 230                 235                 240

Gly Val Asp Asn Gly Ala Leu Arg Phe Arg Ser Val Arg Ile Pro Arg
                245                 250                 255

Asp Asn Leu Leu Asn Arg Phe Gly Glu Val Ser Arg Asp Gly Lys Tyr
            260                 265                 270

Lys Ser Ser Leu Pro Ser Ile Asn Lys Arg Phe Ala Ala Thr Leu Gly
        275                 280                 285

Glu Leu Val Gly Gly Arg Val Gly Leu Ala Tyr Ser Ser Ala Ser Val
    290                 295                 300

Leu Lys Ile Ala Ser Thr Ile Ala Ile Arg Tyr Ser Leu Leu Arg Gln
305                 310                 315                 320

Gln Phe Gly Pro Pro Lys Gln Pro Glu Val Ser Ile Leu Asp Tyr Gln
                325                 330                 335

Ser Gln Gln His Lys Leu Met Pro Met Leu Ala Ser Thr Tyr Ala Phe
            340                 345                 350

His Phe Ser Thr Met Gln Leu Val Glu Lys Tyr Ala Gln Met Lys Lys
        355                 360                 365

Thr His Asp Glu Glu Leu Val Gly Asp Val His Ala Leu Ser Ala Gly
    370                 375                 380

Leu Lys Ala Tyr Val Thr Ser Tyr Thr Ala Lys Ser Leu Ser Thr Cys
385                 390                 395                 400

Arg Glu Ala Cys Gly Gly His Gly Tyr Ala Val Val Asn Arg Phe Gly
                405                 410                 415

Thr Leu Arg Asn Asp His Asp Ile Phe Gln Thr Phe Glu Gly Asp Asn
            420                 425                 430

Thr Val Leu Leu Gln Gln Val Ala Ala Tyr Leu Leu Lys Gln Tyr Gln
        435                 440                 445

Glu Lys Phe Gln Gly Gly Thr Leu Ala Val Thr Trp Asn Tyr Leu Arg
    450                 455                 460

Glu Ser Met Asn Thr Tyr Leu Ser Gln Pro Asn Pro Val Thr Ala Arg
465                 470                 475                 480

Trp Glu Ser Ala Asp His Leu Arg Asp Pro Lys Phe Gln Leu Asp Ala
                485                 490                 495

Phe Gln Tyr Arg Thr Ser Arg Leu Leu Gln Ser Val Ala Val Arg Leu
            500                 505                 510

Arg Lys His Thr Lys Asn Leu Gly Ser Phe Gly Ala Trp Asn Arg Cys
        515                 520                 525
```

Leu Asn His Leu Leu Thr Leu Ala Glu Ser His Ile Glu Ser Val Ile
    530                 535                 540

Leu Ala Gln Phe Ile Glu Ser Val Gln Arg Cys Pro Asn Ala Asn Thr
545                 550                 555                 560

Gln Ala Thr Leu Lys Leu Val Cys Asp Leu Tyr Ala Leu Asp Arg Ile
                565                 570                 575

Trp Asn Asp Ile Gly Thr Tyr Arg Asn Val Asp Tyr Val Ala Pro Asn
            580                 585                 590

Lys Ala Lys Ala Ile His Lys Leu Thr Glu Tyr Leu Cys Phe Gln Val
        595                 600                 605

Arg Asn Ile Ala Gln Glu Leu Val Asp Ala Phe Asp Leu Pro Asp His
    610                 615                 620

Val Thr Arg Ala Pro Ile Ala Met Lys Ser Asn Ala Tyr Ser Gln Tyr
625                 630                 635                 640

Thr Gln Tyr Ile Gly Phe Asp Gln Ile Thr Ser Val Gly Ser Ser Ser
                645                 650                 655

Lys Leu

<210> SEQ ID NO 30
<211> LENGTH: 672
<212> TYPE: PRT
<213> ORGANISM: Homo sapiens

<400> SEQUENCE: 30

Met Asn Pro Asp Leu Arg Arg Glu Arg Asp Ser Ala Ser Phe Asn Pro
1               5                   10                  15

Glu Leu Leu Thr His Ile Leu Asp Gly Ser Pro Glu Lys Thr Arg Arg
            20                  25                  30

Arg Arg Glu Ile Glu Asn Met Ile Leu Asn Asp Pro Asp Phe Gln His
        35                  40                  45

Glu Asp Leu Asn Phe Leu Thr Arg Ser Gln Arg Tyr Glu Val Ala Val
    50                  55                  60

Arg Lys Ser Ala Ile Met Val Lys Lys Met Arg Glu Phe Gly Ile Ala
65                  70                  75                  80

Asp Pro Asp Glu Ile Met Trp Phe Lys Asn Phe Val His Arg Gly Arg
                85                  90                  95

Pro Glu Pro Leu Asp Leu His Leu Gly Met Phe Leu Pro Thr Leu Leu
            100                 105                 110

His Gln Ala Thr Ala Glu Gln Gln Glu Arg Phe Phe Met Pro Ala Trp
        115                 120                 125

Asn Leu Glu Ile Ile Gly Thr Tyr Ala Gln Thr Glu Met Gly His Gly
    130                 135                 140

Thr His Leu Arg Gly Leu Glu Thr Thr Ala Thr Tyr Asp Pro Glu Thr
145                 150                 155                 160

Gln Glu Phe Ile Leu Asn Ser Pro Thr Val Thr Ser Ile Lys Trp Trp
                165                 170                 175

Pro Gly Gly Leu Gly Lys Thr Ser Asn His Ala Ile Val Leu Ala Gln
            180                 185                 190

Leu Ile Thr Lys Gly Lys Cys Tyr Gly Leu His Ala Phe Ile Val Pro
        195                 200                 205

Ile Arg Glu Ile Gly Thr His Lys Pro Leu Pro Gly Ile Thr Val Gly
    210                 215                 220

Asp Ile Gly Pro Lys Phe Gly Tyr Asp Glu Ile Asp Asn Gly Tyr Leu
225                 230                 235                 240

```
Lys Met Asp Asn His Arg Ile Pro Arg Glu Asn Met Leu Met Lys Tyr
                245                 250                 255

Ala Gln Val Lys Pro Asp Gly Thr Tyr Val Lys Pro Leu Ser Asn Lys
            260                 265                 270

Leu Thr Tyr Gly Thr Met Val Phe Val Arg Ser Phe Leu Val Gly Glu
        275                 280                 285

Ala Ala Arg Ala Leu Ser Lys Ala Cys Thr Ile Ala Ile Arg Tyr Ser
    290                 295                 300

Ala Val Arg His Gln Ser Glu Ile Lys Pro Gly Glu Pro Glu Pro Gln
305                 310                 315                 320

Ile Leu Asp Phe Gln Thr Gln Gln Tyr Lys Leu Phe Pro Leu Leu Ala
                325                 330                 335

Thr Ala Tyr Ala Phe Gln Phe Val Gly Ala Tyr Met Lys Glu Thr Tyr
            340                 345                 350

His Arg Ile Asn Glu Gly Ile Gly Gln Gly Asp Leu Ser Glu Leu Pro
        355                 360                 365

Glu Leu His Ala Leu Thr Ala Gly Leu Lys Ala Phe Thr Ser Trp Thr
    370                 375                 380

Ala Asn Thr Gly Ile Glu Ala Cys Arg Met Ala Cys Gly Gly His Gly
385                 390                 395                 400

Tyr Ser His Cys Ser Gly Leu Pro Asn Ile Tyr Val Asn Phe Thr Pro
                405                 410                 415

Ser Cys Thr Phe Glu Gly Glu Asn Thr Val Met Met Leu Gln Thr Ala
            420                 425                 430

Arg Phe Leu Met Lys Ser Tyr Asp Gln Val His Ser Gly Lys Leu Val
        435                 440                 445

Cys Gly Met Val Ser Tyr Leu Asn Asp Leu Pro Ser Gln Arg Ile Gln
    450                 455                 460

Pro Gln Gln Val Ala Val Trp Pro Thr Met Val Asp Ile Asn Ser Pro
465                 470                 475                 480

Glu Ser Leu Thr Glu Ala Tyr Lys Leu Arg Ala Ala Arg Leu Val Glu
                485                 490                 495

Ile Ala Ala Lys Asn Leu Gln Lys Glu Val Ile His Arg Lys Ser Lys
            500                 505                 510

Glu Val Ala Trp Asn Leu Thr Ser Val Asp Leu Val Arg Ala Ser Glu
        515                 520                 525

Ala His Cys His Tyr Val Val Val Lys Leu Phe Ser Glu Lys Leu Leu
    530                 535                 540

Lys Ile Gln Asp Lys Ala Ile Gln Ala Val Leu Arg Ser Leu Cys Leu
545                 550                 555                 560

Leu Tyr Ser Leu Tyr Gly Ile Ser Gln Asn Ala Gly Asp Phe Leu Gln
                565                 570                 575

Gly Ser Ile Met Thr Glu Pro Gln Ile Thr Gln Val Asn Gln Arg Val
            580                 585                 590

Lys Glu Leu Leu Thr Leu Ile Arg Ser Asp Ala Val Ala Leu Val Asp
        595                 600                 605

Ala Phe Asp Phe Gln Asp Val Thr Leu Gly Ser Val Leu Gly Arg Tyr
    610                 615                 620

Asp Gly Asn Val Tyr Glu Asn Leu Phe Glu Trp Ala Lys Asn Ser Pro
625                 630                 635                 640

Leu Asn Lys Ala Glu Val His Glu Ser Tyr Lys His Leu Lys Ser Leu
                645                 650                 655
```

Gln Ser Lys Leu Asp Gln Ile Thr Ser Val Gly Ser Ser Ser Lys Leu
660 665 670

<210> SEQ ID NO 31
<211> LENGTH: 715
<212> TYPE: PRT
<213> ORGANISM: Paenarthrobacter ureafaciens

<400> SEQUENCE: 31

Met Thr Glu Val Val Asp Arg Ala Ser Ser Pro Ala Ser Pro Gly Ser
1 5 10 15

Thr Thr Ala Ala Ala Asp Gly Ala Lys Val Ala Val Glu Pro Arg Val
20 25 30

Asp Val Ala Ala Leu Gly Glu Gln Leu Leu Gly Arg Trp Ala Asp Ile
35 40 45

Arg Leu His Ala Arg Asp Leu Ala Gly Arg Glu Val Val Gln Lys Val
50 55 60

Glu Gly Leu Thr His Thr Glu His Arg Ser Arg Val Phe Gly Gln Leu
65 70 75 80

Lys Tyr Leu Val Asp Asn Asn Ala Val His Arg Ala Phe Pro Ser Arg
85 90 95

Leu Gly Gly Ser Asp Asp His Gly Gly Asn Ile Ala Gly Phe Glu Glu
100 105 110

Leu Val Thr Ala Asp Pro Ser Leu Gln Ile Lys Ala Gly Val Gln Trp
115 120 125

Gly Leu Phe Gly Ser Ala Val Met His Leu Gly Thr Arg Glu His His
130 135 140

Asp Lys Trp Leu Pro Gly Ile Met Ser Leu Glu Ile Pro Gly Cys Phe
145 150 155 160

Ala Met Thr Glu Thr Gly His Gly Ser Asp Val Ala Ser Ile Ala Thr
165 170 175

Thr Ala Thr Tyr Asp Glu Glu Thr Gln Glu Phe Val Ile Asp Thr Pro
180 185 190

Phe Arg Ala Ala Trp Lys Asp Tyr Ile Gly Asn Ala Ala Asn Asp Gly
195 200 205

Leu Ala Ala Val Val Phe Ala Gln Leu Ile Thr Arg Lys Val Asn His
210 215 220

Gly Val His Ala Phe Tyr Val Asp Leu Arg Asp Pro Ala Thr Gly Asp
225 230 235 240

Phe Leu Pro Gly Ile Gly Gly Glu Asp Asp Gly Ile Lys Gly Gly Leu
245 250 255

Asn Gly Ile Asp Asn Gly Arg Leu His Phe Thr Asn Val Arg Ile Pro
260 265 270

Arg Thr Asn Leu Leu Asn Arg Tyr Gly Asp Val Ala Val Asp Gly Thr
275 280 285

Tyr Ser Ser Thr Ile Glu Ser Pro Gly Arg Arg Phe Phe Thr Met Leu
290 295 300

Gly Thr Leu Val Gln Gly Arg Val Ser Leu Asp Gly Ala Ala Val Ala
305 310 315 320

Ala Ser Lys Val Ala Leu Gln Ser Ala Ile His Tyr Ala Ala Glu Arg
325 330 335

Arg Gln Phe Asn Ala Thr Ser Pro Thr Glu Glu Val Leu Leu Asp
340 345 350

Tyr Gln Arg His Gln Arg Arg Leu Phe Thr Arg Leu Ala Thr Thr Tyr
355 360 365

Ala Ala Ser Phe Ala His Glu Gln Leu Leu Gln Lys Phe Asp Asp Val
370 375 380

Phe Ser Gly Ala His Asp Thr Asp Ala Asp Arg Gln Asp Leu Glu Thr
385 390 395 400

Leu Ala Ala Ala Leu Lys Pro Leu Ser Thr Trp His Ala Leu Asp Thr
405 410 415

Leu Gln Glu Cys Arg Glu Ala Cys Gly Gly Ala Gly Phe Leu Ile Glu
420 425 430

Asn Arg Phe Ala Ser Leu Arg Ala Asp Leu Asp Val Tyr Val Thr Phe
435 440 445

Glu Gly Asp Asn Thr Val Leu Leu Gln Leu Val Ala Lys Arg Leu Leu
450 455 460

Ala Asp Tyr Ala Lys Glu Phe Arg Gly Ala Asn Phe Gly Val Leu Ala
465 470 475 480

Arg Tyr Val Val Asp Gln Ala Ala Gly Val Ala Leu His Arg Thr Gly
485 490 495

Leu Arg Gln Val Ala Gln Phe Val Ala Asp Ser Gly Ser Val Gln Lys
500 505 510

Ser Ala Leu Ala Leu Arg Asp Glu Glu Gly Gln Arg Thr Leu Leu Thr
515 520 525

Asp Arg Val Gln Ser Met Val Ala Glu Val Gly Ala Ala Leu Lys Gly
530 535 540

Ala Gly Lys Leu Pro Gln His Gln Ala Ala Ala Leu Phe Asn Gln His
545 550 555 560

Gln Asn Glu Leu Ile Glu Ala Ala Gln Ala His Ala Glu Leu Leu Gln
565 570 575

Trp Glu Ala Phe Thr Glu Ala Leu Ala Lys Val Asp Asp Ala Gly Thr
580 585 590

Lys Glu Val Leu Thr Arg Leu Arg Asp Leu Phe Gly Leu Ser Leu Ile
595 600 605

Glu Lys His Leu Ser Trp Tyr Leu Met Asn Gly Arg Leu Ser Met Gln
610 615 620

Arg Gly Arg Thr Val Gly Thr Tyr Ile Asn Arg Leu Leu Val Lys Ile
625 630 635 640

Arg Pro His Ala Leu Asp Leu Val Asp Ala Phe Gly Tyr Gly Ala Glu
645 650 655

His Leu Arg Ala Ala Ile Ala Thr Gly Ala Glu Ala Thr Arg Gln Asp
660 665 670

Glu Ala Arg Thr Tyr Phe Arg Gln Gln Arg Ala Ser Gly Ser Ala Pro
675 680 685

Ala Asp Glu Lys Thr Leu Leu Ala Ile Lys Ala Gly Lys Ser Arg Asp
690 695 700

Gln Ile Thr Ser Val Gly Ser Ser Ser Lys Leu
705 710 715

<210> SEQ ID NO 32
<211> LENGTH: 673
<212> TYPE: PRT
<213> ORGANISM: Rattus norvegicus

<400> SEQUENCE: 32

Met Asn Pro Asp Leu Arg Lys Glu Arg Ala Ser Ala Thr Phe Asn Pro
1 5 10 15

Glu Leu Ile Thr His Ile Leu Asp Gly Ser Pro Glu Asn Thr Arg Arg

```
            20                  25                  30

Arg Arg Glu Ile Glu Asn Leu Ile Leu Asn Asp Pro Asp Phe Gln His
        35                  40                  45

Glu Asp Tyr Asn Phe Leu Thr Arg Ser Gln Arg Tyr Glu Val Ala Val
    50                  55                  60

Lys Lys Ser Ala Thr Met Val Lys Lys Met Arg Glu Tyr Gly Ile Ser
65                  70                  75                  80

Asp Pro Glu Glu Ile Met Trp Phe Lys Asn Ser Val His Arg Gly His
                85                  90                  95

Pro Glu Pro Leu Asp Leu His Leu Gly Met Phe Leu Pro Thr Leu Leu
            100                 105                 110

His Gln Ala Thr Ala Glu Gln Gln Glu Arg Phe Phe Met Pro Ala Trp
        115                 120                 125

Asn Leu Glu Ile Thr Gly Thr Tyr Ala Gln Thr Glu Met Gly His Gly
    130                 135                 140

Thr His Leu Arg Gly Leu Glu Thr Thr Ala Thr Tyr Asp Pro Lys Thr
145                 150                 155                 160

Gln Glu Phe Ile Leu Asn Ser Pro Thr Val Thr Ser Ile Lys Trp Trp
                165                 170                 175

Pro Gly Gly Leu Gly Lys Thr Ser Asn His Ala Ile Val Leu Ala Gln
            180                 185                 190

Leu Ile Thr Gln Gly Glu Cys Tyr Gly Leu His Ala Phe Val Val Pro
        195                 200                 205

Ile Arg Glu Ile Gly Thr His Lys Pro Leu Pro Gly Ile Thr Val Gly
    210                 215                 220

Asp Ile Gly Pro Lys Phe Gly Tyr Glu Glu Met Asp Asn Gly Tyr Leu
225                 230                 235                 240

Lys Met Asp Asn Tyr Arg Ile Pro Arg Glu Asn Met Leu Met Lys Tyr
                245                 250                 255

Ala Gln Val Lys Pro Asp Gly Thr Tyr Val Lys Pro Leu Ser Asn Lys
            260                 265                 270

Leu Thr Tyr Gly Thr Met Val Phe Val Arg Ser Phe Leu Val Gly Asn
        275                 280                 285

Ala Ala Gln Ser Leu Ser Lys Ala Cys Thr Ile Ala Ile Arg Tyr Ser
    290                 295                 300

Ala Val Arg Arg Gln Ser Glu Ile Lys Gln Ser Glu Pro Glu Pro Gln
305                 310                 315                 320

Ile Leu Asp Phe Gln Thr Gln Gln Tyr Lys Leu Phe Pro Leu Leu Ala
                325                 330                 335

Thr Ala Tyr Ala Phe His Phe Val Gly Arg Tyr Met Lys Glu Thr Tyr
            340                 345                 350

Leu Arg Ile Asn Glu Ser Ile Gly Gln Gly Asp Leu Ser Glu Leu Pro
        355                 360                 365

Glu Leu His Ala Leu Thr Ala Gly Leu Lys Ala Phe Thr Thr Trp Thr
    370                 375                 380

Ala Asn Ala Gly Ile Glu Glu Cys Arg Met Ala Cys Gly Gly His Gly
385                 390                 395                 400

Tyr Ser His Ser Ser Gly Ile Pro Asn Ile Tyr Val Thr Phe Thr Pro
                405                 410                 415

Ala Cys Thr Phe Glu Gly Glu Asn Thr Val Met Met Leu Gln Thr Ala
            420                 425                 430

Arg Phe Leu Met Lys Ile Tyr Asp Gln Val Arg Ser Gly Lys Leu Val
        435                 440                 445
```

Gly Gly Met Val Ser Tyr Leu Asn Asp Leu Pro Ser Gln Arg Ile Gln
450 455 460

Pro Gln Gln Val Ala Val Trp Pro Thr Met Val Asp Ile Asn Ser Leu
465 470 475 480

Glu Gly Leu Thr Glu Ala Tyr Lys Leu Arg Ala Ala Arg Leu Val Glu
485 490 495

Ile Ala Ala Lys Asn Leu Gln Thr His Val Ser His Arg Lys Ser Lys
500 505 510

Glu Val Ala Trp Asn Leu Thr Ser Val Asp Leu Val Arg Ala Ser Glu
515 520 525

Ala His Cys His Tyr Val Val Val Lys Val Phe Ser Asp Lys Leu Pro
530 535 540

Lys Ile Gln Asp Lys Ala Val Gln Ala Val Leu Arg Asn Leu Cys Leu
545 550 555 560

Leu Tyr Ser Leu Tyr Gly Ile Ser Gln Lys Gly Gly Asp Phe Leu Glu
565 570 575

Gly Ser Ile Ile Thr Gly Ala Gln Leu Ser Gln Val Asn Ala Arg Ile
580 585 590

Leu Glu Leu Leu Thr Leu Ile Arg Pro Asn Ala Val Ala Leu Val Asp
595 600 605

Ala Phe Asp Phe Lys Asp Met Thr Leu Gly Ser Val Leu Gly Arg Tyr
610 615 620

Asp Gly Asn Val Tyr Glu Asn Leu Phe Glu Trp Ala Lys Lys Ser Pro
625 630 635 640

Leu Asn Lys Thr Glu Val His Glu Ser Tyr His Lys His Leu Lys Pro
645 650 655

Leu Gln Ser Lys Leu Asp Gln Ile Thr Ser Val Gly Ser Ser Ser Lys
660 665 670

Leu

<210> SEQ ID NO 33
<211> LENGTH: 510
<212> TYPE: PRT
<213> ORGANISM: Saccharomyces cerevisiae

<400> SEQUENCE: 33

Met Pro Thr Ser Gly Thr Thr Ile Glu Leu Ile Asp Asp Gln Phe Pro
1 5 10 15

Lys Asp Asp Ser Ala Ser Ser Gly Ile Val Asp Glu Val Asp Leu Thr
20 25 30

Glu Ala Asn Ile Leu Ala Thr Gly Leu Asn Lys Lys Ala Pro Arg Ile
35 40 45

Val Asn Gly Phe Gly Ser Leu Met Gly Ser Lys Glu Met Val Ser Val
50 55 60

Glu Phe Asp Lys Lys Gly Asn Glu Lys Lys Ser Asn Leu Asp Arg Leu
65 70 75 80

Leu Glu Lys Asp Asn Gln Glu Lys Glu Glu Ala Lys Thr Lys Ile His
85 90 95

Ile Ser Glu Gln Pro Trp Thr Leu Asn Asn Trp His Gln His Leu Asn
100 105 110

Trp Leu Asn Met Val Leu Val Cys Gly Met Pro Met Ile Gly Trp Tyr
115 120 125

Phe Ala Leu Ser Gly Lys Val Pro Leu His Leu Asn Val Phe Leu Phe
130 135 140

Ser Val Phe Tyr Tyr Ala Val Gly Gly Val Ser Ile Thr Ala Gly Tyr
145 150 155 160

His Arg Leu Trp Ser His Arg Ser Tyr Ser Ala His Trp Pro Leu Arg
165 170 175

Leu Phe Tyr Ala Ile Phe Gly Cys Ala Ser Val Glu Gly Ser Ala Lys
180 185 190

Trp Trp Gly His Ser His Arg Ile His His Arg Tyr Thr Asp Thr Leu
195 200 205

Arg Asp Pro Tyr Asp Ala Arg Arg Gly Leu Trp Tyr Ser His Met Gly
210 215 220

Trp Met Leu Leu Lys Pro Asn Pro Lys Tyr Lys Ala Arg Ala Asp Ile
225 230 235 240

Thr Asp Met Thr Asp Asp Trp Thr Ile Arg Phe Gln His Arg His Tyr
245 250 255

Ile Leu Leu Met Leu Leu Thr Ala Phe Val Ile Pro Thr Leu Ile Cys
260 265 270

Gly Tyr Phe Phe Asn Asp Tyr Met Gly Gly Leu Ile Tyr Ala Gly Phe
275 280 285

Ile Arg Val Phe Val Ile Gln Gln Ala Thr Phe Cys Ile Asn Ser Leu
290 295 300

Ala His Tyr Ile Gly Thr Gln Pro Phe Asp Asp Arg Arg Thr Pro Arg
305 310 315 320

Asp Asn Trp Ile Thr Ala Ile Val Thr Phe Gly Glu Gly Tyr His Asn
325 330 335

Phe His His Glu Phe Pro Thr Asp Tyr Arg Asn Ala Ile Lys Trp Tyr
340 345 350

Gln Tyr Asp Pro Thr Lys Val Ile Ile Tyr Leu Thr Ser Leu Val Gly
355 360 365

Leu Ala Tyr Asp Leu Lys Lys Phe Ser Gln Asn Ala Ile Glu Glu Ala
370 375 380

Leu Ile Gln Gln Glu Gln Lys Lys Ile Asn Lys Lys Lys Ala Lys Ile
385 390 395 400

Asn Trp Gly Pro Val Leu Thr Asp Leu Pro Met Trp Asp Lys Gln Thr
405 410 415

Phe Leu Ala Lys Ser Lys Glu Asn Lys Gly Leu Val Ile Ile Ser Gly
420 425 430

Ile Val His Asp Val Ser Gly Tyr Ile Ser Glu His Pro Gly Gly Glu
435 440 445

Thr Leu Ile Lys Thr Ala Leu Gly Lys Asp Ala Thr Lys Ala Phe Ser
450 455 460

Gly Gly Val Tyr Arg His Ser Asn Ala Ala Gln Asn Val Leu Ala Asp
465 470 475 480

Met Arg Val Ala Val Ile Lys Glu Ser Lys Asn Ser Ala Ile Arg Met
485 490 495

Ala Ser Lys Arg Gly Glu Ile Tyr Glu Thr Gly Lys Phe Phe
500 505 510

<210> SEQ ID NO 34
<211> LENGTH: 482
<212> TYPE: PRT
<213> ORGANISM: Yarrowia lipolytica

<400> SEQUENCE: 34

Met Val Lys Asn Val Asp Gln Val Asp Leu Ser Gln Val Asp Thr Ile

```
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Glu Phe Gln Glu Gln Ala
        355                 360                 365

Lys Thr Arg Asp Leu Val Leu Ile Ser Gly Ile Val His Asp Val Ser
    370                 375                 380

Ala Phe Val Glu His His Pro Gly Gly Lys Ala Leu Ile Met Ser Ala
385                 390                 395                 400

Val Gly Lys Asp Gly Thr Ala Val Phe Asn Gly Gly Val Tyr Arg His
                405                 410                 415

Ser Asn Ala Gly His Asn Leu Leu Ala Thr Met Arg Val Ser Val Ile
            420                 425                 430
```

Arg Gly Gly Met Glu Val Glu Val Trp Lys Thr Ala Gln Asn Glu Lys
        435                 440                 445

Lys Asp Gln Asn Ile Val Ser Asp Glu Ser Gly Asn Arg Ile His Arg
    450                 455                 460

Ala Gly Leu Gln Ala Thr Arg Val Glu Asn Pro Gly Met Ser Gly Met
465                 470                 475                 480

Ala Ala

<210> SEQ ID NO 35
<211> LENGTH: 335
<212> TYPE: PRT
<213> ORGANISM: Choristoneura rosaceana

<400> SEQUENCE: 35

Met Ala Pro Asn Val Glu Asp Met Glu Ser Asp Leu Pro Glu Ser Glu
1               5                   10                  15

Glu Lys Leu Glu Lys Leu Val Ala Pro Gln Ala Ala Pro Arg Lys Tyr
            20                  25                  30

Gln Ile Ile Tyr Thr Asn Leu Leu Thr Phe Gly Tyr Trp His Ile Ala
        35                  40                  45

Gly Leu Tyr Gly Leu Tyr Leu Cys Phe Thr Ser Ala Lys Trp Gln Thr
    50                  55                  60

Ile Ile Leu Ala Leu Ile Leu Asn Glu Met Ala Ile Leu Gly Ile Thr
65                  70                  75                  80

Ala Gly Ala His Arg Leu Trp Ala His Arg Ser Tyr Lys Ala Thr Val
                85                  90                  95

Pro Leu Gln Ile Ile Leu Ile Ile Phe Asn Ser Leu Ser Phe Gln Asn
            100                 105                 110

Ser Ala Ile His Trp Ile Arg Asp His Arg Met His His Lys Tyr Ser
        115                 120                 125

Asp Thr Asp Gly Asp Pro His Asn Ala Ser Arg Gly Phe Phe Tyr Ser
    130                 135                 140

His Val Gly Trp Leu Leu Val Lys Lys His Pro Glu Val Lys Lys Arg
145                 150                 155                 160

Ala Lys Thr Ile Asp Met Ser Asp Ile Tyr Ser Asn Pro Ile Leu Arg
                165                 170                 175

Phe Gln Lys Lys Tyr Ala Ile Pro Phe Ile Gly Met Ile Cys Phe Val
            180                 185                 190

Leu Pro Thr Ile Ile Pro Met Tyr Phe Trp Gly Glu Thr Leu Ser Asn
        195                 200                 205

Ala Trp His Ile Thr Met Leu Arg Tyr Val Phe Ser Leu Asn Ser Ile
    210                 215                 220

Phe Leu Val Asn Ser Ala Ala His Leu Tyr Gly Tyr Arg Pro Tyr Asp
225                 230                 235                 240

Lys Asn Ile Leu Pro Ala Glu Asn Lys Met Thr Phe Ile Ala Cys Leu
                245                 250                 255

Gly Glu Asn Phe His Asn Tyr His His Val Phe Pro Trp Asp Tyr Arg
            260                 265                 270

Ala Ser Glu Leu Gly Asn Ile Gly Met Asn Trp Thr Ala Lys Phe Ile
        275                 280                 285

Asp Phe Phe Ala Trp Ile Gly Trp Ala Tyr Asp Leu Lys Thr Ala Ser
    290                 295                 300

Asp Glu Asn Ile Lys Ser Arg Met Lys Arg Thr Gly Asp Gly Thr Asp
305                 310                 315                 320

Val Ser Gly Gln Lys Tyr Ser Cys Glu Ser Ser Glu Val Leu Gln
325 330 335

<210> SEQ ID NO 36
<211> LENGTH: 329
<212> TYPE: PRT
<213> ORGANISM: Ostrinia nubilalis

<400> SEQUENCE: 36

Met Val Pro Tyr Ala Thr Thr Ala Asp Gly His Pro Glu Lys Asp Glu
1 5 10 15

Cys Phe Glu Asp Asn Glu Ile Lys Ser Asn Ser Leu Pro Lys Leu Glu
20 25 30

Ile Leu Tyr Phe Asn Val Met Thr Phe Thr Phe Leu His Leu Ser Ala
35 40 45

Leu Tyr Gly Leu Tyr Leu Gly Phe Thr Ser Val Lys Trp Ala Thr Ile
50 55 60

Gly Leu Gly Ile Ile Phe Tyr Phe Phe Ala Glu Ile Gly Ile Thr Ala
65 70 75 80

Gly Ala His Arg Leu Trp Ser His Arg Ser Tyr Lys Ala Lys Leu Pro
85 90 95

Leu Glu Ile Leu Leu Met Val Phe Asn Ser Met Ala Phe Gln Asn Thr
100 105 110

Ala Leu Ser Trp Ala Arg Asp His Arg Val His His Lys Cys Pro Asp
115 120 125

Thr Asn Gly Asp Pro His Asn Ala Asn Arg Gly Phe Phe Tyr Ser His
130 135 140

Val Gly Trp Leu Met Thr Lys Lys Ser Asp Glu Val Ile Lys Gln Gly
145 150 155 160

Lys Leu Cys Asp Val Ala Asp Leu Tyr Ser Asn Pro Val Leu Arg Phe
165 170 175

Gln Lys Lys Tyr Ala Val Pro Phe Ile Gly Thr Leu Cys Phe Val Leu
180 185 190

Pro Thr Leu Ile Pro Met Tyr Phe Trp Gly Glu Thr Leu Asn Asn Ala
195 200 205

Trp His Phe Asn Met Phe Arg Tyr Val Ile Asn Leu Asn Ala Thr Phe
210 215 220

Cys Val Asn Ser Val Val His Lys Trp Gly Tyr Lys Pro Tyr Asp Lys
225 230 235 240

Asn Ile Cys Pro Thr Gln Asn Val Leu Leu Asn Leu Ala Val Leu Gly
245 250 255

Glu Ala Phe His Asn Tyr His His Val Phe Pro Trp Asp Tyr Arg Ala
260 265 270

Ala Glu Leu Gly Asn Gln Lys Met Asn Pro Thr Thr Leu Phe Ile Asp
275 280 285

Phe Phe Ala Trp Ile Gly Trp Ala Tyr Asp Leu Lys Thr Ala Ser Lys
290 295 300

Glu Met Ile Lys Ser Arg Ser Glu Arg Thr Gly Asp Gly Thr Asp Leu
305 310 315 320

Trp Gly His Ser Ala Asp Lys Leu Lys
325

<210> SEQ ID NO 37
<211> LENGTH: 347
<212> TYPE: PRT

<213> ORGANISM: Thaumetopoea pityocampa

<400> SEQUENCE: 37

```
Met Ala Pro Asn Thr Arg Glu Asn Glu Thr Ile Tyr Asp Glu Val Glu
1               5                   10                  15

His Lys Leu Glu Lys Leu Val Pro Pro Gln Ala Gly Pro Trp Asn Tyr
            20                  25                  30

Lys Ile Val Tyr Leu Asn Leu Leu Thr Phe Ser Tyr Trp Leu Ile Ala
        35                  40                  45

Gly Ala Tyr Gly Leu Tyr Leu Cys Phe Thr Ser Ala Lys Trp Ala Thr
    50                  55                  60

Ile Ile Phe Glu Phe Ile Leu Phe Phe Phe Ala Glu Met Gly Ile Thr
65                  70                  75                  80

Ala Gly Ala His Arg Leu Trp Thr His Lys Ser Tyr Lys Ala Lys Leu
                85                  90                  95

Pro Leu Glu Ile Phe Leu Met Val Leu Asn Ser Val Ala Phe Gln Asn
            100                 105                 110

Thr Ala Thr Asp Trp Val Arg Asp His Arg Leu His His Lys Tyr Ser
        115                 120                 125

Asp Thr Asp Ala Asp Pro His Asn Ala Ala Arg Gly Leu Phe Phe Ser
    130                 135                 140

His Val Gly Trp Leu Leu Val Arg Lys His Asp Glu Val Lys Lys Arg
145                 150                 155                 160

Gly Lys Phe Thr Asp Met Ser Asp Ile Tyr Asn Asn Pro Val Leu Lys
                165                 170                 175

Phe Gln Lys Lys Tyr Ala Ile Pro Phe Ile Gly Ala Val Cys Phe Ile
            180                 185                 190

Leu Pro Thr Val Ile Pro Met Tyr Phe Trp Gly Glu Ser Leu Asn Asn
        195                 200                 205

Ala Trp His Ile Cys Ile Leu Arg Tyr Ala Met Asn Leu Asn Val Thr
    210                 215                 220

Phe Ser Val Asn Ser Leu Ala His Ile Trp Gly Asn Lys Pro Tyr Asp
225                 230                 235                 240

Lys Asp Ile Lys Pro Ala Gln Asn Phe Gly Val Thr Leu Ala Thr Phe
                245                 250                 255

Gly Glu Gly Phe His Asn Tyr His His Val Phe Pro Trp Asp Tyr Arg
            260                 265                 270

Thr Ser Glu Leu Gly Asp Asn Lys Phe Asn Phe Thr Thr Lys Phe Ile
        275                 280                 285

Asn Phe Phe Glu Arg Ile Gly Leu Ala Tyr Asp Leu Lys Thr Val Ser
    290                 295                 300

Asp Asp Val Ile Ala Gln Arg Ala Lys Arg Thr Gly Asp Gly Thr His
305                 310                 315                 320

Leu Trp Asp Cys Ala Asp Lys Asn Asn Asn Asp Val Val Gln Thr Lys
                325                 330                 335

Ala Gln Ile Asp Thr Leu Cys Thr Lys His Glu
            340                 345
```

<210> SEQ ID NO 38
<211> LENGTH: 352
<212> TYPE: PRT
<213> ORGANISM: Dendrophilus punctatus

<400> SEQUENCE: 38

```
Met Ala Pro Lys Glu Ala Asp Val Asn Gly Val Leu Phe Glu Ser Asp
```

```
1               5                   10                  15

Ala Thr Thr Pro Asp Met Ala Leu Pro Thr Thr Pro Val Gln Gln Ala
            20                  25                  30

Asp Asn Tyr Pro Lys Lys Leu Val Trp Arg Asn Ile Leu Leu Phe Ala
        35                  40                  45

Tyr Leu His Leu Ala Ala Leu Tyr Gly Gly Tyr Leu Phe Leu Phe Ser
    50                  55                  60

Ala Lys Trp Gln Thr Asp Ile Phe Ala Tyr Ile Leu Tyr Ile Met Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Val Leu Phe Asn Thr
            100                 105                 110

Leu Ala Phe Gln Asp Ser Ala Ile Asp Trp Ala Arg Asp His Arg Met
        115                 120                 125

His His Lys Tyr Ser Glu Thr Asp Ala Asp Pro His Asn Ala Thr Arg
    130                 135                 140

Gly Phe Phe Phe Ser His Ile Gly Trp Leu Leu Val Arg Lys His Pro
145                 150                 155                 160

Glu Leu Lys Lys Lys Gly Lys Gly Leu Asp Ile Ser Asp Leu Tyr Ala
                165                 170                 175

Asp Pro Ile Leu Arg Phe Gln Lys Lys Tyr Tyr Leu Leu Leu Met Pro
            180                 185                 190

Leu Gly Cys Phe Ile Leu Pro Thr Val Ile Pro Val Tyr Leu Trp Asn
        195                 200                 205

Glu Thr Trp Ser Asn Ala Phe Leu Val Ala Ala Leu Phe Arg Tyr Ala
    210                 215                 220

Val Ile Leu Asn Val Thr Trp Leu Val Asn Ser Ala Ala His Lys Trp
225                 230                 235                 240

Gly Asp Lys Pro Tyr Asp Lys Ser Ile Lys Pro Ser Glu Asn Leu Ser
                245                 250                 255

Val Ala Leu Phe Ala Leu Gly Glu Gly Phe His Asn Tyr His His Thr
            260                 265                 270

Phe Pro Trp Asp Tyr Lys Thr Ala Glu Leu Gly Asn Asn Arg Leu Asn
        275                 280                 285

Phe Thr Thr Thr Phe Ile Asn Phe Phe Ala Lys Ile Gly Trp Ala Tyr
    290                 295                 300

Asp Met Lys Thr Val Ser Asp Glu Ile Ile Gln Asn Arg Val Lys Arg
305                 310                 315                 320

Thr Gly Asp Gly Ser His His Leu Trp Gly Trp Gly Asp Lys Asp His
                325                 330                 335

Ser Lys Glu Glu Ile Asn Ala Ala Ile Arg Ile Asn Pro Lys Asp Asp
            340                 345                 350


<210> SEQ ID NO 39
<211> LENGTH: 346
<212> TYPE: PRT
<213> ORGANISM: Grapholita molesta

<400> SEQUENCE: 39

Met Pro Pro Glu Ser Lys Asn Val Pro Ile Gln Gln Asn Phe Arg Lys
1               5                   10                  15

Pro Leu Glu Phe Leu Pro Arg Lys Tyr Asp Val Val Tyr Glu Asn Val
            20                  25                  30
```

```
Phe Leu His Ile Ala Gly His Ile Ser Ala Ala Tyr Gly Leu Tyr Leu
        35                  40                  45

Cys Phe Thr Val Ala Lys Trp Gln Thr Ile Ala Leu Ala Phe Val Trp
    50                  55                  60

Tyr His Leu Gly Lys Ile Gly Ile Ile Cys Gly Ala His Arg Leu Trp
65                  70                  75                  80

Ser His Arg Cys Tyr Lys Ala Lys Met Pro Leu His Ile Ile Leu Met
                85                  90                  95

Ile Cys Asn Cys Ile Gly Phe Glu Asn Thr Ala Ile Asn Trp Val Arg
            100                 105                 110

Asn His Arg Met His His Lys His Ser Asp Thr Asp Gly Asp Pro His
        115                 120                 125

Asn Ser Asn Arg Gly Ala Phe Phe Ser His Ile Gly Trp Leu Cys Val
    130                 135                 140

Arg Lys His Pro Glu Thr Arg Asn Cys Lys Val Asp Met Ser Asp Ile
145                 150                 155                 160

Tyr Ser Asn Pro Val Leu Val Phe Gln Lys Arg Tyr Lys Tyr Pro Leu
                165                 170                 175

Val Gly Phe Leu Cys Tyr Gly Leu Pro Thr Phe Ile Pro Met Tyr Phe
            180                 185                 190

Trp Gly Glu Thr Leu Val Thr Ala Trp His Val Asn Ile Leu Arg Tyr
        195                 200                 205

Phe Leu Ser Met Asn Ala Val Phe Leu Val Asn Ser Leu Ala His Leu
    210                 215                 220

Tyr Gly Asn Lys Pro Tyr Asp Ile Ser Ile Cys Pro Arg Gln Ser Pro
225                 230                 235                 240

Phe Val Ser Leu Leu Thr Ile Gly Glu Gly Phe His Asn Tyr His His
                245                 250                 255

Thr Phe Pro Trp Asp Tyr Arg Ala Ala Glu Leu Gly Asn Asn Tyr Leu
            260                 265                 270

Asn Val Gly Lys Trp Val Ile Asp Phe Phe Ala Met Ile Gly Trp Ala
        275                 280                 285

Tyr Asp Leu Lys Thr Val Pro Asp Glu Thr Ile Lys Arg Arg Met Lys
    290                 295                 300

Arg Thr Gly Asp Gly Thr Asn Cys Trp Gly Trp Gly Asp Lys Asp Met
305                 310                 315                 320

Thr Arg Glu Asp Arg Asp Ile Ala Lys Ile Ile Tyr Pro Glu Ser Ile
                325                 330                 335

Ser Lys Glu Glu Arg Asp Ile Ile Ala Met
            340                 345


<210> SEQ ID NO 40
<211> LENGTH: 332
<212> TYPE: PRT
<213> ORGANISM: Epiphyas postvittana

<400> SEQUENCE: 40

Met Ala Pro Asn Val Glu Glu Ile Glu Thr Asp Leu Thr Glu Thr Glu
1               5                   10                  15

Glu Lys Trp Glu Lys Leu Val Ala Pro Gln Ala Ala Pro Arg Lys His
            20                  25                  30

Glu Ile Leu Tyr Thr Asn Leu Leu Ile Phe Gly Tyr Gly His Leu Ala
        35                  40                  45

Gly Leu Tyr Gly Leu Tyr Leu Cys Phe Thr Ser Ala Arg Leu Gln Thr
    50                  55                  60
```

```
Ile Ile Leu Ala Phe Ile Leu His Ala Met Ala Ile Leu Gly Ile Thr
65                  70                  75                  80

Ala Gly Ala His Arg Leu Trp Thr His Arg Ser Tyr Lys Ala Thr Met
                85                  90                  95

Pro Leu Gln Ile Ile Leu Ile Ile Phe Asn Ser Leu Ser Phe Gln Asn
            100                 105                 110

Ser Ala Ile Asn Trp Val Arg Asp His Arg Ser His His Lys Tyr Cys
        115                 120                 125

Asp Thr Asp Ala Asp Pro His Asn Ala Ala Arg Gly Leu Phe Tyr Ser
    130                 135                 140

His Ile Gly Trp Leu Leu Val Lys Lys His Pro Glu Val Lys Lys Arg
145                 150                 155                 160

Gly Lys Met Thr Asp Met Ser Asp Val Tyr Arg Asn Pro Val Leu Arg
                165                 170                 175

Phe Gln Lys Lys Tyr Ala Val Pro Phe Ile Gly Thr Ile Cys Phe Val
            180                 185                 190

Leu Pro Thr Ile Ile Pro Met Tyr Phe Trp Gly Glu Ser Leu Asn Asn
        195                 200                 205

Ala Trp His Ile Thr Leu Leu Arg Tyr Ile Phe Ser Met His Thr Ile
    210                 215                 220

Phe Leu Val Asn Ser Val Ala His Leu Trp Gly Asn Arg Pro Tyr Asp
225                 230                 235                 240

Lys Asn Ile Leu Pro Ala Asp Asn Arg Thr Leu Ser Ile Ala Thr Leu
                245                 250                 255

Gly Glu Ala Ser His Asn Tyr His His Thr Phe Pro Trp Asp Tyr Arg
            260                 265                 270

Ser Thr Glu Leu Gly Tyr Leu Pro Thr Asn Phe Thr Thr Asn Phe Ile
        275                 280                 285

Asp Phe Phe Ala Trp Ile Gly Trp Ala Tyr Asp Leu Lys Thr Thr Ser
    290                 295                 300

Gly Glu Ile Ile Asn Ser Arg Ile Gln Arg Thr Gly Asp Gly Thr His
305                 310                 315                 320

Ser Arg Ser Lys Lys Asn Ile Ser Thr Gln Asp Glu
                325                 330
```

<210> SEQ ID NO 41
<211> LENGTH: 338
<212> TYPE: PRT
<213> ORGANISM: Spodoptera littoralis

<400> SEQUENCE: 41

```
Met Ala Gln Cys Val Gln Thr Thr Thr Ile Leu Glu Gln Lys Glu Glu
1               5                   10                  15

Lys Thr Val Thr Leu Leu Val Pro Gln Ala Gly Lys Arg Lys Phe Glu
            20                  25                  30

Ile Val Tyr Phe Asn Ile Ile Thr Phe Ala Tyr Trp His Ile Ala Gly
        35                  40                  45

Leu Tyr Gly Leu Tyr Leu Cys Phe Thr Ser Thr Lys Trp Ala Thr Val
    50                  55                  60

Leu Phe Ser Phe Phe Leu Phe Val Val Ala Glu Val Gly Val Thr Ala
65                  70                  75                  80

Gly Ser His Arg Leu Trp Ser His Lys Thr Tyr Lys Ala Lys Leu Pro
                85                  90                  95

Leu Gln Ile Leu Leu Met Val Met Asn Ser Leu Ala Phe Gln Asn Thr
```

```
            100                 105                 110

Val Ile Asp Trp Val Arg Asp His Arg Leu His His Lys Tyr Ser Asp
        115                 120                 125

Thr Asp Ala Asp Pro His Asn Ala Ser Arg Gly Phe Phe Tyr Ser His
    130                 135                 140

Val Gly Trp Leu Leu Val Arg Lys His Pro Asp Val Lys Lys Arg Gly
145                 150                 155                 160

Lys Glu Ile Asp Ile Ser Asp Ile Tyr Asn Asn Pro Val Leu Arg Phe
                165                 170                 175

Gln Lys Lys Tyr Ala Ile Pro Phe Ile Gly Ala Val Cys Phe Val Leu
            180                 185                 190

Pro Thr Leu Ile Pro Val Tyr Gly Trp Gly Glu Thr Trp Thr Asn Ala
        195                 200                 205

Trp His Val Ala Met Leu Arg Tyr Ile Met Asn Leu Asn Val Thr Phe
    210                 215                 220

Leu Val Asn Ser Ala Ala His Ile Tyr Gly Lys Arg Pro Tyr Asp Lys
225                 230                 235                 240

Lys Ile Leu Pro Ser Gln Asn Ile Ala Val Ser Ile Ala Thr Phe Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Phe Pro Thr Lys Phe Ile Asp
        275                 280                 285

Phe Phe Ala Trp Ile Gly Trp Ala Tyr Asp Leu Lys Thr Val Ser Lys
    290                 295                 300

Glu Met Ile Lys Gln Arg Ser Lys Arg Thr Gly Asp Gly Thr Asn Leu
305                 310                 315                 320

Trp Gly Leu Glu Asp Val Asp Thr Pro Glu Asp Leu Lys Asn Thr Lys
                325                 330                 335

Gly Glu
```

<210> SEQ ID NO 42
<211> LENGTH: 334
<212> TYPE: PRT
<213> ORGANISM: Choristoneura parallela

<400> SEQUENCE: 42

```
Met Ala Pro Asn Val Glu Asp Met Glu Ser Asp Met Pro Glu Ser Glu
1               5                   10                  15

Lys Trp Glu Lys Leu Val Ala Pro Gln Ala Ala Pro Arg Lys Tyr Glu
            20                  25                  30

Ile Ile Tyr Thr Asn Leu Leu Thr Phe Gly Tyr Gly His Ile Ala Gly
        35                  40                  45

Leu Tyr Gly Leu Tyr Leu Cys Phe Thr Ser Ala Lys Trp Gln Thr Val
    50                  55                  60

Ile Leu Ala Ile Ile Leu Asn Glu Met Ala Ile Leu Gly Ile Thr Ala
65                  70                  75                  80

Gly Ala His Arg Leu Trp Ser His Arg Ser Tyr Lys Ala Ala Val Pro
                85                  90                  95

Leu Gln Ile Ile Leu Met Ile Phe Asn Ser Leu Ala Phe Gln Asn Ser
            100                 105                 110

Ala Ile Asn Trp Val Arg Asp His Arg Met His His Lys Tyr Ser Asp
        115                 120                 125

Thr Asp Gly Asp Pro His Asn Ala Ser Arg Gly Phe Phe Tyr Ser His
```

```
    130                 135                 140

Val Gly Trp Leu Leu Val Lys Lys His Pro Glu Val Lys Lys Arg Gly
145                 150                 155                 160

Lys Met Ile Asp Met Ser Asp Ile Tyr Ser Asn Pro Val Leu Arg Phe
                165                 170                 175

Gln Lys Lys Tyr Ala Ile Pro Phe Ile Gly Met Ile Cys Phe Val Leu
            180                 185                 190

Pro Thr Ile Ile Pro Met Tyr Phe Trp Gly Glu Thr Leu Ser Asn Ala
        195                 200                 205

Trp His Ile Thr Met Leu Arg Tyr Val Phe Ser Leu Asn Ser Ile Phe
    210                 215                 220

Leu Val Asn Ser Ala Ala His Leu Tyr Gly Tyr Arg Pro Tyr Asp Lys
225                 230                 235                 240

Asn Ile Leu Pro Ala Glu Asn Lys Ile Ala Leu Ile Ala Cys Leu Gly
                245                 250                 255

Asp Ser Phe His Asn Tyr His His Val Phe Pro Trp Asp Tyr Arg Ala
            260                 265                 270

Ser Glu Leu Gly Asn Ile Gly Met Asn Trp Thr Ala Gln Phe Ile Asp
        275                 280                 285

Phe Phe Ala Trp Ile Gly Trp Ala Tyr Asp Leu Lys Thr Ala Ser Asp
    290                 295                 300

Glu Asn Ile Asn Ser Arg Met Lys Arg Thr Gly Asp Gly Thr Asp Ile
305                 310                 315                 320

Ser Gly Gln Lys Tyr Ser Cys Glu Ser Ser Glu Val Leu Gln
                325                 330


<210> SEQ ID NO 43
<211> LENGTH: 337
<212> TYPE: PRT
<213> ORGANISM: Lobesia botrana

<400> SEQUENCE: 43

Met Val Pro Arg Ala Ala Ser Glu Glu Thr Asp Leu Lys Glu Ala Thr
1               5                   10                  15

Gln Leu Glu Pro Arg Lys Tyr Glu Ile Val Tyr Thr Asn Val Ile Tyr
            20                  25                  30

Phe Thr Tyr Trp His Ile Ala Gly Leu Tyr Gly Leu Tyr Leu Cys Phe
        35                  40                  45

Thr Ser Ala Lys Trp Glu Thr Ile Val Phe Ala Trp Ala Trp Tyr Val
    50                  55                  60

Leu Gly Glu Leu Gly Val Ile Ala Gly Ala His Arg Leu Trp Ala His
65                  70                  75                  80

Arg Thr Tyr Lys Ala Lys Met Pro Leu Gln Ile Ile Leu Met Leu Phe
                85                  90                  95

Asn Cys Ile Gly Phe Gln Asn Thr Ala Thr Asp Trp Val Arg Asp His
            100                 105                 110

Arg Val His His Lys His Ser Asp Thr Asp Ala Asp Pro His Asn Ser
        115                 120                 125

Gln Arg Gly Phe Phe Phe Ser His Val Gly Trp Leu Leu Thr Arg Lys
    130                 135                 140

His Arg Leu Val Lys Glu Lys Gly Glu Ala Val Asp Met Thr Asp Ile
145                 150                 155                 160

Tyr Ser Asn Pro Val Leu Arg Phe Gln Lys Lys Tyr Ser Leu Pro Leu
                165                 170                 175
```

Ile Gly Thr Leu Cys Phe Ala Leu Pro Thr Leu Leu Pro Ala Tyr Cys
180 185 190

Trp Gly Glu Ala Val Gly Thr Ala Trp Asn Ile Asn Leu Leu Arg Tyr
195 200 205

Cys Leu Asn Leu Asn Gly Thr Phe Leu Thr Asn Ser Ala Ala His Lys
210 215 220

Phe Gly Ser Lys Pro Tyr Asp Lys Thr Ile Pro Pro Thr Gln Asn Leu
225 230 235 240

Leu Val Ser Phe Met Thr Leu Gly Glu Gly Phe His Asn Tyr His His
245 250 255

Val Phe Ser Trp Asp Tyr Arg Ala Ala Glu Leu Gly Asn Thr Tyr Leu
260 265 270

Asn Met Thr Thr Ile Phe Ile Asp Phe Phe Ala Leu Ile Gly Trp Ala
275 280 285

Tyr Asp Leu Lys Thr Val Pro Glu Asp Val Ile Lys Lys Arg Met Ala
290 295 300

Arg Thr Gly Asp Gly Thr Asn Leu Trp Gly Trp Gly Asp Lys Asp Met
305 310 315 320

Thr Lys Glu Asp Val Val Asp Thr Glu Ile Arg Phe His Ala Lys Lys
325 330 335

Glu

<210> SEQ ID NO 44
<211> LENGTH: 416
<212> TYPE: PRT
<213> ORGANISM: Drosophila grimshawi

<400> SEQUENCE: 44

Met Phe Ser Glu Tyr Tyr Val Tyr Arg Arg Lys Leu Leu Gly Ile Ser
1 5 10 15

Ser Val Gln Ile Ala Arg Gln Ile Asp Arg Leu Ile Lys Pro Ser Thr
20 25 30

Leu Lys Met Pro Pro Asn Ala Ile Ser Ser Pro Pro Asp Ala Leu Pro
35 40 45

Thr Cys Pro Glu Asp Gln Val Leu Ser Gly Ser Gln Ser Gly Ala Gly
50 55 60

Gly Ala Ser Lys Gln Thr Gly Val Leu Phe Glu Ala Asp Ala Asp Thr
65 70 75 80

Asn Asp Gly Gly Leu Thr Met Asp Ile Thr Gln Phe Lys Asn Ala Glu
85 90 95

Lys Arg Lys Leu Lys Trp Val Trp Arg Asn Ile Val Leu Phe Ala Tyr
100 105 110

Val His Val Ala Ala Leu Tyr Gly Gly Tyr Leu Leu Val Thr Gln Ala
115 120 125

Lys Trp Ala Thr Ile Val Phe Ser Met Phe Leu Tyr Ser Ala Gly Met
130 135 140

Ile Gly Ile Thr Gly Gly Ala His Arg Leu Trp Ala His Arg Ser Tyr
145 150 155 160

Lys Ala Lys Trp Pro Leu Arg Val Ile Leu Val Ala Phe Asn Ser Ile
165 170 175

Ala Phe Gln Asp Ala Ala Tyr His Trp Ala Arg Asp His Arg Val His
180 185 190

His Lys Phe Ser Glu Thr Asp Ala Asp Pro His Asn Ala Thr Arg Gly
195 200 205

```
Phe Phe Phe Ser His Val Gly Trp Leu Leu Cys Lys Lys His Pro Asp
    210                 215                 220

Val Val Ala Lys Gly Lys Ser Leu Asp Leu Ser Asp Leu Arg Ala Asp
225                 230                 235                 240

Arg Val Leu Met Phe Gln Lys Lys His Tyr Phe Val Leu Met Pro Leu
                245                 250                 255

Ala Cys Phe Ile Leu Pro Thr Cys Ile Pro Met Leu Cys Trp Asn Glu
            260                 265                 270

Ser Leu Leu Cys Ser Val Leu Val Pro Thr Ile Phe Arg Trp Cys Leu
        275                 280                 285

Gln Leu Asn Met Thr Trp Leu Val Asn Ser Ala Ala His Lys Phe Gly
    290                 295                 300

Gly Arg Pro Tyr Asp Lys Asn Ile Asn Pro Ser Gln Ser Pro Tyr Val
305                 310                 315                 320

Ser Leu Phe Thr Leu Gly Glu Gly Trp His Asn Tyr His His Val Phe
                325                 330                 335

Pro Trp Asp Tyr Lys Thr Ala Glu Trp Gly Asn Tyr Ser Leu Asn Met
            340                 345                 350

Thr Thr Ala Phe Ile Asp Leu Phe Ala Lys Ile Gly Trp Ala Tyr Asp
        355                 360                 365

Leu Lys Ser Val Val Pro Glu Thr Val Glu Arg Arg Val Arg Arg Thr
    370                 375                 380

Gly Asp Gly Ser His Glu Leu Trp Gly Trp Gly Asp Lys Asp Leu Thr
385                 390                 395                 400

Pro Glu Asp Gly Gln Ser Val Leu His Val Leu Asp Lys Lys Ser Asn
                405                 410                 415


<210> SEQ ID NO 45
<211> LENGTH: 381
<212> TYPE: PRT
<213> ORGANISM: Drosophila virilis

<400> SEQUENCE: 45

Met Pro Pro Asn Ala Ile Thr Ser Pro Ser Asn Val Leu Ala Thr Cys
1               5                   10                  15

Pro Glu Val Glu Gln Leu Pro Ser Gly Glu Cys Ala Ser Thr Ala Ser
            20                  25                  30

Ser Lys Gln Thr Gly Val Leu Phe Glu Gly Asp Ala Asp Thr Ala Asp
        35                  40                  45

Cys Ala Leu Asp Val Asp Val Lys Lys Leu Lys Lys Ala Glu Lys Arg
    50                  55                  60

Lys Leu Lys Leu Val Trp Arg Asn Ile Met Leu Phe Gly Tyr Leu His
65                  70                  75                  80

Leu Ala Ala Val Tyr Gly Gly Tyr Leu Met Leu Thr Gln Ala Lys Trp
                85                  90                  95

Ala Thr Val Val Phe Ser Phe Phe Leu Tyr Thr Ala Gly Met Ile Gly
            100                 105                 110

Ile Thr Gly Gly Ala His Arg Leu Trp Ala His Arg Ser Tyr Lys Ala
        115                 120                 125

Lys Trp Pro Leu Arg Val Ile Leu Val Thr Phe Asn Thr Ile Ala Phe
    130                 135                 140

Gln Asp Ala Ala Phe His Trp Ala Arg Asp His Arg Val His His Lys
145                 150                 155                 160

Phe Ser Glu Thr Asp Ala Asp Pro His Asn Ala Thr Arg Gly Phe Phe
                165                 170                 175
```

Phe Ser His Val Gly Trp Leu Leu Cys Lys Lys His Pro Asp Val Val
180 185 190

Ala Lys Gly Lys Ser Leu Asp Val Thr Asp Leu Arg Ala Asp Arg Ile
195 200 205

Leu Met Phe Gln Leu Lys His Tyr Phe Val Leu Met Pro Leu Ala Cys
210 215 220

Phe Ile Leu Pro Thr Ile Ile Pro Met Ile Cys Trp Asn Glu Ser Leu
225 230 235 240

Leu Cys Ser Trp Phe Val Ala Thr Met Phe Arg Trp Cys Phe Gln Leu
245 250 255

Asn Met Thr Trp Leu Val Asn Ser Ala Ala His Lys Phe Gly Gly Arg
260 265 270

Pro Tyr Asp Lys Asn Ile Asn Pro Ser Gln Ser Pro Tyr Val Ser Ala
275 280 285

Phe Thr Phe Gly Glu Gly Trp His Asn Tyr His His Val Phe Pro Trp
290 295 300

Asp Tyr Lys Thr Ala Glu Trp Gly Arg Tyr Ser Leu Asn Met Thr Thr
305 310 315 320

Ala Phe Ile Asp Phe Phe Ala Lys Ile Gly Trp Ala Tyr Glu Leu Lys
325 330 335

Ser Val Ala Pro Glu Thr Ile Glu Arg Arg Val Arg Arg Thr Gly Asp
340 345 350

Gly Thr His Glu Leu Trp Gly Trp Gly Asp Lys Asp Leu Thr Ala Glu
355 360 365

Asp Ala Gln His Val Leu Phe Val Asp Lys Lys Ala Ala
370 375 380

<210> SEQ ID NO 46
<211> LENGTH: 297
<212> TYPE: PRT
<213> ORGANISM: Synechococcus sp

<400> SEQUENCE: 46

Met Val Ala Gln Thr Phe Asn Leu Asp Thr Tyr Leu Ser Gln Arg Gln
1 5 10 15

Gln Gln Val Glu Glu Ala Leu Ser Ala Ala Leu Val Pro Ala Tyr Pro
20 25 30

Glu Arg Ile Tyr Glu Ala Met Arg Tyr Ser Leu Leu Ala Gly Gly Lys
35 40 45

Arg Leu Arg Pro Ile Leu Cys Leu Ala Ala Cys Glu Leu Ala Gly Gly
50 55 60

Ser Val Glu Gln Ala Met Pro Thr Ala Cys Ala Leu Glu Met Ile His
65 70 75 80

Thr Met Ser Leu Ile His Asp Asp Leu Pro Ala Met Asp Asn Asp Asp
85 90 95

Phe Arg Arg Gly Lys Pro Thr Asn His Lys Val Phe Gly Glu Asp Ile
100 105 110

Ala Ile Leu Ala Gly Asp Ala Leu Leu Ala Tyr Ala Phe Glu His Ile
115 120 125

Ala Ser Gln Thr Arg Gly Val Pro Pro Gln Leu Val Leu Gln Val Ile
130 135 140

Ala Arg Ile Gly His Ala Val Ala Ala Thr Gly Leu Val Gly Gly Gln
145 150 155 160

Val Val Asp Leu Glu Ser Glu Gly Lys Ala Ile Ser Leu Glu Thr Leu

```
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295


<210> SEQ ID NO 47
<211> LENGTH: 574
<212> TYPE: PRT
<213> ORGANISM: Artemisia annua

<400> SEQUENCE: 47

Met Ser Thr Leu Pro Ile Ser Ser Val Ser Phe Ser Ser Ser Thr Ser
1               5                   10                  15

Pro Leu Val Val Asp Asp Lys Val Ser Thr Lys Gln Asp Val Ile Arg
            20                  25                  30

His Thr Met Asn Phe Asn Ala Ser Ile Trp Gly Asp Gln Phe Leu Thr
        35                  40                  45

Tyr Asp Glu Pro Glu Asp Leu Val Met Lys Lys Gln Leu Val Glu Glu
    50                  55                  60

Leu Lys Glu Glu Val Lys Lys Glu Leu Ile Thr Ile Lys Gly Ser Asn
65                  70                  75                  80

Glu Pro Met Gln His Val Lys Leu Leu Glu Leu Ile Asp Ala Val Gln
                85                  90                  95

Arg Leu Gly Ile Ala Tyr His Phe Glu Glu Glu Ile Glu Glu Ala Leu
            100                 105                 110

Gln His Ile His Val Thr Tyr Gly Glu Gln Trp Val Asp Lys Glu Asn
        115                 120                 125

Leu Gln Ser Ile Ser Leu Trp Phe Arg Leu Leu Arg Gln Gln Gly Phe
    130                 135                 140

Asn Val Ser Ser Gly Val Phe Lys Asp Phe Met Asp Glu Lys Gly Lys
145                 150                 155                 160

Phe Lys Glu Ser Leu Cys Asn Asp Ala Gln Gly Ile Leu Ala Leu Tyr
                165                 170                 175

Glu Ala Ala Phe Met Arg Val Glu Asp Glu Thr Ile Leu Asp Asn Ala
            180                 185                 190

Leu Glu Phe Thr Lys Val His Leu Asp Ile Ile Ala Lys Asp Pro Ser
        195                 200                 205

Cys Asp Ser Ser Leu Arg Thr Gln Ile His Gln Ala Leu Lys Gln Pro
    210                 215                 220

Leu Arg Arg Arg Leu Ala Arg Ile Glu Ala Leu His Tyr Met Pro Ile
225                 230                 235                 240
```

Tyr Gln Gln Glu Thr Ser His Asn Glu Val Leu Leu Lys Leu Ala Lys
245 250 255

Leu Asp Phe Ser Val Leu Gln Ser Met His Lys Lys Glu Leu Ser His
260 265 270

Ile Cys Lys Trp Trp Lys Asp Leu Asp Leu Gln Asn Lys Leu Pro Tyr
275 280 285

Val Arg Asp Arg Val Val Glu Gly Tyr Phe Trp Ile Leu Ser Ile Tyr
290 295 300

Tyr Glu Pro Gln His Ala Arg Thr Arg Met Phe Leu Met Lys Thr Cys
305 310 315 320

Met Trp Leu Val Val Leu Asp Asp Thr Phe Asp Asn Tyr Gly Thr Tyr
325 330 335

Glu Glu Leu Glu Ile Phe Thr Gln Ala Val Glu Arg Trp Ser Ile Ser
340 345 350

Cys Leu Asp Met Leu Pro Glu Tyr Met Lys Leu Ile Tyr Gln Glu Leu
355 360 365

Val Asn Leu His Val Glu Met Glu Glu Ser Leu Glu Lys Glu Gly Lys
370 375 380

Thr Tyr Gln Ile His Tyr Val Lys Glu Met Ala Lys Glu Leu Val Arg
385 390 395 400

Asn Tyr Leu Val Glu Ala Arg Trp Leu Lys Glu Gly Tyr Met Pro Thr
405 410 415

Leu Glu Glu Tyr Met Ser Val Ser Met Val Thr Gly Thr Tyr Gly Leu
420 425 430

Met Ile Ala Arg Ser Tyr Val Gly Arg Gly Asp Ile Val Thr Glu Asp
435 440 445

Thr Phe Lys Trp Val Ser Ser Tyr Pro Pro Ile Ile Lys Ala Ser Cys
450 455 460

Val Ile Val Arg Leu Met Asp Asp Ile Val Ser His Lys Glu Glu Gln
465 470 475 480

Glu Arg Gly His Val Ala Ser Ser Ile Glu Cys Tyr Ser Lys Glu Ser
485 490 495

Gly Ala Ser Glu Glu Glu Ala Cys Glu Tyr Ile Ser Gly Lys Val Glu
500 505 510

Asp Ala Trp Lys Val Ile Asn Arg Glu Ser Leu Arg Pro Thr Ala Val
515 520 525

Pro Phe Pro Leu Leu Met Pro Ala Ile Asn Leu Ala Arg Met Cys Glu
530 535 540

Val Leu Tyr Ser Val Asn Asp Gly Phe Thr His Ala Glu Gly Asp Met
545 550 555 560

Lys Ser Tyr Met Lys Ser Phe Phe Val His Pro Met Val Val
565 570

<210> SEQ ID NO 48
<211> LENGTH: 348
<212> TYPE: PRT
<213> ORGANISM: Cydia pomonella
<220> FEATURE:
<221> NAME/KEY: MISC_FEATURE
<222> LOCATION: (1)..(348)
<223> OTHER INFORMATION: C. pomonella CPO_CPRQ desaturase (AHW98354)

<400> SEQUENCE: 48

Met Pro Pro Arg Glu Ser Lys Lys Val Ala Leu Arg Ser Tyr Glu Thr
1 5 10 15

Pro Val Ala Ser Leu Pro Pro Arg Lys Tyr Glu Ile Ile Tyr Leu Asn

```
            20                  25                  30

Leu Phe Leu His Ile Ala Gly His Ile Ser Ala Val Tyr Gly Leu Tyr
        35                  40                  45

Leu Cys Phe Thr Ala Ala Gln Trp Lys Thr Ile Phe Phe Ala Tyr Leu
    50                  55                  60

Trp Leu Leu Met Gly Glu Leu Gly Val Val Cys Gly Ala His Arg Leu
65                  70                  75                  80

Trp Ser His Arg Ser Phe Lys Val Lys Pro Pro Leu Glu Ile Met Leu
                85                  90                  95

Met Leu Phe Asn Cys Ile Gly Phe Gln Asn Thr Ala Thr Asp Trp Val
            100                 105                 110

Arg Asn His Arg Leu His His Lys His Ser Asp Thr Asp Ala Asp Pro
        115                 120                 125

His Asn Ser Asn Arg Gly Met Leu Phe Ser His Ile Gly Trp Leu Cys
    130                 135                 140

Val Arg Lys His Pro Asp Val Lys Glu Arg Gly Lys Thr Thr Asp Met
145                 150                 155                 160

Ser Asp Ile Tyr Ser Asn Pro Val Leu Arg Phe Gln Lys Lys His Lys
                165                 170                 175

Val Pro Leu Phe Gly Ala Met Cys Phe Gly Leu Pro Thr Leu Ile Pro
            180                 185                 190

Thr Leu Trp Gly Glu Asp Ile Val Thr Ala Trp His Val Asn Leu Leu
        195                 200                 205

Arg Phe Val Leu Asn Leu Asn Ser Ile Leu Leu Val Asn Ser Ile Ala
    210                 215                 220

His Lys Tyr Gly Thr Arg Pro Tyr Asp Arg Thr Ile Cys Pro Arg Gln
225                 230                 235                 240

Asn Thr Thr Cys Asn Met Met Thr Leu Gly Glu Gly Phe His Asn Tyr
                245                 250                 255

His His Thr Phe Pro Trp Asp Tyr Arg Ser Ala Glu Leu Gly Lys Asn
            260                 265                 270

Tyr Leu Asn Phe Thr Lys Trp Phe Ile Asp Phe Phe Ala Leu Ile Gly
        275                 280                 285

Trp Ala Tyr Asp Leu Lys Thr Val Pro Asp Asp Met Ile Gln Arg Arg
    290                 295                 300

Met Lys Arg Thr Gly Asp Gly Ser Asn Ser Trp Gly Trp Gly Asp Lys
305                 310                 315                 320

Asp Met Thr Lys Glu Glu Arg Asp Ser Ala Thr Ile Ile Tyr Pro Glu
                325                 330                 335

Lys Lys Asp Asp Ile Lys Met Ile Ser Lys Lys Asn
            340                 345
```

<210> SEQ ID NO 49
<211> LENGTH: 1050
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(1050)
<223> OTHER INFORMATION: Cpo_NPVE, codon-optimised for Y. lipolytica

<400> SEQUENCE: 49

```
atgccccctc agggacagcc tcccgcctgg gtcctggacg agtccgatgc agtgaccgag      60

gacaaggacg tggccacccc cgctcccgaa gccgagaagc gaaagctgca gatcgtttgg     120
```

agaaacgtga ccctgttcgt gtttctgcac atcggagctc tgtacggagg atacctgttc 180
tttaccaagg ccatgtggac tacccgaatt ttcactgtgc tgctgtacat tatgtctggg 240
ctgggtatca ccgccggcgc ccatcgactc tgggctcaca agtcttacaa ggcccgactg 300
cccctgcgac tgctgctgac cctcttcaac accatcgcct ttcaggactc cgttctggat 360
tgggcccgag atcaccgaat gcaccataag tactctgaaa ccgacgcaga tccccacaat 420
gctacccgag gcttcttctt ctctcacgtg ggctggctgc tggtgcgaaa gcacccccag 480
atcaaggcca agggacatac tatcgacatg tctgacctgc tggccgatcc cgtgctgcga 540
ttccagaaga agtactacct gacactgatg cccttgtgct gcttcatcct gccctcttac 600
attcccaccc tctggggaga gtctctgtgg aacgcttact ttgtgtgcgc catcttccga 660
tactgttacg ttctgaacgt gacttggctg gtgaactccg ctgcccacaa atggggtgac 720
cgaccttacg acaagaacat caaccctgtg gagactaagc ctgtgtctct ggtggttttc 780
ggagagggat tccacaacta ccaccacacc ttcccctggg attacaagac cgccgagctg 840
ggcggatact ctctgaacct ttccaaactg ttcatcgata ctatgtccaa gattggatgg 900
gcctacgacc tgaagtccgt ttcccctgac atcgtggaga agcgagtgaa gcgcaccggc 960
gacggatctc accacgtgtg gggatgggac gatgctccct ctgagcaaaa ggtggctgcc 1020
accatcgtga accccgataa gaccgagtaa 1050

<210> SEQ ID NO 50
<211> LENGTH: 334
<212> TYPE: PRT
<213> ORGANISM: Cydia pomonella

<400> SEQUENCE: 50

Met Ala Pro Tyr Ser Glu Glu Tyr Glu Ile Leu Lys Glu Asn Thr Lys
1 5 10 15

Pro Val Ser Pro Gln Ala Ala Pro Arg Glu Tyr Thr Val Val Tyr Ser
20 25 30

Val Val Leu Ile Phe Val Tyr Trp His Ile Gly Ala Leu Tyr Gly Leu
35 40 45

Tyr Leu Gly Phe Thr Ser Ala Lys Trp Ala Thr Ile Ile Phe Asn Tyr
50 55 60

Leu Ile Tyr Val Ser Gly Gly Phe Ala Ile Thr Ala Gly Ser His Arg
65 70 75 80

Leu Trp Ser His Arg Ala Phe Lys Ala Lys Leu Pro Leu Gln Ile Leu
85 90 95

Leu Met Leu Leu Gln Thr Met Ser Cys Gln Lys Ser Val Leu Asn Trp
100 105 110

Val Arg Asp His Arg Leu His His Met Tyr Cys Asp Thr Asp Ala Asp
115 120 125

Pro Tyr Asn Ser Thr Arg Gly Ile Phe Tyr Ser His Ile Gly Trp Leu
130 135 140

Met Val Lys Lys His Pro Glu Val Ile Arg Lys Gly Arg Thr Ile Asp
145 150 155 160

Met Ser Asp Leu Glu Asn Asn Pro Val Leu Lys Phe Gln Lys Lys Phe
165 170 175

Tyr Pro Ile Leu Val Thr Leu Met Ala Phe Ile Leu Pro Ala Leu Ile
180 185 190

Pro Val Ile Phe Trp Gln Glu Ser Leu Asn Ile Ala His His Val Ser
195 200 205

-continued

```
Leu Val His Leu Val Val Gly Ser His Met Thr Phe Ala Ile Asn Ser
    210                 215                 220

Ile Ala His Ala Phe Gly Ser Lys Pro Cys Asp Lys Thr Ile Ser Pro
225                 230                 235                 240

Thr Gln Ser Ile Ser Leu Ser Leu Val Thr Phe Gly Glu Gly Tyr His
                245                 250                 255

Asn Tyr His His Val Phe Pro Phe Asp Tyr Arg Val Ala Glu Leu Gly
            260                 265                 270

Asn Asn Tyr Leu Asn Leu Thr Thr Asn Phe Ile Asp Phe Phe Ala Trp
        275                 280                 285

Ile Gly Trp Ala Tyr Asp Leu Lys Tyr Ala Ser Pro Asp Met Val Ala
    290                 295                 300

Lys Arg Ala Lys Arg Thr Gly Asp Gly Thr Asp Leu Trp Gly Arg Ala
305                 310                 315                 320

Ile Glu His Ala Asp Ile Gln Ala Lys Arg Val His Pro Ser
                325                 330
```

METHODS FOR PRODUCTION, RECOVERY AND SECRETION OF HYDROPHOBIC COMPOUNDS IN A FERMENTATION

TECHNICAL FIELD

The present invention relates to improved methods for producing a hydrophobic compound, in particular a hydrophobic compound which is a pheromone such as an insect pheromone, in a fermentation process involving cultivation of a microorganism such as a yeast, said microorganism producing said hydrophobic compound, wherein the methods facilitate recovery of the hydrophobic compound from the fermentation broth, increase the titer of the hydrophobic compound and/or increase secretion of the hydrophobic compound from the microorganism.

BACKGROUND

Living cells, in particular microbial cells, are widely used nowadays for the biological production of a number of compounds. Examples of such compounds are fatty alcohols, fatty acyl acetates and fatty aldehydes, such as insect pheromones, which can be produced in e.g. yeast cells. Such compounds have applications in agriculture, and can for example be used as green pest repellents. Other useful compounds which can be produced by cells, e.g. genetically engineered cells, are terpenes and terpenoids. Terpenes are naturally produced by plants, and have a number of industrial applications in the field of food, pharmaceutics, cosmetics and biotechnology. They are for example used as part of natural agricultural pesticides. Terpenoids (also termed isoprenoids) are modified terpenes containing additional groups, usually O-containing groups. They are often used for their aromatic qualities and as part of traditional herbal remedies. While terpenes and terpenoids occur widely, their extraction from natural sources is often problematic. Consequently, they are typically produced by chemical synthesis, usually from petrochemicals.

A common property of the above compounds is that they are hydrophobic or lipophilic. Their recovery from a fermentation broth typically involves several organic solvents, which introduces a number of challenges, including process safety, the need for multiple extraction steps, the need for removal of solvent residues from the final products, and significant labour and costs (both monetary and environmental).

Another challenge posed by fermentation processes involving recombinant microorganisms is that the compound of interest may largely retained intracellularly. Limited secretion of the product(s) from the cell into the fermentation broth may thus limit recovery of the compound of interest, or at best require additional steps involving cellular lysis in order to release the compound into the broth. Secretion of the product from the cell into the fermentation broth presents multiple advantages, such as reduced product inhibition and degradation, reduced effect on the host cell, higher titers, and easier and cheaper recovery process (Borodina I., 2019). Particular process advantage is achieved, when a secreted lipophilic product can be recovered in a separate phase.

Thus there is a need for improved methods for recovering hydrophobic fermentation products, as well as improved methods for increasing secretion of a hydrophobic compound from a cell in fermentation processes.

SUMMARY

The present methods solve the above challenges.

Herein is provided a method for producing a hydrophobic compound such as a fatty alcohol, a fatty alcohol ester, a fatty acyl acetate, a fatty aldehyde and/or a terpene such as a terpenoid in a fermentation, said method comprising the step of providing a microorganism capable of producing said hydrophobic compound and culturing said microorganism in a culture medium under conditions allowing production of said hydrophobic compound, wherein the culture medium comprises an extractant in an amount equal to or greater than its cloud concentration measured in an aqueous solution, wherein the extractant a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, the method optionally further comprising the step of recovering the hydrophobic compound. Hence is provided herein a method for producing a hydrophobic compound selected from a fatty alcohol, a fatty alcohol ester, a fatty acyl acetate, a fatty aldehyde and a terpene in a fermentation, said method comprising the step of providing a yeast cell capable of producing said hydrophobic compound and culturing said yeast cell in a culture medium under conditions allowing production of said hydrophobic compound, wherein the culturing step is performed at a cultivation temperature, wherein the culture medium comprises an extractant in an amount equal to or greater than its cloud concentration measured in an aqueous solution such as the culture medium at the cultivation temperature, wherein the extractant is a non-ionic ethoxylated surfactant, the method further comprising the step of recovering the hydrophobic compound.

Also provided herein is a method for increasing the titer of a hydrophobic compound such as a fatty alcohol, a fatty alcohol ester, a fatty acyl acetate, a fatty aldehyde and/or a terpene such as a terpenoid in a fermentation, said method comprising culturing a microorganism capable of producing said hydrophobic compound in a culture medium under conditions allowing production of said hydrophobic compound, wherein the culture medium comprises an extractant in an amount equal to or greater than its cloud concentration in an aqueous solution, wherein the extractant is a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, whereby the titer of the hydrophobic compound is increased compared to a fermentation performed under similar conditions in the absence of extractant or in the presence of extractant in an amount lower than its cloud concentration in an aqueous solution. Also provided herein is a method for increasing the titer of a hydrophobic compound selected from a fatty alcohol, a fatty alcohol ester, a fatty acyl acetate, a fatty aldehyde and a terpene in a fermentation, said method comprising culturing a yeast cell capable of producing said hydrophobic compound in a culture medium under conditions allowing production of said hydrophobic compound, wherein the culturing step is performed at a cultivation temperature, wherein the culture medium comprises an extractant in an amount equal to or greater than its cloud concentration measured in an aqueous solution at the cultivation temperature, wherein the extractant is a non-ionic ethoxylated surfactant, whereby the titer of the hydrophobic compound is increased compared to a fermentation performed under the same conditions but either in the absence of extractant or in the presence of extractant in an amount lower than its cloud concentration in an aqueous solution at the cultivation temperature.

Also provided herein is a method for increasing the secretion of a hydrophobic compound such as a fatty alcohol, a fatty alcohol ester, a fatty acyl acetate, a fatty aldehyde and/or a terpene such as a terpenoid from a microorganism capable of producing said hydrophobic compound in a fermentation, said method comprising culturing said microorganism in a culture medium under conditions allowing production of said hydrophobic compound, wherein the culture medium comprises an extractant in an amount equal to or greater than its cloud concentration measured in an aqueous solution, wherein the extractant is a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, whereby the secretion of the hydrophobic compound from the microorganism is increased compared to a fermentation performed under similar conditions in the absence of extractant or in the presence of extractant in an amount lower than its cloud concentration measured in an aqueous solution. Also provided herein is a method for increasing the secretion of a hydrophobic compound selected from a fatty alcohol, a fatty alcohol ester, a fatty acyl acetate, a fatty aldehyde and a terpene from a yeast cell capable of producing said hydrophobic compound in a fermentation, said method comprising culturing said yeast cell in a culture medium under conditions allowing production of said hydrophobic compound, wherein the culturing step is performed at a cultivation temperature, wherein the culture medium comprises an extractant in an amount equal to or greater than its cloud concentration measured in an aqueous solution at the cultivation temperature, wherein the extractant is a non-ionic ethoxylated surfactant, whereby the secretion of the hydrophobic compound from the yeast cell is increased compared to a fermentation performed under the same conditions but either in the absence of extractant or in the presence of extractant in an amount lower than its cloud concentration in an aqueous solution at the cultivation temperature.

Also provided herein is a hydrophobic compound obtainable by the methods disclosed herein, preferably wherein the hydrophobic compound is selected from a fatty alcohol, a fatty alcohol ester, a fatty acyl acetate, a fatty aldehyde and a terpene.

Also provided herein is a method of monitoring the presence of pest or disrupting the mating of pest, said method comprising the steps of:

i) producing a hydrophobic compound by the methods described herein, wherein the hydrophobic compound is as defined herein,
ii) formulating said desaturated fatty alcohol, desaturated fatty acyl acetate and/or desaturated fatty aldehyde as a pheromone composition, and
iii) employing said pheromone composition as an integrated pest management composition.

DETAILED DESCRIPTION OF THE INVENTION

Figure 1:
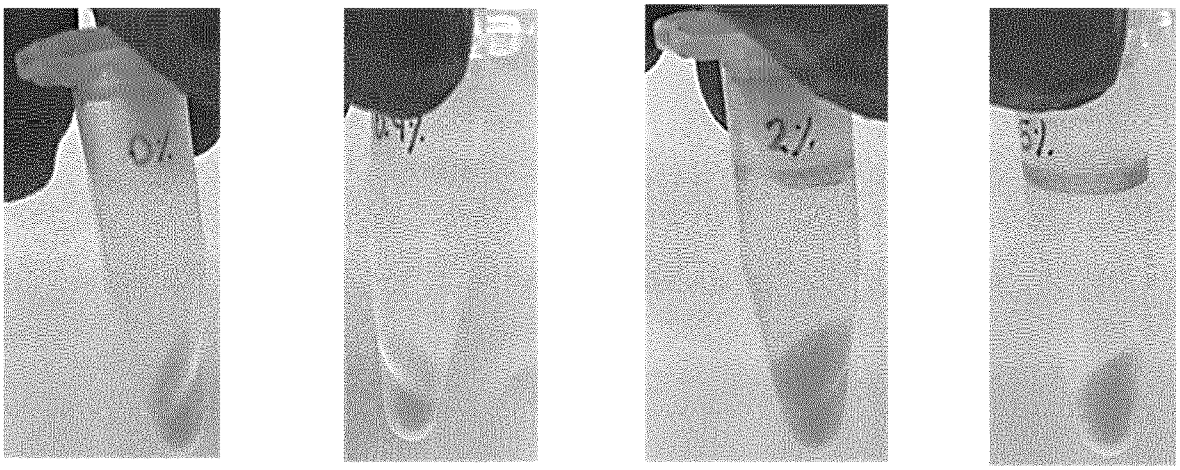
FIG. 1 In situ extraction and recovery of fatty alcohols produced by fermentation. Antifoam A was added at a concentration of: 0% vol/vol (A); 0.4% vol/vol (B); 2% vol/vol (C) or 5% vol/vol (D) in a fermentation of a *Yarrowia lipolytica* strain capable of producing fatty alcohols. When antifoam A is absent (A) or at 0.4% vol/vol (B), the fermentation broth after centrifugation consists of two phases (a solid cellular fraction and a water phase). When antifoam A is added at 2% vol/vol (C) or 5% vol/vol (D), an additional immiscible phase is observed. The fermentation broth after centrifugation consists of three phases: a solid cellular phase, a water phase and a product phase comprising the antifoam and the fatty alcohols. The fatty alcohols are thus isolated in this phase.
Figure 2:
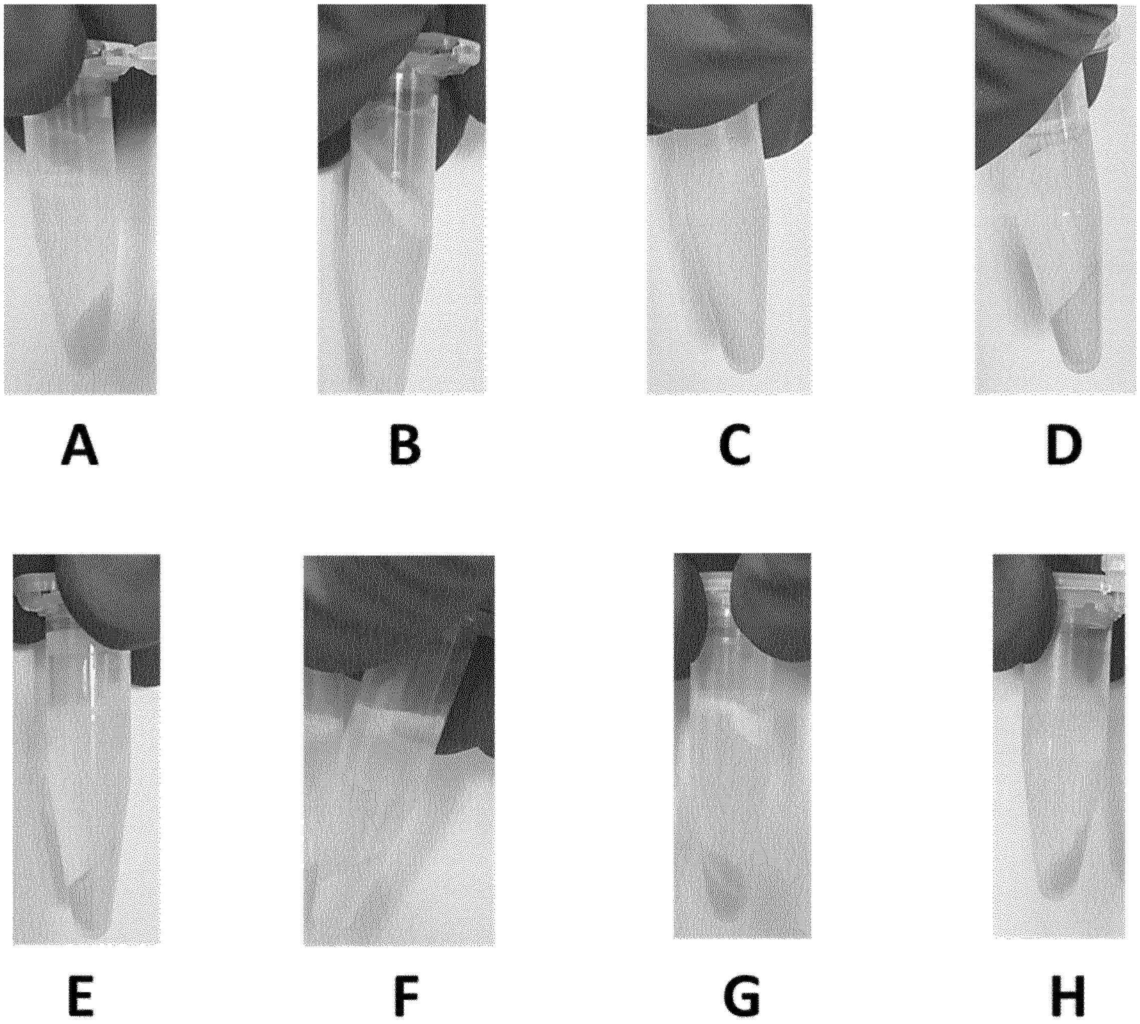
FIG. 2 Antifoaming agents and oils as extractants. Various antifoams were added at a concentration of 3% vol/vol in a fermentation of a *Yarrowia lipolytica* strain capable of producing fatty alcohols. (A) no antifoam; (B) corn oil; (C) oleic acid; (D) antifoam A; (E) Kolliphor® P407; (F) A-204; (G) simethicone; (H) dodecane. After centrifugation, three phases, including a product phase, were observed in fermentation broths to which antifoam A (D), Kolliphor® P407 (E), A-204 (F) or simethicone (G) were added.

The present disclosure relates to the finding that fermentation of a microorganism, particularly a yeast, capable of producing a hydrophobic compound can be improved in several ways by including a non-ionic surfactant, in particular a non-ionic ethoxylated surfactant, for example an antifoaming agent, in an amount equal to or greater than its cloud concentration in an aqueous system. Under such conditions, the non-ionic ethoxylated surfactant acts as an extractant, whereby recovery of the hydrophobic compound is facilitated. In addition, the presence of the non-ionic ethoxylated surfactant surprisingly increases the titer of the hydrophobic compound in the fermentation, and may also increase the secretion of the hydrophobic compound from the yeast cell, thereby further increasing production and facilitating recovery.

Definitions

Surfactant: the term refers to compounds that lower the surface tension (or interfacial tension) between two liquids, between a gas and a liquid, or between a liquid and a solid. Surfactants may act as detergents, wetting agents, emulsifiers, antifoaming agents, and dispersants. Surfactants are usually organic compounds that are amphiphilic, meaning they contain both hydrophobic groups (their tails) and hydrophilic groups (their heads). Therefore, a surfactant typically contains both a water-insoluble (or oil-soluble) component and a water-soluble component. Most commonly, surfactants are classified according to polar head group. A non-ionic surfactant has no charged groups in its head.

Extractant: the term "extractant" as used herein refers to a non-ionic surfactant, more particularly a non-ionic ethoxylated surfactant such as an agent that can be also used as antifoaming agent which facilitates recovery of hydrophobic compounds produced in a fermentation, in particular an ethoxylated surfactant such as a fatty alcohol alkoxylate or a polyethoxylated surfactant selected from: a polyethylene polypropylene glycol, a mixture of polyether dispersions, an agent or an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. Non-ionic ethoxylated surfactants are often also referred to as low-foaming antifoaming agents.

Polyethoxylated surfactant: the term herein refers to ethoxylated surfactants which may be polyethoxylated surfactants, i.e. non-ionic surfactants.

Ethoxylated and propoxylated $C_{16}$-$C_{18}$ alcohol-based agent or ethoxylated and propoxylated $C_{16}$-$C_{18}$ alcohol-based antifoaming agent: the term refers to a group of polyethoxylated, non-ionic surfactants which comprise or mainly consist of ethoxylated and propoxylated alcohols in $C_{16}$-$C_{18}$, for example CAS number 68002-96-0, also termed $C_{16}$-$C_{18}$ alkyl alcohol ethoxylate propoxylate or $C_{16}$-$C_{18}$ alcohols ethoxylated propoxylated polymer. Some compounds in this group are commonly used as antifoaming agents, while others are not and are thus generally referred to as "ethoxylated and propoxylated $C_{16}$-$C_{18}$ alcohol-based agents" herein.

Polyethylene polypropylene glycol: the term refers to a group of polyethoxylated nonionic surfactants which comprise or mainly consist of PEG-PPG-PEG block copolymer antifoaming agents, for example Kolliphor® P407 (CAS number 9003-11-6), also termed poly(ethylene glycol)-block-poly(propylene glycol)-block-poly(ethylene glycol).

Mixture of polyether dispersions: the term refers to a group of polyethoxylated non-ionic surfactants which comprise or mainly consist of a mixture of polyether dispersions, for example organic antifoam 204 from Sigma Aldrich (product number Δ6426 and Δ8311, MDL number MFCD00130523).

Simethicone: the term refers to a group of polyethoxylated non-ionic surfactants which comprise or mainly consist of simethicone, also termed simethicone (CAS number 8050-81-5), dimethyl polysiloxane, or activated Polymethylsiloxane. Simethicone is a silicone-based emulsion containing also 1.2-1.6% polyethylene glycol monostearate.

Cloud point: The cloud point of a surfactant, in particular non-ionic, or a glycol solution, in a solution, for example an aqueous solution, is the temperature at which a mixture of said surfactant and said solution, for example said aqueous solution, starts to phase-separate, and two phases appear, thus becoming cloudy. This behavior is characteristic of non-ionic surfactants containing polyoxyethylene chains, which exhibit reverse solubility versus temperature behavior in water and therefore "cloud out" at some point as the temperature is raised. Glycols demonstrating this behavior are known as "cloud-point glycols". The cloud point is affected by salinity, being generally lower in more saline fluids.

Cloud concentration: the term will herein be used to refer to the concentration of a surfactant, in particular non-ionic, or a glycol solution, in a solution above which, at a given temperature, a mixture of said surfactant and said solution starts to phase-separate, and two phases appear, thus becoming cloudy. For example, the cloud concentration of a surfactant in an aqueous solution at a given temperature is the minimal concentration of said surfactant which, when mixed with the aqueous solution, gives rise to two phases. The cloud concentration can be obtained from the manufacturer of the surfactant, or it may be determined experimentally, by making a dosage curve and determining the concentration at which the mixture phase separates. For example, the method used in Example 7 can be applied. The cloud concentration can be determined at room temperature in an aqueous solution, for example in the culture medium which is used in the present methods. It can also be determined at the cultivation temperature at which the cultivation step is performed, for example at 30° C. In the case of surfactants that can be used as antifoaming agents, the cloud concentration is typically greater than the concentration recommended by the manufacturer for foam management.

Non-Ionic Ethoxylated Surfactant

The present methods rely on the use of a non-ionic ethoxylated surfactant, for example an antifoaming agent, which essentially acts as an extractant in the fermentation broth, where the non-ionic ethoxylated surfactant is present in an amount equal to or greater than its cloud concentration measured in an aqueous solution. Thereby the produced hydrophobic compound is produced with a higher titer, is secreted more readily from the producing microorganism, in particular the producing yeast cell, into the broth, and/or is more easily recovered compared to a fermentation performed with an amount of the same non-ionic ethoxylated surfactant lower than its cloud concentration measured in aqueous solution, such as in the absence of the non-ionic ethoxylated surfactant.

While non-ionic surfactants, including non-ionic ethoxylated surfactants, in particular antifoaming agents, are routinely used in fermentation processes to prevent the formation of foam, the present inventors have found that non-ionic ethoxylated surfactants when included in the fermentation broth in an amount equal to or greater than their cloud concentration measured in an aqueous solution result in increased titer, increased secretion and facilitate recovery of a hydrophobic compound. The cloud concentration in an aqueous solution is determined at a given temperature, preferably at room temperature or at the temperature at which the fermentation is to be performed, for example 30° C.; this temperature is herein referred to as "cultivation temperature". The term "extractant" as used herein refers to a non-ionic surfactant, more particularly a non-ionic ethoxylated surfactant, in particular an antifoaming agent, which facilitates recovery of hydrophobic compounds produced in a fermentation. For example, the nonionic surfactant is a fatty alcohol alkoxylate or a polyethoxylated surfactant, for example selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

Non-ionic surfactants particularly useful for the present methods are ethoxylated and polyethoxylated surfactants, some of which are also routinely used as antifoaming agents, although their application as antifoaming agent is normally associated with their use at lower concentrations than described herein, i.e. at concentrations lower than their cloud concentration as measured in an aqueous solution. These include polyethylene fatty alcohol alkoxylates, and polyethoxylated surfactants, such as polypropylene glycol, mixtures of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

Thus in one embodiment, the non-ionic surfactant acting as extractant is an antifoaming agent. In some embodiments, the non-ionic ethoxylated surfactant is a fatty alcohol alkoxylate. In some embodiments, the non-ionic ethoxylated surfactant is a polyethoxylated surfactant. In some embodiments, the antifoaming agent is polyethylene polypropylene glycol. In another embodiment, the antifoaming agent is a mixture of polyether dispersions. In another embodiment, the antifoaming agent is an antifoaming agent comprising polyethylene glycol monostearate or simethicone. In another embodiment, the antifoaming agent is an ethoxylated and propoxylated $C_{16}$-$C_{18}$ alcohol-based agent or an ethoxylated and propoxylated $C_{16}$-$C_{18}$ alcohol-based antifoaming agent. In some embodiments, the extractant is a mixture of said agents or antifoaming agents and/or non-ionic ethoxylated surfactants.

In preferred embodiments of the present methods, the non-ionic surfactant is a nonionic ethoxylated surfactant such as an antifoaming agent comprising or consisting of an ethoxylated and propoxylated $C_{16}$-$C_{18}$ alcohol-based agent or an ethoxylated and propoxylated $C_{16}$-$C_{18}$ alcohol-based antifoaming agent. For example, $C_{16}$-$C_{18}$ alkyl alcohol ethoxylate propoxylate (CAS number 68002-96-0), Agnique BP420 (CAS number 68002-96-0), a polyethylene polypropylene glycol, antifoam 204, a surfactant comprising polyethylene glycol monostearate and fatty alcohol alkoxylates, in particular the fatty alcohol alkoxylates described below, have been found particularly advantageous. Thus in one embodiment the antifoaming agent is $C_{16}$-$C_{18}$ alkyl alcohol ethoxylate propoxylate (CAS number 68002-96-0).

In another embodiment of the present methods, the non-ionic surfactant is a non-ionic ethoxylated surfactant such as an antifoaming agent comprising or consisting of a polyethylene polypropylene glycol. For example, the antifoaming agent is Kolliphor® P407 (CAS number 9003-11-6).

In another embodiment of the present methods, the non-ionic surfactant is a non-ionic ethoxylated surfactant such as an antifoaming agent comprising or consisting of a mixture of polyether dispersions. For example, the antifoaming agent is Antifoam 204 from Sigma Aldrich (product number Δ6426 or Δ8311).

In another embodiment of the present methods, the non-ionic surfactant is a non-ionic ethoxylated surfactant such as an antifoaming agent comprising or consisting of an antifoaming agent comprising polyethylene glycol monostearate or simethicone (CAS number 8050-81-5), preferably simethicone.

In another embodiment of the present methods, the non-ionic surfactant is a non-ionic ethoxylated surfactant such as Agnique BP420 (CAS number 68002-96-0).

In another embodiment of the present methods, the non-ionic surfactant is a non-ionic ethoxylated surfactant such as antifoam 204.

In some embodiments of the present methods, the non-ionic ethoxylated surfactant is a fatty alcohol alkoxylate, preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574.

In one embodiment, the extractant is Plurafac® LF300 (CAS number 196823-11-7). In another embodiment, the extractant is Plurafac® LF1300 (68002-96-0). In another embodiment, the extractant is Plurafac® SLF180 (CAS number 196823-11-7). In another embodiment, the extractant is Dehypon® 2574 (CAS number 68154-97-2). In another embodiment, the extractant is Imbentin SG/251 (CAS number 68002-96-0).

The inventors have found that the above non-ionic surfactants, in particular the above non-ionic ethoxylated surfactants, some of which are routinely for foam management in fermentations, when added in an amount equal to or greater than their cloud concentration in an aqueous solution, i.e. an amount higher than required for foam management, result in increased titer, increased secretion and facilitate recovery of the hydrophobic compound produced in the fermentation. The cloud concentration of a surfactant is the concentration of surfactant at which, when it is mixed in an aqueous solution, the mixture starts to phase-separate, and two phases appear, thus the mixture becomes cloudy.

In order to determine the cloud concentration of a surfactant, and hence determine the minimal amount of surfactant to use in the present methods, the person of skill in the art will know how to perform a dosage curve, where the surfactant is added to a solution, preferably an aqueous solution, at a given temperature, to determine the concentration of surfactant at which the appearance of two phases in the mixture is observed. The cloud concentration may be determined at room temperature, i.e. between 18 and 25° C., for example at 19° C., 20° C., 21° C., 22° C., 23° C. or 24° C., or at a temperature suitable for the envisaged fermentation process, e.g. 30° C. or 37° C. The temperature of the fermentation broth may be adjusted after fermentation in order to enhance the phase separation as described herein. Example 7 describes one way to determine the cloud concentration of a surfactant.

In some embodiments, the non-ionic surfactant, or the non-ionic ethoxylated surfactant, is added in an amount greater than its cloud concentration measured in an aqueous solution. In some embodiments, the ethoxylated surfactant, such as the fatty alcohol alkoxylate or the polyethoxylated surfactant, is added in an amount greater than its cloud concentration measured in an aqueous solution. The cloud concentration may be determined at room temperature, or at the cultivation temperature.

In some embodiments, the culture medium comprises the extractant, i.e. the non-ionic surfactant, in particular the non-ionic ethoxylated surfactant, in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more, where the cloud concentration preferably is measured in an aqueous solution, for example at room temperature or at the cultivation temperature.

The extractant is preferably a fatty alcohol alkoxylate or an ethoxylated surfactant, such as a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

In some embodiments, the culture medium comprises the extractant, i.e. a non-ionic ethoxylated surfactant such as a fatty alcohol alkoxylate or a polyethoxylated surfactant selected from: Agnique BP420 (CAS number 68002-96-0), antifoam 204, a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more, where the cloud concentration preferably is measured in an aqueous solution, for example at room temperature or at the cultivation temperature.

In some embodiments, the culture medium comprises the extractant, i.e. a non-ionic ethoxylated surfactant such as a fatty alcohol alkoxylate selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more, where the cloud concentration preferably is measured in an aqueous solution, for example at room temperature or at the cultivation temperature.

In other embodiments, the culture medium comprises the extractant, i.e. the non-ionic surfactant, in particular the non-ionic ethoxylated surfactant such as a fatty alcohol alkoxylate or the polyethoxylated surfactant, in an amount at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration, where the cloud concentration preferably is measured in an aqueous solution, for example at room temperature or at the cultivation temperature.

In other embodiments, the culture medium comprises the extractant, i.e. a non-ionic ethoxylated surfactant such as a fatty alcohol alkoxylate selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, in an amount at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration, where the cloud concentration preferably is measured in an aqueous solution, for example at room temperature or at the cultivation temperature.

In some embodiments, the culture medium comprises the extractant, i.e. the non-ionic ethoxylated surfactant such as a fatty alcohol alkoxylate or a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, in an amount at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration, where the cloud concentration preferably is measured in an aqueous solution, for example at room temperature or at the cultivation temperature.

In some embodiments, the culture medium comprises the extractant, i.e. the non-ionic ethoxylated surfactant such as a fatty alcohol alkoxylate selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, in an amount at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration, where the cloud concentration preferably is measured in an aqueous solution, for example at room temperature or at the cultivation temperature.

In some embodiments, the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant, wherein the extractant is a non-ionic surfactant. In some embodiments, the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant, wherein the extractant is a non-ionic ethoxylated surfactant such as a fatty alcohol alkoxylate such as a fatty alcohol alkoxylate selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, or a polyethoxylated surfactant, such as selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

In some embodiments, the non-ionic surfactant is a non-ionic ethoxylated surfactant, in particular an antifoaming agent comprising or consisting of an ethoxylated and propoxylated $C_{16}$-$C_{18}$ alcohol-based agent or an ethoxylated and propoxylated $C_{16}$-$C_{18}$ alcohol-based antifoaming agent, for example, $C_{16}$-$C_{18}$ alkyl alcohol ethoxylate propoxylate (CAS number 68002-96-0). The cloud concentration of $C_{16}$-$C_{18}$ alkyl alcohol ethoxylate propoxylate (CAS number 68002-96-0) is about 1% vol/vol at room temperature. Accordingly, when this antifoaming agent is used, the culture medium preferably comprises at least 1% vol/vol of $C_{16}$-$C_{18}$ alkyl alcohol ethoxylate propoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol $C_{16}$-$C_{18}$ alkyl alcohol ethoxylate propoxylate, or more.

In some embodiments, the non-ionic surfactant is a non-ionic ethoxylated surfactant, in particular an antifoaming agent comprising or consisting of a polyethylene polypropylene glycol, for example Kolliphor® P407 (CAS number 9003-11-6), also termed poly(ethylene glycol)-block-poly (propylene glycol)-block-poly(ethylene glycol). The cloud concentration of Kolliphor® P407 is 10% at a temperature above 100° C. Accordingly, when a polyethylene polypropylene glycol such as Kolliphor® P407 is used, the culture medium preferably comprises at least 10% vol/vol of polyethylene polypropylene glycol such as Kolliphor® P407, such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Kolliphor® P407, or more.

In some embodiments, the non-ionic surfactant is a non-ionic ethoxylated surfactant, in particular an antifoaming agent comprising or consisting of a mixture of polyether dispersions, such as antifoam 204 (product number Δ6426 or Δ8311 from Sigma Aldrich). The cloud concentration of antifoam 204 is 1% in an aqueous solution at a temperature of 18.0 to 21.0° C. Accordingly, when a mixture of polyether dispersions such as antifoam 204 is used, the culture medium preferably comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of polyether dispersions such as antifoam 204, or more.

In some embodiments, the non-ionic surfactant is a non-ionic ethoxylated surfactant, in particular an antifoaming agent comprising or consisting of an antifoaming agent comprising polyethylene glycol monostearate or simethicone. Simethicone comprises polyethylene glycol monostearate, which, without being bound by theory, appears to be the compound important for the ability of simethicone to act as an extractant. Polyethylene glycol monostearate has a cloud point of 1% in an aqueous solution at 5° C. Accordingly, when simethicone or a surfactant comprising polyethylene glycol monostearate is used as antifoaming agent, the culture medium preferably comprises at least 1% vol/vol of polyethylene glycol monostearate or simethicone, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol polyethylene glycol monostearate or simethicone, or more.

In some embodiments, the non-ionic surfactant is a non-ionic ethoxylated surfactant, in particular Agnique BP420 (CAS number 68002-96-0). Agnique BP420 (CAS number 68002-96-0) has a cloud point of 1% in an aqueous solution at room temperature. Accordingly, when Agnique BP420 (CAS number 68002-96-0) is used as antifoaming agent, the culture medium preferably comprises at least 1% vol/vol of Agnique BP420 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Agnique BP420 (CAS number 68002-96-0).

In some embodiments, the non-ionic surfactant is a non-ionic ethoxylated surfactant, in particular a fatty alcohol alkoxylate such as Plurafac® LF300 (CAS number 196823-11-7). The cloud concentration of Plurafac® LF300 (CAS number 196823-11-7) is about 1% vol/vol at room temperature. Accordingly, when Plurafac® LF300 (CAS number 196823-11-7) is used, the culture medium preferably comprises at least 1% vol/vol of Plurafac® LF300 (CAS number 196823-11-7), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Plurafac® LF300 (CAS number 196823-11-7), or more.

In some embodiments, the non-ionic surfactant is a non-ionic ethoxylated surfactant, in particular a fatty alcohol alkoxylate such as Plurafac® LF1300 (68002-96-0). The cloud concentration of Plurafac® LF1300 (68002-96-0) is about 1% vol/vol at room temperature. Accordingly, when Plurafac® LF1300 (68002-96-0) is used, the culture medium preferably comprises at least 1% vol/vol of Plurafac® LF1300 (68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Plurafac® LF1300 (68002-96-0), or more.

In some embodiments, the non-ionic surfactant is a non-ionic ethoxylated surfactant, in particular a fatty alcohol alkoxylate such as Plurafac® SLF180 (CAS number 196823-11-7). The cloud concentration of Plurafac® SLF180 (CAS number 196823-11-7) is about 1% vol/vol at room temperature. Accordingly, when Plurafac® SLF180 (CAS number 196823-11-7) is used, the culture medium preferably comprises at least 1% vol/vol of Plurafac® SLF180 (CAS number 196823-11-7), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Plurafac® SLF180 (CAS number 196823-11-7), or more.

In some embodiments, the non-ionic surfactant is a non-ionic ethoxylated surfactant, in particular a fatty alcohol alkoxylate such as Dehypon® 2574 (CAS number 68154-97-2). The cloud concentration of Dehypon® 2574 (CAS number 68154-97-2) is about 1% vol/vol at room temperature. Accordingly, when Dehypon® 2574 (CAS number 68154-97-2) is used, the culture medium preferably comprises at least 1% vol/vol of Dehypon® 2574 (CAS number 68154-97-2), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Dehypon® 2574 (CAS number 68154-97-2), or more.

In some embodiments, the non-ionic surfactant is a non-ionic ethoxylated surfactant, in particular a fatty alcohol alkoxylate such as Imbentin SG/251 (CAS number 68002-96-0). The cloud concentration of Imbentin SG/251 (CAS number 68002-96-0) is about 1% vol/vol at room temperature. Accordingly, when Imbentin SG/251 (CAS number 68002-96-0) is used, the culture medium preferably comprises at least 1% vol/vol of Imbentin SG/251 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Imbentin SG/251 (CAS number 68002-96-0), or more.

Hydrophobic Compound

The herein disclosed methods are useful for facilitating recovery of a hydrophobic compound from a fermentation broth, for increasing the titer of the hydrophobic compound in the fermentation and for increasing secretion of the hydrophobic compound from the producing microorganism.

The hydrophobic compound may be any hydrophobic compound produced by the microorganism in the fermentation. The microorganism is in preferred embodiments a yeast cell. In particular, the hydrophobic compound may be selected from: a fatty alcohol, a fatty alcohol ester, a fatty acyl acetate, a fatty aldehyde and a terpene such as a terpenoid. The hydrophobic compound may be several hydrophobic compounds, for example a mixture of one or more of at least one fatty alcohol, at least one fatty acyl acetate, at least one fatty aldehyde and at least one terpene such as at least one terpenoid. In some embodiments the hydrophobic compound is a mixture of one or more fatty alcohols, one or more fatty acyl acetates and/or one or more fatty aldehydes. In some embodiments the hydrophobic compound is a mixture of one or more terpenes, such as a mixture of one ore more terpenoids or a mixture of one or more terpenes and one or more terpenoids.

The present methods are particularly useful for producing and recovering hydrophobic compounds which are pheromones, in particular insect pheromones.

Fatty Alcohols

The fatty alcohol may be a saturated fatty alcohol, a desaturated fatty alcohol or a mixture thereof. In one embodiment, the fatty alcohol has a chain length of 8. In another embodiment, the fatty alcohol has a chain length of 9. In another embodiment, the fatty alcohol has a chain length of 10. In another embodiment, the fatty alcohol has a chain length of 11. In another embodiment, the fatty alcohol has a chain length of 12. In another embodiment, the fatty alcohol has a chain length of 13. In another embodiment, the fatty alcohol has a chain length of 14. In another embodiment, the fatty alcohol has a chain length of 15. In another embodiment, the fatty alcohol has a chain length of 16. In another embodiment, the fatty alcohol has a chain length of 17. In another embodiment, the fatty alcohol has a chain length of 18. In another embodiment, the fatty alcohol has a chain length of 19. In another embodiment, the fatty alcohol has a chain length of 20. In another embodiment, the fatty alcohol has a chain length of 21. In another embodiment, the fatty alcohol has a chain length of 22.

In some embodiments, the fatty alcohol is a desaturated fatty alcohol. Such compounds are naturally produced e.g. by insect cells, where they act as pheromones. The desaturated fatty alcohols may be:

- (Z)-Δ3 desaturated fatty alcohols having a carbon chain length of 8, 9, 10, 11, 12, 13, 14, 15, 16, 17, 18, 19, 20, 21 or 22;
- (E)-Δ3 desaturated fatty alcohols having a carbon chain length of 8, 9, 10, 11, 12, 13, 14, 15, 16, 17, 18, 19, 20, 21 or 22;
- (Z)-Δ5 desaturated fatty alcohols having a carbon chain length of 8, 9, 10, 11, 12, 13, 14, 15, 16, 17, 18, 19, 20, 21 or 22;
- (E)-Δ5 desaturated fatty alcohols having a carbon chain length of 8, 9, 10, 11, 12, 13, 14, 15, 16, 17, 18, 19, 20, 21 or 22;
- (Z)-Δ6 desaturated fatty alcohols having a carbon chain length of 8, 9, 10, 11, 12, 13, 14, 15, 16, 17, 18, 19, 20, 21 or 22;
- (E)-Δ6 desaturated fatty alcohols having a carbon chain length of 8, 9, 10, 11, 12, 13, 14, 15, 16, 17, 18, 19, 20, 21 or 22;
- (Z)-Δ7 desaturated fatty alcohols having a carbon chain length of 8, 9, 10, 11, 12, 13, 14, 15, 16, 17, 18, 19, 20, 21 or 22;
- (E)-Δ7 desaturated fatty alcohols having a carbon chain length of 8, 9, 10, 11, 12, 13, 14, 15, 16, 17, 18, 19, 20, 21 or 22;
- (Z)-Δ8 desaturated fatty alcohols having a carbon chain length of 9, 10, 11, 12, 13, 14, 15, 16, 17, 18, 19, 20, 21 or 22;

(E)-Δ8 desaturated fatty alcohols having a carbon chain length of 9, 10, 11, 12, 13, 14, 15, 16, 17, 18, 19, 20, 21 or 22;
(Z)-Δ9 desaturated fatty alcohols having a carbon chain length of 10, 11, 12, 13, 14, 15, 16, 17, 18, 19, 20, 21 or 22;
(E)-Δ9 desaturated fatty alcohols having a carbon chain length of 10, 11, 12, 13, 14, 15, 16, 17, 18, 19, 20, 21 or 22;
(Z)-Δ10 desaturated fatty alcohols having a carbon chain length of 11, 12, 13, 14, 15, 16, 17, 18, 19, 20, 21 or 22;
(E)-Δ10 desaturated fatty alcohols having a carbon chain length of 11, 12, 13, 14, 15, 16, 17, 18, 19, 20, 21 or 22;
(Z)-Δ11 desaturated fatty alcohols having a carbon chain length of 12, 13, 14, 15, 16, 17, 18, 19, 20, 21 or 22;
(E)-Δ11 desaturated fatty alcohols having a carbon chain length of 12, 13, 14, 15, 16, 17, 18, 19, 20, 21 or 22;
(Z)-Δ12 desaturated fatty alcohols having a carbon chain length of 13, 14, 15, 16, 17, 18, 19, 20, 21 or 22;
(E)-Δ12 desaturated fatty alcohols having a carbon chain length of 13, 14, 15, 16, 17, 18, 19, 20, 21 or 22;
(Z)-Δ13 desaturated fatty alcohols having a carbon chain length of 14, 15, 16, 17, 18, 19, 20, 21 or 22; and
(E)-Δ13 desaturated fatty alcohols having a carbon chain length of 14, 15, 16, 17, 18, 19, 20, 21 or 22.

In some embodiments, the fatty alcohols are desaturated fatty alcohols having a carbon chain length of 14, such as:

(Z)-Δ5 desaturated fatty alcohols having a carbon chain length of 14;
(E)-Δ5 desaturated fatty alcohols having a carbon chain length of 14;
(Z)-Δ6 desaturated fatty alcohols having a carbon chain length of 14;
(E)-Δ6 desaturated fatty alcohols having a carbon chain length of 14;
(Z)-Δ7 desaturated fatty alcohols having a carbon chain length of 14;
(E)-Δ7 desaturated fatty alcohols having a carbon chain length of 14;
(Z)-Δ8 desaturated fatty alcohols having a carbon chain length of 14;
(E)-Δ8 desaturated fatty alcohols having a carbon chain length of 14;
(Z)-Δ9 desaturated fatty alcohols having a carbon chain length of 14;
(E)-Δ9 desaturated fatty alcohols having a carbon chain length of 14;
(Z)-Δ10 desaturated fatty alcohols having a carbon chain length of 14;
(E)-Δ10 desaturated fatty alcohols having a carbon chain length of 14;
(Z)-Δ11 desaturated fatty alcohols having a carbon chain length of 14;
(E)-Δ11 desaturated fatty alcohols having a carbon chain length of 14;
(Z)-Δ12 desaturated fatty alcohols having a carbon chain length of 14;
(E)-Δ12 desaturated fatty alcohols having a carbon chain length of 14;
(Z)-Δ13 desaturated fatty alcohols having a carbon chain length of 14; and
(E)-Δ13 desaturated fatty alcohols having a carbon chain length of 14.

In some embodiments, the fatty alcohols are desaturated fatty alcohols having a carbon chain length of 16, such as:

(Z)-Δ5 desaturated fatty alcohols having a carbon chain length of 16;

(E)-Δ5 desaturated fatty alcohols having a carbon chain length of 16;
(Z)-Δ6 desaturated fatty alcohols having a carbon chain length of 16;
(E)-Δ6 desaturated fatty alcohols having a carbon chain length of 16;
(Z)-Δ7 desaturated fatty alcohols having a carbon chain length of 16;
(E)-Δ7 desaturated fatty alcohols having a carbon chain length of 16;
(Z)-Δ8 desaturated fatty alcohols having a carbon chain length of 16;
(E)-Δ8 desaturated fatty alcohols having a carbon chain length of 16;
(Z)-Δ9 desaturated fatty alcohols having a carbon chain length of 16;
(E)-Δ9 desaturated fatty alcohols having a carbon chain length of 16;
(Z)-Δ10 desaturated fatty alcohols having a carbon chain length of 16;
(E)-Δ10 desaturated fatty alcohols having a carbon chain length of 16;
(Z)-Δ11 desaturated fatty alcohols having a carbon chain length of 16;
(E)-Δ11 desaturated fatty alcohols having a carbon chain length of 16;
(Z)-Δ12 desaturated fatty alcohols having a carbon chain length of 16;
(E)-Δ12 desaturated fatty alcohols having a carbon chain length of 16;
(Z)-Δ13 desaturated fatty alcohols having a carbon chain length of 16; and
(E)-Δ13 desaturated fatty alcohols having a carbon chain length of 16.

The desaturated fatty alcohols may be desaturated in more than one position. The desaturated fatty alcohols may be desaturated in at least two positions, such as at least three positions, such as four positions.

For example, the fatty alcohol is an (E)7, (Z)9 desaturated fatty alcohol having a carbon chain length of 10, 11, 12, 13, 14, 15, 16, 17, 18, 19, 20, 21 or 22. In some embodiments, the fatty alcohol is an (E)3, (Z)8, (Z)11 desaturated fatty alcohol having a carbon chain length of 12, 13, 14, 15, 16, 17, 18, 19, 20, 21 or 22, for example 14. In some embodiments, the fatty alcohol is a (Z)9, (E)11, (E)13 desaturated fatty alcohol having a carbon chain length of 14, 15, 16, 17, 18, 19, 20, 21 or 22. In other embodiments, the fatty alcohol is an (E)7, (Z)9 desaturated fatty alcohol having a carbon chain length of 14. In other embodiments, the desaturated fatty alcohol is an (E)3, (Z)8, (Z)11 desaturated fatty alcohol having a carbon chain length of 14. In other embodiments, the desaturated fatty alcohol is a (Z)9, (E)11, (E)13 desaturated fatty alcohol having a carbon chain length of 14. For example, the fatty alcohol is an (E)7, (Z)9 desaturated fatty alcohol having a carbon chain length of 12. In other embodiments, the desaturated fatty alcohol is an (E)3, (Z)8, (Z)11 desaturated fatty alcohol having a carbon chain length of 12. In other embodiments, the desaturated fatty alcohol is a (Z)9, (E)11, (E)13 desaturated fatty alcohol having a carbon chain length of 12. In other embodiments, the desaturated fatty alcohol is a (E)8, (E)10 desaturated fatty alcohol having a carbon chain length of 12.

In a particular embodiment, the fatty alcohol is (Z)-11-hexadecen-1-ol or (Z)-9-tetradecen-1-ol.

Fatty Alcohols Esters

The fatty alcohol ester may be a saturated fatty alcohol ester, a desaturated fatty alcohol ester or a mixture thereof.

In one embodiment, the fatty alcohol ester has a chain length of 8. In another embodiment, the fatty alcohol ester has a chain length of 9. In another embodiment, the fatty alcohol ester has a chain length of 10. In another embodiment, the fatty alcohol ester has a chain length of 11. In another embodiment, the fatty alcohol ester has a chain length of 12. In another embodiment, the fatty alcohol ester has a chain length of 13. In another embodiment, the fatty alcohol ester has a chain length of 14. In another embodiment, the fatty alcohol ester has a chain length of 15. In another embodiment, the fatty alcohol ester has a chain length of 16. In another embodiment, the fatty alcohol ester has a chain length of 17. In another embodiment, the fatty alcohol ester has a chain length of 18. In another embodiment, the fatty alcohol ester has a chain length of 19. In another embodiment, the fatty alcohol ester has a chain length of 20. In another embodiment, the fatty alcohol ester has a chain length of 21. In another embodiment, the fatty alcohol ester has a chain length of 22.

In some embodiments, the fatty alcohol ester is a desaturated fatty alcohol ester. Such compounds are naturally produced e.g. by insect cells, where they act as pheromones. The desaturated fatty alcohol esters may be:

- (Z)-Δ3 desaturated fatty alcohol esters having a carbon chain length of 8, 9, 10, 11, 12, 13, 14, 15, 16, 17, 18, 19, 20, 21 or 22;
- (E)-Δ3 desaturated fatty alcohol esters having a carbon chain length of 8, 9, 10, 11, 12, 13, 14, 15, 16, 17, 18, 19, 20, 21 or 22;
- (Z)-Δ5 desaturated fatty alcohol esters having a carbon chain length of 8, 9, 10, 11, 12, 13, 14, 15, 16, 17, 18, 19, 20, 21 or 22;
- (E)-Δ5 desaturated fatty alcohol esters having a carbon chain length of 8, 9, 10, 11, 12, 13, 14, 15, 16, 17, 18, 19, 20, 21 or 22;
- (Z)-Δ6 desaturated fatty alcohol esters having a carbon chain length of 8, 9, 10, 11, 12, 13, 14, 15, 16, 17, 18, 19, 20, 21 or 22;
- (E)-Δ6 desaturated fatty alcohol esters having a carbon chain length of 8, 9, 10, 11, 12, 13, 14, 15, 16, 17, 18, 19, 20, 21 or 22;
- (Z)-Δ7 desaturated fatty alcohol esters having a carbon chain length of 8, 9, 10, 11, 12, 13, 14, 15, 16, 17, 18, 19, 20, 21 or 22;
- (E)-Δ7 desaturated fatty alcohol esters having a carbon chain length of 8, 9, 10, 11, 12, 13, 14, 15, 16, 17, 18, 19, 20, 21 or 22;
- (Z)-Δ8 desaturated fatty alcohol esters having a carbon chain length of 9, 10, 11, 12, 13, 14, 15, 16, 17, 18, 19, 20, 21 or 22;
- (E)-Δ8 desaturated fatty alcohol esters having a carbon chain length of 9, 10, 11, 12, 13, 14, 15, 16, 17, 18, 19, 20, 21 or 22;
- (Z)-Δ9 desaturated fatty alcohol esters having a carbon chain length of 10, 11, 12, 13, 14, 15, 16, 17, 18, 19, 20, 21 or 22;
- (E)-Δ9 desaturated fatty alcohol esters having a carbon chain length of 10, 11, 12, 13, 14, 15, 16, 17, 18, 19, 20, 21 or 22;
- (Z)-Δ10 desaturated fatty alcohol esters having a carbon chain length of 11, 12, 13, 14, 15, 16, 17, 18, 19, 20, 21 or 22;
- (E)-Δ10 desaturated fatty alcohol esters having a carbon chain length of 11, 12, 13, 14, 15, 16, 17, 18, 19, 20, 21 or 22;
- (Z)-Δ11 desaturated fatty alcohol esters having a carbon chain length of 12, 13, 14, 15, 16, 17, 18, 19, 20, 21 or 22;
- (E)-Δ11 desaturated fatty alcohol esters having a carbon chain length of 12, 13, 14, 15, 16, 17, 18, 19, 20, 21 or 22;
- (Z)-Δ12 desaturated fatty alcohol esters having a carbon chain length of 13, 14, 15, 16, 17, 18, 19, 20, 21 or 22;
- (E)-Δ12 desaturated fatty alcohol esters having a carbon chain length of 13, 14, 15, 16, 17, 18, 19, 20, 21 or 22;
- (Z)-Δ13 desaturated fatty alcohol esters having a carbon chain length of 14, 15, 16, 17, 18, 19, 20, 21 or 22; and
- (E)-Δ13 desaturated fatty alcohol esters having a carbon chain length of 14, 15, 16, 17, 18, 19, 20, 21 or 22.

In some embodiments, the fatty alcohol esters are desaturated fatty alcohol esters having a carbon chain length of 14, such as:

- (Z)-Δ5 desaturated fatty alcohol esters having a carbon chain length of 14;
- (E)-Δ5 desaturated fatty alcohol esters having a carbon chain length of 14;
- (Z)-Δ6 desaturated fatty alcohol esters having a carbon chain length of 14;
- (E)-Δ6 desaturated fatty alcohol esters having a carbon chain length of 14;
- (Z)-Δ7 desaturated fatty alcohol esters having a carbon chain length of 14;
- (E)-Δ7 desaturated fatty alcohol esters having a carbon chain length of 14;
- (Z)-Δ8 desaturated fatty alcohol esters having a carbon chain length of 14;
- (E)-Δ8 desaturated fatty alcohol esters having a carbon chain length of 14;
- (Z)-Δ9 desaturated fatty alcohol esters having a carbon chain length of 14;
- (E)-Δ9 desaturated fatty alcohol esters having a carbon chain length of 14;
- (Z)-Δ10 desaturated fatty alcohol esters having a carbon chain length of 14;
- (E)-Δ10 desaturated fatty alcohol esters having a carbon chain length of 14;
- (Z)-Δ11 desaturated fatty alcohol esters having a carbon chain length of 14;
- (E)-Δ11 desaturated fatty alcohol esters having a carbon chain length of 14;
- (Z)-Δ12 desaturated fatty alcohol esters having a carbon chain length of 14;
- (E)-Δ12 desaturated fatty alcohol esters having a carbon chain length of 14;
- (Z)-Δ13 desaturated fatty alcohol esters having a carbon chain length of 14; and
- (E)-Δ13 desaturated fatty alcohol esters having a carbon chain length of 14.

In some embodiments, the fatty alcohol esters are desaturated fatty alcohol esters having a carbon chain length of 16, such as:

- (Z)-Δ5 desaturated fatty alcohol esters having a carbon chain length of 16;
- (E)-Δ5 desaturated fatty alcohol esters having a carbon chain length of 16;
- (Z)-Δ6 desaturated fatty alcohol esters having a carbon chain length of 16;
- (E)-Δ6 desaturated fatty alcohol esters having a carbon chain length of 16;
- (Z)-Δ7 desaturated fatty alcohol esters having a carbon chain length of 16;

(E)-Δ7 desaturated fatty alcohol esters having a carbon chain length of 16;
(Z)-Δ8 desaturated fatty alcohol esters having a carbon chain length of 16;
(E)-Δ8 desaturated fatty alcohol esters having a carbon chain length of 16;
(Z)-Δ9 desaturated fatty alcohol esters having a carbon chain length of 16;
(E)-Δ9 desaturated fatty alcohol esters having a carbon chain length of 16;
(Z)-Δ10 desaturated fatty alcohol esters having a carbon chain length of 16;
(E)-Δ10 desaturated fatty alcohol esters having a carbon chain length of 16;
(Z)-Δ11 desaturated fatty alcohol esters having a carbon chain length of 16;
(E)-Δ11 desaturated fatty alcohol esters having a carbon chain length of 16;
(Z)-Δ12 desaturated fatty alcohol esters having a carbon chain length of 16;
(E)-Δ12 desaturated fatty alcohol esters having a carbon chain length of 16;
(Z)-Δ13 desaturated fatty alcohol esters having a carbon chain length of 16; and
(E)-Δ13 desaturated fatty alcohol esters having a carbon chain length of 16.

The desaturated fatty alcohol esters may be desaturated in more than one position. The desaturated fatty alcohol esters may be desaturated in at least two positions, such as at least three positions, such as four positions.

For example, the fatty alcohol ester is an (E)7, (Z)9 desaturated fatty alcohol ester having a carbon chain length of 10, 11, 12, 13, 14, 15, 16, 17, 18, 19, 20, 21 or 22. In some embodiments, the fatty alcohol ester is an (E)3, (Z)8, (Z)11 desaturated fatty alcohol ester having a carbon chain length of 12, 13, 14, 15, 16, 17, 18, 19, 20, 21 or 22, for example 14. In some embodiments, the fatty alcohol ester is a (Z)9, (E)11, (E)13 desaturated fatty alcohol ester having a carbon chain length of 14, 15, 16, 17, 18, 19, 20, 21 or 22. In other embodiments, the fatty alcohol ester is an (E)7, (Z)9 desaturated fatty alcohol ester having a carbon chain length of 14. In other embodiments, the desaturated fatty alcohol ester is an (E)3, (Z)8, (Z)11 desaturated fatty alcohol ester having a carbon chain length of 14. In other embodiments, the desaturated fatty alcohol ester is a (Z)9, (E)11, (E)13 desaturated fatty alcohol ester having a carbon chain length of 14. For example, the fatty alcohol ester is an (E)7, (Z)9 desaturated fatty alcohol ester having a carbon chain length of 12. In other embodiments, the desaturated fatty alcohol ester is an (E)3, (Z)8, (Z)11 desaturated fatty alcohol ester having a carbon chain length of 12. In other embodiments, the desaturated fatty alcohol ester is a (Z)9, (E)11, (E)13 desaturated fatty alcohol ester having a carbon chain length of 12. In other embodiments, the desaturated fatty alcohol ester is a (E)8, (E)10 desaturated fatty alcohol ester having a carbon chain length of 12.

In a particular embodiment, the fatty alcohol ester is (Z)-11-hexadecen-1-ol ester or (Z)-9-tetradecen-1-ol ester.

The fatty alcohol ester may be a fatty alcohol acetate ester.

Fatty Acyl Acetates

The fatty acyl acetates may be saturated fatty acyl acetates or desaturated fatty acyl acetates or a mixture thereof. Fatty acyl acetates, in particular desaturated fatty acyl acetates, are also naturally comprised within pheromones, in particular pheromones produced by species belonging to the Lepidoptera order.

In one embodiment, the fatty acyl acetate has a chain length of 8. In another embodiment, the fatty acyl acetate has a chain length of 9. In another embodiment, the fatty acyl acetate has a chain length of 10. In another embodiment, the fatty acyl acetate has a chain length of 11. In another embodiment, the fatty acyl acetate has a chain length of 12. In another embodiment, the fatty acyl acetate has a chain length of 13. In another embodiment, the fatty acyl acetate has a chain length of 14. In another embodiment, the fatty acyl acetate has a chain length of 15. In another embodiment, the fatty acyl acetate has a chain length of 16. In another embodiment, the fatty acyl acetate has a chain length of 17. In another embodiment, the fatty acyl acetate has a chain length of 18. In another embodiment, the fatty acyl acetate has a chain length of 19. In another embodiment, the fatty acyl acetate has a chain length of 20. In another embodiment, the fatty acyl acetate has a chain length of 21. In another embodiment, the fatty acyl acetate has a chain length of 22.

In some embodiments, the fatty acyl acetate is a desaturated fatty acyl acetate. The desaturated fatty acyl acetate may be a desaturated fatty acyl acetate having a carbon chain length of 8, 9, 10, 11, 12, 13, 14, 15, 16, 17, 18, 19, 20, 21 or 22, such as:
(Z)-Δ3 desaturated fatty alcohols having a carbon chain length of 8, 9, 10, 11, 12, 13, 14, 15, 16, 17, 18, 19, 20, 21 or 22;
(E)-Δ3 desaturated fatty alcohols having a carbon chain length of 8, 9, 10, 11, 12, 13, 14, 15, 16, 17, 18, 19, 20, 21 or 22;
(Z)-Δ5 desaturated fatty acyl acetates having a carbon chain length of 8, 9, 10, 11, 12, 13, 14, 15, 16, 17, 18, 19, 20, 21 or 22;
(E)-Δ5 desaturated fatty acyl acetates having a carbon chain length of 8, 9, 10, 11, 12, 13, 14, 15, 16, 17, 18, 19, 20, 21 or 22;
(Z)-Δ6 desaturated fatty acyl acetates having a carbon chain length of 8, 9, 10, 11, 12, 13, 14, 15, 16, 17, 18, 19, 20, 21 or 22;
(E)-Δ6 desaturated fatty acyl acetates having a carbon chain length of 8, 9, 10, 11, 12, 13, 14, 15, 16, 17, 18, 19, 20, 21 or 22;
(Z)-Δ7 desaturated fatty acyl acetates having a carbon chain length of 8, 9, 10, 11, 12, 13, 14, 15, 16, 17, 18, 19, 20, 21 or 22;
(E)-Δ7 desaturated fatty acyl acetates having a carbon chain length of 8, 9, 10, 11, 12, 13, 14, 15, 16, 17, 18, 19, 20, 21 or 22;
(Z)-Δ8 desaturated fatty acyl acetates having a carbon chain length of 9, 10, 11, 12, 13, 14, 15, 16, 17, 18, 19, 20, 21 or 22;
(E)-Δ8 desaturated fatty acyl acetates having a carbon chain length of 9, 10, 11, 12, 13, 14, 15, 16, 17, 18, 19, 20, 21 or 22;
(Z)-Δ9 desaturated fatty acyl acetates having a carbon chain length of 10, 11, 12, 13, 14, 15, 16, 17, 18, 19, 20, 21 or 22;
(E)-Δ9 desaturated fatty acyl acetates having a carbon chain length of 10, 11, 12, 13, 14, 15, 16, 17, 18, 19, 20, 21 or 22;
(Z)-Δ10 desaturated fatty acyl acetates having a carbon chain length of 11, 12, 13, 14, 15, 16, 17, 18, 19, 20, 21 or 22;
(E)-Δ10 desaturated fatty acyl acetates having a carbon chain length of 11, 12, 13, 14, 15, 16, 17, 18, 19, 20, 21 or 22;

(Z)-Δ11 desaturated fatty acyl acetates having a carbon chain length of 12, 13, 14, 15, 16, 17, 18, 19, 20, 21 or 22;

(E)-Δ11 desaturated fatty acyl acetates having a carbon chain length of 12, 13, 14, 15, 16, 17, 18, 19, 20, 21 or 22;

(Z)-Δ12 desaturated fatty acyl acetates having a carbon chain length of 13, 14, 15, 16, 17, 18, 19, 20, 21 or 22;

(E)-Δ12 desaturated fatty acyl acetates having a carbon chain length of 13, 14, 15, 16, 17, 18, 19, 20, 21 or 22;

(Z)-Δ13 desaturated fatty acyl acetates having a carbon chain length of 14, 15, 16, 17, 18, 19, 20, 21 or 22; and (E)-Δ13 desaturated fatty acyl acetates having a carbon chain length of 14, 15, 16, 17, 18, 19, 20, 21 or 22.

In some embodiments, the fatty acyl acetates are desaturated fatty acyl acetates having a carbon chain length of 14, such as:

(Z)-Δ5 desaturated fatty acyl acetates having a carbon chain length of 14;

(E)-Δ5 desaturated fatty acyl acetates having a carbon chain length of 14;

(Z)-Δ6 desaturated fatty acyl acetates having a carbon chain length of 14;

(E)-Δ6 desaturated fatty acyl acetates having a carbon chain length of 14;

(Z)-Δ7 desaturated fatty acyl acetates having a carbon chain length of 14;

(E)-Δ7 desaturated fatty acyl acetates having a carbon chain length of 14;

(Z)-Δ8 desaturated fatty acyl acetates having a carbon chain length of 14;

(E)-Δ8 desaturated fatty acyl acetates having a carbon chain length of 14;

(Z)-Δ9 desaturated fatty acyl acetates having a carbon chain length of 14;

(E)-Δ9 desaturated fatty acyl acetates having a carbon chain length of 14;

(Z)-Δ10 desaturated fatty acyl acetates having a carbon chain length of 14;

(E)-Δ10 desaturated fatty acyl acetates having a carbon chain length of 14;

(Z)-Δ11 desaturated fatty acyl acetates having a carbon chain length of 14;

(E)-Δ11 desaturated fatty acyl acetates having a carbon chain length of 14;

(Z)-Δ12 desaturated fatty acyl acetates having a carbon chain length of 14;

(E)-Δ12 desaturated fatty acyl acetates having a carbon chain length of 14;

(Z)-Δ13 desaturated fatty acyl acetates having a carbon chain length of 14; and (E)-Δ13 desaturated fatty acyl acetates having a carbon chain length of 14.

In some embodiments, the fatty acyl acetates are desaturated fatty acyl acetates having a carbon chain length of 16, such as:

(Z)-Δ5 desaturated fatty acyl acetates having a carbon chain length of 16;

(E)-Δ5 desaturated fatty acyl acetates having a carbon chain length of 16;

(Z)-Δ6 desaturated fatty acyl acetates having a carbon chain length of 16;

(E)-Δ6 desaturated fatty acyl acetates having a carbon chain length of 16;

(Z)-Δ7 desaturated fatty acyl acetates having a carbon chain length of 16;

(E)-Δ7 desaturated fatty acyl acetates having a carbon chain length of 16;

(Z)-Δ8 desaturated fatty acyl acetates having a carbon chain length of 16;

(E)-Δ8 desaturated fatty acyl acetates having a carbon chain length of 16;

(Z)-Δ9 desaturated fatty acyl acetates having a carbon chain length of 16;

(E)-Δ9 desaturated fatty acyl acetates having a carbon chain length of 16;

(Z)-Δ10 desaturated fatty acyl acetates having a carbon chain length of 16;

(E)-Δ10 desaturated fatty acyl acetates having a carbon chain length of 16;

(Z)-Δ11 desaturated fatty acyl acetates having a carbon chain length of 16;

(E)-Δ11 desaturated fatty acyl acetates having a carbon chain length of 16;

(Z)-Δ12 desaturated fatty acyl acetates having a carbon chain length of 16;

(E)-Δ12 desaturated fatty acyl acetates having a carbon chain length of 16;

(Z)-Δ13 desaturated fatty acyl acetates having a carbon chain length of 16; and (E)-Δ13 desaturated fatty acyl acetates having a carbon chain length of 16.

The desaturated fatty acyl acetates may be desaturated in more than one position. The desaturated fatty acyl acetates may be desaturated in at least two positions, such as at least three positions, such as four positions.

For example, the fatty acyl acetate is an (E)7, (Z)9 desaturated fatty acyl acetate having a carbon chain length of 10, 11, 12, 13, 14, 15, 16, 17, 18, 19, 20, 21 or 22. In some embodiments, the fatty acyl acetate is an (E)3, (Z)8, (Z)11 desaturated fatty acyl acetate having a carbon chain length of 12, 13, 14, 15, 16, 17, 18, 19, 20, 21 or 22. In some embodiments, the fatty acyl acetate is an (Z)9, (E)11, (E)13 desaturated fatty acyl acetate having a carbon chain length of 14, 15, 16, 17, 18, 19, 20, 21 or 22. In other embodiments, the fatty acyl acetate is an (E)7, (Z)9 desaturated fatty acyl acetate having a carbon chain length of 14. In some embodiments, the fatty acyl acetate is an (E)3, (Z)8, (Z)11 desaturated fatty acyl acetate having a carbon chain length of 14. In some embodiments, the fatty acyl acetate is a (Z)9, (E)11, (E)13 desaturated fatty acyl acetate having a carbon chain length of 14. In other embodiments, the fatty acyl acetate is an (E)7, (Z)9 desaturated fatty acyl acetate having a carbon chain length of 12. In some embodiments, the fatty acyl acetate is an (E)3, (Z)8, (Z)11 desaturated fatty acyl acetate having a carbon chain length of 12.

In a particular embodiment, the fatty acyl acetate is (Z)-11-hexadecen-1-yl acetate or (Z)-9-tetradecen-1-yl acetate.

The fatty acyl acetates may be produced by the microorganism in the fermentation, e.g. where the microorganism is capable of converting a fatty alcohol to the corresponding fatty acyl acetate, or they may be obtained by chemical conversion as is known in the art.

Fatty Aldehydes

The fatty aldehydes may be saturated fatty aldehydes or desaturated fatty aldehydes or a mixture thereof. Fatty aldehydes, in particular desaturated fatty aldehydes, are also naturally comprised within pheromones, in particular insect pheromones.

In one embodiment, the fatty aldehyde has a chain length of 8. In another embodiment, the fatty aldehyde has a chain length of 9. In another embodiment, the fatty aldehyde has a chain length of 10. In another embodiment, the fatty aldehyde has a chain length of 11. In another embodiment, the fatty aldehyde has a chain length of 12. In another embodiment, the fatty aldehyde has a chain length of 13. In another embodiment, the fatty aldehyde has a chain length of 14. In another embodiment, the fatty aldehyde has a chain length of 15. In another embodiment, the fatty aldehyde has a chain length of 16. In another embodiment, the fatty aldehyde has a chain length of 17. In another embodiment, the fatty aldehyde has a chain length of 18. In another embodiment, the fatty aldehyde has a chain length of 19. In another embodiment, the fatty aldehyde has a chain length of 20. In another embodiment, the fatty aldehyde has a chain length of 21. In another embodiment, the fatty aldehyde has a chain length of 22.

In some embodiments, the fatty aldehyde is a desaturated fatty aldehyde. The desaturated fatty aldehyde may have a carbon chain length of 8, 9, 10, 11, 12, 13, 14, 15, 16, 17, 18, 19, 20, 21 or 22, such as:

- (Z)-Δ3 desaturated fatty aldehydes having a carbon chain length of 8, 9, 10, 11, 12, 13, 14, 15, 16, 17, 18, 19, 20, 21 or 22;
- (E)-Δ3 desaturated fatty aldehydes having a carbon chain length of 8, 9, 10, 11, 12, 13, 14, 15, 16, 17, 18, 19, 20, 21 or 22;
- (Z)-Δ5 desaturated fatty aldehydes having a carbon chain length of 8, 9, 10, 11, 12, 13, 14, 15, 16, 17, 18, 19, 20, 21 or 22;
- (E)-Δ5 desaturated fatty aldehydes having a carbon chain length of 8, 9, 10, 11, 12, 13, 14, 15, 16, 17, 18, 19, 20, 21 or 22;
- (Z)-Δ6 desaturated fatty aldehydes having a carbon chain length of 8, 9, 10, 11, 12, 13, 14, 15, 16, 17, 18, 19, 20, 21 or 22;
- (E)-Δ6 desaturated fatty aldehydes having a carbon chain length of 8, 9, 10, 11, 12, 13, 14, 15, 16, 17, 18, 19, 20, 21 or 22;
- (Z)-Δ7 desaturated fatty aldehydes having a carbon chain length of 8, 9, 10, 11, 12, 13, 14, 15, 16, 17, 18, 19, 20, 21 or 22;
- (E)-Δ7 desaturated fatty aldehydes having a carbon chain length of 8, 9, 10, 11, 12, 13, 14, 15, 16, 17, 18, 19, 20, 21 or 22;
- (Z)-Δ8 desaturated fatty aldehydes having a carbon chain length of 9, 10, 11, 12, 13, 14, 15, 16, 17, 18, 19, 20, 21 or 22;
- (E)-Δ8 desaturated fatty aldehydes having a carbon chain length of 9, 10, 11, 12, 13, 14, 15, 16, 17, 18, 19, 20, 21 or 22;
- (Z)-Δ9 desaturated fatty aldehydes having a carbon chain length of 10, 11, 12, 13, 14, 15, 16, 17, 18, 19, 20, 21 or 22;
- (E)-Δ9 desaturated fatty aldehydes having a carbon chain length of 10, 11, 12, 13, 14, 15, 16, 17, 18, 19, 20, 21 or 22;
- (Z)-Δ10 desaturated fatty aldehydes having a carbon chain length of 11, 12, 13, 14, 15, 16, 17, 18, 19, 20, 21 or 22;
- (E)-Δ10 desaturated fatty aldehydes having a carbon chain length of 11, 12, 13, 14, 15, 16, 17, 18, 19, 20, 21 or 22;
- (Z)-Δ11 desaturated fatty aldehydes having a carbon chain length of 12, 13, 14, 15, 16, 17, 18, 19, 20, 21 or 22;
- (E)-Δ11 desaturated fatty aldehydes having a carbon chain length of 12, 13, 14, 15, 16, 17, 18, 19, 20, 21 or 22;
- (Z)-Δ12 desaturated fatty aldehydes having a carbon chain length of 13, 14, 15, 16, 17, 18, 19, 20, 21 or 22;
- (E)-Δ12 desaturated fatty aldehydes having a carbon chain length of 13, 14, 15, 16, 17, 18, 19, 20, 21 or 22;
- (Z)-Δ13 desaturated fatty aldehydes having a carbon chain length of 14, 15, 16, 17, 18, 19, 20, 21 or 22; and
- (E)-Δ13 desaturated fatty aldehydes having a carbon chain length of 14, 15, 16, 17, 18, 19, 20, 21 or 22.

In some embodiments, the fatty aldehydes are desaturated fatty aldehydes having a carbon chain length of 14, such as:

- (Z)-Δ5 desaturated fatty aldehydes having a carbon chain length of 14;
- (E)-Δ5 desaturated fatty aldehydes having a carbon chain length of 14;
- (Z)-Δ6 desaturated fatty aldehydes having a carbon chain length of 14;
- (E)-Δ6 desaturated fatty aldehydes having a carbon chain length of 14;
- (Z)-Δ7 desaturated fatty aldehydes having a carbon chain length of 14;
- (E)-Δ7 desaturated fatty aldehydes having a carbon chain length of 14;
- (Z)-Δ8 desaturated fatty aldehydes having a carbon chain length of 14;
- (E)-Δ8 desaturated fatty aldehydes having a carbon chain length of 14;
- (Z)-Δ9 desaturated fatty aldehydes having a carbon chain length of 14;
- (E)-Δ9 desaturated fatty aldehydes having a carbon chain length of 14;
- (Z)-Δ10 desaturated fatty aldehydes having a carbon chain length of 14;
- (E)-Δ10 desaturated fatty aldehydes having a carbon chain length of 14;
- (Z)-Δ11 desaturated fatty aldehydes having a carbon chain length of 14;
- (E)-Δ11 desaturated fatty aldehydes having a carbon chain length of 14;
- (Z)-Δ12 desaturated fatty aldehydes having a carbon chain length of 14;
- (E)-Δ12 desaturated fatty aldehydes having a carbon chain length of 14;
- (Z)-Δ13 desaturated fatty aldehydes having a carbon chain length of 14; and
- (E)-Δ13 desaturated fatty aldehydes having a carbon chain length of 14.

In some embodiments, the fatty aldehydes are desaturated fatty aldehydes having a carbon chain length of 16, such as:

- (Z)-Δ5 desaturated fatty aldehydes having a carbon chain length of 16;
- (E)-Δ5 desaturated fatty aldehydes having a carbon chain length of 16;
- (Z)-Δ6 desaturated fatty aldehydes having a carbon chain length of 16;
- (E)-Δ6 desaturated fatty aldehydes having a carbon chain length of 16;
- (Z)-Δ7 desaturated fatty aldehydes having a carbon chain length of 16;
- (E)-Δ7 desaturated fatty aldehydes having a carbon chain length of 16;
- (Z)-Δ8 desaturated fatty aldehydes having a carbon chain length of 16;
- (E)-Δ8 desaturated fatty aldehydes having a carbon chain length of 16;
- (Z)-Δ9 desaturated fatty aldehydes having a carbon chain length of 16;

(E)-Δ9 desaturated fatty aldehydes having a carbon chain length of 16;
(Z)-Δ10 desaturated fatty aldehydes having a carbon chain length of 16;
(E)-Δ10 desaturated fatty aldehydes having a carbon chain length of 16;
(Z)-Δ11 desaturated fatty aldehydes having a carbon chain length of 16;
(E)-Δ11 desaturated fatty aldehydes having a carbon chain length of 16;
(Z)-Δ12 desaturated fatty aldehydes having a carbon chain length of 16;
(E)-Δ12 desaturated fatty aldehydes having a carbon chain length of 16;
(Z)-Δ13 desaturated fatty aldehydes having a carbon chain length of 16; and
(E)-Δ13 desaturated fatty aldehydes having a carbon chain length of 16.

The desaturated fatty aldehydes produced may be desaturated in more than one position. The desaturated fatty aldehydes may be desaturated in at least two positions, such as at least three positions, such as four positions.

For example, the fatty aldehyde is an (E)7, (Z)9 desaturated fatty aldehyde having a carbon chain length of 10, 11, 12, 13, 14, 15, 16, 17, 18, 19, 20, 21 or 22, such as 14. In some embodiments, the fatty aldehyde is an (E)3, (Z)8, (Z)11 desaturated fatty aldehyde having a carbon chain length of 14. In some embodiments, the fatty aldehyde is a (Z)9, (E)11, (E)13 desaturated fatty aldehydes having a carbon chain length of 14, 15, 16, 17, 18, 19, 20, 21 or 22, such as 14. In some embodiments, the desaturated fatty aldehyde is an (E)7, (Z)9 desaturated fatty aldehyde having a carbon chain length of 12. In other embodiments, the fatty aldehyde is an (E)3, (Z)8, (Z)11 desaturated fatty aldehydes having a carbon chain length of 12. In some embodiments, the fatty aldehyde is a (Z)9, (E)11, (E)13 desaturated fatty aldehyde having a carbon chain length of 12.

In a particular embodiment, the fatty aldehyde is (Z)-11-hexadecenal.

The fatty aldehydes may be produced by the microorganism in the fermentation, e.g. where the microorganism is capable of converting a fatty alcohol to the corresponding fatty aldehyde, or they may be obtained by chemical conversion as is known in the art.

Terpenes and Terpenoids

Terpenes are naturally produced by plants, and have a number of industrial applications in the field of food, pharmaceutics, cosmetics and biotechnology. They are for example used as part of natural agricultural pesticides. Terpenoids (also termed isoprenoids) are modified terpenes containing additional groups, usually O-containing groups. They are often used for their aromatic qualities and as part of traditional herbal remedies.

In some embodiments of the present methods, the hydrophobic compound is a terpene, such as a hemiterpene, a monoterpene, a sesquiterpene, a disesterterpene, a triterpene, a sesquarterpene, a tetraterpene, or a polyterpene. In some embodiments, the terpene is a monoterpene such as geraniol, terpineol, limonene, myrcene, linalool, pinene or menthol. In some embodiments, the terpene is a sesquiterpene such as humulene, farnesene or farnesol. In some embodiments, the terpene is a triterpene such as squalene. In some embodiments, the terpene is a tetraterpene such as lycopene, and carotenes such as α-carotene, β-carotene and γ-carotene.

In some embodiments the hydrophobic compound is a terpene such as a terpenoid, such as a hemiterpenoid, a monoterpenoid, a sesquiterpenoid, a disesterterpenoid, a triterpenoid, a sesquiterpenoid, a tetraterpenoid or a polyterpenoid. In some embodiments, the terpenoid is a monoterpenoid such as monocyclic monoterpenoids, e.g. menthol, thymol or carvacrol, or bicyclic monoterpenoids, for example camphor, borneol or eucalyptol. In some embodiments, the terpenoid is a sesquiterpenoid such as geosmin, vetivazulene, guaiazulene or farnesol. In some embodiments, the terpenoid is a diterpenoid such as a taxene, retinol or phytol. In some embodiments, the terpenoid is a triterpenoid such as a steroid, for example a sterol or a cucurbitacin. In some embodiments the terpenoid is a tetraterpenoid such as a carotenoid.

Microorganism

The present methods are useful for recovering hydrophobic compounds produced in a fermentation by a microorganism, and/or for increasing the titer of the hydrophobic compound and/or for increasing the secretion of the hydrophobic compound from the microorganism. Preferably, the microorganism is a yeast.

The microorganism may be a bacteria or a eukaryote. In some embodiments, the microorganism is a yeast cell.

In some embodiments, the microorganism or the yeast cell has been modified at the genomic level, e.g. by gene editing in the genome. The cell may also be modified by insertion of at least one nucleic acid construct such as at least one vector. The vector may be designed as is known to the skilled person to either enable integration of nucleic acid sequences in the genome, or to enable expression of a polypeptide encoded by a nucleic acid sequence comprised in the vector without genome integration. In other embodiments, the microorganism is a natural producer of the desired hydrophobic compound, for example a yeast which naturally produces a fatty alcohol, a fatty alcohol ester, a fatty acyl acetate, a fatty aldehyde and a terpene.

In certain embodiments of the disclosure, yeast or fungi of genera including, but not limited to, *Blakeslea, Candida, Cryptococcus, Cunninghamella, Lipomyces, Mortierella, Mucor, Phycomyces, Pythium, Rhodosporidium, Rhodotorula, Trichosporon, Saccharomyces* and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutinis, R. gracilis, R. graminis, R. mucilaginosa, R. pinicola, Trichosporon* pullans, *T. cutaneum, Saccharomyces cerevisiae* and *Yarrowia lipolytica* are used. In preferred embodiments, the microorganism is a yeast, in particular *Yarrowia lipolytica* or *Saccharomyces cerevisiae.*

Several microorganisms, in particular yeast cells, have been described which can produce hydrophobic compounds, in particular fatty alcohols, fatty acyl acetates and fatty aldehydes, which can be formulated in pheromone compositions and used as pest repellants. The present methods can be employed in fermentation processes where such yeast cells are cultivated to produce such compounds and facilitate their recovery, increase their titer and/or increase their secretion from the cell. Such yeast cells and the resulting products are described in detail in e.g. WO 2016/207339, WO 2018/109163, WO 2018/109167, international application PCT/EP2020/053306 and EP application 19218703.7 filed on 20 Dec. 2019 by same applicant and entitled “Yeast cells and methods for production of E8,E10-dodecadienyl coenzyme A, codlemone and derivatives thereof".

In general, yeast cells useful for production of such compounds rely on the expression of several enzymes, particularly heterologous enzymes, for example a desaturase such as a Δ11 desaturase (EC 1.14.19.5), a fatty acyl reductase (FAR) (EC 1.2.1.84), a fatty acyl-CoA synthetase (FAA) (EC 2.3.1.86), an acetyltransferase (EC 2.3.1.84) or an acyl-CoA oxidase (EC 1.3.3.6).

Herein below are described some specific embodiments.

Desaturated Fatty Alcohols

In some embodiments, the microorganism is yeast cell such as an oleaginous yeast cell and the hydrophobic compound is a desaturated fatty alcohol. The yeast cell, for example a *Yarrowia* cell such as a *Yarrowia lipolytica* cell, capable of producing the desaturated fatty alcohol:

- expresses at least one heterologous desaturase capable of introducing at least one double bond in a fatty acyl-CoA; and
- expresses at least one heterologous fatty acyl-CoA reductase, capable of converting at least part of said desaturated fatty acyl-CoA to a desaturated fatty alcohol; and
- has a mutation resulting in reduced activity of Fao1 (SEQ ID NO: 11) and a mutation resulting in reduced activity of at least one of Hfd1 (SEQ ID NO: 12), Hfd4 (SEQ ID NO: 13), Pex10 (SEQ ID NO: 14) and GPAT (SEQ ID NO: 15) or has a mutation resulting in reduced activity of at least one protein having at least 90% homology to Fao1 (SEQ ID NO: 11) and a mutation resulting in reduced activity of at least one of Hfd1 (SEQ ID NO: 12), Hfd4 (SEQ ID NO: 13), Pex10 (SEQ ID NO: 14) and GPAT (SEQ ID NO: 15), such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 11) and at least one of Hfd1 (SEQ ID NO: 12), Hfd4 (SEQ ID NO: 13), Pex10 (SEQ ID NO: 14) and GPAT (SEQ ID NO: 15).

Throughout the present disclosure, it will be understood that mutations resulting in reduced activity of a protein or enzyme are preferably mutations in the genes encoding said protein or enzyme. The mutation is preferably in the promoter of the gene, or in the coding sequence of the gene, or both.

The desaturase is preferably selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase, a Δ13 desaturase and a Δ14 desaturase, preferably wherein the desaturase is derived from an insect, such as from the Lepidoptera order, preferably the desaturase is a Δ11 desaturase having at least 60% homology to the Δ11 desaturase from *Amyelois transitella* as set forth in SEQ ID NO: 1 or a Δ9 desaturase having at least 60% homology to the Δ9 desaturase from *Drosophila melanogaster* as set forth in SEQ ID NO: 16. In some embodiments, the fatty acyl reductase is selected from:

i) a FAR having at least 80% homology to the FAR from *Helicoverpa armigera* as set forth in SEQ ID NO: 5;
ii) a FAR having at least 80% homology to the FAR from *Helicoverpa assulta* as set forth in SEQ ID NO: 7;
iii) a FAR having at least 80% homology to the FAR from *Heliothis subflexa* as set forth in SEQ ID NO: 6; and
iv) a FAR having at least 80% homology to the FAR from *Bicyclus anynana* as set forth in SEQ ID NO: 17, preferably the FAR has at least 80% homology to the FAR from *Helicoverpa armigera* or to the FAR from *Heliothis subflexa*.

Such yeast cells are well suited for producing hydrophobic compounds as defined herein, in particular desaturated fatty alcohols, fatty acyl acetates and fatty aldehydes, and are described in detail in WO 2016/207339.

In some embodiments, the microorganism is a yeast cell such as a *Yarrowia* cell, for example a *Yarrowia lipolytica* cell, capable of producing said desaturated fatty alcohol, said yeast cell expressing:

- at least one heterologous desaturase capable of introducing at least one double bond in a fatty acyl-CoA having a carbon chain length of 14; and
- at least one heterologous fatty acyl-CoA reductase (FAR), capable of converting at least part of said desaturated fatty acyl-CoA to a desaturated fatty alcohol.

Preferably, the desaturase in such embodiments has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA. Such yeast cells are well suited for producing desaturated fatty alcohols of carbon chain length 14, and are described in detail in WO 2018/109167.

In such embodiments, the at least one heterologous desaturase may be derived from an organism selected from *Pelargonium hortorum, Ricinus communis, Drosophila* melanogaster, *Spodoptera litura* and *Tribolium castaneum*, preferably the desaturase is derived from *Drosophila melanogaster*, preferably the at least one heterologous desaturase is selected from the group consisting of:

i) a Δ9 desaturase having at least 60% homology to the Δ9 desaturase from *Drosophila melanogaster* as set forth in SEQ ID NO: 16;
ii) a Δ9 desaturase having at least 60% homology to the Δ9 desaturase from *Spodoptera litura* as set forth in SEQ ID NO: 18;
iii) a desaturase having at least 60% homology to the desaturase from *Lobesia botrana* as set forth in SEQ ID NO: 43;
iv) a desaturase having at least 60% homology to the desaturase from *Drosophila grimshawi* as set forth in SEQ ID NO: 44; and
v) a desaturase having at least 60% homology to the desaturase from *Drosophila virilis* as set forth in SEQ ID NO: 45,
vi) a Δ11 desaturase having at least 60% homology to the Δ11 desaturase from *Choristoneura parallela* as set forth in SEQ ID NO: 42;
vii) a Δ11 desaturase having at least 60% homology to the Δ11 desaturase from *Choristoneura rosaceana* as set forth in SEQ ID NO: 35.

A desaturase having at least 60% homology to a given desaturase has at least 60% homology, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72% homology, such as at least 73% homology, such as at least 74% homology, such as at least 75% homology, such as at least 76% homology, such as at least 77% homology, such as at least 78% homology, such as at least 79% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology.

The fatty acyl reductase may be selected from:

i) a FAR having at least 80% homology to the FAR from *Helicoverpa armigera* as set forth in SEQ ID NO: 5;

ii) a FAR having at least 80% homology to the FAR from *Helicoverpa assulta* as set forth in SEQ ID NO: 7;

iii) a FAR having at least 80% homology to the FAR from *Heliothis subflexa* as set forth in SEQ ID NO: 6; and iv) a FAR having at least 80% homology to the FAR from *Bicyclus anynana* as set forth in SEQ ID NO: 17, preferably the FAR is a FAR having at least 80% homology to the FAR from *Helicoverpa armigera* as set forth in SEQ ID NO: 5.

A FAR having at least 80% homology to a given FAR has at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology.

In some embodiments, the hydrophobic compound is a desaturated fatty alcohol and the microorganism is a yeast cell capable of producing said desaturated fatty alcohol, which yeast cell:

has one or more mutations resulting in reduced activity of one or more native acyl-CoA oxidases; and expresses at least one first group of enzymes comprising at least one acyl-CoA oxidase capable of oxidising a fatty acyl-CoA, wherein the first group of enzymes is capable of shortening a fatty acyl-CoA of a first carbon chain length X to a shortened fatty acyl-CoA having a second carbon chain length X', wherein X'≤X−2; and expresses at least one heterologous desaturase capable of introducing at least one double bond in said fatty acyl-CoA and/or in said shortened fatty acyl-CoA; and expresses at least one heterologous fatty acyl-CoA reductase, capable of converting at least part of said desaturated fatty acyl-CoA to a desaturated fatty alcohol.

Such yeast cells are described in detail in application WO 2020/169389.

The native acyl-CoA oxidase and/or the heterologous acyl-CoA oxidase may be a peroxisomal acyl-CoA oxidase. In some embodiments, the at least one acyl-CoA oxidase of the first group of enzymes is a native acyl-CoA oxidase or a heterologous acyl-CoA oxidase, which may be overexpressed compared to a reference yeast strain not expressing said at least one first group of enzymes. In some embodiments, the at least one acyl-CoA oxidase of the first group of enzymes is a heterologous acyl-CoA oxidase. In some embodiments, the at least one first group of enzymes comprises an acyl-CoA oxidase derived from an organism of a genus selected from *Yarrowia, Agrotis, Arabidopsis, Aspergillus, Cucurbita, Homo, Paenarthrobacter* and *Rattus*. Preferably the at least one first group of enzymes comprises an acyl-CoA oxidase derived from *Yarrowia lipolytica, Agrotis segetum, Arabidopsis thaliana, Aspergillus nidulans, Cucurbita maxima, Homo sapiens*, Paenarthrobacterureafaciens or *Rattus norvegicus*. In particular embodiments, preferably the at least one acyl-CoA oxidase of the first group of enzymes is an acyl-CoA oxidase selected from the group consisting of Yli_POX1 (SEQ ID NO: 19), Yli_POX2 (SEQ ID NO: 20), Yli_POX3 (SEQ ID NO: 21), Yli_POX4 (SEQ ID NO: 22), Yli_POX5 (SEQ ID NO: 23), Yli_POX6 (SEQ ID NO: 24), Ase_POX (SEQ ID NO: 25), Ath_POX1 (SEQ ID NO: 26), Ath_POX2 (SEQ ID NO: 27), Ani_POX (SEQ ID NO: 28), Cma_POX (SEQ ID NO: 29), Hsa_POX1-2 (SEQ ID NO: 30), Pur_POX (SEQ ID NO: 31), and Rno_POX2 (SEQ ID NO: 32), or a functional variant thereof having at least 60% homology thereto, such as at least 65%, such as at least 70%, such as at least 75%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% homology thereto.

In some embodiments, the at least one heterologous desaturase is selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase, a Δ13 desaturase and a Δ14 desaturase, and/or wherein the desaturase is derived from a yeast such as *Saccharomyces* or *Yarrowia*, such as *Saccharomyces cerevisiae* or *Yarrowia lipolytica*, or from an insect, such as from the *Diptera*, the Coleoptera, or the Lepidoptera order, such as of the genus *Amyelois, Choristoneura, Drosophila, Ostrinia, Thaumetopoea, Dendrophilus, Grapholita, Cydia, Epiphyas*, or *Spodoptera*, such as *Drosophila melanogaster, Amyelois transitella, Choristoneura rosaceana, Ostrinia nubilalis, Thaumetopoea pityocampa, Dendrophilus punctatus, Grapholita molesta, Cydia pomonella, Epiphyas postvittana, Spodoptera littoralis* or *Choristoneura parallela*. For example, the desaturase is a $\Delta_{Z9}$-desaturase such as Sce_OLE1 (SEQ ID NO: 33), Yli-_OLE1 (SEQ ID NO: 34) or Dme_D9 (SEQ ID NO: 16), a $\Delta_{Z11}$-desaturase such as Atr_D11 (SEQ ID NO: 1), Cro_Z11 (SEQ ID NO: 35), Onu_11 (SEQ ID NO: 36), Tpi_D13 (SEQ ID NO: 37), a $\Delta_{E9}$-desaturase such as Dpu_E9-14 (SEQ ID NO: 38), a $\Delta_{Z/E10}$-desaturase such as Gmo_CPRQ (SEQ ID NO: 39), or a desaturase such as Epo_E11 (SEQ ID NO: 40), SIs_ZE11 (SEQ ID NO: 41), Lbo_PPTQ (SEQ ID NO: 43), Dgd9 (SEQ ID NO: 44), Dvd9 (SEQ ID NO: 45) or Cpa_E11 (SEQ ID NO: 42), or a functional variant thereof having at least 60% homology thereto, such as at least 65%, such as at least 70%, such as at least 75%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% homology thereto.

In some embodiments, the fatty acyl-CoA reductase is derived from an insect such as an insect of the Lepidoptera order, such as of the genus *Helicoverpa, Heliothis* or *Bicyclus*, preferably the fatty acyl-CoA reductase is a fatty acyl-CoA reductase native to *Helicoverpa armigera, Helicoverpa assulta, Heliothis subflexa, Bicyclus anynana*, or a functional variant thereof, preferably the fatty acyl-CoA reductase is selected from the group consisting of a fatty acyl-CoA reductase having at least 80% homology to Har_FAR (SEQ ID NO: 5), Has_FAR (SEQ ID NO: 7), Ban_FAR (SEQ ID NO: 17) or Hs_FAR (SEQ ID NO: 6).

The yeast cell producing the desaturated fatty alcohols may further express a fatty acyl synthetase (FAA) such as Sc_FAA1 (SEQ ID NO: 8) or Yl_FAA (SEQ ID NO: 9) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 8) or Yl_FAA (SEQ ID NO: 9).

The microorganism may be further modified to express an acetyltransferase such as a heterologous acetyltransferase (AcT) or to overexpress a native acetyltransferase, wherein said acetyltransferase is capable of converting at least part of the produced desaturated fatty alcohols into the corresponding fatty acyl acetates. In some embodiments the acetyltransferase is Sc_Atf1 (SEQ ID NO: 10) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

The desaturated fatty alcohols may also be converted to the corresponding fatty acyl acetates by chemical conversion, for example by performing an acetylation reaction using the desaturated fatty alcohols produced by the cell as substrate.

(Z)-11-hexadecen-1-ol

In some embodiments, the hydrophobic compound is (Z)-11-hexadecen-1-ol. In some embodiments, the microorganism is a yeast cell capable of producing (Z)-11-hexadecen-1-ol with a titer of at least 0.2 mg/L. The yeast cell expresses:

- a Δ11-desaturase selected from the group consisting of the *Amyelois transitella* Δ11-desaturase (Atr_Δ11; SEQ ID NO: 1), the *Spodoptera littoralis* Δ11-desaturase (Sl_Δ11; SEQ ID NO: 2), the *Agrotis segetum* Δ11-desaturase (As_Δ11; SEQ ID NO: 3) and the *Trichoplusia* niΔ11-desaturase (Tni_Δ11; SEQ ID NO: 4) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 1), Sl_Δ11 (SEQ ID NO: 2), As_Δ11 (SEQ ID NO: 3), or Tni_Δ11 (SEQ ID NO: 4), and
- an alcohol-forming fatty acyl-CoA reductase (FAR) selected from the group consisting of Har_FAR (SEQ ID NO: 5), Hs_FAR (SEQ ID NO: 6), and Has_FAR (SEQ ID NO: 7), or a variant thereof having at least 80% homology, such as at least 85%, such as at least 90%, such as at least 95%, such as 100% homology to Har_FAR (SEQ ID NO: 5), Hs_FAR (SEQ ID NO: 6), or Has_FAR (SEQ ID NO: 7);

whereby

- the Δ11-desaturase is capable of converting at least part of said hexadecanoyl-CoA to (Z)11-hexadecenoyl-CoA; and
- the FAR is capable of converting at least part of said (Z)11-hexadecenoyl-CoA to (Z)-11-hexadecanol. In some embodiments, the yeast cell is a *Saccharomyces cerevisiae* cell.

The yeast cell producing (Z)-11-hexadecen-1-ol may further express a fatty acyl synthetase (FAA) such as Sc_FAA1 (SEQ ID NO: 8) or Yl_FAA (SEQ ID NO: 9) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 8) or Yl_FAA (SEQ ID NO: 9).

The microorganism may be further modified to express an acetyltransferase such as a heterologous acetyltransferase (AcT) or to overexpress a native acetyltransferase, wherein said acetyltransferase is capable of converting at least part of the (Z)-11-hexadecen-1-ol into (Z)11-hexadecen-1-yl acetate. In some embodiments the acetyltransferase is Sc_Atf1 (SEQ ID NO: 10) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

(Z)-11-hexadecen-1-ol may also be converted to (Z)11-hexadecen-1-yl acetate by chemical conversion, for example by performing an acetylation reaction using the (Z)11-hexadecen-1-ol produced by the cell as substrate.

Such yeast cells are well suited for producing hydrophobic compounds as defined herein, in particular desaturated fatty alcohols, fatty acyl acetates and fatty aldehydes, and are described in detail in WO 2016/207339.

Codlemone

In some embodiments, the hydrophobic compound is codlemone (E8,E10-dodecadien-1-ol), or one or more of its derivatives E8,E10-dodecadienyl acetate and/or E8,E10-dodecadienal.

Yeast cells capable of producing codlemone or one or more of its derivatives preferably express at least one heterologous desaturase capable of introducing one or more double bonds in a fatty acyl-CoA having a carbon chain length of 12, thereby converting said fatty acyl-CoA to a desaturated fatty acyl-CoA, wherein at least part of said desaturated fatty acyl-CoA is E8,E10-dodecadienyl coenzyme A (E8,E10-C12:CoA), and further express at least one heterologous fatty acyl-CoA reductase (EC 1.2.1.84) capable of converting at least part of said desaturated fatty acyl-CoA to a desaturated fatty alcohol, wherein the fatty acyl-CoA reductase is capable of converting at least part of said E8,E10-dodecadienyl coenzyme A (E8,E10-C12:CoA) to E8,E10-dodecadien-1-ol. Such yeast cells are described in detail in European application 19218703.7, entitled "Yeast cells and methods for production of E8,E10-dodecadienyl coenzyme A, codlemone and derivatives thereof" filed on 20 Dec. 2019 by the same applicant as the present application. This application describes desaturases and fatty acyl-CoA reductases which are particularly useful for production of codlemone and its derivatives, in particular in the section entitled "Desaturase" (p. 12 to 16 of EP 19218703.7) and in the section entitled "Fatty acyl-CoA reductase (EC 1.2.1.84)" (p. 16 to 20 of EP 19218703.7). Codlemone can be further converted to E8,E10-dodecadienyl acetate; this can be done ex vivo, as is known in the art, e.g. by chemical conversion, or it can be done in vivo by the action of an acetyltransferase (EC 2.3.1.84) capable of converting at least part of the E8,E10-dodecadien-1-ol produced by the cell into E8,E10-dodecadienyl acetate, as described in the section entitled "Production of E8,E10-dodecadienyl acetate" (p. 37-38 of EP 19218703.7). It may also be of interest to further convert at least part of the E8,E10-dodecadien-1-ol produced by the cell into E8,E10-dodecadienal. This can be done by chemical conversion or by further engineering the yeast cell, for example as described in the section entitled "Production of E8,E10-dodecadienal" (p. 39-40 of EP 19218703.7).

Method for Producing a Hydrophobic Compound

Herein are disclosed methods for producing a hydrophobic compound, which may be any of the hydrophobic compounds described herein above. The methods comprise the step of providing a microorganism capable of producing said hydrophobic compound, and culturing said microorganism in a culture medium under conditions allowing production of said hydrophobic compound, wherein the culture medium comprises an extractant in an amount equal to or greater than its cloud concentration measured in an aqueous solution, preferably at the cultivation temperature, or at room temperature. As detailed above, such agents are routinely used in fermentations for foam management, however when used as antifoaming agents the agents are used at a concentration lower than the cloud concentration measured in an aqueous solution. Preferably the microorganism is a yeast. The extractant is a non-ionic surfactant, in particular a nonionic ethoxylated surfactant, such as a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, or a polyethoxylated surfactant such as an antifoaming agent, for example a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The method may also further comprise a step of recovering the hydrophobic compound from the fermentation broth.

The present methods are particularly useful for facilitating recovery of hydrophobic compounds produced by fermentation of a microorganism capable of producing these compounds, for example any of the microorganisms described in the above section "Microorganism". The hydrophobic compound may be any compound described in the above section "Hydrophobic compound", in particular a fatty alcohol, a fatty alcohol ester, a fatty acyl acetate, a fatty aldehyde and/or a terpene such as a terpenoid.

The present inventors have found that when a non-ionic surfactant, in particular a nonionic ethoxylated surfactant which is preferably a fatty alcohol alkoxylate or a polyethoxylated surfactant, such as an antifoaming agent, in particular any of the non-ionic surfactants and antifoaming agents described in the above section "Non-ionic ethoxylated surfactant", is included in the culture medium or fermentation broth in an amount equal to or greater than its cloud concentration measured in an aqueous solution, preferably at the cultivation temperature, the non-ionic surfactant acts as an in situ extractant and facilitates recovery of the hydrophobic compound from the fermentation broth. Accordingly, herein is provided a method for producing a hydrophobic compound such as a fatty alcohol, a fatty alcohol ester, a fatty acyl acetate, a fatty aldehyde and/or a terpene such as a terpenoid in a fermentation, said method comprising the step of providing a microorganism capable of producing said hydrophobic compound and culturing said microorganism in a culture medium under conditions allowing production of said hydrophobic compound, wherein the culture medium comprises an extractant in an amount equal to or greater than its cloud concentration measured in an aqueous solution, wherein the extractant is a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, the method optionally further comprising the step of recovering the hydrophobic compound from the fermentation broth. Hence is provided herein a method for producing a hydrophobic compound selected from a fatty alcohol, a fatty alcohol ester, a fatty acyl acetate, a fatty aldehyde and a terpene in a fermentation, said method comprising the step of providing a yeast cell capable of producing said hydrophobic compound and culturing said yeast cell in a culture medium under conditions allowing production of said hydrophobic compound, wherein the culturing step is performed at a cultivation temperature, wherein the culture medium comprises an extractant in an amount equal to or greater than its cloud concentration measured in an aqueous solution such as the culture medium at the cultivation temperature, wherein the extractant is a non-ionic ethoxylated surfactant, the method further comprising the step of recovering the hydrophobic compound.

In some embodiments, the hydrophobic compound is a fatty alcohol, a fatty alcohol ester, a fatty acyl acetate or a fatty aldehyde as described herein. In other embodiments, the hydrophobic compound is a terpene such as a terpenoid as described herein. In some embodiments, the hydrophobic compound is a mixture of hydrophobic compounds, such as a mixture of fatty alcohols, fatty acyl acetates, fatty aldehydes and/or terpenes such as terpenoids as described herein. In particular embodiments, the hydrophobic compound is a desaturated fatty alcohol, a desaturated fatty acyl acetate or a desaturated fatty aldehyde as described herein.

In some embodiments, the non-ionic surfactant is a nonionic ethoxylated surfactant, for example a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, or a non-ionic polyethoxylated surfactant, for example an antifoaming agent. The antifoaming agent is preferably a polyethoxylated surfactant, such as a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents, or a combination thereof.

In some embodiments, the non-ionic surfactant is added in an amount greater than its cloud concentration measured in an aqueous solution. In some embodiments, the nonionic ethoxylated surfactant is added in an amount greater than its cloud concentration measured in an aqueous solution. In some embodiments, the polyethoxylated surfactant is added in an amount greater than its cloud concentration in an aqueous solution. In some embodiments, the fatty alcohol alkoxylate is added in an amount greater than its cloud concentration measured in an aqueous solution. The cloud concentration may be determined in the cultivation medium, for example at room temperature or at the cultivation temperature, as detailed herein elsewhere.

In some embodiments, the non-ionic surfactant is present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. Preferably the cloud concentration is determined in the cultivation medium, for example at room temperature or at the cultivation temperature.

In some embodiments, the non-ionic surfactant is a non-ionic ethoxylated surfactant present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. Preferably the cloud concentration is determined in the cultivation medium, for example at room temperature or at the cultivation temperature.

In some embodiments, the non-ionic surfactant is a fatty alcohol alkoxylate present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. Preferably the cloud concentration is determined in the cultivation medium, for example at room temperature or at the cultivation temperature. In some embodiments, the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof.

In some embodiments, the non-ionic surfactant is a polyethoxylated surfactant, which is present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. Preferably the cloud concentration is determined in the cultivation medium, for example at room temperature or at the cultivation temperature. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

In some embodiments, the amount of non-ionic surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. Preferably the cloud concentration is determined in the cultivation medium, for example at room temperature or at the cultivation temperature.

In some embodiments, the amount of non-ionic ethoxylated surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the ethoxylated surfactant is a fatty alcohol alkoxylate. Preferably the cloud concentration is determined in the cultivation medium, for example at room temperature or at the cultivation temperature.

In some embodiments, the non-ionic surfactant is a polyethoxylated surfactant, and the amount of polyethoxylated surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. Preferably the cloud concentration is determined in the cultivation medium, for example at room temperature or at the cultivation temperature.

In some embodiments, the non-ionic surfactant is a fatty alcohol alkoxylate, and the amount of fatty alcohol alkoxylate (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. Preferably the cloud concentration is determined in the cultivation medium, for example at room temperature or at the cultivation temperature.

In some embodiments, the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant, wherein the extractant is a non-ionic surfactant, preferably a non-ionic ethoxylated surfactant such as a fatty alcohol alkoxylate or a non-ionic polyethoxylated surfactant. In some embodiments the non-ionic surfactant is a polyethoxylated surfactant, such as selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof.

In some embodiments, the non-ionic ethoxylated surfactant is an ethoxylated and propoxylated $C_{16}$-$C_{18}$ alcohol-based agent or an ethoxylated and propoxylated $C_{16}$-$C_{18}$ alcohol-based antifoaming agent, for example, $C_{16}$-$C_{18}$ alkyl alcohol ethoxylate propoxylate (CAS number 68002-96-0). The cloud concentration of $C_{16}$-$C_{18}$ alkyl alcohol ethoxylate propoxylate (CAS number 68002-96-0) is about 1% vol/vol at room temperature. Accordingly, when this antifoaming agent is used, the culture medium preferably comprises at least 1% vol/vol of $C_{16}$-$C_{18}$ alkyl alcohol ethoxylate propoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol $C_{16}$-$C_{18}$ alkyl alcohol ethoxylate propoxylate, or more.

In some embodiments, the non-ionic ethoxylated surfactant is a polyethylene polypropylene glycol, for example Kolliphor® P407 (CAS number 9003-11-6), also termed poly(ethylene glycol)-block-poly(propylene glycol)-block-poly(ethylene glycol). The cloud concentration of Kolliphor® P407 is 10% at a temperature above 100° C. Accordingly, when a polyethylene polypropylene glycol such as Kolliphor® P407 is used, the culture medium preferably comprises at least 10% vol/vol of polyethylene polypropylene glycol such as Kolliphor® P407, such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Kolliphor® P407, or more.

In some embodiments, the non-ionic ethoxylated surfactant is a mixture of polyether dispersions, such as antifoam 204 (product number Δ6426 or Δ8311 from Sigma Aldrich). The cloud concentration of antifoam 204 is 1% in an aqueous solution at a temperature of 18.0 to 21.0° C. Accordingly, when a mixture of polyether dispersions such as antifoam 204 is used, the culture medium preferably comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of polyether dispersions such as antifoam 204, or more.

In some embodiments, the non-ionic ethoxylated surfactant is Agnique BP420 (CAS number 68002-96-0). The cloud concentration of Agnique BP420 (CAS number 68002-96-0) is 1% in an aqueous solution at a temperature of 18.0 to 21.0° C. Accordingly, when a mixture of polyether dispersions such as antifoam 204 is used, the culture medium preferably comprises at least 1% vol/vol of Agnique BP420 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of Agnique BP420 (CAS number 68002-96-0), or more.

In some embodiments, the non-ionic ethoxylated surfactant is an antifoaming agent comprising polyethylene glycol monostearate or simethicone. Simethicone comprises polyethylene glycol monostearate, which, without being bound by theory, appears to be the compound important for the ability of simethicone to act as an extractant. Polyethylene glycol monostearate has a cloud point of 1% in an aqueous solution at 5° C. Accordingly, when simethicone or a surfactant comprising polyethylene glycol monostearate is used, the culture medium preferably comprises at least 1% vol/vol of polyethylene glycol monostearate or simethicone, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol polyethylene glycol monostearate or simethicone, or more.

In some embodiments, the non-ionic surfactant is a fatty alcohol alkoxylate such as Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574. The cloud concentration of these surfactants is about 1% vol/vol at room temperature. Accordingly, when Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0) is used, the culture medium preferably comprises at least 1% vol/vol of Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), or more.

The fermentation itself may be performed as is known in the art. In some embodiments, the fermentation is performed in a bioreactor. The fermentation is conducted under conditions that allow the microorganism present in the fermentation to produce the hydrophobic compound of interest.

The addition of an extractant, i.e. a non-ionic ethoxylated surfactant, preferably a fatty alcohol alkoxylate or a polyethoxylated surfactant such as any of the antifoaming agents described herein, results in the generation of an emulsion in the fermentation broth, where the hydrophobic compound produced by the microorganism, preferably a yeast cell, is present in the emulsion. The method thus may also comprise a step of breaking the emulsion to recover a product phase comprising the extractant and the hydrophobic compound. Once the emulsion is broken, the fermentation broth is separated in three phases: a water phase, comprising mainly water and aqueous compounds, a phase comprising cells and cellular debris, and a product phase mainly comprising the extractant and the hydrophobic compound. Thus a composition is obtained consisting of three phases. In preferred embodiments, most of the hydrophobic compound of the fermentation broth is present in the product phase. For example, at least 50% of the hydrophobic compound is present in the product phase, such as at least 55%, such as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99%, such as 100% of the hydrophobic compound is present in the product phase. In some embodiments, the product phase comprises at least 50% of the hydrophobic compound initially present in the fermentation broth, such as at least 55%, such as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99%, such as 100% of the hydrophobic compound initially present in the fermentation broth.

The step of breaking the emulsion may be performed as is known in the art, for example by submitting the emulsion to a step of phase separation as is known in the art. In some embodiments, the step of phase separation is a centrifugation, for example 5 minutes at 10 000 g. In some embodiments, the centrifugation is performed for 1 minute or more, such as for 2 minutes or more, such as for 3 minutes or more, such as for 4 minutes or more, such as for 5 minutes or more, such as for 6 minutes or more, such as for 7 minutes or more, such as for 8 minutes or more, such as for 9 minutes or more, such as for 10 minutes or more. In some embodiments, the centrifugation is performed at 3,000 g or more, such as at 4,000 g or more, such as at 5,000 g or more, such as at 6,000 g or more, such as at 7,000 g or more, such as at 8,000 g or more, such as at 9,000 g or more, such as at 10 000 g or more, such as at 11,000 g or more, such as at 12,000 g or more, such as at 13,000 g or more, such as at 14,000 g or more, such as at 15,000 g or more, such as at 17,500 g or more, such as at 20 000 g or more.

Following the step of breaking the emulsion, the product phase comprising the extractant and the hydrophobic compound may be recovered from the composition. The method may in such embodiments further comprise the step of separating the hydrophobic compound from the extractant. This can be performed by methods known in the art, such as by distillation, for example a distillation under reduced pressure, or a column purification. The extractant may be recycled, e.g. it may be recirculated back to the fermentation.

In some embodiments, the method involves culturing a microorganism capable of producing a fatty alcohol, such as a desaturated fatty alcohol or a mixture of (saturated and/or desaturated) fatty alcohols. In some embodiments, the method involves culturing a yeast cell capable of producing a fatty alcohol, such as a desaturated fatty alcohol or a mixture of (saturated and/or desaturated) fatty alcohols. The desaturated fatty alcohol may be recovered as described above. In such embodiments, the method may further comprise a step of recovering the produced fatty alcohol and chemically converting at least part thereof to the corresponding fatty acyl acetate and/or to the corresponding fatty aldehyde. The term "corresponding" here refers to a compound, fatty acyl acetate or fatty aldehyde, having the same carbon chain length and double bond position(s) as the fatty alcohol it is obtained from.

Thus, when a microorganism such as a yeast cell produces fatty alcohols, the methods may further comprise the step of recovering said fatty alcohols, for example as described above, and chemically converting at least part of the fatty alcohols to the corresponding fatty acyl acetates. This can be done by performing an acetylation reaction as is known in the art, for example as described in Fritz et al., 1959, or Mattson et al., 1964. The methods may additionally or alternatively comprise the step of chemically converting at least part of the fatty alcohols to the corresponding fatty aldehydes. This can be done by performing an oxidation reaction as is known in the art, for example as described in Steves et al., 2013. The resulting fatty acyl acetates and/or fatty aldehydes may then be recovered.

Acetylation for example may be carried out with acetic anhydride using pyridine as catalyst. The resulting fatty acetates are then extracted from the reaction mix with an organic solvent and the solvent is removed by evaporation.

Oxidation may for example be carried out using known procedures for the oxidation of primary alcohols including, but not limited to, those published by Hoover et al., 2011, using Tetrakisacetonitrile copper(I) triflate/TEMPO catalyst system, Omura et al. (1978), Corey et al. (1972), Ratcliffe et al. (1970), Ley et al. (1994), or Anelli et al. (1987). The resulting fatty aldehydes are then extracted from the reaction mix with an organic solvent and the solvent can be removed by evaporation and the aldehydes are purified using distillation or column chromatography.

Method for Increasing the Titer of a Hydrophobic Compound in a Fermentation

Herein are disclosed methods for increasing the titer of a hydrophobic compound in a fermentation. The methods comprise the step of culturing a microorganism capable of producing said hydrophobic compound in a culture medium under conditions allowing production of said hydrophobic compound, wherein the culture medium comprises an extractant in an amount equal to or greater than its cloud concentration measured in an aqueous solution. Preferably, the microorganism is a yeast cell. Preferably, the cloud concentration is determined at room temperature or at the cultivation temperature. The extractant is a non-ionic surfactant, in particular a non-ionic ethoxylated surfactant, preferably selected from a fatty alcohol alkoxylate, preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, and a polyethoxylated surfactant, such as an antifoaming agent, for example a polyethoxylated non-ionic surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The method may also further comprise a step of recovering the hydrophobic compound from the fermentation broth.

The present methods are particularly useful for increasing the titer of hydrophobic compounds produced by fermentation of a microorganism, for example a yeast cell, capable of producing these compounds, for example any of the microorganisms described in the above section "Microorganism". The hydrophobic compound may be any compound described in the above section "Hydrophobic compound", in particular a fatty alcohol, a fatty alcohol ester, a fatty acyl acetate, a fatty aldehyde and a terpene such as a terpenoid. The presence of a non-ionic surfactant, in particular a non-ionic ethoxylated surfactant, preferably selected from a fatty alcohol alkoxylate such as Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, or an antifoaming agent, in particular a polyethoxylated surfactant, to the culture medium, results in an increase in the titer of the hydrophobic compound compared to the titer obtained in a fermentation performed in similar conditions but with an amount of non-ionic surfactant which is lower than its cloud concentration. Thus the present methods are useful for increasing the titer of the hydrophobic compound compared to a fermentation performed under the same conditions but either in the absence of extractant or in the presence of extractant in an amount lower than its cloud concentration in an aqueous solution at the cultivation temperature or at room temperature.

In some embodiments, the hydrophobic compound is a fatty alcohol, a fatty alcohol ester, a fatty acyl acetate or a fatty aldehyde as described herein. In other embodiments, the hydrophobic compound is a terpene such as a terpenoid as described herein. In some embodiments, the hydrophobic compound is a mixture of hydrophobic compounds, such as a mixture of fatty alcohols, fatty alcohol esters, fatty acyl acetates, fatty aldehydes and terpenes such as terpenoids as described herein. In particular embodiments, the hydrophobic compound is a desaturated fatty alcohol, a desaturated fatty alcohol ester, a desaturated fatty acyl acetate or a desaturated fatty aldehyde as described herein.

The non-ionic surfactant is preferably a non-ionic ethoxylated surfactant or a fatty alcohol alkoxylate, preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, or an antifoaming agent such as a polyethoxylated surfactant, for example selected from: polyethoxylated non-ionic surfactants, such as a polyethylene polypropylene glycol, mixtures of polyether dispersions, antifoaming agents comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents, or a combination thereof.

In some embodiments, the non-ionic surfactant or the non-ionic ethoxylated surfactant is added in an amount greater than its cloud concentration measured in an aqueous solution, preferably at room temperature or at the cultivation temperature. In some embodiments, the non-ionic ethoxylated surfactant, preferably a fatty alcohol alkoxylate or a polyethoxylated surfactant, is added in an amount greater than its cloud concentration measured in an aqueous solution, preferably at room temperature or at the cultivation temperature.

In some embodiments, the non-ionic surfactant is present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. The cloud concentration may be determined in the cultivation medium, for example at room temperature or at the cultivation temperature.

In some embodiments, the non-ionic surfactant is an antifoaming agent such as a polyethoxylated surfactant. The polyethoxylated surfactant is then preferably present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The cloud concentration may be determined in the cultivation medium, for example at room temperature or at the cultivation temperature.

In some embodiments, the non-ionic surfactant is a fatty alcohol alkoxylate such as Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574. The fatty alcohol alkoxylate is then preferably present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, and combinations thereof. The cloud concentration may be determined in the cultivation medium, for example at room temperature or at the cultivation temperature.

In some embodiments, the amount of non-ionic surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. The cloud concentration may be determined in the cultivation medium, for example at room temperature or at the cultivation temperature.

In some embodiments the non-ionic surfactant is a polyethoxylated surfactant. In some embodiments the amount of polyethoxylated surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The cloud concentration may be determined in the cultivation medium, for example at room temperature or at the cultivation temperature.

In some embodiments the non-ionic surfactant is a fatty alcohol alkoxylate. In some embodiments the amount of fatty alcohol alkoxylate (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, and combinations thereof. The cloud concentration may be determined in the cultivation medium, for example at room temperature or at the cultivation temperature.

In some embodiments, the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant, wherein the extractant is a non-ionic surfactant. In some embodiments the non-ionic surfactant is a non-ionic ethoxylated surfactant such as a polyethoxylated surfactant or a fatty alcohol alkoxylate. In some embodiments the polyethoxylated surfactant is selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2) or Imbentin SG/251 (CAS number 68002-96-0), preferably Plurafac® LF300 or Dehypon® 2574, and combinations thereof.

In some embodiments, the non-ionic surfactant is an antifoaming agent. In some embodiments, the antifoaming agent is an ethoxylated and propoxylated $C_{16}$-$C_{18}$ alcohol-based agent or an ethoxylated and propoxylated $C_{16}$-$C_{18}$ alcohol-based antifoaming agent, for example, $C_{16}$-$C_{18}$ alkyl alcohol ethoxylate propoxylate (CAS number 68002-96-0). The cloud concentration of $C_{16}$-$C_{18}$ alkyl alcohol ethoxylate propoxylate (CAS number 68002-96-0) is about 1% vol/vol at room temperature. Accordingly, when this antifoaming agent is used, the culture medium preferably comprises at least 1% vol/vol of $C_{16}$-$C_{18}$ alkyl alcohol ethoxylate propoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol $C_{16}$-$C_{18}$ alkyl alcohol ethoxylate propoxylate, or more.

In some embodiments, the antifoaming agent is a polyethylene polypropylene glycol, for example Kolliphor® P407 (CAS number 9003-11-6), also termed poly(ethylene glycol)-block-poly(propylene glycol)-block-poly(ethylene glycol). The cloud concentration of Kolliphor® P407 is 10% at a temperature above 100° C. Accordingly, when a polyethylene polypropylene glycol such as Kolliphor® P407 is used, the culture medium preferably comprises at least 10% vol/vol of polyethylene polypropylene glycol such as Kolliphor® P407, such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Kolliphor® P407, or more.

In some embodiments, the antifoaming agent is a mixture of polyether dispersions, such as antifoam 204 (product number Δ6426 or Δ8311 from Sigma Aldrich). The cloud concentration of antifoam 204 is 1% in an aqueous solution at a temperature of 18.0 to 21.0° C. Accordingly, when a mixture of polyether dispersions such as antifoam 204 is used, the culture medium preferably comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of polyether dispersions such as antifoam 204, or more.

In some embodiments, the antifoaming agent is Agnique BP420 (CAS number 68002-96-0). The cloud concentration of Agnique BP420 (CAS number 68002-96-0) is 1% in an aqueous solution at a temperature of 18.0 to 21.0° C. Accordingly, when Agnique BP420 (CAS number 68002-96-0) is used, the culture medium preferably comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of Agnique BP420 (CAS number 68002-96-0), or more.

In some embodiments, the antifoaming agent is an antifoaming agent comprising polyethylene glycol monostearate or simethicone. Simethicone comprises polyethylene glycol monostearate, which, without being bound by theory, appears to be the compound important for the ability of simethicone to act as an extractant. Polyethylene glycol monostearate has a cloud point of 1% in an aqueous solution at 5° C. Accordingly, when simethicone or a surfactant comprising polyethylene glycol monostearate is used, the culture medium preferably comprises at least 1% vol/vol of polyethylene glycol monostearate or simethicone, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol polyethylene glycol monostearate or simethicone, or more.

In some embodiments, the extractant is a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. These fatty alcohol alkoxylates have a cloud point of 1% in an aqueous solution at room temperature. Accordingly, when a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, is used, the culture medium preferably comprises at least 1% vol/vol of said fatty alcohol alkoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof.

The microorganism, which is preferably a yeast cell, used in the present methods may already be engineered or selected for producing the hydrophobic compound at a high titer. The present methods may further increase the titer. In some embodiments, the titer of the hydrophobic compound is increased by at least 5% compared to the titer obtained in a fermentation performed under similar conditions in the absence of extractant or in the presence of extractant in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more. The term "similar conditions" here refers to a fermentation of the same microorganism or yeast cell, which is performed under the same conditions but either in the absence of extractant or in the presence of extractant in an amount lower than its cloud concentration in an aqueous solution at the cultivation temperature or at room temperature. In some embodiments, the hydrophobic compound is a fatty alcohol, a fatty alcohol ester, a fatty acyl acetate and/or a fatty aldehyde. In some embodiments, the hydrophobic compound is a terpene such as a terpenoid.

Thus, when a microorganism such as a yeast cell produces fatty alcohols, the methods may further comprise the step of recovering said fatty alcohols, for example as described above, and chemically converting at least part of the fatty alcohols to the corresponding fatty acyl acetates. This can be done by performing an acetylation reaction as is known in the art, for example as described in Fritz et al., 1959, or Mattson et al., 1964. The methods may additionally or alternatively comprise the step of chemically converting at least part of the fatty alcohols to the corresponding fatty aldehydes. This can be done by performing an oxidation reaction as is known in the art, for example as described in Steves et al., 2013. The resulting fatty acyl acetates and/or fatty aldehydes may then be recovered.

Acetylation may be carried out with acetic anhydride using pyridine as catalyst. The resulting fatty acetates are then extracted from the reaction mix with an organic solvent and the solvent is removed by evaporation.

Oxidation may be carried out using known procedures for the oxidation of primary alcohols including, but not limited to, those published by Hoover et al., 2011, using Tetrakisacetonitrile copper(I) triflate/TEMPO catalyst system, Omura et al. (1978), Corey et al. (1972), Ratcliffe et al. (1970), Ley et al. (1994), or Anelli et al. (1987). The resulting fatty aldehydes are then extracted from the reaction mix with an organic solvent and the solvent may be removed by evaporation and the aldehydes are purified using distillation or column chromatography.

Method for Increasing the Secretion of a Hydrophobic Compound in a Fermentation

Herein are disclosed methods for increasing the secretion of a hydrophobic compound in a fermentation. The methods comprise the step of culturing a microorganism capable of producing said hydrophobic compound in a culture medium under conditions allowing production of said hydrophobic compound, wherein the culture medium comprises an extractant in an amount equal to or greater than its cloud concentration measured in an aqueous solution. The methods thus preferably comprise culturing a yeast cell in a culture medium under conditions allowing production of said hydrophobic compound, wherein the culturing step is performed at a cultivation temperature, wherein the culture medium comprises an extractant in an amount equal to or greater than its cloud concentration measured in an aqueous solution at the cultivation temperature, wherein the extractant is a non-ionic ethoxylated surfactant, whereby the secretion of the hydrophobic compound from the yeast cell is increased compared to a fermentation performed under the same conditions but either in the absence of extractant or in the presence of extractant in an amount lower than its cloud concentration in an aqueous solution at the cultivation temperature. The extractant is a non-ionic surfactant, preferably a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, or a non-ionic ethoxylated surfactant such as an antifoaming agent, for example a polyethoxylated surfactant selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The method may also further comprise a step of recovering the hydrophobic compound from the fermentation broth. The methods thus result in an increased secretion compared to a fermentation performed under similar conditions in the absence of extractant or in the presence of extractant in an amount lower than its cloud concentration in an aqueous solution. The term "similar conditions" here refers to a fermentation of the same microorganism or yeast cell, which is performed under the same conditions but either in the absence of extractant or in the presence of extractant in an amount lower than its cloud concentration in an aqueous solution at the cultivation temperature or at room temperature.

The present methods are particularly useful for increasing the secretion of hydrophobic compounds produced by fermentation of a microorganism capable of producing these compounds, preferably a yeast cell, or for example any of the microorganisms described in the above section "Microorganism". The hydrophobic compound may be any compound described in the above section "Hydrophobic compound", in particular a fatty alcohol, a fatty alcohol ester, a fatty acyl acetate, a fatty aldehyde and a terpene such as a terpenoid. The presence of a non-ionic surfactant, in particular a non-ionic ethoxylated surfactant such as an antifoaming agent, preferably a fatty alcohol alkoxylate or a polyethoxylated surfactant, in the culture medium, results in an increase in the secretion of the hydrophobic compound from the microorganism compared to the secretion observed in a fermentation performed in similar conditions but with an amount of non-ionic surfactant which is lower than its cloud concentration.

In some embodiments, the hydrophobic compound is a fatty alcohol, a fatty alcohol ester, a fatty acyl acetate or a fatty aldehyde as described herein. In other embodiments, the hydrophobic compound is a terpene such as a terpenoid as described herein. In some embodiments, the hydrophobic compound is a mixture of hydrophobic compounds, such as a mixture of fatty alcohols, fatty acyl acetates, fatty aldehydes and/or terpenes such as terpenoids as described herein. In particular embodiments, the hydrophobic compound is a desaturated fatty alcohol, a desaturated fatty acyl acetate or a desaturated fatty aldehyde as described herein.

The non-ionic surfactant is a non-ionic ethoxylated surfactant which may be an antifoaming agent. The antifoaming agent is preferably a polyethoxylated non-ionic surfactant, such as a polyethylene polypropylene glycol, a mixtures of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents, or a combination thereof.

In some embodiments, the non-ionic surfactant is a non-ionic ethoxylated surfactant, preferably selected from a fatty alcohol alkoxylate and a polyethoxylated surfactant, and is added in an amount greater than its cloud concentration measured in an aqueous solution. In some embodiments, the non-ionic ethoxylated surfactant is a polyethoxylated surfactant and is added in an amount greater than its cloud concentration measured in an aqueous solution. The cloud concentration may be determined in the cultivation medium, for example at room temperature or at the cultivation temperature.

In some embodiments, the non-ionic surfactant is a non-ionic ethoxylated surfactant present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. The cloud concentration may be determined in the cultivation medium, for example at room temperature or at the cultivation temperature.

In some embodiments, the non-ionic surfactant is a non-ionic ethoxylated surfactant preferably selected from a fatty alcohol alkoxylate and a polyethoxylated surfactant and is present in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more. In some embodiments the polyethoxylated surfactant is selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. In some embodiments, the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. The cloud concentration may be determined in the cultivation medium, for example at room temperature or at the cultivation temperature.

In some embodiments, the amount of non-ionic ethoxylated surfactant is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. The cloud concentration may be determined in the cultivation medium, for example at room temperature or at the cultivation temperature.

In some embodiments, the non-ionic surfactant is a polyethoxylated surfactant. In some embodiments the amount of polyethoxylated surfactant (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the polyethoxylated surfactant is selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. The cloud concentration may be determined in the cultivation medium, for example at room temperature or at the cultivation temperature.

In some embodiments, the non-ionic surfactant is a fatty alcohol alkoxylate. In some embodiments the amount of fatty alcohol alkoxylate (extractant) is at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. The cloud concentration may be determined in the cultivation medium, for example at room temperature or at the cultivation temperature.

In some embodiments, the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant, wherein the extractant is a non-ionic ethoxylated surfactant such as a fatty alcohol alkoxylate or a polyethoxylated surfactant. In some embodiments the polyethoxylated surfactant is selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof. In some embodiments the fatty alcohol alkoxylate is selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. The cloud concentration may be determined in the cultivation medium, for example at room temperature or at the cultivation temperature.

In some embodiments, the non-ionic surfactant is an antifoaming agent. In some embodiments the antifoaming agent is an ethoxylated and propoxylated $C_{16}$-$C_{18}$ alcohol-based agent or an ethoxylated and propoxylated $C_{16}$-$C_{18}$ alcohol-based antifoaming agent, for example, $C_{16}$-$C_{18}$ alkyl alcohol ethoxylate propoxylate (CAS number 68002-96-0). The cloud concentration of $C_{16}$-$C_{18}$ alkyl alcohol ethoxylate propoxylate (CAS number 68002-96-0) is about 1% vol/vol at room temperature. Accordingly, when this antifoaming agent is used, the culture medium preferably comprises at least 1% vol/vol of $C_{16}$-$C_{18}$ alkyl alcohol ethoxylate propoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol $C_{16}$-$C_{18}$ alkyl alcohol ethoxylate propoxylate, or more.

In some embodiments, the antifoaming agent is a polyethylene polypropylene glycol, for example Kolliphor® P407 (CAS number 9003-11-6), also termed poly(ethylene glycol)-block-poly(propylene glycol)-block-poly(ethylene glycol). The cloud concentration of Kolliphor® P407 is 10% at a temperature above 100° C. Accordingly, when a polyethylene polypropylene glycol such as Kolliphor® P407 is used, the culture medium preferably comprises at least 10% vol/vol of polyethylene polypropylene glycol such as Kolliphor® P407, such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Kolliphor® P407, or more.

In some embodiments, the non-ionic surfactant is an antifoaming agent. In some embodiments the antifoaming agent is Agnique BP420 (CAS number 68002-96-0). The cloud concentration of Agnique BP420 (CAS number 68002-96-0) is about 1% vol/vol at room temperature. Accordingly, when this antifoaming agent is used, the culture medium preferably comprises at least 1% vol/vol of Agnique BP420 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Agnique BP420 (CAS number 68002-96-0), or more.

In some embodiments, the antifoaming agent is a mixture of polyether dispersions, such as antifoam 204 (product number Δ6426 or Δ8311 from Sigma Aldrich). The cloud concentration of antifoam 204 is 1% in an aqueous solution at a temperature of 18.0 to 21.0° C. Accordingly, when a mixture of polyether dispersions such as antifoam 204 is used, the culture medium preferably comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of polyether dispersions such as antifoam 204, or more.

In some embodiments, the antifoaming agent is an antifoaming agent comprising polyethylene glycol monostearate or simethicone. Simethicone comprises polyethylene glycol monostearate, which, without being bound by theory, appears to be the compound important for the ability of simethicone to act as an extractant. Polyethylene glycol monostearate has a cloud point of 1% in an aqueous solution at 5° C. Accordingly, when simethicone or a surfactant comprising polyethylene glycol monostearate is used, the culture medium preferably comprises at least 1% vol/vol of polyethylene glycol monostearate or simethicone, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol polyethylene glycol monostearate or simethicone, or more.

In some embodiments, the extractant is a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof. These fatty alcohol alkoxylates have a cloud point of 1% in an aqueous solution at room temperature. Accordingly, when a fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, is used, the culture medium preferably comprises at least 1% vol/vol of said fatty alcohol alkoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol fatty alcohol alkoxylate, preferably selected from: Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof.

The microorganism used in the present methods may already be engineered or selected for producing the hydrophobic compound. Preferably the microorganism is a yeast cell. The present methods may further help increase the secretion of the hydrophobic compound. In some embodiments, the secretion of the hydrophobic compound from the cell is increased by at least 5% compared to the secretion observed in a fermentation performed under similar conditions in the absence of extractant or in the presence of extractant in an amount lower than its cloud concentration in an aqueous solution, such as by at least 5%, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more. The term "similar conditions" here refers to a fermentation of the same microorganism or yeast cell, which is performed under the same conditions but either in the absence of extractant or in the presence of extractant in an amount lower than its cloud concentration in an aqueous solution at the cultivation temperature or at room temperature.

In some embodiments, the hydrophobic compound is a fatty alcohol, a fatty alcohol ester, a fatty acyl acetate and/or a fatty aldehyde. In some embodiments, the hydrophobic compound is a terpene such as a terpenoid.

Thus, when a microorganism, in particular a yeast, produces fatty alcohols, the methods may further comprise the step of recovering said fatty alcohols, for example as described above, and chemically converting at least part of the fatty alcohols to the corresponding fatty acyl acetates. This can be done by performing an acetylation reaction as is known in the art, for example as described in Fritz et al., 1959, or Mattson et al., 1964. The methods may additionally or alternatively comprise the step of chemically converting at least part of the fatty alcohols to the corresponding fatty aldehydes. This can be done by performing an oxidation reaction as is known in the art, for example as described in Steves et al., 2013. The resulting fatty acyl acetates and/or fatty aldehydes may then be recovered.

For example, acetylation may be carried out with acetic anhydride using pyridine as catalyst. The resulting fatty acetates are then extracted from the reaction mix with an organic solvent and the solvent is removed by evaporation.

Oxidation may for example be carried out using known procedures for the oxidation of primary alcohols including, but not limited to, those published by Hoover et al., 2011, using Tetrakisacetonitrile copper(I) triflate/TEMPO catalyst system, Omura et al. (1978), Corey et al. (1972), Ratcliffe et al. (1970), Ley et al. (1994), or Anelli et al. (1987). The resulting fatty aldehydes are then extracted from the reaction mix with an organic solvent and the solvent is removed by evaporation and the aldehydes are purified using distillation or column chromatography.

Product Phase Comprising the Hydrophobic Compound**

The fermentation itself may be performed as is known in the art. In some embodiments, the fermentation is performed in a bioreactor. The fermentation is conducted under conditions that allow the microorganism present in the fermentation to produce the hydrophobic compound of interest. Such conditions which are suitable for production of a hydrophobic compound such as a fatty alcohol, a fatty alcohol ester, a fatty acyl acetate, a fatty aldehyde and/or a terpene such as a terpenoid by a yeast cell are readily available to the skilled person. Suitable microorganisms, in particular yeast cells, are known in the art, e.g. such yeast cells are described in e.g. WO 2016/207339, WO 2018/109163, WO 2018/109167, international application PCT/EP2020/053306 and EP application 19218703.7, and have also been described herein.

The addition of an extractant, i.e. a non-ionic surfactant, in particular a non-ionic ethoxylated surfactant, preferably selected from a fatty alcohol alkoxylate or a polyethoxylated surfactant, for example any of the non-ionic surfactants, non-ionic ethoxylated surfactants, antifoaming agents or polyethoxylated surfactants described herein, results in the generation of an emulsion in the fermentation broth, where the hydrophobic compound produced by the microorganism is present in the emulsion. Similarly, the addition of such surfactants in a concentration equal to or greater than their cloud concentration measured in an aqueous solution, for example at the cultivation temperature or at room temperature, in a fermentation where the microorganism is a yeast cell, likewise results in the generation of an emulsion in the fermentation broth, which contains the hydrophobic compound. Any of the present methods thus may also comprise a step of breaking the emulsion to recover a product phase comprising the extractant and the hydrophobic compound. Once the emulsion is broken, the fermentation broth is separated in three phases: a water phase, comprising mainly water and aqueous compounds, a phase comprising cells and cellular debris, and a product phase mainly comprising the extractant and the hydrophobic compound. Thus a composition is obtained consisting of three phases.

Thus in some embodiments, the method is for producing a hydrophobic compound and comprises the step of providing a microorganism, preferably a yeast cell, capable of producing said hydrophobic compound, and culturing said microorganism in a culture medium under conditions allowing production of said hydrophobic compound, wherein the culture medium comprises a non-ionic surfactant, more particularly a non-ionic ethoxylated surfactant, preferably selected from a fatty alcohol alkoxylate preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, and a polyethoxylated surfactant, such as a polyethoxylated surfactant or an antifoaming agent selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, in an amount equal to or greater than its cloud concentration measured in an aqueous solution, preferably at the cultivation temperature or at room temperature, whereby a composition consisting of three phases is obtained in the fermentation broth, and the method further comprises the step of recovering the product phase.

In some embodiments, the method is for increasing the titer of a hydrophobic compound in a fermentation as described herein above and comprises the step of providing a microorganism, preferably a yeast cell, capable of producing said hydrophobic compound, and culturing said microorganism or yeast cell in a culture medium under conditions allowing production of said hydrophobic compound, wherein the culture medium comprises a non-ionic surfactant, more particularly a non-ionic ethoxylated surfactant, preferably selected from a fatty alcohol alkoxylate, preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, and a polyethoxylated surfactant, such as a polyethoxylated surfactant or an antifoaming agent selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, in an amount equal to or greater than its cloud concentration measured in an aqueous solution, preferably at the cultivation temperature or at room temperature, whereby a composition consisting of three phases is obtained in the fermentation broth, and the method further comprises the step of recovering the product phase.

In some embodiments, the method is for increasing secretion of a hydrophobic compound in a fermentation as described herein above and comprises the step of providing a microorganism, preferably a yeast cell, capable of producing said hydrophobic compound, and culturing said microorganism or yeast cell in a culture medium under conditions allowing production of said hydrophobic compound, wherein the culture medium comprises a non-ionic surfactant, more particularly a non-ionic ethoxylated surfactant, preferably selected from a fatty alcohol alkoxylate, preferably selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and combinations thereof, and a polyethoxylated surfactant, such as an antifoaming agent selected from: Agnique BP420 (CAS number 68002-96-0), a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, in an amount equal to or greater than its cloud concentration measured in an aqueous solution, preferably at the cultivation temperature or at room temperature, whereby a composition consisting of three phases is obtained in the fermentation broth, and the method further comprises the step of recovering the product phase.

In preferred embodiments, most of the hydrophobic compound of the fermentation broth is present in the product phase. For example, at least 50% of the hydrophobic compound is present in the product phase, such as at least 55%, such as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99%, such as 100% of the hydrophobic compound is present in the product phase. In some embodiments, the product phase comprises at least 50% of the hydrophobic compound initially present in the fermentation broth, such as at least 55%, such as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99%, such as 100% of the hydrophobic compound initially present in the fermentation broth. In some embodiments, the hydrophobic compound is a fatty alcohol, a fatty alcohol ester, a fatty acyl acetate and/or a fatty aldehyde. In some embodiments, the hydrophobic compound is a terpene such as a terpenoid.

The step of breaking the emulsion may be performed as is known in the art, for example by submitting the emulsion to a step of phase separation as is known in the art. In some embodiments, the step of phase separation is a step of centrifugation, for example 5 minutes at 10 000 g. In some embodiments, the centrifugation is performed for 1 minute or more, such as for 2 minutes or more, such as for 3 minutes or more, such as for 4 minutes or more, such as for 5 minutes or more, such as for 6 minutes or more, such as for 7 minutes or more, such as for 8 minutes or more, such as for 9 minutes or more, such as for 10 minutes or more. In some embodiments, the centrifugation is performed at 3,000 g or more, such as at 4,000 g or more, such as at 5,000 g or more, such as at 6,000 g or more, such as at 7,000 g or more, such as at 8,000 g or more, such as at 9,000 g or more, such as at 10 000 g or more, such as at 11,000 g or more, such as at 12,000 g or more, such as at 13,000 g or more, such as at 14,000 g or more, such as at 15,000 g or more, such as at 17,500 g or more, such as at 20 000 g or more.

Following the step of breaking the emulsion, the product phase comprising the extractant and the hydrophobic compound may be recovered from the composition. The method may in such embodiments further comprise the step of separating the hydrophobic compound from the extractant. This can be performed by methods known in the art, such as by distillation, for example distillation under reduced pressure, or by column purification, or any other suitable method. The extractant may be recirculated to the fermentor or bioreactor.

In some embodiments, the method involves culturing a microorganism, preferably a yeast cell, capable of producing a fatty alcohol, such as a desaturated fatty alcohol or a mixture of (saturated and/or desaturated) fatty alcohols. The desaturated fatty alcohol may be recovered as described above. In such embodiments, the method may further comprise a step of recovering the produced fatty alcohol and chemically converting at least part thereof to the corresponding fatty acyl acetate and/or to the corresponding fatty aldehyde. The term "corresponding" here refers to a compound, fatty acyl acetate or fatty aldehyde, having the same carbon chain length as the fatty alcohol it is obtained from.

Thus, when a microorganism, preferably a yeast cell, produces fatty alcohols, the methods may further comprise the step of recovering said fatty alcohols, for example as described above, and chemically converting at least part of the fatty alcohols to the corresponding fatty acyl acetates. This can be done by performing an acetylation reaction as is known in the art, for example as described in Fritz et al., 1959, or Mattson et al., 1964. The methods may additionally or alternatively comprise the step of chemically converting at least part of the fatty alcohols to the corresponding fatty aldehydes. This can be done by performing an oxidation reaction as is known in the art, for example as described in Steves et al., 2013. The resulting fatty acyl acetates and/or fatty aldehydes may then be recovered.

Acetylation for example may be carried out with acetic anhydride using pyridine as catalyst. The resulting fatty acetates are then extracted from the reaction mix with an organic solvent and the solvent is removed by evaporation.

Oxidation may for example be carried out according to Stahl protocol using Tetrakisacetonitrile copper(I) triflate/TEMPO catalyst system. The resulting fatty aldehydes are then extracted from the reaction mix with an organic solvent and the solvent may be removed by evaporation.

Hydrophobic Compound Obtainable by the Present Methods

The present disclosure also provides a hydrophobic compound obtainable by the methods described herein.

In particular, a fatty alcohol, a fatty alcohol ester, a fatty acyl acetate, a fatty aldehyde and a terpene such as a terpenoid obtainable by the present methods are disclosed.

In some embodiments, the hydrophobic compound obtained by the present methods is a fatty alcohol. The fatty alcohol may be saturated or desaturated. Biological production of fatty alcohols from microorganisms such as yeast cells, in particular microorganisms and yeast cells engineered to produce fatty alcohols of interest, may yield a mixture of fatty alcohols comprising odd-chain fatty alcohols—in contrast to what is observed in chemical synthesis processes, where only even-chain fatty alcohols are obtained.

Thus, in some embodiments, the hydrophobic compound obtained by the present methods comprises or consists of a mixture of fatty alcohols which comprises odd-chain fatty alcohols in addition to even-chain fatty alcohols. The term "odd-chain" fatty alcohols refers to fatty alcohols having a carbon chain length which is an odd number of carbon atoms, such as 1, 3, 5, 7, 9, 11, 13, 15, 17, 19, 21, or 23 carbon atoms. The term "even-chain" fatty alcohols refers to fatty alcohols having a carbon chain length which is an even number of carbon atoms, such as 8, 10, 12, 14, 16, 18, 20 or 22 carbon atoms.

The present method allows recovering the different fatty alcohols produced by the microorganism, preferably a yeast cell, in a single process. When expressing insect desaturases and reductases, the resulting mix of fatty alcohols produced by the microorganism will typically have a similar composition as the one produced in the pheromone glands of the insects. This allows for the production of pheromone mixes suitable for various insects instead of producing individual pheromone components in separate processes that then need to be mixed in appropriate proportions. Nevertheless, as shown in example 5, the resulting mixture of fatty alcohols may contain by-products characteristic of biological production. Thus in some embodiments where production of a desired desaturated fatty alcohol is performed, the produced fatty alcohols comprise at least 1%, such as at least 2%, such as at least 3%, such as at least 4%, such as at least 5%, such as at least 10%, such as at least 15%, such as at least 20% of a desaturated fatty alcohol having a desaturation at another position than the desired fatty alcohol and/or at least 1%, such as at least 2%, such as at least 3%, such as at least 4%, such as at least 5%, such as at least 10%, such as at least 15%, such as at least 20% of the corresponding saturated fatty alcohol. If the mix of fatty alcohols recovered from the fermentation broth is chemically oxidized into aldehydes or acetylated into acetates, then corresponding mixes of aldehydes and acetates are produced.

In some embodiments, the hydrophobic compound obtained by the present methods is a fatty alcohol ester, which may be saturated or desaturated. In some embodiments, the hydrophobic compound obtained by the present methods comprises or consists of a mixture of fatty alcohol esters which comprises odd-chain fatty alcohol esters in addition to even-chain fatty alcohol esters. The term “odd-chain” alcohol esters refers to fatty alcohol esters having a carbon chain length which is an odd number of carbon atoms, such as 1, 3, 5, 7, 9, 11, 13, 15, 17, 19, 21, or 23 carbon atoms. The term “even-chain” fatty alcohol esters refers to fatty alcohol esters having a carbon chain length which is an even number of carbon atoms, such as 8, 10, 12, 14, 16, 18, 20 or 22 carbon atoms.

In some embodiments, the hydrophobic compound obtained by the present methods is a fatty aldehyde, which may be saturated or desaturated. In some embodiments, the hydrophobic compound obtained by the present methods comprises or consists of a mixture of fatty aldehydes which comprises odd-chain fatty aldehydes in addition to even-chain fatty aldehydes. The term “odd-chain” fatty aldehydes refers to fatty aldehydes having a carbon chain length which is an odd number of carbon atoms, such as 1, 3, 5, 7, 9, 11, 13, 15, 17, 19, 21, or 23 carbon atoms. The term “even-chain” fatty aldehydes refers to fatty aldehydes having a carbon chain length which is an even number of carbon atoms, such as 8, 10, 12, 14, 16, 18, 20 or 22 carbon atoms.

In some embodiments, the hydrophobic compound obtained by the present methods is a fatty acyl acetate, which may be saturated or desaturated. In some embodiments, the hydrophobic compound obtained by the present methods comprises or consists of a mixture of fatty acyl acetates which comprises odd-chain fatty acyl acetates in addition to even-chain fatty acyl acetates. The term “odd-chain” fatty acyl acetates refers to fatty acyl acetates having a carbon chain length which is an odd number of carbon atoms, such as 1, 3, 5, 7, 9, 11, 13, 15, 17, 19, 21, or 23 carbon atoms. The term “even-chain” fatty acyl acetates refers to fatty acyl acetates having a carbon chain length which is an even number of carbon atoms, such as 8, 10, 12, 14, 16, 18, 20 or 22 carbon atoms.

In some embodiments, the hydrophobic compound obtained by the present methods is a terpene such as a terpenoid, for example as described herein above.

Pheromone Composition

Also disclosed herein is a pheromone composition comprising a desaturated fatty alcohol, a desaturated fatty acyl acetate and/or a desaturated fatty aldehyde. For example, a pheromone composition may comprise (Z)-11-hexadecanol, (Z)-11-hexadecenal and/or (Z)-11-hexadecen-1-yl acetate. For example, the pheromone composition may comprise codlemone (E8,E10-dodecadien-1-ol), E8,E10-dodecadienyl acetate and/or E8,E10-dodecadienal. At least one of the desaturated fatty alcohol, the desaturated fatty acyl acetate and the desaturated fatty aldehyde is preferably obtainable by the methods disclosed herein above.

In some embodiments of the present disclosure, the pheromone composition comprises (Z)-11-hexadecanol, (Z)-11-hexadecenal and (Z)-11-hexadecen-1-yl acetate, where at least one of the (Z)-11-hexadecanol, (Z)-11-hexadecenal or (Z)-11-hexadecen-1-yl acetate and is obtainable by the methods disclosed herein above. In other embodiments, the pheromone composition comprises codlemone (E8,E10-dodecadien-1-ol), E8,E10-dodecadienyl acetate and/or E8,E10-dodecadienal.

Accordingly, the present methods may further comprise the step of formulating the recovered desaturated fatty alcohol, desaturated fatty acyl acetate or desaturated fatty aldehyde into a pheromone composition. The present pheromone compositions may be used as integrated pest management products, which can be used in a method of monitoring the presence of pest or in a method of disrupting the mating of pest.

Pheromone compositions as disclosed herein may be used as biopesticides. Such compositions can be sprayed or dispensed on a culture, in a field or in an orchard. They can also, as is known in the art, be soaked e.g. onto a rubber septa, or mixed with other components. This can result in mating disruption, thereby preventing pest reproduction, or it can be used in combination with a trapping device to entrap the pests. Non-limiting examples of pests against which the present pheromone compositions can be used are: cotton bollworm (*Helicoverpa armigera*), striped stemborer (*Chilo suppressalis*), diamond back moth (*Plutella xylostella*), cabbage moth (*Mamestra brassicae*), large cabbage-heart caterpillar (*Crocidolomia binotalis*), European corn stalk borer (*Sesamia nonagrioides*), currant clearwing (*Synanthedon tipuliformis*) and artichoke plume moth (*Platyptilia carduidactylal*). Accordingly, use of the present compositions on a culture can lead to increased crop yield, with substantially no environmental impact.

The relative amounts of the different compounds in the present pheromone compositions may vary depending on the nature of the crop and/or of the pest to be controlled; geographical variations may also exist. Determining the optimal relative amounts may thus require routine optimisation.

Examples of compositions used as repellents can be found in Kehat & Dunkelblum, 1993, for *H. armigera*, in Alfaro et al., 2009, for *C. suppressalis*, in Eizaguirre et al., 2002, for *S. nonagrioides*; in Wu et al., 2012, for *P. xylostella*; in Bari et al., 2003, for P. carduidactyla In some embodiments of the present disclosure, the pheromone composition may further comprise one or more additional compounds such as a liquid or solid carrier or substrate. For example, suitable carriers or substrate include vegetable oils, refined mineral oils or fractions thereof, rubbers, plastics, silica, diatomaceous earth, wax matrix and cellulose powder.

The pheromone composition may be formulated as is known in the art. For example, it may be under the form of a solution, a gel, a powder. The pheromone composition may be formulated so that it can be easily dispensed, as is known in the art.

EXAMPLES

All strains are described in Table 6.

Example 1—In Situ Extraction of Fatty Alcohols Produced by Fermentation

Engineered *Yarrowia lipolytica* strains ST8327 and ST8762 are capable of producing fatty alcohols (saturated and unsaturated). Strain ST8327 has been engineered to produce (Z)11-hexadecen-1-ol. It also produces smaller amounts of (Z)9-hexadecen-1-ol and hexadecanol. The strain expresses the Δ11 desaturase from *Amyelois transitella* (SEQ ID NO: 1) and fatty acyl-CoA reductase from *Helicoverpa armigera* (SEQ ID NO: 5). Strain ST8762 has been engineered to produce (Z)9-tetradecen-1-ol. The strain expresses the Δ9 desaturase from *Drosophila melanogaster* (SEQ ID NO: 16) and fatty acyl-CoA reductase from *Helicoverpa armigera* (SEQ ID NO: 5). Both strains have additional modifications that decrease degradation of fatty alcohols and improve fatty acid biosynthesis. A strain was inoculated from a YPD agar plate (10 g/L yeast extract, 10 g/L peptone, 20 g/L glucose, 15 g/L agar agar) to an initial $OD_{600}$ of 0.1-0.2 into 2.5 mL YPG medium (10 g/L yeast extract, 10 g/L peptone, 40 g/L glycerol) in 24 well-plate (EnzyScreen). The plate was incubated at 28° C. and 300 rpm for 22 hours. The well-plate was centrifuged at 3,500 g for 5 min at 4° C., the medium was removed and the cells were resuspended in 1.25 mL production medium (50 g/L glycerol, 5 g/L yeast extract, 4 g/L $KH_2PO_4$, 1.5 g/L $MgSO_4$, 0.2 g/L NaCl, 0.265 g/L $CaCl_2 \cdot 2H_2O$, 2 mL/L trace elements solution: 4.5 g/L $CaCl_2 \cdot 2H_2O$, 4.5 g/L $ZnSO_4 \cdot 7H_2O$, 3 g/L $FeSO_4 \cdot 7H_2O$, 1 g/L $H_3BO_3$, 1 g/L $MnCl_2 \cdot 4H_2O$, 0.4 g/L N $Na_2MoO_4 \cdot 2H_2O$, 0.3 g/L $CoCl_2 \cdot 6H_2O$, 0.1 g/L $CuSO_4 \cdot 5H_2O$, 0.1 g/L KI, 15 g/L EDTA). At the same time, 95 μL of Antifoam A (ethoxylated and propoxylated C16-18 alcohols, CAS No. 68002-96-0), corresponding to ~7 v/v % (i.e. above the recommended dose of 0.1 v/v % for foam management and above the cloud concentration), was added. The plate was incubated at 28° C. and 300 rpm for 28 hours. Each experiment was performed in biological triplicates.

The intracellular and extracellular concentrations of fatty alcohols were assessed as follows. 1000 μL of culture broth was transferred to a 4 mL gas-tight glass extraction vial. The sample was centrifuged at 3,500 g for 5 min at room temperature. The supernatant was transferred into a new glass vial with 990 μL of hexane and 10 μL of internal standard (IS) solution (20 mg/L of methyl Z10-heptadecanoate in ethyl acetate). The vial was vortexed for 10 s and centrifuged as before. 250 μL of the upper hexane phase was transferred to a GC vial for GC-MS analysis of the extracellular fatty alcohol concentration. The pellet remaining after the removal of the supernatant from the centrifuged culture broth was resuspended in 990 μL of solvent mixture (EtOAc and EtOH) and 10 μL of IS solution as above. The sample was incubated for 1 h with periodic mixing. 300 μL water was added and the vials were centrifuged at 3,500 g for 5 min at room temperature. 250 μL of the upper organic phase was transferred to a GC vial for GC-MS analysis of the intracellular fatty alcohols. GC-MS analyses were performed on an Agilent 7820A GC coupled to a mass selective detector Agilent 5977B. The GC was equipped with an DB Fatwax column (30 m×0.25 mm×0.25 μm), and helium was used as carrier gas. The MS was operated in electron impact mode (70 eV), scanning between m/z 30 and 400, and the injector was configured in split mode 20:1 at 220° C. Oven temperature was set to 80° C. for 1 min, then increased at a rate of 20° C./min to 210° C., followed by a hold at 210° C. for 7 min, and then increased at a rate of 20° C./min to 230° C. Compounds were identified by comparison of retention times and mass spectra of the reference compounds. Compounds were quantified by the ion 55.1 m/z. Data were analysed by the Agilent Masshunter software. The concentrations of fatty alcohols were calculated based on standard calibration curves prepared with reference standards.

Results are shown in Table 1, the standard deviations were calculated from biological triplicates. The addition of the antifoaming agent has two beneficial effects: first, the fatty alcohol total titer was increased; second, the extracellular fraction of the total fatty alcohols produced was increased (from 2-8% to 70-73%). These effects simplify the downstream processing and improve the overall economics of the process.

The example thus demonstrates that adding an extractant in an amount greater than its cloud concentration results in an increase in the titer of both a saturated fatty alcohol and of an unsaturated fatty alcohol, as well as in an increase in extracellular concentrations of the same. This is independent of the genotype of the strains, as it is observed in two different strains, and confirmed in other strains (see example 12).

In situ extraction of fatty alcohols produced by fermentation.

| Strain | ST8327 | | ST8762 | |
|---|---|---|---|---|
| Antifoam A addition | no | Yes (7 v/v %) | no | Yes (7 v/v %) |
| Unsaturated fatty alcohol | Z11-hexadecen-1-ol | | Z9-tetradecen-1-ol | |
| Saturated fatty alcohol | Hexadecanol | | Tetradecanol | |
| Total concentration of unsaturated fatty alcohol (mg/L) | 801.1 ± 82.0 | 1520.1 ± 210.0 | 101.5 ± 10.9 | 163.3 ± 11.6 |
| Extracellular concentration of unsaturated | 18.6 ± 22.9 (2.3%) | 1057.7 ± 126.7 (69.6%) | 4.9 ± 2.3 (4.9%) | 119.5 ± 11.1 (73.2%) |

-continued

In situ extraction of fatty alcohols produced by fermentation.

| Strain | ST8327 | | ST8762 | |
|---|---|---|---|---|
| fatty alcohol (mg/L) (fraction of total) | | | | |
| Total concentration of saturated fatty alcohol (mg/L) | 380.6 ± 26.4 | 862.7 ± 136.2 | 385.0 ± 23.1 | 414.2 ± 29.1 |
| Extracellular concentration of saturated fatty alcohol (mg/L) (fraction of total) | 8.5 ± 8.8 (2.2%) | 629.1 ± 83.9 (72.9%) | 29.6 ± 5.6 (7.7%) | 303.3 ± 27.5 (73.2%) |

Example 2—In Situ Extraction and Recovery of Fatty Alcohols Produced by Fermentation Here we investigated different amounts of antifoam added and the influence on the recovery of fatty alcohols in a separate phase. Substances like Antifoam A commonly used as antifoaming agents in microbial fermentations are known emulsifiers. The cloud concentration of Antifoam A was experimentally determined to be ~1 v/v % antifoam in an aqueous solution. The dose recommended for foam management by the manufacturer is 0.1 v/v %.

The experiments were performed with engineered *Y. lipolytica* strain ST8881 following the procedures as in Example 1. The strain ST8881 is similar to ST8327, but has several additional genetic modifications that further enhance the fatty acid biosynthesis. Antifoam A was added at 0, 0.4, 2, or 5% v/v concentrations. Results are shown in Table 2 and FIG. 1.

When antifoam A is added in 0.4 v/v %, below its cloud concentration with aqueous systems, Antifoam A acts as an emulsifier in the fermentation culture (FIG. 1B). In this case the secretion of the target hydrophobic compound was 14.5%, the majority of the product remaining intracellular. Applying centrifugation for 5 min at 16,000 g at room temperature resulted in separation of the solid cellular fraction from the liquid phase. However, centrifugation for 5 min at 16,000 g at room temperature did not result in successful emulsion break, implying the need for complicated recovery of the hydrophobic target compound using organic solvents and cell disruption.

When antifoam A is added in 2 and 5 v/v %, above its cloud concentration with aqueous systems, it constitutes a separate immiscible light phase (FIGS. 1C and 1D). This separate immiscible oily phase apparently acts as an in situ extractant, and resulted in 66.5% and 78.0% secretion of the target hydrophobic compound. Applying centrifugation for 5 min at 16,000 g at room temperature successfully separated the three present phases, resulting in isolation of the hydrophobic target compound in the oily phase without applying costly cell disruption techniques and extraction with organic solvents for product recovery.

TABLE 2

In situ extraction and recovery of fatty alcohols produced by fermentation.

| | Antifoam A concentration v/v % | | | |
|---|---|---|---|---|
| | 0 | 0.4 | 2 | 5 |
| Concentration of extracellular Z11-hexadecen-1-ol (mg/L) | 0.4 ± 0.6 | 213.6 ± 5.4 | 965.2 ± 142.5 | 1249.6 ± 245.4 |
| % secretion (calculated as fraction of extracellular concentration in relation to total concentration) | 0.02% | 14.5% | 66.5% | 78.0% |
| Phase separation after centrifugation | 2 phases (water, cells) FIG. 1A | 2 phases (water, cells) FIG. 1B | 3 phases (antifoam/fatty alcohols, water, cells) FIG. 1C | 3 phases (antifoam/fatty alcohols, water, cells) FIG. 1D |

Example 3—In Situ Extraction and Recovery of Fatty Alcohols Produced by Fermentation Using Various Antifoaming Agents Here we investigated the effect of different antifoaming oils and agents on the recovery of fatty alcohols in a separate phase. The experiments were performed with engineered *Y. lipolytica* strain ST8881 following the procedures as in Example 1.

The following commonly used antifoaming oils and agents were tested at 3 v/v %:

- corn oil,
- oleic acid,
- Antifoam A,
- Kolliphor® P407 (a poly(ethylene glycol)-block-poly (propylene glycol)-block-poly(ethylene glycol)),
- A-204 (a mixture of organic polyether dispersions),
- Simethicone (a silicone emulsion), and
- dodecane.

The suppliers are indicated in Table 3. The control experiment was performed without addition of any antifoaming oil or agent. Antifoaming oils and agents are added at 3 vol/vol % to the culture broth, which is a significantly lower amount than the concentration of organic phase in classic biphasic fermentations as known in the art (above 5-10 v/v %).

The in situ extraction performance of commonly used antifoaming oils and agents is shown in Table 3. Cultures with Corn oil, Antifoam A, Kolliphor® P407, A-204 and Simethicone showed increased concentration of fatty alcohols compared to control cultivations. Cultures with Corn oil, Antifoam A, Kolliphor® P407, A-204 and Simethicone presented also higher secretion rates of fatty alcohols compared to control cultivations.

In the case of oleic acid, Antifoam A, Kolliphor® P407, A-204 and Simethicone, applying centrifugation for 5 min at 10,000 g at 30° C. resulted in separation of the solid cellular fraction from the liquid phase (FIG. 2C, FIG. 2D, FIG. 2E, FIG. 2F and FIG. 2G, respectively). In the case of corn oil and dodecane, the solid cellular fraction constituted a dispersion with the organic upper phase (FIG. 2B and FIG. 2H, respectively).

In the case of Antifoam A, Kolliphor® P407, A-204 and Simethicone, centrifugation for 5 min at 10,000 g at 30° C. resulted in successful water-oil emulsion break.

TABLE 3

In situ extraction and recovery of fatty alcohols produced by fermentation using antifoaming agents

| Anti-foaming agent | Provider | CAS No | Total concentration of Z11-hexa-decen-1-ol (mg/L) | Extracellular concentration of Z11.hexa-decen-1-ol (% secretion) | Phase separation after centri-fugation 10,000 × g for 5 min at 30° C. |
|---|---|---|---|---|---|
| Control without anti-foam addition | — | — | 2190.0 ± 320.0 | 0 (0%) | Phase 1: Water<br>Phase 2: cells<br>FIG. 2A |
| Corn oil | Roquette | 8001-30-7 | 2699.6 ± 42.3 | 646.6 ± 437.1 (24%) | Phase 1: suspension of oil and cells<br>Phase 2: water<br>FIG. 2B |
| Oleic acid | Merck | 112-80-1 | 1008.4 ± 648.6 | 0 (0%) | Phase 1: emulsion of oil and water<br>Phase 2: cells<br>FIG. 2C |
| Anti-foam A | Bekchem | 68002-96-0 | 3406.6 ± 276.3 | 1354.8 ± 365.1 (39.8%) | Phase 1: organic<br>Phase 2: water<br>Phase 3: cells<br>FIG. 2D |
| Kolliphor ® P407 | Merck | 9003-11-6 | 2546.5 ± 96.4 | 177.7 ± 34.1 (6.9%) | Phase 1: organic<br>Phase 2: water<br>Phase 3: cells<br>FIG. 2E |
| A-204 | Sigma | | 2946.2 ± 459.5 | 723.5 ± 1040.99 (24.6%) | Phase 1: organic<br>Phase 2: water<br>Phase 3: cells<br>FIG. 2F |
| Simethicone | Dow | 9004-67-5<br>63231-67-4<br>9004-99-3 | 1919.0 ± 153.9 | 222.5 ± 58.0 11.6%) | Phase 1: organic<br>Phase 2: water<br>Phase 3: cells<br>FIG. 2G |
| Dodecane | Merck | 112-40-3 | 720.0 ± 95.6 | 0 (0%) | Phase 1: organic with cells<br>Phase 2: water<br>Phase 3: cells<br>FIG. 2H |

Example 4—In Situ Extraction and Recovery of Other Lipophilic/Hydrophobic Compounds Microorganisms capable of producing various lipophilic compounds, e.g. engineered to produce free fatty acids, fatty acyl acetates, fatty aldehydes and terpenes such as terpenoids, are cultivated in the presence of antifoaming agents such as a polyethoxylated surfactant at concentrations equal to or higher than their cloud concentration.

The resulting fermentation broth is subjected to centrifugation and the light phase containing non-ionic surfactant and the product is separated by centrifugation. The light phase is further subjected to distillation, possibly under vacuum, in order to separate the product from the non-ionic surfactant and other non-volatile impurities. The distilled product can be for example a mix of fatty alcohols. The fatty alcohols mix can be acetylated into the corresponding fatty alcohol acetates or oxidized into the corresponding fatty aldehydes.

Acetylation is carried out with acetic anhydride using pyridine as catalyst. The resulting fatty alcohol acetates are then extracted from the reaction mix with an organic solvent and the solvent is removed by evaporation. Oxidation is carried out according to Stahl protocol using Tetrakisacetonitrile copper(I) triflate/TEMPO catalyst system. The resulting fatty aldehydes are then extracted from the reaction mix with an organic solvent and the solvent is removed by evaporation. The resulting fatty alcohol acetates or fatty aldehydes are formulated and used for plant protection from insects.

Example 5—Biological Activity of Pheromone Preparations Obtained by Fermentation (Z)11-hexadecen-1-ol (Z11-16:OH) produced by fermentation in *Yarrowia lipolytica*, for example, will typically co-occur with (Z)9-hexadecen-1-ol (Z9-16:OH), which is produced due to the action of the native *Yarrowia lipolytica* desaturase OLE1. In engineered strains, Z9-16:OH was also produced in the amounts of 5-20% of the amount of Z11-16:OH. Saturated fatty alcohols of carbon chain 16 were also produced as byproducts, when reductase acts directly on the saturated substrate hexadecenyl-CoA.

When the mix of fatty alcohols recovered from the fermentation broth is chemically oxidized into aldehydes or acetylated into acetates, then corresponding mixes of aldehydes and acetates are produced.

In an exemplary sample preparation, the composition was as follows: 65% Z11-16:Ald, 4% Z9-16:Ald, 10% 16:Ald.

Fermented Z11-16:Ald can be used for controlling cotton bollworm *Helicoverpa armigera* by mating disruption. The pheromone glands of *H. armigera* contain Z11-16:Ald, Z9-16:Ald, and 16:Ald.

The ratio between Z11-16:Ald and Z9-16:Ald varies from 99:1 to 90:10 (http://www.pherobase.com/database/species/species-*Helicoverpa*-armigera.php). Z9-16:Ald is a minor component of *H. armigera* pheromone mix and it was reported to enhance the activity of an artificial pheromone formulation, when it was added to Z11-16:Ald (Kehat et al., 1990). n-Hexadecanal 16:Ald is also present in *H. armigera* pheromone glands at 4-20%, but it is neutral in regard to behavioral response.

Fermented Z11-16:Ald can be used for controlling the Asiatic rice borer *Chilo suppressalis* by mating disruption. The pheromone glands of *C. suppressalis* also contain Z11-16:Ald, Z9-16:Ald, and 16:Ald. The ratio between Z11-16:Ald and Z9-16:Ald is 10:1 (http://www.pherobase-.com/database/species/species-*Chilo*-suppressalis.php). Z9-16:Ald is synergistic to the two primary pheromone components Z11-16:Ald and Z13-18:Ald (Tatsuki et al., 2983). n-Hexadecanal 16:Ald is a neutral component and does not elicit a behavioral response.

Fermented Z11-16:Ald can be used for controlling the Yellow rice stemborer *Scirpophaga incertulas* by mating disruption. The pheromone glands of *S. incertulas* contain Z11-16:Ald, Z9-16:Ald, and 16:Ald. The ratio between Z11-16:Ald and Z9-16:Ald is 4:1 to 2:1 (http://www.pherobase.com/database/species/speciesScirpophaga-incertulas-.php).

Hence the two key by-products that were produced by engineered yeasts are present in amounts similar to the natural range of pheromone composition in insects. Z9-16 compounds are usually biologically active and beneficial for the behavioral activity.

Example 6—Strain Construction

Strains ST3705 (Example 2 and Table 4 of WO 2016/207339) and ST5290 (Example 4 of WO 2018/109167) are *Saccharomyces cerevisiae* strains engineered to produce (Z)11-hexadecen-1-ol and Z9-tetradecenyl acetate, respectively. Strain ST3705 expresses the Δ11 desaturase from *Amyelois transitella* and fatty acyl-CoA reductase from *Helicoverpa armigera*. Strain ST5290 expresses Δ9 desaturase from *Drosophila melanogaster*, fatty acyl-CoA reductase from *Helicoverpa armigera* and acetyltransferase ATF1 from *Saccharomyces cerevisiae*.

Strain ST4840 is a *Yarrowia lipolytica* wild-type strain. *Y. lipolytica* strain ST6629 is a *Yarrowia lipolytica* strain and has been described previously in WO 2018/109167 (Example 9 of WO 2018/109167). In this strain, the open-reading frame of genes HFD4 (YALI0B01298g), HFD3 (YALI0A17875), HFD2 (YALI0E15400) and HFD1 (YALI0F23793g), as well as nucleotides −1130 to −100 upstream of the coding sequence of GPAT (YALI0C00209g) were deleted. A premature Stop-codon and frameshift was introduced in PEX10 (YALI0C01023g) and FAO1 (YALI0B14014g) resulting in non-functional genes.

In *Y. lipolytica* strain ST9426 was engineered to improve the mevalonate pathway flux and used as a terpenoids platform strain. In this strain, the open reading frame of genes KU70 (YALI0C08701g) and PEX10 (YALI0C01023g), as well as nucleotides −529 to −50 upstream of the coding sequence of squalene synthase (SQS1, YALI0Δ10076g) were deleted. Furthermore, genes isopentenyl-diphosphate delta-isomerase (IDI1, YALI0F04015g), farnesyl diphosphate synthase (ERG20, YALI0E05753g), 3-hydroxy-3-methylglutaryl coenzyme A reductase (HMG1, YALI0E04807g) and geranylgeranyl pyrophosphate synthase (GGPPS, SEQ ID: 46) were also overexpressed.

*Y. lipolytica* strains ST7982, ST8327, ST9253, ST10229, ST10230, ST10231, ST9423, ST9424, and ST10151 were constructed as follows.

All heterologous genes were synthesized by GeneArt (Life Technologies) in codon optimized versions for *Y. lipolytica*. All genes were amplified by PCR using Phusion U Hot Start DNA Polymerase (ThermoFisher) to obtain the fragments for cloning into yeast expression vectors. The primers and the resulting DNA fragments (BioBricks) are listed in Table 4. The PCR products were separated on a 1%-agarose gel containing RedSafe™ (iNtRON Biotechnology). PCR products of the correct size were excised from the gel and purified using the Nucleospin Gel and PCR Clean-up kit (Macherey-Nagel).

Integrative yeast vectors with USER cassette were linearized with FastDigest SfaAI (ThermoFisher) for 2 hours at 37° C. and then nicked with Nb.BsmI (New England Biolabs) for 1 hour at 65° C. The resulting vectors containing sticky ends were separated by gel electrophoresis, excised from the gel, and gel-purified using the Nucleospin Gel and PCR Clean-up kit (Macherey-Nagel). The DNA fragments were cloned into the so prepared vectors by USER-cloning as described in (Holkenbrink et al., 2018). The reaction was transformed into chemically competent *E. coli* DHalpha cells and the cells were plated on Lysogeny Broth (LB) agar plates with 100 mg/L ampicillin. The plates were incubated overnight at 37° C. and the resulting colonies were screened by colony PCR. The plasmids were purified from overnight *E. coli* liquid cultures and the correct cloning was confirmed by sequencing. The constructed vectors are listed in Table 5.

Yeast strains were constructed by transformation of DNA vectors as described in Holkenbrink et al., 2018. Integrative vectors were linearized with FastDigest NotI prior to transformation. When needed, helper vectors to promote the integration into specific genomic regions were co-transformed with the integrative plasmid or DNA repair fragments (Tables 4 and 5). Strains were selected on yeast peptone dextrose (YPD) agar with appropriate antibiotics selection. Correct genotype was confirmed by colony PCR and when needed by sequencing. The resulting strains are listed in Table 6.

TABLE 4

DNA fragments (BioBricks) obtained by PCR using the indicated template and primers.

| DNA fragment name | Description | Fw_primer (5'->3') Hybridises at positions | Rv_primer (5'->3') Hybridises at positions | Template DNA |
|---|---|---|---|---|
| BB2311 | 5' end of FAS2 (I1220F) repair fragment | Yali0B 2566672 . . . 2566691 | Yali0B 2567146 . . . 2567159 | *Y. lipolytica* genomic DNA |
| BB2312 | 3' end of FAS2 (I1220F) repair fragment | Yali0B 2567171 . . . 2567190 | Yali0B 2567645 . . . 2567662 | *Y. lipolytica* genomic DNA |
| BB2313 | FAS2 (I1220F) | BB2311 1 . . . 20 | BB2312 475 . . . 492 | BB2311, BB2312 |
| BB1006 | Linearized vector PL3405 | 1097 . . . 1129 | 1696 . . . 1727 | PL3405* |
| BB1005 | Hygromycin resistance cassette | 2894 . . . 2923 | 3906 . . . 3935 | PL4132* |
| BB1135 | Vector backbone | 2306 . . . 2336 | 5129 . . . 5152; 1 . . . 13 | PL6681* |
| BB8388 | Region from *Y. lipolytica* genome | Yali0F 2011922 . . . 2011937 | Yali0F 2012405 . . . 2012421 | *Y. lipolytica* genomic DNA |
| BB1631 | Y. *lipolytica* PEX20 and LIP2 terminator | 516 . . . 546 | 1789 . . . 1815 | PL6371* |
| BB8389 | Region from *Y. lipolytica* genome | Yali0F 2012722 . . . 2012743 | Yali0F 2013206 . . . 2013221 | *Y. lipolytica* genomic DNA |
| BB2608 | *Y. lipolytica* LIP2 terminator | Yali0A 2187638 . . . 2187643 | Yali0A 2188554 . . . 2188574 | *Y. lipolytica* genomic DNA |
| BB8049 | Desaturase from *Amyelois transitella* expressed under *Y. lipolytica* TEF promoter and LIP2 terminator | BB2093 1 . . . 14 | BB2608 2188554 . . . 2188574 | BB2093, BB8047, BB2608 |
| BB8048 | *Y. lipolytica* TEF promoter | Yali0C 1244246 . . . 1244265 | Yali0C 1243743 . . . 1243761 | *Y. lipolytica* genomic DNA |
| BB8047 | Desaturase from *Amyelois transitella* | 4 . . . 23 | 963 . . . 981 | SEQ ID NO: 1 |
| BB8169 | Linearized vector PL6677 | 1814 . . . 1833 | 840 . . . 857 | PL6677* |
| BB8269 | Linearized vector PL8006 | 1739 . . . 1756 | 765 . . . 782 | PL8006 |
| BB8167 | Fatty acyl reductase from *H. armigera* expressed under *Y. lipolytica* TEF promoter and LIP2 terminator | 867 . . . 891 | 3703 . . . 3723 | PL8236 |

TABLE 4-continued

DNA fragments (BioBricks) obtained by PCR using the indicated template and primers.

| DNA fragment name | Description | Fw_primer (5'->3') Hybridises at positions | Rv_primer (5'->3') Hybridises at positions | Template DNA |
|---|---|---|---|---|
| BB8168 | Fatty acyl reductase from *H. armigera* expressed under *Y. lipolytica* TEF promoter and LIP2 terminator | 878 . . . 897 | 3705 . . . 3723 | PL8236 |
| BB8212 | Fatty acyl reductase from *H. armigera* expressed under *Y. lipolytica* TEF promoter and LIP2 terminator | 878 . . . 891 | 3703 . . . 3723 | PL8236 |
| BB8213 | Fatty acyl reductase from *H. armigera* expressed under *Y. lipolytica* TEF promoter | 878 . . . 897 | 2753 . . . 2773 | PL8236 |
| BB2719 | Tef promoter of *Y. lipolytica* | Yali0C 1244252 . . . 1244265 | Yali0C 1243743 . . . 1243761 | *Y. lipolytica* genomic DNA |
| BB2693 | Desaturase from *L. brotana* | 4 . . . 22 | 997 . . . 1014 | SEQ ID NO: 43 |
| BB1688 | Tef promoter of *Y. lipolytica* | Yali0C 1244254 . . . 1244265 | Yali0C 1243743 . . . 1243762 | *Y. lipolytica* genomic DNA |
| BB1740 | Fatty acyl reductase from *H. armigera* | 4 . . . 21 | 1348 . . . 1368 | SEQ ID NO: 5 |
| BB1635 | tRNA from *Y. lipolytica* | 3154 . . . 3183 | 3342 . . . 3371 | PL4589 |
| BB1636 | region from *Y. lipolytica* genome | 3392 . . . 3424 | 3458 . . . 3498 | PL4589 |
| BB7970 | FAS1 from *Y. lipolytica* | Yali0B 2006887 . . . 2006907 | Yali0B 2000650 . . . 2000673 | *Y. lipolytica* genomic DNA |
| BB2209 | Tef promoter of *Y. lipolytica* | Yali0C 1244252 . . . 1244265 | Yali0C 1243743 . . . 1243761 | *Y. lipolytica* genomic DNA |
| BB2093 | Tef promoter of *Y. lipolytica* | Yali0C 1244252 . . . 1244265 | Yali0C 1243743 . . . 1243761 | *Y. lipolytica* genomic DNA |
| BB8969 | Desaturase of *Drosophila grimshawi* | 4 . . . 18 | 1137 . . . 1149 | SEQ ID NO: 44 |
| BB8971 | Desaturase of *Drosophila virilis* | 4 . . . 18 | 1131 . . . 1146 | SEQ ID NO: 45 |
| BB8662 | FAS2 (I1220F) | Yali0B 3170 . . . 3189 | Yali0B 4143 . . . 4160 | Genomic DNA of strain ST7982 |
| BB7983 | Region from Y. *lipolytica* genome | Yali0B 1644153 . . . 1644173 | Yali0B 1644632 . . . 1644647 | *Y. lipolytica* genomic DNA |
| BB7984 | Region from *Y. lipolytica* genome | Yali0B 1644658 . . . 1644677 | Yali0B 1645125 . . . 1645143 | *Y. lipolytica* genomic DNA |

TABLE 4-continued

DNA fragments (BioBricks) obtained by PCR using the indicated template and primers.

| DNA fragment name | Description | Fw_primer (5'->3') Hybridises at positions | Rv_primer (5'->3') Hybridises at positions | Template DNA |
|---|---|---|---|---|
| BB7985 | Region from *Y. lipolytica* genome | BB7983 1 . . . 21 | BB7984 468 . . . 486 | BB7983, BB7984 |
| BB9296 | Desaturase of *Drosophila melanogaster* | 4 . . . 19 | 1071 . . . 1086 | SEQ ID NO: 16 |
| BB8386 | Region from *Y. lipolytica* genome | YALI0F 3823053 . . . 3823069 | YALI0F 3823536 . . . 3823552 | *Y. lipolytica* genomic DNA |
| BB8387 | Region from *Y. lipolytica* genome | YALI0F 3823853 . . . 3823869 | YALI0F 3824332 . . . 3824352 | *Y. lipolytica* genomic DNA |
| BB8663 | Region from *Y. lipolytica* genome | YALI0C 406284 . . . 406298 | YALI0C 405783 . . . 405802 | *Y. lipolytica* genomic DNA |
| BB8664 | Region from *Y. lipolytica* genome | YALI0C 405647 . . . 405665 | YALI0C 405163 . . . 405177 | *Y. lipolytica* genomic DNA |
| BB2722 | *Y. lipolytica* EXP promoter | YALI0C 1663140 . . . 1663158 | YALI0C 1664123 . . . 1664141 | *Y. lipolytica* genomic DNA |
| BB8644 | *Y. lipolytica* GPD promoter | YALI0C 825834 . . . 825853 | YALI0C 826740 . . . 826766 | *Y. lipolytica* genomic DNA |
| BB8836 | HMG1 | YALI0E 539630 . . . 539649 | YALI0E 542627 . . . 542629 | *Y. lipolytica* genomic DNA |
| BB8837 | ERG20 | YALI0E 642319 . . . 642337 | YALI0E 641303 . . . 641324 | *Y. lipolytica* genomic DNA |
| BB8838 | IDI1 | YALI0F 601747 . . . 601765 | YALI0F 600953 . . . 600970 | *Y. lipolytica* genomic DNA |
| BB8847 | geranyl-geranyl pyrophosphate synthase of *Synechococcus* sp. | 1 . . . 17 | 878 . . . 894 | SEQ ID NO: 46 |
| BB9273 | ß-farnesene synthase of *Artemisia annua* | 4 . . . 20 | 1710 . . . 1725 | SEQ ID NO: 47 |

TABLE 5

List of vectors used

| Expression vector | Parent vector | DNA fragments cloned into parent vector (crRNA sequence, if applicable) |
|---|---|---|
| PL4589* | | |
| PL3431 | | BB1006, BB1005 |
| PL8264 | | BB1135, BB8388, BB1631, BB8389 |
| PL9002 | PL3405 | BB8955 |
| PL7981 | PL6371* | BB8049, BB8048, BB8047 |
| PL8037 | PL6684* | BB8049, BB8048, BB8047 |
| PL8033 | PL3431 | BB1635, BB1636, (YALI0D; 2193232 . . . 2193213) |
| PL8071 | PL6679* | BB8212, BB8213 |
| PL8034 | PL3431 | BB1635, BB1636, (YALI0E; 1722566 . . . 1722585) |
| PL8053 | | BB8169, BB8167, BB8168 |
| PL7983 | PL3405* | BB1635, BB1636, (YALI0B; 1644658 . . . 1644677 |
| PL8158 | PL3431 | BB1635, BB1636 (YALI0A; 1556748 . . . 1556767) |

TABLE 5-continued

List of vectors used

| Expression vector | Parent vector | DNA fragments cloned into parent vector (crRNA sequence, if applicable) |
|---|---|---|
| PL8150 | | BB8269, BB8167, BB8168 |
| PL8071 | PL6679 | BB8212, BB8213 |
| PL6638 | PL3405 | BB1635, BB1636 (YALI0E; 2882052 . . . 2882071) |
| PL6631 | PL3405 | BB1635, BB1636, (YALI0D; 2193232 . . . 2193213) |
| PL7912 | PL6684 | BB2719, BB2693 |
| PL8680 | PL6371 | BB2209, BB2693 |
| PL6630 | PL3405 | BB1635, BB1636 (YALI0C; 568875 . . . 568856) |
| PL8655 | PL8264 | BB2209, BB7970 |
| PL8646 | PL3431 | BB1635, BB1636, (YALI0F; 2012605 . . . 2012624) |
| PL8236 | PL6679 | BB1688, BB1740 |
| PL8655 | PL8264 | BB7970, BB2209 |
| PL9023 | PL9002 | BB2093, BB8969 |

TABLE 5-continued

List of vectors used

| Expression vector | Parent vector | DNA fragments cloned into parent vector (crRNA sequence, if applicable) |
|---|---|---|
| PL9025 | PL9002 | BB2093, BB8971 |
| PL7088 | PL3405 | BB1635, BB1636, YALI0B; 2567145 . . . 2567164) |
| PL9003 | PL3405 | BB2093, BB9296 |
| PL8863 | PL3431 | BB1635, BB1636 (YALI0A; 1017584 . . . 1017603) |
| PL8263 | | BB1135, BB8386, BB1631, BB8387 |
| PL8622 | | BB1135, BB8663, BB1631, BB8664 |
| PL8864 | PL8263 | BB8838, BB2722, BB8644, BB8837 |
| PL8540 | PL3405 | BB1635, BB1636 (YALI0F; 3823780 . . . 3823799) |
| PL8865 | PL8622 | BB8836, BB2722, BB8644, BB8847 |
| PL8625 | PL3405 | BB1635, BB1636 (YALI0C; 405763 . . . 405782) |
| PL5239 | PL3405 | BB1635, BB1636 (YALI0C; 140578 . . . 140597) |
| PL9389 | PL6371* | BB2093, BB9273 |
| PL8032 | PL3431 | BB1635, BB1636 (YALI0C, 568856 . . . 568875) |

TABLE 6

Yeast strains.

| Strain name | Intrinsic genome edits | Over-expressed genes | Parent strain (integrated vector) |
|---|---|---|---|
| ST3705 | | Atrd11 HarFAR | |
| ST5290 | | Dmd9 HarFAR ScATF1 | |
| ST6629 | Δhfd1-4 Δfao1 Δpex10 Δ-1130-100_PrGPAT | | |
| ST7982 | B19382* | | ST6629 (PL7088, BB2313) |
| ST8200 | | Atrd11 | ST6629 (PL7981, PL6630) |
| ST8201 | | Atrd11 | ST8200 (PL8037, PL8033) |
| ST8223 | | Atrd11 HarFAR | ST8201 (PL6638, PL8071) |
| ST8246 | | Atrd11 HarFAR | ST8223 (PL8034, PL8053) |
| ST8264 | B12342* | Atrd11 HarFAR | ST8246 (PL7983, BB7985) |
| ST8327 | B12342* | Atrd11 HarFAR | ST8264 (PL8158, PL8150) |
| ST8225 | B19382* | HarFAR | ST7982 (PL6638, PL8071) |
| ST8373 | B19382* | HarFAR LboPPTQ | ST8225 (PL7912, PL6631) |
| ST9136 | B19382* | HarFAR LboPPTQ | ST8373 (PL8680, PL6630) |
| ST9253 | B19382* | HarFAR LboPPTQ YlFAS1 | ST9136 (PL8655,PL8646) |
| ST10229 | B19382* | HarFAR YlFAS1 Dgd9 | ST8225 (PL9023) |
| ST10230 | B19382* | HarFAR YlFAS1 Dvd9 | ST8225 (PL9025) |
| ST10231 | B19382* | HarFAR YlFAS1 Dmd9 | ST8225 (PL9003) |

TABLE 6-continued

Yeast strains.

| Strain name | Intrinsic genome edits | Over-expressed genes | Parent strain (integrated vector) |
|---|---|---|---|
| ST6029 | Δku70 | | ST4840 (PL6364, Marella et al., 2020) |
| ST9423 | SQS_Pr50 bp | | ST6029 (YALI0A; 1017515 . . . 1017559; 1018039 . . . 1018083, PL8863) |
| ST9424 | | IDI1 ERG20 | ST9423 (PL8864, PL8540) |
| ST9425 | | HMG1 SynGGPPs7 | ST9424 (PL8865, PL8625) |
| ST9426 | Δpex10 | | ST9425 (YALI0C; 139673 . . . 139717; 140852 . . . 140896, PL5239) |
| ST10151 | | AaBFS | ST9426 (PL9389, PL8032) |

Example 7—Selection of Surfactants: Ethoxylates/Ethoxylated Non-Ionic Surfactants Selected non-ionic ethoxylated surfactants with trade name, manufacturer, chemical name, CAS No., cloud point (° C., by provider), cloud concentration (v/v %, in aqueous systems at room temperature, experimentally measured), recommended dose for foam management (%, by provider) were tested (Table 7).

Simple model mixture experiments were performed using 1 mL production medium (50 g/L glycerol, 5 g/L yeast extract, 4 g/L $KH_2PO_4$, 1.5 g/L $MgSO_4$, 0.2 g/L NaCl, 0.265 g/L $CaCl_2 \cdot 2H_2O$, 2 mL/L trace elements solution: 4.5 g/L $CaCl_2 \cdot 2H_2O$, 4.5 g/L $ZnSO_4 \cdot 7H_2O$, 3 g/L $FeSO_4 \cdot 7H_2O$, 1 g/L $H_3BO_3$, 1 g/L $MnCl_2 \cdot 4H_2O$, 0.4 g/L N $Na_2MoO_4 \cdot 2H_2O$, 0.3 g/L $CoCl_2 \cdot 6H_2O$, 0.1 g/L $CuSO_4 \cdot 5H_2O$, 0.1 g/L KI, 15 g/L EDTA) supplemented with 0 v/v %, 0.1 v/v % (below the measured cloud concentration, close to recommended dose for foam management), and 3 v/v % (above the measured cloud concentration) surfactants in 2 mL spin tubes. The tubes were vortexed for 5 s to mimic mixing conditions during the fermentation process. Spin tests were carried out at room temperature at 15,000 g for 5 min in a benchtop centrifuge.

The spin tests revealed that when the surfactants were applied at the recommended low doses for foam management in a fermentation process (0.1 v/v %, below their cloud concentrations), no phase separation was detected (only one homogeneous aqueous phase). However, when the surfactants were used in a concentration higher than their cloud concentrations, the hydrophobic oily and the hydrophilic aqueous phase could be easily separated by the applied centrifugal force during the spin tests. Applying a surfactant above its recommended dose for foam management, and above its cloud concentration enables increased production, secretion by in-situ extraction of hydrophobic pheromone products of a fermentation. In addition, by simple mechanical separation, the easy and economic recovery of hydrophobic pheromone products of a fermentation is facilitated.

TABLE 7

Measured cloud concentration: measured in aqueous systems (production media - example A) at room temperature (v/v %). Foam management dose: Dose recommended dose for foam management (%) by provider.

| Surfactant trade name | Manufacturer | Chemical name | CAS No. | Cloud Point ° C.- by provider | Measured cloud concentration | Foam management dose (%) | Spin test |
|---|---|---|---|---|---|---|---|
| Antifoam A | Bekchem | ethoxylated and propoxylated C16-18 alcohols | 68002-96-0 | 23-27 (butyldiglycol) | approx. 1 | Up to 0.1 | OW |
| Plurafac ® LF300 | BASF | Oxirane, methyl-, polymer with oxirane, monoisotridecyl ether, block | 196823-11-7 | 22 (1% aqueous) | approx. 1 | | OW* |
| Agnique BP420 | BASF | ethoxylated and propoxylated C16-18 alcohols | 68002-96-0 | 26 (butyldiglycol) | approx. 1 | | OW |
| Plurafac ® LF1300 | BASF | ethoxylated and propoxylated C16-18 alcohols | 68002-96-0 | 26 (butyldiglycol) | approx. 1 | | OW |
| Plurafac ® SLF180 | BASF | Ethoxylated alkyl alkohol | No CAS, Ref. No 02-211963 0747-33-0000 | 16-21 (1% aqueous) | approx. 1 | 0.1-0.5 | OW* |
| Dehypon ® 2574 | BASF | Fatty alcohol, ethoxylated and propoxylated | 68154-97-2 | 40 (butyldiglycol) | approx. 1 | | OW |
| Imbentin SG/251 | KLK Oleo | Alcohols C8-18, ethoxylated, propoxylated | 68002-96-0 | 21-26 (butyldiglycol) | approx. 1 | 0.1 | OW** |
| A-204 | Sigma | mixture of organic polyether dispersions | -(product number A6426 and A8311, MDL number MFCD00130523) | 18-21 (1% aqueous) | approx. 1 | 0.005-0.01 | OW |

OW: visible oil-water phase separation only above cloud concentration;
OW*: visible oil-water phase separation only above cloud concentration (water phase cloudy - some miscibility of surfactant with water);
OW**: visible oil-water phase separation only above cloud concentration, some cloudiness in the interface of the two separated phases.

Example 8—In Situ Extraction and Recovery of Fatty Alcohols Produced by Fermentation Here we investigated different amounts of antifoam added and the influence on the recovery of fatty alcohols in a separate phase. Substances like Antifoam A (Bekchem) commonly used as antifoaming agents in microbial fermentations are known emulsifiers. The cloud concentration of Antifoam A was experimentally determined to be ~1 v/v % antifoam in an aqueous solution. The dose recommended for foam management by the manufacturer is 0.1 v/v %.

The experiments were performed with engineered *Y. lipolytica* strain ST8327 following the procedures as in Example 1. Antifoam A was added at 0, 0.4, 2, or 5% v/v concentrations. Results are shown in Table 8.

When antifoam A is added in 0.4 v/v %, below its cloud concentration measured in an aqueous solution, Antifoam A acts as an emulsifier in the fermentation culture, similar to what was observed in Example 2. In this case the secretion of the target hydrophobic compound was 20-25%, the majority of the product remaining intracellular. Applying centrifugation for 5 min at 16,000 g at room temperature resulted in separation of the solid cellular fraction from the liquid phase. However, centrifugation for 5 min at 16,000 g at room temperature did not result in successful emulsion break, implying the need for complicated recovery of the hydrophobic target compound using organic solvents and cell disruption.

When antifoam A is added in 2 and 5 v/v %, above its cloud concentration measured in an aqueous solution, it constitutes a separate immiscible light phase (as also seen in FIGS. 1C and 1D). This separate immiscible oily phase apparently acts as an in situ extractant, and resulted in 73-74% and 67% secretion of the target hydrophobic compound. Applying centrifugation for 5 min at 16,000 g at room temperature successfully separated the three present phases, resulting in isolation of the hydrophobic target compound in the oily phase without applying costly cell disruption techniques and extraction with organic solvents for product recovery.

TABLE 8

In situ extraction and recovery of fatty alcohols produced by fermentation.

| | Antifoam A concentration v/v % | | | |
|---|---|---|---|---|
| | 0 | 0.4 | 2 | 5 |
| Concentration of extracellular Z11-hexadecen-1-ol (mg/L)/ Z9-hexadecen- | 35.3 ± 8.2/ 0.3 ± 0.5 | 219.6 ± 81.1/ 40.9 ± 16.5 | 664.3 ± 73.9/ 136.6 ± 21.6* | 1149 ± 167.9/ 271.8 ± 33.4 |

TABLE 8-continued

In situ extraction and recovery of fatty alcohols produced by fermentation.

| | Antifoam A concentration v/v % | | | |
|---|---|---|---|---|
| | 0 | 0.4 | 2 | 5 |
| 1-ol (mg/L) | | | | |
| % secretion (calculated as fraction of extracellular concentration in relation to total concentration) | 3.5%/0.2% | 24.5%/19.8% | 74.3%/72.8% | 67.1%/66.8% |
| Phase separation after centrifugation | 2 phases (water, cells) FIG. 1A | 2 phases (water, cells) FIG. 1B | 3 phases (antifoam/fatty alcohols, water, cells) FIG. 1C | 3 phases (antifoam/fatty alcohols, water, cells) FIG. 1D |

*Technical duplicates only

Example 9—Increased Production, Secretion, and Recovery of Fatty Alcohols by the Yeast *Saccharomyces cerevisiae*

Here the increased production, secretion, and recovery of fatty alcohols by the engineered yeast *Saccharomyces cerevisiae* was demonstrated.

Strain ST3705 was inoculated from a YPD agar plate (10 g/L yeast extract, 10 g/L peptone, 20 g/L glucose, 15 g/L agar agar) to an initial $OD_{600}$ of 0.1-0.2 into 2.5 mL YPD medium (10 g/L yeast extract, 10 g/L peptone, 40 g/L glucose) in 24 well-plate (EnzyScreen). The plate was incubated at 28° C. and 300 rpm for 22 hours. The well-plate was centrifuged at 3,500 g for 5 min at 4° C., the medium was removed and the cells were resuspended in 1.25 mL production medium (50 g/L glucose, 20 mg/L uracil, 5 g/L yeast extract, 4 g/L $KH_2PO_4$, 1.5 g/L $MgSO_4$, 0.2 g/L NaCl, 0.265 g/L $CaCl_2 \cdot 2H_2O$, 2 mL/L trace elements solution: 4.5 g/L $CaCl_2 \cdot 2H_2O$, 4.5 g/L $ZnSO_4 \cdot 7H_2O$, 3 g/L $FeSO_4 \cdot 7H_2O$, 1 g/L $H_3BO_3$, 1 g/L $MnCl_2 \cdot 4H_2O$, 0.4 g/L N $Na_2MoO_4 \cdot 2H_2O$, 0.3 g/L $CoCl_2 \cdot 6H_2O$, 0.1 g/L $CuSO_4 \cdot 5H_2O$, 0.1 g/L KI, 15 g/L EDTA). At the same time, control 1, 0 v/v % surfactant, control 2, 0.1 v/v % surfactant (approximate recommended dose by manufacturer for foam management) and 3 v/v % (above the cloud concentration of the surfactant) was added of the following surfactants: Antifoam A (Bekchem; ethoxylated and propoxylated C16-18 alcohols, CAS No. 68002-96-0); Agnique BP420 (BASF; ethoxylated and propoxylated C16-18 alcohols, CAS No. 68002-96-0); Plurafac® LF1300 (BASF; ethoxylated and propoxylated C16-18 alcohols, CAS No. 68002-96-0); Dehypon® 2574 (BASF; Fatty alcohol, ethoxylated and propoxylated, CAS-nummer: 68154-97-2). The plate was incubated at 28° C. and 300 rpm for 28 hours. Each experiment was performed in biological triplicates.

The intracellular and extracellular concentrations of fatty alcohols were assessed as follows. 1000 μL of appropriately diluted culture broth was transferred to a 4 mL gas-tight glass extraction vial. The sample was centrifuged at 3,500 g for 5 min at room temperature. The supernatant was transferred into a new glass vial with 1000 μL of hexane and 10 μL of internal standard (IS) solution (20 mg/L of methyl nonadecanoate in ethyl acetate). The vial was vortexed for 10 s and centrifuged as before. 250 μL of the upper hexane phase was transferred to a GC vial for GC-MS analysis of the extracellular fatty alcohol concentration. The pellet remaining after the removal of the supernatant from the centrifuged culture broth was resuspended in 1000 μL of solvent mixture (EtOAc and EtOH) and 10 μL of IS solution as above. The sample was incubated for 1 h with periodic mixing. 300 μL water was added and the vials were centrifuged at 3,500 g for 5 min at room temperature. 250 μL of the upper organic phase was transferred to a GC vial for GC-MS analysis of the intracellular fatty alcohols.

GC-MS analyses were performed on an Agilent 7820A GC coupled to a mass selective detector Agilent 5977B. The GC was equipped with an DB Fatwax column (30 m×0.25 mm×0.25 μm), and helium was used as carrier gas. The MS was operated in electron impact mode (70 eV), scanning between m/z 30 and 400, and the injector was configured in split mode 20:1 at 220° C. Oven temperature was set to 80° C. for 1 min, then increased at a rate of 20° C./min to 210° C., followed by a hold at 210° C. for 7 min, and then increased at a rate of 20° C./min to 230° C. Compounds were identified by comparison of retention times and mass spectra of the reference compounds. Compounds were quantified by the ion 55.1 m/z. Data were analyzed by the Agilent Masshunter software. The concentrations of fatty alcohols were calculated based on standard calibration curves prepared with reference standards.

Results are shown in Table 9. Significant amount of extracellular of fatty alcohols was obtained when the surfactant was added in high concentrations, i.e. above its cloud concentration. In addition, the total production of fatty alcohols also increased when the surfactant was added in high concentrations (3 v/v %). When the surfactant was dosed above its cloud concentration, it constituted a separate immiscible hydrophobic phase together with the in-situ extracted fatty alcohols. Therefore, phase separation and product recovery could be facilitated by simple mechanical phase separation, without the use of organic solvents or costly separation methods.

TABLE 9

| | ST3705 | | | | | |
|---|---|---|---|---|---|---|
| | 0 v/v % surfactant | | 0.1 v/v % surfactant | | 3 v/v % surfactant | |
| Surfactant | Total concentration (mg/L) | Extracellular concentration (mg/L) (fraction of total) | Total concentration (mg/L) | Extracellular concentration (mg/L) (fraction of total) | Total concentration (mg/L) | Extracellular concentration (mg/L) (fraction of total) |
| Unsaturated fatty alcohol Z11-hexadecen-1-ol | | | | | | |
| Antifoam A | 23.2 ± 43.4 | 0.0 ± 0.0 (0%) | 23.3 ± 13.5 | 1.7 ± 0.6 (7%) | 10.2 ± 1.0 | 3.5 ± 0.8 (34%) |

TABLE 9-continued

| Surfactant | 0 v/v % surfactant: Total concentration (mg/L) | 0 v/v % surfactant: Extracellular concentration (mg/L) (fraction of total) | 0.1 v/v % surfactant: Total concentration (mg/L) | 0.1 v/v % surfactant: Extracellular concentration (mg/L) (fraction of total) | 3 v/v % surfactant: Total concentration (mg/L) | 3 v/v % surfactant: Extracellular concentration (mg/L) (fraction of total) |
|---|---|---|---|---|---|---|
| ST3705 | | | | | | |
| Agnique BP420 | | | 9.5 ± 3.2 | 0.3 ± 0.4 (0%) | 16.0 ± 4.4 | 8.7 ± 3.7 (54%) |
| Plurafac ® LF1300 | | | 9.5 ± 3.2 | 0.3 ± 0.4 (0%) | 16.0 ± 4.4 | 8.7 ± 3.7 (54%) |
| Dehypon ® 2574 | | | 9.0 ± 0.2 | 0.0 ± 0.0 (0%) | 20.2 ± 1.7 | 10.5 ± 1.5 (52%) |
| Saturated fatty alcohol Hexadecanol | | | | | | |
| Antifoam A | 11.6 ± 6.6 | 2.7 ± 0.5 (23%) | 56.1 ± 13.3 | 47.0 ± 11.4 (84%) | 190 ± 15 | 179.7 ± 8.5 (94%) |
| Agnique BP420 | | | 24.8 ± 17.1 | 11.5 ± 10.8 (46%) | 116 ± 35 | 104.6 ± 27.1 (90%) |
| Plurafac ® LF1300 | | | 24.8 ± 17.1 | 11.5 ± 10.8 (46%) | 116 ± 35 | 104.6 ± 27.1 (90%) |
| Dehypon ® 2574 | | | 4.3 ± 0.5 | 0.0 ± 0.0 (0%) | 15 ± 2 | 14.0 ± 2.0 (94%) |

Example 10—Increased Production, Secretion, and Recovery of Fatty Alcohol Acetate Esters by the Yeast *Saccharomyces cerevisiae*

Here the increased production, secretion, and recovery of fatty alcohol acetate esters by the engineered yeast *Saccharomyces cerevisiae* was demonstrated.

The experiments were performed following the procedures using strain ST5290 as in Example 9, with the modification of supplementing the production medium with an additional 76 mg/L histidine, 0.5 g/L myristic acid methyl ester. For acetate esters of fatty alcohols, GC-MS analyses were performed following the procedures as in Example 9. Apart from acetate esters of fatty alcohols, untargeted screen of data for other esters revealed no significant production of other ester compounds.

The results are shown in Table 10. Significant production and secretion of fatty alcohol acetate esters were observed when the cultivation was supplemented with surfactant above its cloud concentration (at 3 v/v %). When the surfactant was dosed above its cloud concentration, it constituted a separate immiscible hydrophobic phase together with the in-situ extracted fatty alcohols. Therefore, phase separation and product recovery could be facilitated by simple mechanical phase separation, without the use of organic solvents or costly separation methods.

TABLE 10

| Surfactant | 0 v/v % surfactant: Total concentration (mg/L) | 0 v/v % surfactant: Extracellular concentration (mg/L) (fraction of total) | 0.1 v/v % surfactant: Total concentration (mg/L) | 0.1 v/v % surfactant: Extracellular concentration (mg/L) (fraction of total) | 3 v/v % surfactant: Total concentration (mg/L) | 3 v/v % surfactant: Extracellular concentration (mg/L) (fraction of total) |
|---|---|---|---|---|---|---|
| ST5290 | | | | | | |
| Acetate ester of unsaturated fatty alcohol Z9-tetradecen-1-yl acetate | | | | | | |
| Antifoam A | 0 ± 0 | 0 ± 0 (0%) | 0 ± 0 | 0 ± 0 (0%) | 4.5 ± 1.8 | 4.4 ± 1.8 (99%) |
| Agnique BP420 | | | 0 ± 0 | 0 ± 0 (0%) | 1.5 ± 1.4 | 1.5 ± 1.4 (100%) |
| Plurafac ® LF1300 | | | 0 ± 0 | 0 ± 0 (0%) | 0 ± 0 | 1.5 ± 1.4 (100%) |
| Dehypon ® 2574 | | | 0.5 ± 0.5 | 0 ± 0 (0%) | 0.5 ± 0.4 | 0.5 ± 0.4 (100%) |
| Acetate ester of saturated fatty alcohol tetradecanyl acetate | | | | | | |
| Antifoam A | 2.1 ± 1.9 | 0 ± 0 (0%) | 5.7 ± 3.2 | 1.8 ± 2.2 (32%) | 28.8 ± 8.0 | 25.2 ± 4.7 (88%) |
| Agnique BP420 | | | 1.7 ± 2.4 | 0.5 ± 0.5 (27%) | 22.5 ± 16.4 | 19.6 ± 13.2 (87%) |
| Plurafac ® LF1300 | | | 1.7 ± 2.4 | 0.5 ± 0.5 (27%) | 22.5 ± 16.4 | 19.6 ± 13.2 (87%) |
| Dehypon ® 2574 | | | 1.8 ± 0.6 | 0 ± 0 (0%) | 0.2 ± 0.2 | 0.2 ± 0.2 (100%) |

Example 11—Increased Production, Secretion, and Recovery of Fatty Alcohols by the Yeast *Yarrowia lipolytica*

Here the increased production, secretion, and recovery of fatty alcohols by the engineered yeast *Yarrowia lipolytica* was demonstrated.

Using strains ST8327 and ST9253, the experiments were following the procedures as in Example 9, with the modification of using YPG medium (10 g/L yeast extract, 10 g/L peptone, 40 g/L glycerol), and production medium (50 g/L glycerol, 5 g/L yeast extract, 4 g/L $KH_2PO_4$, 1.5 g/L $MgSO_4$, 0.2 g/L NaCl, 0.265 g/L $CaCl_2{\cdot}2H_2O$, 2 mL/L trace elements solution: 4.5 g/L $CaCl_2{\cdot}2H_2O$, 4.5 g/L $ZnSO_4{\cdot}7H_2O$, 3 g/L $FeSO_4{\cdot}7H_2O$, 1 g/L $H_3BO_3$, 1 g/L $MnCl_2{\cdot}4H_2O$, 0.4 g/L N $Na_2MoO_4{\cdot}2H_2O$, 0.3 g/L $CoCl_2{\cdot}6H_2O$, 0.1 g/L $CuSO_4{\cdot}5H_2O$, 0.1 g/L KI, 15 g/L EDTA).

For strain ST8327, GC-MS analyses were performed as in example 9. For strain ST9253, oven temperature was set to 80° C. for 1 min, then increased at a rate of 20° C./min to 150° C., and then increased at a rate of 1° C./min to 200° C., and then increased at a rate of 20° C./min to 230°.

Results are shown in Table 11 and Table 12. A significant increase in total titer and secretion was observed when surfactants were supplemented above their cloud concentrations (3 v/v %). When the surfactant was dosed above its cloud concentration, it constituted a separate immiscible hydrophobic phase together with the in-situ extracted fatty alcohols. Therefore, phase separation and product recovery could be facilitated by simple mechanical phase separation, without the use of organic solvents or costly separation methods.

TABLE 11

| ST8327 | | | | | | |
|---|---|---|---|---|---|---|
| | 0 v/v % surfactant | | 0.1 v/v % surfactant | | 3 v/v % surfactant | |
| Surfactant | Total concentration (mg/L) | Extracellular concentration (mg/L) (fraction of total) | Total concentration (mg/L) | Extracellular concentration (mg/L) (fraction of total) | Total concentration (mg/L) | Extracellular concentration (mg/L) (fraction of total) |
| Unsaturated fatty alcohol Z11-hexadecen-1-ol | | | | | | |
| Antifoam A | 761 ± 47 | 17 ± 7 (2%) | 914 ± 68 | 41 ± 43 (5%) | 1721 ± 314 | 1371 ± 224 (80%) |
| Agnique BP420 | | | 1141 ± 266 | 53 ± 38 (5%) | 1052 ± 224 | 521 ± 36 (50%) |
| Plurafac ® LF1300 | | | 1141 ± 266 | 53 ± 38 (5%) | 1052 ± 224 | 521 ± 36 (50%) |
| Dehypon ® 2574 | | | 827 ± 275 | 304 ± 164 (37%) | 1217 ± 73 | 709 ± 50 (58%) |
| Unsaturated fatty alcohol Z9-hexadecen-1-ol | | | | | | |
| Antifoam A | 77 ± 3 | 0 ± 0 (0%) | 105 ± 13 | 1 ± 2 (1%) | 163 ± 28 | 133 ± 17 (81%) |
| Agnique BP420 | | | 128 ± 24 | 2 ± 3 (2%) | 119 ± 27 | 58 ± 3 (48%) |
| Plurafac ® LF1300 | | | 128 ± 24 | 2 ± 3 (2%) | 119 ± 27 | 58 ± 3 (48%) |
| Dehypon ® 2574 | | | 72 ± 25 | 26 ± 15 (36%) | 129 ± 19 | 71 ± 15 (55%) |
| Saturated fatty alcohol hexadecanol | | | | | | |
| Antifoam A | 456 ± 149 | 9 ± 4 (2%) | 560 ± 91 | 24 ± 26 (4%) | 1155 ± 214 | 890 ± 126 (77%) |
| Agnique BP420 | | | 751 ± 149 | 48 ± 43 (6%) | 740 ± 202 | 363 ± 11 (49%) |
| Plurafac ® LF1300 | | | 751 ± 149 | 48 ± 43 (6%) | 740 ± 202 | 363 ± 11 (49%) |
| Dehypon ® 2574 | | | 764 ± 298 | 262 ± 144 (34%) | 560 ± 33 | 342 ± 24 (61%) |

TABLE 12

| ST9253 | | | | | | |
|---|---|---|---|---|---|---|
| | 0 v/v % surfactant | | 0.1 v/v % surfactant | | 3 v/v % surfactant | |
| Surfactant | Total concentration (mg/L) | Extracellular concentration (mg/L) (fraction of total) | Total concentration (mg/L) | Extracellular concentration (mg/L) (fraction of total) | Total concentration (mg/L) | Extracellular concentration (mg/L) (fraction of total) |
| Unsaturated fatty alcohol Z11-tetradecen-1-ol | | | | | | |
| Antifoam A | 18.8 ± 0.8 | 3.1 ± 0.1 (16%) | 17.9 ± 0.9 | 3.8 ± 0.2 (22%) | 35.3 ± 2.8 | 30.6 ± 2.0 (87%) |
| Agnique BP420 | | | 21.0 ± 12.5 | 10.7 ± 6.5 (51%) | 28.5 ± 6.1 | 23.7 ± 5.4 (83%) |
| Plurafac ® LF1300 | | | 21.0 ± 12.5 | 10.7 ± 6.5 (51%) | 28.5 ± 6.1 | 23.7 ± 5.4 (83%) |
| Dehypon ® 2574 | | | 15.5 ± 2.7 | 6.0 ± 1.1 (39%) | 23.8 ± 2.2 | 15.6 ± 0.9 (66%) |
| Unsaturated fatty alcohol E11-tetradecen-1-ol | | | | | | |
| Antifoam A | 108.7 ± 4.6 | 10.3 ± 0.5 (10%) | 110.3 ± 7.1 | 17.1 ± 3.1 (16%) | 350.7 ± 31.3 | 324.4 ± 23.3 (93%) |
| Agnique BP420 | | | 150.2 ± 107.1 | 81.1 ± 59.4 (54%) | 254.8 ± 65.5 | 228.1 ± 58.7 (90%) |
| Plurafac ® LF1300 | | | 150.2 ± 107.1 | 81.1 ± 59.4 (54%) | 254.8 ± 65.5 | 228.1 ± 58.7 (90%) |
| Dehypon ® 2574 | | | 112.4 ± 16.4 | 44.0 ± 7.9 (39%) | 209.7 ± 10.1 | 153.4 ± 1.1 (73%) |

Example 12—Increased Production, Secretion and Recovery of Fatty Alcohols by the Yeast *Yarrowia lipolytica*

Here the increased production, secretion, and recovery of fatty alcohols by the engineered yeast *Yarrowia lipolytica* was demonstrated.

The experiments were performed following the procedures as in Example 11 using strains ST10229, ST10230 and ST10231, with the modification of supplementing both YPG and production media with 150 mg/L nourseothricin. When the cells were resuspended in production medium, control 1, 0 v/v % Antifoam A, control 2, 0.1 v/v % Antifoam A (approximate recommended dose by manufacturer for foam management) and 3 v/v % (above the cloud concentration of the surfactant) Antifoam A (Bekchem; ethoxylated and propoxylated 16-18 alcohols, CAS No. 68002-96-0) was added. GO-MS analyses were performed as in example 9.

The results are shown in Table 13. Significant production and secretion of fatty alcohols were observed when the cultivation was supplemented with surfactant above its cloud concentration (at 3 v/v %). When the surfactant was dosed above its cloud concentration, it constituted a separate immiscible hydrophobic phase together with the in-situ extracted fatty alcohols. Therefore, phase separation and product recovery could be facilitated by simple mechanical phase separation, without the use of organic solvents or costly separation methods.

TABLE 13

| Unsaturated fatty alcohol Z9-tetradecen-1-ol<br>Saturated fatty alcohols tetradecanol | | | | | | |
|---|---|---|---|---|---|---|
| | 0 v/v % surfactant | | 0.1 v/v % surfactant | | 3 v/v % surfactant | |
| Surfactant | Total concentration of unsaturated/ saturated fatty alcohol (mg/L) | Extracellular concentration of unsaturated/ saturated fatty alcohol (mg/L) (fraction of total) | Total concentration of unsaturated/ saturated fatty alcohol (mg/L) | Extracellular concentration of unsaturated/ saturated fatty alcohol (mg/L) (fraction of total) | Total concentration of unsaturated/ saturated fatty alcohol (mg/L) | Extracellular concentration of unsaturated/ saturated fatty alcohol (mg/L) (fraction of total) |
| ST10229 | | | | | | |
| Antifoam A | 80.5 ± 37.3/ 127.6 ± 64.3 | 0 ± 0 (0%)/ 0 ± 0 (0%) | 79.6 ± 12.9/ 111.9 ± 17.8 | 0 ± 0 (0%)/ 0 ± 0 (0%) | 194.4 ± 22.5/ 215.9 ± 24.9 | 177.8 ± 33.8 (91%)/ 198.1 ± 37.7 (92%) |
| ST10230 | | | | | | |
| Antifoam A | 106.7 ± 7.3/ 189.7 ± 15.0 | 0 ± 0 (0%)/ 0 ± 0 (0%) | 105.7 ± 7.0/ 169.1 ± 13.1 | 1.0 ± 0.5 (1%)/ 0 ± 0 (0%) | 176.9 ± 14.3/ 218.0 ± 18.3 | 145.7 ± 2.2 (81%)/ 179.6 ± 4.2 (82%) |

TABLE 13-continued

| Unsaturated fatty alcohol Z9-tetradecen-1-ol Saturated fatty alcohols tetradecanol | | | | | | |
|---|---|---|---|---|---|---|
| | 0 v/v % surfactant | | 0.1 v/v % surfactant | | 3 v/v % surfactant | |
| Surfactant | Total concentration of unsaturated/ saturated fatty alcohol (mg/L) | Extracellular concentration of unsaturated/ saturated fatty alcohol (mg/L) (fraction of total) | Total concentration of unsaturated/ saturated fatty alcohol (mg/L) | Extracellular concentration of unsaturated/ saturated fatty alcohol (mg/L) (fraction of total) | Total concentration of unsaturated/ saturated fatty alcohol (mg/L) | Extracellular concentration of unsaturated/ saturated fatty alcohol (mg/L) (fraction of total) |
| ST10231 | | | | | | |
| Antifoam A | 22.2 ± 3.2/ 490.8 ± 19.0 | 0 ± 0 (0%)/ 5.2 ± 7.1 (1%) | 44.4 ± 5.6/ 445.0 ± 30.9 | 0 ± 0 (0%)/ 5.7 ± 2.1 (1.2%) | 97.7 ± 0.1/ 443.2 ± 3.8* | 69.3 ± 4.1 (70%)/ 307 ± 18.7 (69%)* |

*only technical duplicates available

Example 13—Increased Secretion and Recovery of Fatty Aldehydes by the Yeast *Yarrowia lipolytica*

Here the increased secretion and recovery of fatty aldehydes by the engineered yeast *Yarrowia lipolytica* was demonstrated.

Using strain ST8327, the experiments were performed following the procedures as in Example 10. GC-MS analyses were performed as in Example 9.

Result are shown in Table 14. Significant secretion was observed when surfactants were supplemented above their cloud concentrations (3 v/v %). When the surfactant was dosed above its cloud concentration, it constituted a separate immiscible hydrophobic phase together with the in-situ extracted fatty alcohols. Therefore, phase separation and product recovery were facilitated by simple mechanical phase separation, without the use of organic solvents or costly separation methods.

TABLE 14

| ST8327 | | | |
|---|---|---|---|
| Surfactant | 0 v/v % surfactant Extracellular concentration (mg/L) (fraction of total) | 0.1 v/v % surfactant Extracellular concentration (mg/L) (fraction of total) | 3 v/v % surfactant Extracellular concentration (mg/L) (fraction of total) |
| Unsaturated fatty aldehyde Z11-hexadecen-1-al | | | |
| Antifoam A | 2.9 ± 0.3 (23%) | 0.8 ± 1.1 (6%) | 15.0 ± 2.9 (80%) |
| Agnique BP420 | | 0.4 ± 0.5 (2%) | 5.0 ± 0.6 (43%) |
| Plurafac ® LF1300 | | 0.4 ± 0.5 (2%) | 5.0 ± 0.6 (43%) |
| Dehypon ® 2574 | | 2.9 ± 1.9 (36%) | 3.9 ± 0.3 (57%) |
| Saturated fatty aldehyde hexadecanal | | | |
| Antifoam A | 0.0 ± 1.3 (0%) | 6.8 ± 11.8 (22%) | 37.6 ± 9.3 (82%) |
| Agnique BP420 | | 0.0 ± 0.0 (0%) | 7.3 ± 0.7 (35%) |
| Plurafac ® LF1300 | | 0.0 ± 0.0 (0%) | 7.3 ± 0.7 (35%) |
| Dehypon ® 2574 | | 8.3 ± 1.4 (46%) | 8.3 ± 1.4 (44%) |

Example 14—Purification of Fatty Alcohols from the Recovered Mixture of Fatty Alcohols and Surfactants The purification of fatty alcohols from the hydrophobic mixture of fatty alcohols and surfactants was demonstrated by distillation.

Model mixtures were prepared of different commercially available ethoxylated surfactants (Antifoam A from Bekchem, Plurafac® LF 1300, Dehypon® 2574) and a technical grade fatty alcohol mixture. The model mixtures were subjected to vacuum distillation in a laboratory scale distillation setup equipped with Vigreux column. The experiments were carried out applying 5 mbar vacuum, 200-210° C. final pot and 170-180° C. final receiver temperature. The light phase was collected and analyzed for mass and composition.

Appropriate amounts of samples were transferred to 50 mL volumetric flasks and weighed on an analytical balance. The samples were dissolved in ethyl acetate in the volumetric flasks and were well mixed. 1 mL of the diluted aliquots were transferred to GC vials and 10 μL of internal standard (IS) solution (20 mg/L of methyl nonadecanoate in ethyl acetate) was added to each GC vial. The vials were vortexed for 10 s before analysis. GC and data analysis were performed as described in Example 11.

Results are shown in Table 15. The composition of the collected light phase from a model mixture distillation experiment demonstrated the enrichment of the target fatty alcohol compounds in the relevant fraction. Distillation is a cost-effective solution to purify the target compounds from the recovered hydrophobic surfactant-fatty alcohol, fatty alcohol ester and fatty aldehyde mixtures presented in Examples 9-11 and 13.

TABLE 15

| Surfactant | Start mass model mixture (g) | Composition start Z11-16: OH (% of mass) | Composition start 16: OH (% of mass) | Composition start Z9-16: OH (5 of mass) |
|---|---|---|---|---|
| Antifoam A | 60.1 | 21.9 | 1.4 | 0.5 |
| Plurafac ® LF 1300 | 60.0 | 21.3 | 1.3 | 0.5 |
| Dehypon ® 2574 | 60.0 | 21.6 | 1.4 | 0.5 |

| Surfactant | Light phase mass (g) | Composition light phase Z11-16: OH (% of mass) | Composition light phase 16: OH (% of mass) | Composition light phase Z9-16: OH (% of mass |
|---|---|---|---|---|
| Antifoam A | 8.7 | 54.7 | 4.1 | 1.7 |
| Plurafac ® LF 1300 | 7.7 | 55.2 | 4.0 | 2.1 |
| Dehypon ® 2574 | 6.8 | 49.3 | 3.5 | 1.8 |

Example 15—Increased Secretion and Recovery of Isoprenoids by the Yeast *Yarrowia lipolytica*

Here the increased secretion, and recovery of isoprenoids by the engineered yeast *Yarrowia lipolytica* was demonstrated.

Engineered *Yarrowia lipolytica* strains ST10151 is capable of producing β-farnesene. The strain expresses the β-farnesene synthase from *Artemisia annua* (SEQ ID NO: 47). The strain has additional modifications that increase mevalonate (MVA) pathway flux.

The experiments were performed following the procedures as in Example 11 using strain ST10151. When the cells were resuspended in production medium, 0 v/v %, 0.1 v/v % or 3 v/v % surfactant was added of the following surfactants: Antifoam A (Bekchem) or A-204 (Sigma). The plates were incubated at 28° C. and 300 rpm for 28 hours. Each experiment was performed in biological triplicates.

The extracellular and intracellular samples for GC-MS analysis were analysed following the procedures as in Example 9, except that Patchouli alcohol (2 g/L of Patchouli alcohol in ethyl acetate) was used as internal standard. The GC-FID analysis for β-farnesene was performed using Agilent GC 7890B with a flame ionization detector (FID) and equipped with a fused-silica capillary column (BP5, 30 m×0.32 mm ID, 0.25 μm, Agilent Technologies). Hydrogen at a constant flow rate of 2.0 mL/min was used as the carrier gas. The GC oven temperature started at 50° C. for 1.5 min and then increased to 170° C. at 30° C./min and hold for 1.5 min. Then from 170 to 300° C. at 15° C./min and hold for 4.5 min. The injector and detector ports were both kept at 300° C. and the injector operated in a split mode of 20:1. For quantification of β-farnesene calibration standards containing β-farnesene with a concentration range of 0.01 mg/ml to 1 mg/ml were prepared. 10 μl of 2 g/l of Patchouli alcohol in ethyl acetate was added to 990 μl standard and a calibration curve was obtained. Data analysis was performed with MassHunter Quantitative Analysis Version 10.1.

Result are shown in Table 16. Significant production and secretion of isoprenoids were observed when surfactants (Antifoam A and A-204) were supplied above their cloud concentrations (3 v/v %). When the surfactants were dosed above their cloud concentration, it constituted a separate immiscible hydrophobic phase together with the in-situ extracted isoprenoids. Therefore, phase separation and product recovery was facilitated by simple mechanical phase separation, without the use of organic solvents or costly separation methods.

TABLE 16

| | 0 v/v % surfactant | | 0.1 v/v % surfactant | | 3 v/v % surfactant | |
|---|---|---|---|---|---|---|
| Surfactant | Total concentration (mg/L) | Extracellular concentration (mg/L) (fraction of total) | Total concentration (mg/L) | Extracellular concentration (mg/L) (fraction of total) | Total concentration (mg/L) | Extracellular concentration (mg/L) (fraction of total) |
| Antifoam A | 3.9 ± 0.1 | 0.0 ± 0.0 (0%) | 4.4 ± 0.1 | 0.0 ± 0.0 (0%) | 27.7 ± 0.2 | 25.7 ± 2.0 (92.8%) |
| A-204 | | | 6.7 ± 1.3 | 0.0 ± 0.0 (0%) | 35.6 ± 5.8 | 17.7 ± 5.0 (69.2%) |

REFERENCES

Anelli P L, Biffi C, Montanar F, and Quici S, *J. Org. Chem.* 1987, 52, 12, 2559-2562

Borodina, I. Understanding metabolite transport gives an upper hand in strain development. *Microb Biotechnol.* 2019 January; 12(1):69-70.

Corey E J; C. U. Kim (1972). *Journal of the American Chemical Society.* 94 (21): 7586-7587. doi:10.1021/ja00776a056

Fritz, J. S. et al. Acid-catalysed acetylation of organic hydroxyl groups. Anal. Chem. 1959, 31, 11, 1808-1812

Holkenbrink C, Dam M I, Kildegaard K R, et al. EasyCloneYALI: CRISPR/Cas9-Based Synthetic Toolbox for Engineering of the Yeast *Yarrowia lipolytica. Biotechnol J.* 2018; 13(9):e1700543. doi:10.1002/biot.201700543

Hoover J. M. et al. Highly Practical Copper(I)/TEMPO Catalyst System for Chemoselective Aerobic Oxidation of Primary Alcohols. *J. Am. Chem. Soc.* 2011, 133, 42, 16901-16910

Kehat et al. (1990), "Behavioral responses of male *Heliothis armigera* (Lepidoptera: Noctuidae) moths in a flight tunnel to combinations of components identified from female sex pheromone glands". Journal of Insect Bhavior, 3(1): 75-83

Ley, Steven V.; Norman, Joanne; Griffith, William P.; Marsden, Stephen P. (1994). *Synthesis.* 1994 (7): 639-666. doi:10.1055/s-1994-25538

Marella E R, Dahlin J, Dam M I, ter Horst J, Christensen H B, Sudarsan S, Wang G, Holkenbrink C, Borodina I. A single-host fermentation process for the production of flavor lactones from non-hydroxylated fatty acids. Metabolic Engineering 2020. doi.org/10.1016/j.ymben.2019.08.009

Mattson, F. H. et al. Esterification of hydroxy compounds by fatty acid anhydrides. J Lipid Res. 1964 July; 5(3):374-7.

Omura, K.; Swern, D. (1978). Tetrahedron. 34 (11): 1651-1660. doi:10.1016/0040-4020(78)80197-5

Ratcliffe R and Rodehorst R (1970). *J. Org. Chem.* 35 (11): 4000-4001. doi:10.1021/jo00836a108

Steves, J. E. et al. Copper(I)/ABNO-catalyzed aerobic alcohol oxidation: alleviating steric and electronic constraints of Cu/TEMPO catalyst systems. J Am Chem Soc. 2013 Oct. 23; 135(42):15742-5

Tatsuki, S., Kurihara, M., Usui, K., Ohguchi, Y., Uchiumi, K., and Fukami, J. 1983. Sex pheromone of the rice stem borer, *Chilo suppressalis* (Walker) (Lepidoptera: Pyralidae): the third component, Z-9-hexadecenal. Appl. Entomol. Zool. 18:443-446

WO 2016/207339

WO 2018/109163

WO 2018/109167

WO 2020/169389

Sequence Overview

| Sequence ID NO: | | Description |
|---|---|---|
| 1 | Atr_Δ11 | *Amyelois transitella* Δ11-desaturase |
| 2 | SI_Δ11 | *Spodoptera littoralis* Δ11-desaturase |
| 3 | As_Δ11 | Agrotis segetum Δ11-desaturase |
| 4 | Tni_Δ11 | Trichoplusia *ni* Δ11-desaturase |
| 5 | Har_FAR | *Helicoverpa armigera* fatty acyl-CoA reductase |
| 6 | Hs_FAR | *Heliothis subflexa* fatty acyl-CoA reductase |
| 7 | Has_FAR | *Helicoverpa assulta* fatty acyl-CoA reductase |
| 8 | ScFAA1 | *Saccharomyces cerevisiae* fatty acyl synthetase |
| 9 | YIFAA | *Yarrowia lipolytica* fatty acyl synthetase |
| 10 | ScATF1 | *Saccharomyces cerevisiae* acetyltransferase |
| 11 | Fao1 | *Yarrowia lipolytica* fatty alcohol oxidase |
| 12 | Hfd1 | *Yarrowia lipolytica* fatty aldehyde dehydrogenase 1 |
| 13 | Hfd4 | *Yarrowia lipolytica* fatty aldehyde dehydrogenase 4 |
| 14 | Pex10 | *Yarrowia lipolytica* peroxisome biogenesis factor 10 |
| 15 | GPAT | *Yarrowia lipolytica* glycerol-3-phosphate acyltransferase |
| 16 | DmeΔ9 | *Drosophila melanogaster* Δ9 desaturase |
| 17 | Ban_FAR | *Bicyclus anynana* fatty acyl reductase |
| 18 | SlΔ9 | *Spodoptera litura* Δ9 desaturase |
| 19 | Yli_POX1 (XP_504703) | *Yarrowia lipolytica* Peroxisomal oxidase 1 |
| 20 | Yli_POX2 (XP_505264) | *Yarrowia lipolytica* Peroxisomal oxidase 2 |
| 21 | Yli_POX3 (XP_503244) | *Yarrowia lipolytica* Peroxisomal oxidase 3 |
| 22 | Yli_POX4 (XP_504475) | *Yarrowia lipolytica* Peroxisomal oxidase 4 |
| 23 | Yli_POX5 (XP_502199) | *Yarrowia lipolytica* Peroxisomal oxidase 5 |
| 24 | Yli_POX6 (XP_503632) | *Yarrowia lipolytica* Peroxisomal oxidase 6 |

-continued

| Sequence ID NO: | | Description |
|---|---|---|
| 25 | Ase_POX | *Agrotis segetum* Peroxisomal oxidase |
| 26 | Ath_POX1 | *Arabidopsis thaliana* Peroxisomal oxidase 1 |
| 27 | Ath_POX2 | *Arabidopsis thaliana* Peroxisomal oxidase 2 |
| 28 | Ani_POX | *Aspergillus nidulans* Peroxisomal oxidase |
| 29 | Cma_POX | *Cucurbita maxima* Peroxisomal oxidase |
| 30 | Hsa_POX1-2 | *Homo sapiens* Peroxisomal oxidase |
| 31 | Pur_POX | *Paenarthrobacter ureafaciens* Peroxisomal oxidase |
| 32 | Rno_POX2 | *Rattus norvegicus* Peroxisomal oxidase |
| 33 | Sce_OLE1 | *Saccharomyces cerevisiae* $\Delta_{Z9}$-desaturase |
| 34 | Yli_OLE1 (XP_501496) | *Yarrowia lipolytica* $\Delta_{Z9}$-desaturase |
| 35 | Cro_Z11 | *Choristoneura rosaceana* ΔZ11-14-desaturase |
| 36 | Onu_11 | *Ostrinia nubilalis* $\Delta_{Z11}$-14-desaturase |
| 37 | Tpi_D13 | *Thaumetopoea pityocampa* $\Delta_{Z11}$-14-desaturase |
| 38 | Dpu_E9-14 | *Dendrophilus punctatus* $\Delta_{E9}$-14-desaturase |
| 39 | Gmo_CPRQ | *Grapholita molesta* $\Delta_{Z/E10}$-14-desaturase |
| 40 | Epo_E11 | *Epiphyas postvittana* desaturase |
| 41 | Sls_ZE11 | *Spodoptera littoralis* desaturase |
| 42 | Cpa_E11 | *Choristoneura parallela* desaturase |
| 43 | LboPPTQ | *Lobesia brotana* desaturase |
| 44 | Dgd9 | *Drosophila grimshawi* desaturase |
| 45 | Dvd9 | *Drosophila virilis* desaturase |
| 46 | SynGGPPs7 | *Synechococcus* sp. geranylgeranyl diphosphate synthase |
| 47 | Aa_BFS | *Artemisia annua* ß-farnesene synthase |
| 48 | Cpo_CPRQ | *Cydia pomonella* CPO_CPRQ desaturase (AHW98354) |
| 49 | Cpo_NPVE | *Cydia pomonella* desaturase |
| 50 | Cpo_SPTQ | *Cydia pomonella* desaturase |

Items

1. A method for producing a hydrophobic compound such as a fatty alcohol, a fatty alcohol ester, a fatty acyl acetate, a fatty aldehyde and/or a terpene such as a terpenoid in a fermentation, said method comprising the step of providing a microorganism, preferably a yeast cell, capable of producing said hydrophobic compound and culturing said microorganism in a culture medium under conditions allowing production of said hydrophobic compound, wherein the culture medium comprises an extractant in an amount equal to or greater than its cloud concentration in an aqueous solution, wherein the extractant a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, the method optionally further comprising the step of recovering the hydrophobic compound.
2. A method for increasing the titer of a hydrophobic compound such as a fatty alcohol, a fatty alcohol ester, a fatty acyl acetate, a fatty aldehyde and/or a terpene such as a terpenoid in a fermentation, said method comprising culturing a microorganism, preferably a yeast cell, capable of producing said hydrophobic compound in a culture medium under conditions allowing production of said hydrophobic compound, wherein the culture medium comprises an extractant in an amount equal to or greater than its cloud concentration in an aqueous solution, wherein the extractant is a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, whereby the titer of the hydrophobic compound is increased compared to a fermentation performed under similar conditions in the absence of extractant or in the presence of extractant in an amount lower than its cloud concentration in an aqueous solution.

3. A method for increasing the secretion of a hydrophobic compound such as a fatty alcohol, a fatty alcohol ester, a fatty acyl acetate, a fatty aldehyde and/or a terpene such as a terpenoid from a microorganism, preferably a yeast cell, capable of producing said hydrophobic compound in a fermentation, said method comprising culturing said microorganism in a culture medium under conditions allowing production of said hydrophobic compound, wherein the culture medium comprises an extractant in an amount equal to or greater than its cloud concentration in an aqueous solution, wherein the extractant is a non-ionic surfactant such as an antifoaming agent, preferably a polyethoxylated surfactant selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof, whereby the secretion of the hydrophobic compound from the microorganism is increased compared to a fermentation performed under similar conditions in the absence of extractant or in the presence of extractant in an amount lower than its cloud concentration in an aqueous solution.

4. The method according to any one of the preceding items, wherein the extractant is a non-ionic ethoxylated surfactant.

5. The method according to any one of the preceding items, wherein the extractant is a fatty alcohol alkoxylate or a polyethoxylated surfactant, preferably selected from: a polyethylene polypropylene glycol, a mixture of polyether dispersions, an antifoaming agent comprising polyethylene glycol monostearate, simethicone and ethoxylated and propoxylated $C_{16}$-$C_{18}$ alcohol-based agents or ethoxylated and propoxylated $C_{16}$-$C_{18}$ alcohol-based antifoaming agents and combinations thereof.

6. The method according to any one of the preceding items, wherein the fatty alcohols are saturated fatty alcohols, desaturated fatty alcohols, or a mixture thereof.

7. The method according to any one of the preceding items, wherein the fatty acyl acetates are saturated fatty acyl acetates, desaturated fatty acyl acetates, or a mixture thereof.

8. The method according to any one of the preceding items, wherein the fatty aldehydes are saturated fatty aldehydes, desaturated fatty aldehydes, or a mixture thereof.

9. The method according to any one of the preceding items, wherein the fatty alcohol esters are saturated fatty alcohol esters, desaturated fatty alcohol esters, or a mixture thereof.

10. The method according to any one of the preceding items, wherein the fatty alcohols, fatty alcohol esters, fatty acyl acetates and/or fatty aldehydes have a carbon chain length of 8, 9, 10, 11, 12, 13, 14, 15, 16, 17, 18, 19, 20, 21 or 22.

11. The method according to any one of the preceding items, wherein the terpene is a hemiterpene, a monoterpene, a sesquiterpene, a disesterterpene, a triterpene, a sesquarterpene, a tetraterpene, or a polyterpene.

12. The method according to any one of the preceding items, wherein the terpene is a terpenoid, such as a hemiterpenoid, a monoterpenoid, a sesquiterpenoid, a disesterterpenoid, a triterpenoid, a sesquiterpenoid, a tetraterpenoid or a polyterpenoid.

13. The method according to any one of the preceding items, wherein the extractant is an ethoxylated and propoxylated $C_{16}$-$C_{18}$ alcohol-based agent or an ethoxylated and propoxylated $C_{16}$-$C_{18}$ alcohol-based antifoaming agent, preferably having a cloud concentration of 1% vol/vol in an aqueous solution.

14. The method according to any one of the preceding items, wherein the extractant is selected from $C_{16}$-$C_{18}$ alkyl alcohol ethoxylate propoxylate (CAS number 68002-96-0), Agnique BP420 (CAS number 68002-96-0), a polyethylene polypropylene glycol, antifoam 204, a surfactant comprising polyethylene glycol monostearate, and a fatty alcohol alkoxylate, such as Kolliphor® P407 (CAS number 9003-11-6), simethicone, Plurafac® LF300 (CAS number 196823-11-7), Plurafac® LF1300 (68002-96-0), Plurafac® SLF180 (CAS number 196823-11-7), Dehypon® 2574 (CAS number 68154-97-2), or Imbentin SG/251 (CAS number 68002-96-0).

15. The method according to any one of the preceding items, wherein the culture medium comprises at least 1% vol/vol extractant, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol extractant.

16. The method according to any one of the preceding items, wherein the non-ionic surfactant is an antifoaming agent.

17. The method according to any one of the preceding items, wherein the non-ionic surfactant is an ethoxylated and propoxylated $C_{16}$-$C_{18}$ alcohol-based agent or an ethoxylated and propoxylated $C_{16}$-$C_{18}$ alcohol-based antifoaming agent, such as $C_{16}$-$C_{18}$ alkyl alcohol ethoxylate propoxylate (CAS number 68002-96-0), and wherein the culture medium comprises at least 1% vol/vol of $C_{16}$-$C_{18}$ alkyl alcohol ethoxylate propoxylate, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol $C_{16}$-$C_{18}$ alkyl alcohol ethoxylate propoxylate, or more.

18. The method according to any one of the preceding items, wherein the non-ionic surfactant is a polyethylene polypropylene glycol, for example Kolliphor® P407 (CAS number 9003-11-6), and wherein the culture medium comprises at least 10% vol/vol of polyethylene polypropylene glycol such as Kolliphor® P407, such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Kolliphor® P407, or more.
19. The method according to any one of the preceding items, wherein the non-ionic surfactant is Agnique BP420 (CAS number 68002-96-0), and wherein the culture medium comprises at least 10% vol/vol of Agnique BP420 (CAS number 68002-96-0), such as at least 11% vol/vol, such as at least 12% vol/vol, such as at least 13% vol/vol, such as at least 14% vol/vol, such as at least 15% vol/vol, such as at least 16% vol/vol, such as at least 17% vol/vol, such as at least 18% vol/vol, such as at least 19% vol/vol, such as at least 20% vol/vol, such as at least 25% vol/vol, such as at least 30% vol/vol, such as at least 35% vol/vol of polyethylene polypropylene glycol such as Agnique BP420 (CAS number 68002-96-0), or more.
20. The method according to any one of the preceding items, wherein the non-ionic surfactant is a mixture of polyether dispersions, such as antifoam 204, and wherein the culture medium comprises at least 1% vol/vol of a mixture of polyether dispersions such as antifoam 204, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol of a mixture of polyether dispersions such as antifoam 204, or more.
21. The method according to any one of the preceding items, wherein the non-ionic surfactant is simethicone, and wherein the culture medium comprises at least 1% vol/vol of simethicone, such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol simethicone, or more.
22. The method according to any one of the preceding claims, wherein the nonionic surfactant is a fatty alcohol alkoxylate selected from Plurafac® LF300 (CAS number 196823-11-7), Plurafac® LF1300 (68002-96-0), Plurafac® SLF180 (CAS number 196823-11-7), Dehypon® 2574 (CAS number 68154-97-2), and Imbentin SG/251 (CAS number 68002-96-0), preferably Plurafac® LF300 or Dehypon® 2574, and wherein the culture medium comprises at least 1% vol/vol of Plurafac® LF300 (CAS number 196823-11-7), Plurafac® LF1300 (68002-96-0), Plurafac® SLF180 (CAS number 196823-11-7), Dehypon® 2574 (CAS number 68154-97-2), Imbentin SG/251 (CAS number 68002-96-0), such as at least 1.5%, such as at least 2%, such as at least 2.5%, such as at least 3%, such as at least 3.5%, such as at least 4%, such as at least 5%, such as at least 6%, such as at least 7%, such as at least 8%, such as at least 9%, such as at least 10%, such as at least 12.5%, such as at least 15%, such as at least 17.5%, such as at least 20%, such as at least 22.5%, such as at least 25%, such as at least 27.5%, such as at least 30% vol/vol Plurafac® LF300 (CAS number 196823-11-7), Plurafac® LF1300 (68002-96-0), Plurafac® SLF180 (CAS number 196823-11-7), Dehypon® 2574 (CAS number 68154-97-2), Imbentin SG/251 (CAS number 68002-96-0), or more.
23. The method according to any one of the preceding items, wherein the culture medium comprises the extractant in an amount greater than its cloud concentration by at least 50%, such as at least 100%, such as at least 150%, such as at least 200%, such as at least 250%, such as at least 300%, such as at least 350%, such as at least 400%, such as at least 500%, such as at least 750%, such as at least 1000%, or more.
24. The method according to any one of the preceding items, wherein the culture medium comprises the extractant in an amount at least 2-fold its cloud concentration, such as at least 3-fold its cloud concentration, such as at least 4-fold its cloud concentration, such as at least 5-fold its cloud concentration, such as at least 6-fold its cloud concentration, such as at least 7-fold its cloud concentration, such as at least 8-fold its cloud concentration, such as at least 9-fold its cloud concentration, such as at least 10-fold its cloud concentration, such as at least 12.5-fold its cloud concentration, such as at least 15-fold its cloud concentration, such as at least 17.5-fold its cloud concentration, such as at least 20-fold its cloud concentration, such as at least 25-fold its cloud concentration, such as at least 30-fold its cloud concentration.
25. The method according to any one of the preceding items, wherein the hydrophobic compound produced by the microorganism is present in an emulsion in the fermentation broth, the method further comprising a step of breaking said emulsion, thereby obtaining a composition comprising a product phase comprising the extractant and the hydrophobic compound.
26. The method according to item 25, wherein the step of breaking the emulsion comprises or consists of a step of phase separation, such as a step of centrifugation, of the fermentation broth, thereby obtaining a composition consisting of three phases: a water phase, a phase comprising cells and cellular debris, and the product phase comprising the extractant and the hydrophobic compound.
27. The method according to item 26, wherein the product phase comprises at least 50% of the hydrophobic compound initially present in the fermentation broth, such as at least 55%, such as at least 60%, such as at least 65%, such as at least 70%, such as at least 75%, such as at least 80%, such as at least 85%, such as at least 90%, such as at least 95% or more.

28. The method according to any one of items 26 to 27, further comprising recovering the product phase comprising the extractant and the hydrophobic compound from the composition, and optionally further separating the hydrophobic compound from the extractant, wherein the separation preferably is a distillation such as a distillation under reduced pressure, or a column purification.
29. The method according to any one of the preceding items, wherein the hydrophobic compound is one or more fatty alcohols, and wherein the method further comprises the steps of:
recovering said one or more fatty alcohols, preferably by a distillation step such as a distillation under reduced pressure, or by a column purification, thereby obtaining a mixture of fatty alcohols,
chemically converting at least part of the fatty alcohols of said mixture to the corresponding fatty acyl acetates and/or to the corresponding fatty aldehydes.
30. The method according to item 29, wherein at least part of the fatty alcohols are converted to the corresponding fatty acyl acetates by acetylation.
31. The method according to any one of items 29 to 30, wherein at least part of the fatty alcohols are converted to the corresponding fatty aldehydes by oxidation.
32. The method according to any one of items 29 to 31, further comprising the step of recovering said corresponding fatty acyl acetates and/or said corresponding fatty aldehydes.
33. The method according to any one of the preceding items, wherein the extractant is recovered from the fermentation broth and optionally recycled to the fermentation broth.
34. The method according to any one of the preceding items, wherein the titer of the hydrophobic compound is increased by at least 5% compared to the titer obtained in a fermentation performed under similar or identical conditions but either in the absence of extractant or in the presence of extractant in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more, preferably wherein the non-ionic surfactant is selected from: Agnique BP420 (CAS number 68002-96-0), a polyethylene polypropylene glycol, a mixture of polyether dispersions, an antifoaming agent comprising polyethylene glycol monostearate, simethicone, ethoxylated and propoxylated $C_{16}$-$C_{18}$ alcohol-based antifoaming agents and ethoxylated and propoxylated $C_{16}$-$C_{18}$ alcohol-based agents and combinations thereof.
35. The method according to any one of the preceding items, wherein the secretion of the hydrophobic compound is increased by at least 5% compared to a fermentation performed under similar or identical conditions but either in the absence of extractant or in the presence of extractant in an amount lower than its cloud concentration measured in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more, preferably wherein the non-ionic surfactant is selected from: Agnique BP420 (CAS number 68002-96-0), a polyethylene polypropylene glycol, a mixture of polyether dispersions, an antifoaming agent comprising polyethylene glycol monostearate, simethicone, ethoxylated and propoxylated $C_{16}$-$C_{18}$ alcohol-based antifoaming agents and ethoxylated and propoxylated $C_{16}$-$C_{18}$ alcohol-based agents and combinations thereof.
36. The method according to any one of the preceding items, wherein the hydrophobic compound is a fatty alcohol, a fatty alcohol ester, a fatty acyl acetate and/or a fatty aldehyde and the extractant is an ethoxylated and propoxylated $C_{16}$-$C_{18}$ alcohol-based agent or antifoaming agent, preferably wherein the medium comprises more than 1% vol/vol of ethoxylated and propoxylated $C_{16}$-$C_{18}$ alcohol-based agent or antifoaming agent.
37. The method according to item 36, wherein the titer of fatty alcohol, the titer of fatty acyl acetate and/or the titer of fatty aldehyde is increased by at least 5% compared to the titer obtained in a fermentation performed under similar or identical conditions but either in the absence of ethoxylated and propoxylated $C_{16}$-$C_{18}$ alcohol-based agent or antifoaming agent or in the presence of ethoxylated and propoxylated $C_{16}$-$C_{18}$ alcohol-based agent or antifoaming agent in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more.
38. The method according to any one of items 36 to 37, wherein the secretion of the fatty alcohol, the fatty acyl acetate and/or the fatty aldehyde is increased by at least 5% compared to a fermentation performed under similar or identical conditions but either in the absence of ethoxylated and propoxylated $C_{16}$-$C_{18}$ alcohol-based agent or antifoaming agent or in the presence of ethoxylated and propoxylated $C_{16}$-$C_{18}$ alcohol-based agent or antifoaming agent in an amount lower than its cloud concentration in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more.
39. The method according to any one of the preceding items, wherein the hydrophobic compound is a fatty alcohol, a fatty alcohol ester, a fatty acyl acetate and/or a fatty aldehyde and the extractant is a polyethylene polypropylene glycol, preferably wherein the medium comprises more than 1% vol/vol of polyethylene polypropylene glycol.
40. The method according to item 39, wherein the titer of fatty alcohol, the titer of fatty acyl acetate and/or the titer of fatty aldehyde is increased by at least 5% compared to the titer obtained in a fermentation performed under similar or identical conditions but either in the absence of polyethylene polypropylene glycol or in the presence of polyethylene polypropylene glycol in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more.

41. The method according to any one of items 39 to 40, wherein the secretion of the fatty alcohol, the fatty acyl acetate and/or the fatty aldehyde is increased by at least 5% compared to a fermentation performed under similar or identical conditions but either in the absence of polyethylene polypropylene glycol or in the presence of polyethylene polypropylene glycol in an amount lower than its cloud concentration in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more.

42. The method according to any one of the preceding items, wherein the hydrophobic compound is a fatty alcohol, a fatty alcohol ester, a fatty acyl acetate and/or a fatty aldehyde and the extractant is a mixture of polyether dispersions, preferably wherein the medium comprises more than 1% vol/vol of a mixture of polyether dispersions.

43. The method according to item 42, wherein the titer of fatty alcohol, the titer of fatty acyl acetate and/or the titer of fatty aldehyde is increased by at least 5% compared to the titer obtained in a fermentation performed under similar or identical conditions but either in the absence of the mixture of polyether dispersions or in the presence of the mixture of polyether dispersions in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more.

44. The method according to any one of items 42 to 43, wherein the secretion of the fatty alcohol, the fatty acyl acetate and/or the fatty aldehyde is increased by at least 5% compared to a fermentation performed under similar or identical conditions but either in the absence of mixture of polyether dispersions or in the presence of the mixture of polyether dispersions in an amount lower than its cloud concentration in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more.

45. The method according to any one of the preceding items, wherein the hydrophobic compound is a fatty alcohol, a fatty alcohol ester, a fatty acyl acetate and/or a fatty aldehyde and the extractant is simethicone, preferably wherein the medium comprises more than 1% vol/vol of simethicone.

46. The method according to item 45, wherein the titer of fatty alcohol, the titer of fatty acyl acetate and/or the titer of fatty aldehyde is increased by at least 5% compared to the titer obtained in a fermentation performed under similar or identical conditions but either in the absence of simethicone or in the presence of simethicone in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more.

47. The method according to any one of items 45 to 46, wherein the secretion of the fatty alcohol, the fatty acyl acetate and/or the fatty aldehyde is increased by at least 5% compared to a fermentation performed under similar or identical conditions but either in the absence of simethicone or in the presence of the antifoaming agent comprising simethicone in an amount lower than its cloud concentration in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more.

48. The method according to any one of the preceding items, wherein the hydrophobic compound is a fatty alcohol, a fatty alcohol ester, a fatty acyl acetate and/or a fatty aldehyde and the extractant is a $C_{16}$-$C_{18}$ alkyl alcohol ethoxylate propoxylate (CAS number 68002-96-0), Agnique BP420 (CAS number 68002-96-0), a polyethylene polypropylene glycol, antifoam 204, a surfactant comprising polyethylene glycol monostearate, and a fatty alcohol alkoxylate, such as Kolliphor® P407 (CAS number 9003-11-6), simethicone, Plurafac® LF300 (CAS number 196823-11-7), Plurafac® LF1300 (68002-96-0), Plurafac® SLF180 (CAS number 196823-11-7), Dehypon® 2574 (CAS number 68154-97-2), or Imbentin SG/251 (CAS number 68002-96-0), preferably wherein the medium comprises more than 1% vol/vol of the extractant.

49. The method according to item 48, wherein the titer of fatty alcohol, the titer of fatty acyl acetate and/or the titer of fatty aldehyde is increased by at least 5% compared to the titer obtained in a fermentation performed under similar or identical conditions but either in the absence of the extractant or in the presence of the extractant in an amount lower than its cloud concentration in an aqueous solution, such as by at least 10%, such as by at least 15%, such as by at least 20%, such as by at least 25%, such as by at least 30%, such as by at least 35%, such as by at least 40%, such as by at least 45%, such as by at least 46%, such as by at least 47%, such as by at least 48%, such as by at least 49%, such as by at least 50%, such as by at least 51%, such as by at least 52%, such as by at least 53%, such as by at least 54%, such as by at least 55% or more.

50. The method according to any one of items 48 to 49, wherein the secretion of the fatty alcohol, the fatty acyl acetate and/or the fatty aldehyde is increased by at least 5% compared to a fermentation performed under similar or identical conditions but either in the absence of the extractant or in the presence of the extractant in an amount lower than its cloud concentration in an aqueous solution, such as by at least 7.5%, such as by at least 10%, such as by at least 12.5%, such as by at least 15%, such as by at least 20%, such as by at least 25%, such as by at least 30%, such as by at least 35%, such as by at least 36%, such as by at least 37%, such as by at least 38%, such as by at least 39%, such as by at least 40%, such as by at least or more.

51. The method according to any one of the preceding items, wherein the microorganism is a yeast such as a yeast of the genus *Saccharomyces, Pichia, Yarrowia, Kluyveromyces, Candida, Rhodotorula, Rhodosporidium, Cryptococcus, Trichosporon* and *Lipomyces*, preferably the genus is *Saccharomyces* or *Yarrowia.*

52. The method according to any one of the preceding items, wherein the microorganism is a yeast of a species selected from *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon* pullulan and *Yarrowia lipolytica*, preferably the yeast cell is a *Saccharomyces cerevisiae* cell or a *Yarrowia lipolytica* cell.

53. The method according to any one of the preceding items, wherein the hydrophobic compound is (Z)-11-hexadecen-1-ol and the microorganism is a yeast cell capable of producing (Z)-11-hexadecen-1-ol with a titer of at least 0.2 mg/L, preferably wherein said yeast cell is a *Saccharomyces cerevisiae* cell, said yeast cell expressing:

a Δ11-desaturase selected from the group consisting of the *Amyelois transitella* Δ11-desaturase (Atr_Δ11; SEQ ID NO: 1), the *Spodoptera littoralis* Δ11-desaturase (SI_Δ11; SEQ ID NO: 2), the *Agrotis segetum* Δ11-desaturase (As_Δ11; SEQ ID NO: 3), the desaturase from *Lobesia botrana* (Lbo_PPTQ; SEQ ID NO: 43), the desaturase from *Drosophila grimshawi* (Dgd9; SEQ ID NO: 44), the desaturase from *Drosophila virilis* (Dvd9; SEQ ID NO: 45) and the *Trichoplusia* ni Δ11-desaturase (Tni_Δ11; SEQ ID NO: 4) or a functional thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 1), SI_Δ11 (SEQ ID NO: 2), As_Δ11 (SEQ ID NO: 3), Lbop_PPTQ (SEQ ID NO: 43), Dgd9 (SEQ ID NO: 44), Dvd9 (SEQ ID NO: 45) or Tni_Δ11 (SEQ ID NO: 4), and an alcohol-forming fatty acyl-CoA reductase (FAR) selected from the group consisting of Har_FAR (SEQ ID NO: 5), Hs_FAR (SEQ ID NO: 6), and Has_FAR (SEQ ID NO: 7), or a variant thereof having at least 80% homology, such as at least 85%, such as at least 90%, such as at least 95%, such as 100% homology to Har_FAR (SEQ ID NO: 5), Hs_FAR (SEQ ID NO: 6), or Has_FAR (SEQ ID NO: 7);

whereby the Δ11-desaturase is capable of converting at least part of said hexadecanoyl-CoA to (Z)11-hexadecenoyl-CoA; and the FAR is capable of converting at least part of said (Z)11-hexadecenoyl-CoA to (Z)-11-hexadecanol.

54. The method according to item 53, wherein the yeast cell further expresses a fatty acyl synthetase (FAA), such as Sc_FAA1 (SEQ ID NO: 8) or YI_FAA (SEQ ID NO: 9) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 8) or YI_FAA (SEQ ID NO: 9).

55. The method according to any one of items 53 to 54, further comprising the step of converting at least part of the (Z)-11-hexadecen-1-ol into (Z)-11-hexadecen1-yl acetate by chemical conversion or by expression of an acetyltransferase such as a heterologous acetyltransferase (AcT) from said yeast cell or by overexpression of a native acetyltransferase from said yeast cell, wherein said acetyltransferase is capable of converting at least part of the (Z)-11-hexadecen1-al into (Z)11-hexadecen-1-yl acetate, preferably wherein the acetyltransferase is Sc_Atf1 (SEQ ID NO: 10) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

56. The method according to any one of items 1 to 55, wherein the hydrophobic compound is a desaturated fatty alcohol and the microorganism is an oleaginous yeast cell such as a *Yarrowia* cell, for example a *Yarrowia lipolytica* cell, capable of producing said desaturated fatty alcohol, said oleaginous yeast cell:

expressing at least one heterologous desaturase capable of introducing at least one double bond in a fatty acyl-CoA; and expressing at least one heterologous fatty acyl-CoA reductase, capable of converting at least part of said desaturated fatty acyl-CoA to a desaturated fatty alcohol; and having a mutation resulting in reduced activity of Fao1 (SEQ ID NO: 11) and a mutation resulting in reduced activity of at least one of Hfd1 (SEQ ID NO: 12), Hfd4 (SEQ ID NO: 13), Pex10 (SEQ ID NO: 14) and GPAT (SEQ ID NO: 15) or having a mutation resulting in reduced activity of at least one protein having at least 90% homology to Fao1 (SEQ ID NO: 11) and a mutation resulting in reduced activity of at least one of Hfd1 (SEQ ID NO: 12), Hfd4 (SEQ ID NO: 13), Pex10 (SEQ ID NO: 14) and GPAT (SEQ ID NO: 15), such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 11) and at least one of Hfd1 (SEQ ID NO: 12), Hfd4 (SEQ ID NO: 13), Pex10 (SEQ ID NO: 14) and GPAT (SEQ ID NO: 15).

57. The method according to item 56, wherein the at least one heterologous desaturase is selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase, a Δ13 desaturase and a Δ14 desaturase, preferably wherein the desaturase is derived from an insect, such as from the Lepidoptera order, preferably the desaturase is a Δ11 desaturase having at least 60% homology to the Δ11 desaturase from *Amyelois* transitella as set forth in SEQ ID NO: 1, a Δ9 desaturase having at least 60% homology to the Δ9 desaturase from *Drosophila melanogaster* as set forth in SEQ ID NO: 16, a desaturase having at least 60% homology to the desaturase from *Lobesia botrana* as set forth in SEQ ID NO: 43, a desaturase having at least 60% homology to the desaturase from *Drosophila grimshawi* as set forth in SEQ ID NO: 44 or a desaturase having at least 60% homology to the desaturase from *Drosophila virilis* as set forth in SEQ ID NO: 45.

58. The method according to any one of items 56 to 57, wherein the fatty acyl reductase (FAR) is selected from:
   i) a FAR having at least 80% homology to the FAR from *Helicoverpa armigera* as set forth in SEQ ID NO: 5;
   ii) a FAR having at least 80% homology to the FAR from *Helicoverpa assulta* as set forth in SEQ ID NO: 7;
   iii) a FAR having at least 80% homology to the FAR from *Heliothis subflexa* as set forth in SEQ ID NO: 6; and
   iv) a FAR having at least 80% homology to the FAR from *Bicyclus anynana* as set forth in SEQ ID NO: 17, preferably the FAR has at least 80% homology to the FAR from *Helicoverpa armigera* or to the FAR from *Heliothis subflexa*.

59. The method according to any one of items 56 to 58, further comprising the step of converting at least part of the desaturated fatty alcohol to a fatty acyl acetate by chemical conversion or by expression of an acetyltransferase such as a heterologous acetyltransferase (AcT) from said oleaginous yeast cell or by overexpression of a native acetyltransferase from said oleaginous yeast cell, wherein said acetyltransferase is capable of converting at least part of the desaturated fatty alcohol to a fatty acyl acetate, preferably wherein the acetyltransferase is Sc_Atf1 (SEQ ID NO: 10) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

60. The method according to any one of items 1 to 52, wherein the hydrophobic compound is a desaturated fatty alcohol and the microorganism is a yeast cell such as a *Yarrowia* cell, for example a *Yarrowia lipolytica* cell, capable of producing said desaturated fatty alcohol, said yeast cell expressing:
   at least one heterologous desaturase capable of introducing at least one double bond in a fatty acyl-CoA having a carbon chain length of 14; and
   at least one heterologous fatty acyl-CoA reductase (FAR), capable of converting at least part of said desaturated fatty acyl-CoA to a desaturated fatty alcohol.

61. The method according to item 60, wherein the at least one heterologous desaturase is derived from an organism selected from *Pelargonium hortorum, Ricinus communis, Drosophila melanogaster, Spodoptera litura* and *Tribolium castaneum*, preferably the desaturase is derived from *Drosophila melanogaster*, preferably wherein the at least one heterologous desaturase is selected from the group consisting of:
   i) a Δ9 desaturase having at least 60% homology to the Δ9 desaturase from *Drosophila melanogaster* as set forth in SEQ ID NO: 16;
   ii) a Δ9 desaturase having at least 60% homology to the Δ9 desaturase from *Spodoptera litura* as set forth in SEQ ID NO: 18;
   iii) a desaturase having at least 60% homology to the desaturase from *Lobesia botrana* as set forth in SEQ ID NO: 43;
   iv) a desaturase having at least 60% homology to the desaturase from *Drosophila grimshawi* as set forth in SEQ ID NO: 44; and
   v) a desaturase having at least 60% homology to the desaturase from *Drosophila virilis* as set forth in SEQ ID NO: 45,
   vi) a Δ11 desaturase having at least 60% homology to the Δ11 desaturase from *Choristoneura parallela* as set forth in SEQ ID NO: 42,
   vii) a Δ11 desaturase having at least 60% homology to the Δ11 desaturase from *Choristoneura rosaceana* as set forth in SEQ ID NO: 35.

62. The method according to any one of items 60 to 61, wherein the fatty acyl-CoA reductase (FAR) is selected from:
   i) a FAR having at least 80% homology to the FAR from *Helicoverpa armigera* as set forth in SEQ ID NO: 5;
   ii) a FAR having at least 80% homology to the FAR from *Helicoverpa assulta* as set forth in SEQ ID NO: 7;
   iii) a FAR having at least 80% homology to the FAR from *Heliothis subflexa* as set forth in SEQ ID NO: 6; and
   iv) a FAR having at least 80% homology to the FAR from *Bicyclus anynana* as set forth in SEQ ID NO: 17, preferably the FAR is a FAR having at least 80% homology to the FAR from *Helicoverpa armigera* as set forth in SEQ ID NO: 5.

63. The method according to any one of items 60 to 62, further comprising the step of converting at least part of the desaturated fatty alcohol to a fatty acyl acetate by chemical conversion or by expression of an acetyltransferase such as a heterologous acetyltransferase (AcT) from said oleaginous yeast cell or by overexpression of a native acetyltransferase from said oleaginous yeast cell, wherein said acetyltransferase is capable of converting at least part of the desaturated fatty alcohol to a fatty acyl acetate, preferably wherein the acetyltransferase is Sc_Atf1 (SEQ ID NO: 10) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

64. The method according to any one of items 1 to 52, wherein the hydrophobic compound is a desaturated fatty alcohol and the microorganism is a yeast cell capable of producing said desaturated fatty alcohol, said yeast cell:
   having one or more mutations resulting in reduced activity of one or more native acyl-CoA oxidases; and
   expressing at least one first group of enzymes comprising at least one acyl-CoA oxidase capable of oxidising a fatty acyl-CoA, wherein the first group of enzymes is capable of shortening a fatty acyl-CoA of a first carbon chain length X to a shortened fatty acyl-CoA having a second carbon chain length X', wherein X'≤X−2; and
   expressing at least one heterologous desaturase capable of introducing at least one double bond in said fatty acyl-CoA and/or in said shortened fatty acyl-CoA; and
   expressing at least one heterologous fatty acyl-CoA reductase, capable of converting at least part of said desaturated fatty acyl-CoA to a desaturated fatty alcohol.

65. The method according to item 64, wherein the native acyl-CoA oxidase and/or the heterologous acyl-CoA oxidase is a peroxisomal acyl-CoA oxidase.

66. The method according to any one of items 64 to 65, wherein the at least one acyl-CoA oxidase of the first group of enzymes is a native acyl-CoA oxidase or a heterologous acyl-CoA oxidase, which is optionally overexpressed compared to a reference yeast strain not expressing said at least one first group of enzymes, preferably the at least one acyl-CoA oxidase of the first group of enzymes is a heterologous acyl-CoA oxidase, optionally wherein the at least one first group of enzymes comprises an acyl-CoA oxidase derived from an organism of a genus selected from *Yarrowia, Agrotis, Arabidopsis, Aspergillus, Cucurbita, Homo, Paenarthrobacter* and *Rattus*, preferably the at least one first group of enzymes comprises an acyl-CoA oxidase derived from *Yarrowia lipolytica, Agrotis segetum, Arabidopsis thaliana, Aspergillus nidulans, Cucurbita maxima, Homo sapiens, Paenarthrobacter ureafaciens* or *Rattus norvegicus*, preferably the at least one acyl-CoA oxidase of the first group of enzymes is an acyl-CoA oxidase selected from the group consisting of Yli_POX1 (SEQ ID NO: 19), Yli_POX2 (SEQ ID NO: 20), Yli_POX3 (SEQ ID NO: 21), Yli_POX4 (SEQ ID NO: 22), Yli_POX5 (SEQ ID NO: 23), Yli_POX6 (SEQ ID NO: 24), Ase_POX (SEQ ID NO: 25), Ath_POX1 (SEQ ID NO: 26), Ath_POX2 (SEQ ID NO: 27), Ani_POX (SEQ ID NO: 28), Cma_POX (SEQ ID NO: 29), Hsa_POX1-2 (SEQ ID NO: 30), Pur_POX (SEQ ID NO: 31), and Rno_POX2 (SEQ ID NO: 32), or a functional variant thereof having at least 60% homology thereto, such as at least 65%, such as at least 70%, such as at least 75%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% homology thereto.

67. The method according to any one of items 64 to 66, wherein the at least one heterologous desaturase is selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase, a Δ13 desaturase and a Δ14 desaturase, and/or wherein the desaturase is derived from a yeast such as *Saccharomyces* or *Yarrowia*, such as *Saccharomyces cerevisiae* or *Yarrowia lipolytica*, or from an insect, such as from the *Diptera*, the Coleoptera, or the Lepidoptera order, such as of the genus *Amyelois, Choristoneura, Drosophila, Ostrinia, Thaumetopoea, Dendrophilus, Grapholita, Cydia, Epiphyas*, or *Spodoptera*, such as *Drosophila melanogaster, Amyelois transitella, Choristoneura rosaceana, Ostrinia nubilalis, Thaumetopoea pityocampa, Dendrophilus punctatus, Grapholita molesta, Cydia pomonella, Epiphyas postvittana, Spodoptera littoralis* or *Choristoneura parallela.*

68. The method according to any one of items 64 to 67, wherein the desaturase is a $\Delta_{Z9}$-desaturase such as Sce_OLE1 (SEQ ID NO: 33), Yli_OLE1 (SEQ ID NO: 34) or Dme_D9 (SEQ ID NO: 16), a $\Delta_{Z11}$-desaturase such as Atr_D11 (SEQ ID NO: 1), Cro_Z11 (SEQ ID NO: 35), Onu_11 (SEQ ID NO: 36), Tpi_D13 (SEQ ID NO: 37), a $\Delta_{E9}$-desaturase such as Dpu_E9-14 (SEQ ID NO: 38), a $\Delta_{Z/E10}$-desaturase such as Gmo_CPRQ (SEQ ID NO: 39), or a desaturase such as Epo_E11 (SEQ ID NO: 40), SIs_ZE11 (SEQ ID NO: 41), Lbo_PPTQ (SEQ ID NO: 43), Dgd9 (SEQ ID NO: 44), Dvd9 (SEQ ID NO: 45) or Cpa_E11 (SEQ ID NO: 42), or a functional variant thereof having at least 60% homology thereto, such as at least 65%, such as at least 70%, such as at least 75%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% homology thereto.

69. The method according to any one of items 64 to 68, wherein the fatty acyl-CoA reductase is derived from an insect such as an insect of the Lepidoptera order, such as of the genus *Helicoverpa, Heliothis* or *Bicyclus*, preferably the fatty acyl-CoA reductase is a fatty acyl-CoA reductase native to *Helicoverpa armigera, Helicoverpa* assulta, *Heliothis subflexa, Bicyclus anynana*, or a functional variant thereof, preferably the fatty acyl-CoA reductase is selected from the group consisting of a fatty acyl-CoA reductase having at least 80% homology to Har_FAR (SEQ ID NO: 5), Has_FAR (SEQ ID NO: 7), Ban_FAR (SEQ ID NO: 17) or Hs_FAR (SEQ ID NO: 6).

70. The method according to any one of items 64 to 69, further comprising the step of converting at least part of the desaturated fatty alcohol to a fatty acyl acetate by chemical conversion or by expression of an acetyltransferase such as a heterologous acetyltransferase (AcT) from said yeast cell or by overexpression of a native acetyltransferase from said yeast cell, wherein said acetyltransferase is capable of converting at least part of the desaturated fatty alcohol to a desaturated fatty acyl acetate, preferably wherein the acetyltransferase is Sc_Atf1 (SEQ ID NO: 10) or a functional variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_Atf1 (SEQ ID NO: 10).

71. The method according to any one of items 64 to 70, further comprising the step of converting at least part of the desaturated fatty alcohol to a desaturated fatty aldehyde by expression of at least one alcohol dehydrogenase and/or at least one fatty alcohol oxidase from said yeast cell.

72. A hydrophobic compound obtainable by the method according to any one of the preceding items.

73. The hydrophobic compound according to item 72, wherein the hydrophobic compound is a fatty alcohol, a fatty alcohol ester, a fatty acyl acetate or a fatty aldehyde, preferably as defined in any one of items 1 to 71.

74. The hydrophobic compound according to any one of items 72 to 73, wherein the hydrophobic compound is one or more fatty alcohols, wherein at least one of said fatty alcohols has a carbon chain length of 1, 3, 5, 7, 9, 11, 13, 15, 17, 19, 21, or 23, preferably of 9, 11, 13, 15, 17, 19, 21, or 23.

75. The hydrophobic compound according to any one of items 72 to 74, wherein the hydrophobic compound is one or more fatty acyl acetates, wherein at least one of said fatty acyl acetates has a carbon chain length of 1, 3, 5, 7, 9, 11, 13, 15, 17, 19, 21, or 23, preferably of 9, 11, 13, 15, 17, 19, 21, or 23.

76. The hydrophobic compound according to any one of items 72 to 75, wherein the hydrophobic compound is one or more fatty aldehydes, wherein at least one of said fatty aldehydes has a carbon chain length of 1, 3, 5, 7, 9, 11, 13, 15, 17, 19, 21, or 23, preferably of 9, 11, 13, 15, 17, 19, 21, or 23.

77. A method of monitoring the presence of pest or disrupting the mating of pest, said method comprising the steps of:
   i) producing a hydrophobic compound by the method of any of items 1 to 71, wherein the hydrophobic compound is a desaturated fatty alcohol, a desaturated fatty acyl acetate and/or a desaturated fatty aldehyde,
   ii) formulating said desaturated fatty alcohol, desaturated fatty acyl acetate and/or desaturated fatty aldehyde as a pheromone composition, and
   iii) employing said pheromone composition as an integrated pest management composition.

The invention claimed is:

1. A method for producing a hydrophobic compound selected from a fatty alcohol, a fatty alcohol ester, a fatty acyl acetate, a fatty aldehyde and a terpene in a fermentation, said method comprising the step of providing an engineered yeast cell capable of producing said hydrophobic compound and culturing said engineered yeast cell in a culture medium under conditions allowing production of said hydrophobic compound, wherein the culturing step is performed at a cultivation temperature, wherein the culture medium comprises an extractant in an amount equal to or greater than its cloud concentration measured in an aqueous solution, wherein the extractant is a non-ionic ethoxylated surfactant, the method further comprising the step of recovering the hydrophobic compound.

2. The method according to claim 1, wherein the non-ionic ethoxylated surfactant is:

a. a fatty alcohol alkoxylate or a polyethoxylated surfactant; or b. a polyethylene polypropylene glycol, a mixture of polyether dispersions, an antifoaming agent comprising polyethylene glycol monostearate, a surfactant comprising polyethylene glycol monostearate, a fatty alcohol alkoxylate, ethoxylated and propoxylated $C_{16}$-$C_{18}$ alcohol-based agents or ethoxylated and propoxylated $C_{16}$-$C_{18}$ alcohol-based antifoaming agents and combinations thereof; or c. $C_{16}$-$C_{18}$ alkyl alcohol ethoxylate propoxylate (CAS number 68002-96-0), Agnique BP420 (CAS number 68002-96-0), simethicone, Kolliphor® P407 (CAS number 9003-11-6), Plurafac® LF300 (CAS number 196823-11-7), Plurafac® LF1300 (CAS number: 68002-96-0), Plurafac® SLF180 (CAS number 196823-11-7), Dehypon® 2574 (CAS number 68154-97-2) or Imbentin SG/251 (CAS number: 68002-96-0).

3. The method according to claim 1, wherein:

a. the fatty alcohols are saturated fatty alcohols, desaturated fatty alcohols, or a mixture thereof; and/or b. the fatty acyl acetates are saturated fatty acyl acetates, desaturated fatty acyl acetates, or a mixture thereof; and/or c. the fatty aldehydes are saturated fatty aldehydes, desaturated fatty aldehydes, or a mixture thereof; and/or d. the terpene is a sesquiterpene; and/or e. the fatty alcohol ester is a fatty alcohol acetate ester.

4. The method according to claim 1, wherein the culture medium comprises:

a. at least 1% vol/vol of the non-ionic ethoxylated surfactant, or more; or b. the extractant in an amount greater than its cloud concentration by at least 50%, or more; or c. the extractant in an amount at least 2-fold its cloud concentration.

5. The method according to claim 1, wherein the hydrophobic compound produced by the microorganism is present in an emulsion in the fermentation broth, the method further comprising a step of breaking said emulsion, thereby obtaining a composition comprising a product phase comprising the extractant and the hydrophobic compound.

6. The method according to claim 5, wherein the step of breaking the emulsion comprises or consists of a step of phase separation of the fermentation broth, thereby obtaining a composition consisting of three phases: a water phase, a phase comprising cells and cellular debris, and the product phase comprising the extractant and the hydrophobic compound.

7. The method according to claim 5, further comprising recovering the product phase comprising the extractant and the hydrophobic compound from the composition.

8. The method according to claim 1, wherein the hydrophobic compound is one or more fatty alcohols, and wherein the method further comprises the step of recovering said one or more fatty alcohols, thereby obtaining a mixture of fatty alcohols.

9. The method according to claim 8, further comprising:

a. chemically converting at least part of the fatty alcohols of said mixture of fatty alcohols to the corresponding fatty acyl acetates; and/or b. chemically converting at least part of the fatty alcohols of said mixture of fatty alcohols to the corresponding fatty aldehydes.

10. The method according claim 9, further comprising the step of recovering said corresponding fatty acyl acetates and/or said corresponding fatty aldehydes.

11. The method according to claim 1, wherein the engineered yeast is of the genus *Saccharomyces, Pichia, Yarrowia, Kluyveromyces, Candida, Rhodotorula, Rhodosporidium, Cryptococcus, Trichosporon* or *Lipomyces*, or wherein the engineered yeast is of a species selected from *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon pullulan* and *Yarrowia lipolytica.*

12. The method according to claim 1, wherein the hydrophobic compound is a desaturated fatty alcohol, an acetate ester of a saturated or desaturated fatty alcohol, or a fatty aldehyde.

13. The method according to claim 12, wherein:

a. the desaturated fatty alcohol is (Z)-11-hexadecen-1-ol, (Z)9-hexadecen-1-ol, (Z)11-tetradecen-1-ol, (E)11-tetradecen-1-ol, (Z)9-tetradecen-1-ol or E8,E10-dodecadien-1-ol; and/or b. the acetate ester of a desaturated fatty alcohol is (Z)9-tetradecen-1-yl acetate or E8,E10-dodecadienyl acetate; and/or c. the fatty aldehyde is an unsaturated fatty aldehyde; and/or d. the fatty aldehyde is (Z)11-hexadecen-1-al or E8,E10-dodecadienal.

14. The method according to claim 1, wherein the engineered yeast cell is capable of producing the hydrophobic compound with a titer of at least 0.2 mg/L.

15. The method according to claim 1, wherein the engineered yeast cell expresses:

a Δ11-desaturase selected from *Amyelois transitella* Δ11-desaturase (Atr_Δ11; SEQ ID NO: 1), the *Spodoptera littoralis* Δ11-desaturase (S1_Δ11; SEQ ID NO: 2), the *Agrotis segetum* Δ11-desaturase (As_Δ11; SEQ ID NO: 3), the desaturase from *Lobesia botrana* (Lbo_PPTQ; SEQ ID NO: 43), the desaturase from *Drosophila grimshawi* (Dgd9; SEQ ID NO: 44), the desaturase from *Drosophila virilis* (Dvd9; SEQ ID NO: 45) and the *Trichoplusia ni* Δ11-desaturase (Tni_Δ11; SEQ ID NO: 4) or a functional variant thereof having at least 65% sequence identity to Atr_Δ11 (SEQ ID NO: 1), SI_Δ11 (SEQ ID NO: 2), As_Δ11 (SEQ ID NO: 3), Lbo_PPTQ (SEQ ID NO: 43), Dgd9 (SEQ ID NO: 44), Dvd9 (SEQ ID NO: 45) or Tni_Δ11 (SEQ ID NO: 4), and an alcohol-forming fatty acyl-CoA reductase (FAR) selected from Har_FAR (SEQ ID NO: 5), Hs_FAR (SEQ ID NO: 6), and Has_FAR (SEQ ID NO: 7), or a functional variant thereof having at least 80% sequence identity to Har_FAR (SEQ ID NO: 5), Hs_FAR (SEQ ID NO: 6), or Has_FAR (SEQ ID NO: 7);

whereby the Δ11-desaturase is capable of converting hexadecanoyl-CoA to (Z)11-hexadecenoyl-CoA; and the FAR is capable of converting at least part of said (Z)11-hexadecenoyl-CoA to (Z)-11-hexadecenol.

16. The method according to claim 1, wherein the hydrophobic compound is a desaturated fatty alcohol and the engineered yeast cell is an engineered oleaginous yeast cell capable of producing said desaturated fatty alcohol, said engineered oleaginous yeast cell:

a. expressing at least one heterologous desaturase capable of introducing at least one double bond in a fatty acyl-CoA, thereby converting said fatty acyl-CoA to a desaturated fatty acyl-CoA; and expressing at least one heterologous fatty acyl-CoA reductase, capable of converting at least part of said desaturated fatty acyl-CoA to a desaturated fatty alcohol; and having a mutation resulting in reduced activity of Fao1 and a mutation resulting in reduced activity of at least one of Hfd1, Hfd4, Pex10 and GPAT or having a mutation resulting in reduced activity of at least one protein having at least 90% sequence identity to Fao1 as set forth in SEQ ID NO: 11 and a mutation resulting in reduced activity of at least one of Hfd1 as set forth in SEQ ID NO: 12, Hfd4 as set forth in SEQ ID NO: 13, Pex10 as set forth in SEQ ID NO: 14 and GPAT as set forth in SEQ ID NO: 15, wherein said mutations resulting in reduced activity are mutations in the genes encoding Fao1, Hfd1, Hfd4, Pex10 or GPAT, respectively; or b. expressing at least one heterologous desaturase capable of introducing at least one double bond in a fatty acyl-CoA having a carbon chain length of 14, thereby converting said fatty acyl-CoA having a carbon chain length of 14 to a desaturated fatty acyl-CoA; and expressing at least one heterologous fatty acyl-CoA reductase (FAR), capable of converting at least part of said desaturated fatty acyl-CoA to a desaturated fatty alcohol; or c. having one or more mutations resulting in reduced activity of one or more native acyl-CoA oxidases, wherein said mutations resulting in reduced activity are mutations in the genes encoding the one or more native acyl-CoA oxidases; and expressing at least one first group of enzymes comprising at least one acyl-CoA oxidase capable of oxidizing a fatty acyl-CoA, wherein the first group of enzymes is capable of shortening a fatty acyl-CoA of a first carbon chain length X to a shortened fatty acyl-CoA having a second carbon chain length X', wherein $X' \leq X-2$; and expressing at least one heterologous desaturase capable of introducing at least one double bond in said fatty acyl-CoA or in said shortened fatty acyl-CoA, thereby converting said fatty acyl-CoA or said shortened fatty acyl-CoA to a desaturated fatty acyl-CoA; and expressing at least one heterologous fatty acyl-CoA reductase, capable of converting at least part of said desaturated fatty acyl-CoA to a desaturated fatty alcohol.

17. The method according to claim 16, further comprising the step of converting at least part of the desaturated fatty alcohol to:

a. a desaturated fatty acyl acetate by chemical conversion or by expression of an acetyltransferase from said engineered yeast cell or by overexpression of a native acetyltransferase from said engineered yeast cell, wherein said acetyltransferase is capable of converting at least part of the desaturated fatty alcohol to a desaturated fatty acyl acetate; and/or b. a desaturated fatty aldehyde by expression of:

i. at least one alcohol dehydrogenase; and/or ii. at least one fatty alcohol oxidase:

from said engineered yeast cell.

* * * * *